(12) United States Patent
Goletz et al.

(10) Patent No.: US 8,592,165 B2
(45) Date of Patent: Nov. 26, 2013

(54) CARBOHYDRATE SPECIFIC CELLULAR IMMUNITY INDUCING MICROORGANISMS AND FRACTIONS THEREOF

(75) Inventors: Steffen Goletz, Glienicke-Nordbahn (DE); Philippe Ulsemer, Berlin (DE); Anja Löffler, Schorfheide (DE)

(73) Assignee: Glycotope GmbH, Berlin (DE)

( * ) Notice: Subject to any disclaimer, the term of this patent is extended or adjusted under 35 U.S.C. 154(b) by 742 days.

(21) Appl. No.: 12/514,200

(22) PCT Filed: Nov. 12, 2007

(86) PCT No.: PCT/EP2007/009765
§ 371 (c)(1),
(2), (4) Date: Nov. 11, 2009

(87) PCT Pub. No.: WO2008/055702
PCT Pub. Date: May 15, 2008

(65) Prior Publication Data
US 2010/0303837 A1 Dec. 2, 2010

(30) Foreign Application Priority Data
Nov. 10, 2006 (EP) ..................................... 06090208
Nov. 10, 2006 (EP) ..................................... 06090209

(51) Int. Cl.
*G01N 33/50* (2006.01)
(52) U.S. Cl.
USPC .......................................................... 435/7.1
(58) Field of Classification Search
None
See application file for complete search history.

(56) References Cited

U.S. PATENT DOCUMENTS

| | | |
|---|---|---|
| 4,931,275 A | 6/1990 | Shinitzky et al. |
| 5,506,343 A | 4/1996 | Kufe |
| 5,547,933 A | 8/1996 | Lin |
| 5,683,674 A | 11/1997 | Taylor-Papadimitriou et al. |
| 5,739,277 A | 4/1998 | Presta et al. |
| 5,804,187 A | 9/1998 | do Couto et al. |
| 5,961,979 A | 10/1999 | Srivastava |
| 6,168,793 B1 | 1/2001 | Srivastava |
| 6,315,997 B1 | 11/2001 | do Couto et al. |
| 6,984,384 B1 | 1/2006 | Subjeck et al. |
| 7,268,120 B1 | 9/2007 | Horton et al. |
| 7,595,192 B2 | 9/2009 | Goletz et al. |
| 8,017,388 B2 | 9/2011 | Goletz et al. |
| 8,088,357 B2 | 1/2012 | Goletz et al. |
| 2002/0132771 A1 | 9/2002 | Madiyalakan |
| 2004/0265998 A1 | 12/2004 | Goletz et al. |
| 2005/0187378 A1 | 8/2005 | Kim |
| 2005/0203010 A1 | 9/2005 | Kim |
| 2006/0127419 A1 | 6/2006 | Goletz et al. |
| 2006/0251668 A1 | 11/2006 | Goletz et al. |
| 2006/0292129 A1 | 12/2006 | Goletz et al. |
| 2007/0015239 A1 | 1/2007 | Bihoreau et al. |
| 2007/0016704 A1 | 1/2007 | Harari et al. |
| 2008/0226681 A1 | 9/2008 | Goletz et al. |
| 2010/0028947 A1 | 2/2010 | Goletz et al. |
| 2010/0158952 A1 | 6/2010 | Goletz |

FOREIGN PATENT DOCUMENTS

| | | |
|---|---|---|
| DE | 43 29 004 A1 | 3/1995 |
| EP | 0 117 060 A2 | 8/1984 |
| EP | 1 167 537 A1 | 1/2002 |
| WO | WO 92/15682 | 9/1992 |
| WO | WO 93/20841 A1 | 10/1993 |
| WO | WO 94/29469 A2 | 12/1994 |
| WO | WO 97/00957 A1 | 1/1997 |
| WO | WO 97/30087 A1 | 8/1997 |
| WO | WO 97/40182 A1 | 10/1997 |
| WO | WO 99/29834 A1 | 6/1999 |
| WO | WO 00/52135 | 9/2000 |
| WO | WO 01/12217 A1 | 2/2001 |
| WO | WO 02/44217 A2 | 6/2002 |
| WO | WO 03/016329 | 2/2003 |
| WO | WO 03/023023 A1 | 3/2003 |
| WO | WO 03/035636 | 5/2003 |
| WO | WO 03/044051 A1 | 5/2003 |
| WO | WO 2004/009632 A2 | 1/2004 |
| WO | WO 2004/018659 A1 | 3/2004 |
| WO | WO 2004/050707 A2 | 6/2004 |
| WO | WO 2005/016962 A2 | 2/2005 |
| WO | WO 2005/017130 A2 | 2/2005 |
| WO | WO 2005/040221 A1 | 5/2005 |
| WO | WO 2005/080585 A1 | 9/2005 |
| WO | WO 2005/108423 A1 | 11/2005 |
| WO | WO 2006/012616 A2 | 2/2006 |
| WO | WO 2008/028686 A2 | 3/2008 |
| WO | WO 2008/055703 A2 | 5/2008 |

OTHER PUBLICATIONS

Bagshawe, K. et al., "Antibody-Directed Enzyme Prodrug Therapy (ADEPT) for Cancer," Expert Opinion on Biological Therapy, vol. 4, No. 11, pp. 1777-1789 (2004).
Benoist, H. et al., "Studies on the Susceptibility to NK-Mediated Lysis and the Simultaneous Expression of Various Surface Molecules in Anthracyclin-Treated K562 Cells and in Four K562 Cell Clones," Immunology Letters, vol. 34, pp. 45-55 (1992).
Cao, Y. et al., "Expression of CD175 (Tn), CD175s (Sialosyl-Tn) and CD176 (Thomsen-Friedenreich Antigen) on Malignant Human Hematopoietic Cells," International Journal of Cancer, vol. 123, pp. 89-99 (2008).
Carbone, M. et al., "Multistep and Multifactorial Carcinogenesis: When Does a Contributing Factor Become a Carcinogen?," Seminars in Cancer Biology, vol. 14, pp. 399-405 (2004).

(Continued)

Primary Examiner — Brian J Gangle
(74) Attorney, Agent, or Firm — Nelson Mullins Riley & Scarborough LLP; Jane E. Remillard, Esq.; Jill Gorny Sloper, Esq.

(57) ABSTRACT

The present invention relates to the field of prevention and treatment of disorders associated with the occurrence of certain carbohydrate epitopes. The present invention relates to the prevention and treatment of carbohydrate epitope positive tumors. The invention relates to formulations and methods for the induction of an effective carbohydrate specific cellular immune response.

19 Claims, 20 Drawing Sheets

(56) References Cited

OTHER PUBLICATIONS

Czuczman, M. et al., "Treatment of Patients with Low-Grade B-Cell Lymphoma with the Combination of Chimeric Anti-CD20 Monoclonal Antibody and CHOP Chemotherapy," Journal of Clinical Oncology, vol. 17, No. 1, pp. 268-276 (1999).
Euhus, D. et al., "Appraisal of Anti-Idiotypic Antibodies in the Treatment of Solid Tumors in Humans," Surgery, Gynecology & Obstetrics, vol. 175, pp. 89-96 (1992).
Goletz, S. et al., "Binding Patterns of 33 TD-4 (MUC1) Antibodies Towards Single-Chain Fragments and Peptides Mimicking the Conformation of the MUC1 PDTRP Epitope," Tumor Biology, vol. 21, Suppl. 1, p. 142 (2000).
Gough, M. et al., "Macrophages Orchestrate the Immune Response to Tumor Cell Death," Cancer Research, vol. 61, No. 9, pp. 7240-7247 (2001).
Hinoda, Y. et al., "Primary Structure of the Variable Regions of a Monoclonal Antibody MUSE11 Recognizing the Tandem Repeat Domain of a Mucin Core Protein, MUC1," Journal of Clinical Laboratory Analysis, vol. 7, pp. 100-104 (1993).
Huang, Q. et al., "Heat-Induced Gene Expression as a Novel Targeted Cancer Gene Therapy Strategy," Cancer Research, vol. 60, pp. 3435-3439 (2000).
Linardou, H. et al., "Deoxyribonuclease I (DNase I)," Cell Biophysics vols. 24/25, pp. 243-248 (1994).
Melcher, A. et al., "Tumor Immunogenicity is Determined by the Mechanism of Cell Death Via Induction of Heat Shock Protein Expression," Nature Medicine, vol. 4, No. 5, pp. 581-587 (1998).
Melcher, A. et al., "Apoptosis or Necrosis for Tumor Immunotherapy: What's in a Name?," Journal of Molecular Medicine, vol. 77, pp. 824-833 (1999).
Mondovi, B. et al., "Increased Immunogenicity of Ehrlich Ascites Cells After Heat Treatment," Cancer, vol. 20, No. 4, pp. 885-888 (1972).
MSNBC News Services, "Mixed Results on New Cancer Drug," Nov. 9, 2000.
Olsvik, O. et al., "Magnetic Separation Techniques in Diagnostic Microbiology," Clinical Microbiology Reviews, vol. 7, No. 1, pp. 43-54 (1994).
Suzuki, T. et al., "A Comparison of the Genotoxicity of Ethylnitrosourea and Ethyl Methanesulfonate in *lacZ* Transgenic Mice (Muta™ Mouse)," Mutation Research, vol. 395, pp. 75-82 (1997).
Thatcher, N. et al., "Anti-T Antibody in Malignant Melanoma Patients, Influence of Response Survival Following Chemotherapy—Changes in Serum Levels Following C parvum, BCG Immunization," Cancer, vol. 46, No. 6, pp. 1378-1382 (1980).
Voshol, H. et al., "Cell Surface Glycoconjugates as Possible Targets for Human Natural Killer Cells: Evidence Against the Involvement of Glycolipids an N-Linked Carbohydrate Chains," Gylcobiology, vol. 3, No. 1, pp. 69-76 (1993).
Wang, Q. et al., "Second-Generation Adenovirus Vectors," Nature Medicine, vol. 2, No. 6, pp. 714-716 (1996).
Werkmeister, J. et al., "Modulation of K562 Cells with Sodium Butyrate. Association of Impaired NK Susceptibility with Sialic Acid and Analysis of Other Parameters," International Journal of Cancer, vol. 32, pp. 71-78 (1983).
Yu, J-Y. et al., "RNA Interference by Expression of Short-Interfering RNAs and Hairpin RNAs in Mammalian Cells," Proceedings of the National Academy of Sciences, vol. 99, No. 9, pp. 6047-6052 (2002).
Zhang, S. et al., "Selection of Tumor Antigens as Targets for Immune Attack Using Immunohistochemistry: II. Blood Group-Related Antigens," International Journal of Cancer, vol. 73, pp. 50-56 (1997).
U.S. Appl. No. 12/440,562, filed May 14, 2009, Goletz et al.
U.S. Appl. No. 12/514,248, filed May 8, 2009, Goletz et al.
Springer, G.F., et al., "Origin of Anti Thomsen Friedenreich and TN Agglutinins in Man and in White Leghorn Chicks," British Journal of Haematology, vol. 47, No. 3, pp. 453-460 (1981).
Klaamas, K., et al., "Expression of Tumor-Associated Thomsen-Friedenreich Antigen (T AG) in *Helicobacter pylori* and Modulation of T AG Specific Immune Response in Infected Individuals," Immunological Investigations, vol. 31, No. 3/4, pp. 191-204 (2002).
Kurtenkov, O., et al., "Better Survival of *Helicobacter pylori* Infected Patients With Early Gastric Cancer Is Related to a Higher Level of Thomsen-Friedenreich Antigen-Specific Antibodies," Immunological Investigations, vol. 32, No. 1-2, pp. 89-93 (2003).
Takahashi et al., "Antitumor Effects of the Intravesical Instillation of Heat Killed Cells of the *Lactobacillus casei* Strain Shirota on the Murine Orthotopic Bladder Tumor MBT-2," Journal of Urology, vol. 166, No. 6, pp. 2506-2511 (2001).
Matsuzaki, T., et al., "Antitumor Effect of Intrapleural Administration of *Lactobacillus-casei* in Mice," Cancer Immunology Immunotherapy, vol. 26, No. 3, pp. 209-214 (1988).
Goletz, S., et al., "Thomsen-Friedenreich Antigen: The Hidden Tumor Antigen," Advances in Experimental Medicine and Biology, vol. 535, pp. 147-162 (2003).
Butschak, G., et al., "Isolation and Characterization of Thomsen-Friedenreich-Specific Antibodies From Human Serum," Tumor Biology, vol. 23, No. 3, pp. 113-122 (2002).
Clausen, H., et al., "Monoclonal Antibodies Directed to the Blood Group A Associated Structure Galactosyl-A Specificity and Relation to the Thomsen-Friedenreich Antigen," Molecular Immunology, vol. 25, No. 2, pp. 199-204 (1988).
Takano, Y., et al., "Lymph Node Metastasis-Related Carbohydrate Epitopes of Gastric Cancer With Submucosal Invasion," Surgery Today 2000, vol. 30, No. 12, pp. 1073-1082 (2000).
Franco, A., "CTL-Based Cancer Preventive/Therapeutic Vaccines for Carcinomas: Role of Tumour-Associated Carbohydrate Antigens," Scandinavian Journal of Immunology, vol. 61, No. 5, pp. 391-397 (2005).
Croce, M.V., et al., "The Use of Carbohydrate Antigens for the Preparation of Vaccines for Therapy in Breast Cancer," Drugs of Today, vol. 38, No. 11, pp. 759-768 (2002).
Maclean, G.D., et al., "Active Immunization of Human Ovarian Cancer Patients Against a Common Carcinoma (Thomsen-Friedenreich) Determinant Using a Synthetic Carbohydrate Antigen," Journal of Immunotherapy, vol. 11, pp. 292-305 (1992).
Slovin, S.F., et al., "Thomsen-Friedenreich (TF) Antigen As a Target for Prostate Cancer Vaccine: Clinical Trial Results With TF cluster (c)-KLH Plus QS21 Conjugate Vaccine in Patients With Biochemically Relapsed Prostate Cancer," Cancer Immunology Immunotherapy, vol. 54, No. 7, pp. 694-702 (2005).
Baumeister and Goletz, "Voll Funktionsfähige Humane Dendritische Zelllinie," Laborwelt [online], vol. 6, 2005, url:http://www.nemod.com/downloads/nemoddc%20IN%20laborwelt%207.2.05.pdf.
Dorai, H., et al., "The Effect of Dihydrofolate Reductase-Mediated Gene Amplification on the Expression of Transfected Immunoglobulin Genes," Journal of Immunology (Baltimore, Md. 1950), Dec. 15, 1987, vol. 139, No. 12, pp. 4232-4241.
Kaneko, Y., et al., "Anti-Inflammatory Activity of Immungloubulin G Resulting from FC Sialylation," Science, American Association for the Advancement of Science, Aug. 2006, vol. 313, No. 5787, p. 671.
Baumeister, H., "Glycoengineering—a Technology for Production of Glycoproteins," Journal of Biotechnology, Nov. 2004, pp. 10-11.
Kanda Yutaka, et al., "Comparison of Cell Lines for Stable Production of Fucose-Negative Antibodies with Enhanced ADCC," Biotechnology and Bioengineering, Jul. 2006, vol. 94, No. 4, pp. 680-688.
Goletz, S., "Turning Glycomics into Health," (2006) XP00243302.
Geneseq, "DHFR—Synuclein Fusion Protein GST-ATSalpha Seq. ID No. 81," (2005) XP002430726.
"Sequence 628 from Patent WO 2005/016962," (2005) XP002430727.
International Search Report for PCT Application No. PCT/EP2007/007877 (WO 2008/028686 A3) dated Apr. 18, 2008.
International Search Report for PCT Application No. PCT/EP2007/009766 (WO 2008/055703 A2) dated Oct. 7, 2008.
International Search Report for PCT Application No. PCT/EP2007/009765 (WO 2008/055702 A1) dated Apr. 15, 2008.
European Search Report for Application No. 11 176193.8, dated Apr. 16, 2012.
European Search Report for Application No. 11 176197.9, dated Apr. 12, 2012.

(56) References Cited

OTHER PUBLICATIONS

European Search Report for Application No. 11 17 6200.1, dated Apr. 12, 2012.
Shinkawa, T. et al. "The Absence of Fucose but Not the Presence of Galactose or Bisecting N-Acetylglucosamine of Human IgG1 Complex-type Oligosaccharides Shows the Critical Rile of Enhancing Antibody-dependent Cellular Cytotoxicity," The Journal of Biological Chemistry, 278(5): 3466-3473 (2003).
U.S. Appl. No. 10/589,447, filed Feb. 7, 2008, Goletz et al.
Baumeister, "A novel expression system for production of higher active biotherapeutics with optimised glycosylation," PharmaChem, 5(4): 21-24 (2006).
Baumeister et al, "GlycoExpress: a novel expression system for the optimal glycosylation of biotherapeutics," Specialty Chemicals Magazine, 25: 46-48 (2005).
Bönig et al. "Gylcosylated vs non-glycosylated granulocyte colony-stimulating factor (G-CSF)—results of a prospective randomised mononcentre study," Bone Marrow Trans. 25: 259-264 (2001).
Fogolin et al. "Choice of the adequate quantification method for recombinant human GM-CSF produced in different host systems," Electronic J. of Biotech. 5: 243-250 (2002).
Fukuda, M. et al. "Structures of novel sialyated O-linked oligosaccharides isolated from human erythrocyte glycophorins," The Journal of Biological Chemistry, 262(25): 11952-11957 (1987).
Hong, Y. et al. "Lec3 Chinese Hamster Ovary Mutants Lack UPD-N-acetylglucosamine 2-EPimerase Activity Because of Mutations in the Epimerase Domain of the Gne Gene," J. Biol. chem 278(52): 53045-53054 (2003).
International Search Report for PCT Application No. PCT/EP2005/01593 (WO 2005/080585) dated Jul. 15, 2005.
Jacobs, C. et al. "Substrate specificity of the sialic acid biosynthetic pathway," Biochemistry 40(43): 12864-12874 (2001).
Jones, M. et al. "Characterization of the cellular uptake and metabolic conversion of acetylated N-acetylmannosamine (ManNAc) analogues to sialic acids," Biotechnology and Bioengineering, 85 (4): 394-405 (2004).
Keppler, O. et al. "UDP-GicNac 2-Epimerase: A Regulator of Cell Surface," Science 284: 1372-1376 (1999).
Mantey, L. et al. "Efficient Biochemical Engineering of Cellular Sialic Acids Using an Unphysiological Sialic Acid Precursor in Cells Lacking UDP-N-acetylglucosamine 2-epimerase," FEBS Letters, 503, Nr-1: 80-84 (2001).
Muramatsu et al., "Glycoprotein-Bound Large Carbohydrates of Early Embryonic Cells: Structural Characteristic of the Glycan Isolated from F9 Carcinoma Cells," J. Biochem. 94:799-810 (1983).
Office Action dated Oct. 13, 2011 in U.S. Appl. No. 12/440,562.
Office Action dated Oct. 28, 2010 in U.S. Appl. No. 12/440,562.
Office Action dated Feb. 3, 2011 in U.S. Appl. No. 10/589,447.
Office Action dated Aug. 26, 2011 in U.S. Appl. No. 10/589,447.
Office Action dated Apr. 9, 2012 in U.S. Appl. No. 10/589,447.
Sigma-Aldrich catalog, Granulocyte Macrophage Colony-Stimulating Factor Human, dowloaded 2011.
Tachibana et al; (Cytotechnology, 1991, vol. 6, pp. 219-226).
Viswanatha, K. et al. "Engineering sialic acid synthetic ability into insect cells: identifying metabolic bottlenecks and devising strategies to overcome them," Biochemistry 42(51): 15215-15225 (2003).
U.S. Appl. No. 10/524,738, filed Sep. 15, 2005, Goletz et al.
U.S. Appl. No. 10/536,834, filed Mar. 20, 2006, Goletz et al.
U.S. Appl. No. 10/568,098, filed Jun. 20, 2006, Goletz et al.
Agrawal, B. et al., "Cancer-Associated MUC1 Mucin Inhibits Human T-Cell Proliferation, which is Reversible by IL-2," Nature Medicine, vol. 4, No. 1, pp. 43-49 (1998).
Albert, M. et al., "Dendritic Cells Acquire Antigen from Apoptotic Cells and Induce Class I-Restricted CTLs," Nature, vol. 392, pp. 86-89 (1998).
Allison, A., "The Role of Cytokines in the Action of Immunological Adjuvants," Vaccine Design: The Role of Cytokine Networks, Gregoriadis, G. et al., Eds., NATO ASI Series A: Life Sciences, vol. 293, pp. 1-9, Plenum Press (1997).
Anderson, W., "Human Gene Therapy," Science, vol. 256, pp. 808-813 (1992).
Berd, D. et al., "Autologous Hapten-Modified Melanoma Vaccine as Postsurgical Adjuvant Treatment After Resection of Nodal Metastases," Journal of Clinical Oncology, vol. 15, No. 6, pp. 2359-2370 (1997).
Berthier-Vergnes, O. et al., "Induction of IgG Antibodies Directed to a $M_r$ 31,000 Melanoma Antigen in Patients Immunized with Vaccinia Virus Melanoma Oncolysates," Cancer Research, vol. 54, pp. 2433-2439 (1994).
Binder, R. et al., "Cutting Edge: Heat Shock Protein gp96 Induces Maturation and Migration of CD11c$^+$ Cells In Vivo," The Journal of Immunology, vol. 165, pp. 6029-6035 (2000).
Boel, E. et al., "Functional Human Monoclonal Antibodies of All Isotypes Constructed from Phage Display Library-Derived Single-Chain Fv Antibody Fragments," Journal of Immunological Methods, vol. 239, Issues 1-2, pp. 153-166 (2000).
Böhm, C. et al., "Carbohydrate Recognition on MUC1-Expressing Targets Enhances Cytotoxicity of a T Cell Subpopulation," Scandinavian Journal of Immunology, vol. 46, pp. 27-34 (1997).
Bomford, R. et al., "The Control of the Antibody Isotype Response to Recombinant Human Immunodeficiency Virus gp120 Antigen by Adjuvants," Aids Research and Human Retroviruses, vol. 8, No. 10, pp. 1765-1771 (1992).
Bourdon, G., "Inhibition of Tumoral Graft Growth by Pretreatment with Normal or Heat-Modified Tumoral Cells," Annales D'Immunologie, vol. 132, No. 1, pp. 43-63 (1981).
Brechbiel, M. et al., "Synthesis of 1-(p-Isothiocyanatobenzyl) Derivatives of DTPA and EDTA. Antibody Labeling and Tumor-Imaging Studies," Inorganic Chemistry, vol. 25, No. 16, pp. 2772-2781 (1986).
Brummelkamp, T. et al., "A System for Stable Expression of Short Interfering RNAs in Mammalian Cells," Science, vol. 296, pp. 550-553 (2002).
Burgess, W. et al., "Possible Dissociation of the Heparin-Binding and Mitogenic Activities of Heparin-Binding (Acidic Fibroblast) Growth Factor-1 from its Receptor-Binding Activities by Site-Directed Mutagenesis of a Single Lysine Residue," The Journal of Cell Biology, vol. 111, No. 5, pp. 2129-2138 (1990).
Cao, Y. et al., "Immunodetection of Epithelial Mucin (MUC1, MUC3) and Mucin-Associated Glycotopes (TF, Tn, and Sialosyl-Tn) in Benign and Malignant Lesions of Colonic Epithelium Apolar Localization Corresponds to Malignant Transformation," Virchows Archiv, vol. 431, pp. 159-166 (1997).
Casset, F. et al., "A Peptide Mimetic of an Anti-CD4 Monoclonal Antibody by Rational Design," Biochemical and Biophysical Research Communications, vol. 307, Issue 1, pp. 198-205 (2003).
Cavaliere, R. et al., "Selective Heat Sensitivity of Cancer Cells. Biochemical and Clinical Studies," Cancer, vol. 20, No. 9, pp. 1351-1381 (1967).
Check, J. et al., "Protection Against Transplanted and Spontaneous Lymphoma by Inoculation of Heat-Altered Syngeneic Tumor Cells in Splenectomized Mice," Cancer, vol. 34, No. 1, pp. 197-203 (1974).
Chen, Y. et al., "Selection and Analysis of an Optimized Anti-VEGF Antibody: Crystal Structure of an Affinity-Matured FAB in Complex with Antigen," Journal of Molecular Biology, vol. 293, Issue 4, pp. 865-881 (1999).
Chen, Z. et al., "Efficient Antitumor Immunity Derived from Maturation of Dendritic Cells that had Phagocytosed Apoptotic/Necrotic Tumor Cells," International Journal of Cancer, vol. 93, No. 4, pp. 539-548 (2001).
Chothia, C. et al., "The Predicted Structure of Immunoglobulin D1.3 and its Comparison with the Crystal Structure," Science, vol. 233, pp. 755-758 (1986).
Chothia, C. et al., "Canonical Structures for the Hypervariable Regions of Immunoglobulins," Journal of Molecular Biology, vol. 196, Issue 4, pp. 901-917 (1987).
Chothia, C. et al., "Conformations of Immunoglobulin Hypervariable Regions," Nature, vol. 342, pp. 877-883 (1989).
Chothia, C. et al., "Structural Repertoire of the Human $V_H$ Segments," Journal of Molecular Biology, vol. 227, Issue 3, pp. 799-817 (1992).

(56) References Cited

OTHER PUBLICATIONS

Clayman, C., Ed., The American Medical Association Encyclopedia of Medicine, Random House, New York, pp. 573-574, 576, and 1034 (1989).
Cox, J. et al., "Adjuvants—A Classification and Review of Their Modes of Action," Vaccine, vol. 15, No. 3, pp. 248-256 (1997).
Cox, J. et al., "Development of an Influenza-ISCOM™ Vaccine," Vaccine Design: The Role of Cytokine Networks, Gregoriadis, G. et al., Eds., Plenum Press, New York, pp. 33-49 (1997).
Cryz, S., Ed., Immunotherapy and Vaccines, pp. 3-11, VCH, Weinheim, Germany (1991).
Dai, J. et al., "Effect of Desialyation on Binding, Affinity, and Specificity of 56 Monoclonal Antibodies Against MUC1 Mucin," Tumor Biology, vol. 19, pp. 100-110 (1998).
Dall'Olio, F. et al., "Expression of β-Galactoside α2,6-Sialyltransferase Does Not Alter the Susceptibility of Human Colon Cancer Cells to NK-mediated Cell Lysis," Gycobiology, vol. 7, No. 4, pp. 507-513 (1997).
Dermer, G., "Another Anniversary for the War on Cancer," Bio/Technology, vol. 12, p. 320 (1994).
Dickson, J., "Hyperthermia in the Treatment of Cancer," Lancet, vol. 1, pp. 202-205 (1979).
Dictionary of Immunology, Herbert, W. et al., Eds., Third Edition, Blackwell Scientific Publications, Oxford, pp. 3, 7, 46, 87-88, 94, 97, 105, and 116 (1985).
Dressel, R. et al., "Heat Shock Protein 70 is Able to Prevent Heat Shock-Induced Resistance of Target Cells to CTL," The Journal of Immunology, vol. 164, pp. 2362-2371 (2000).
Duk, M. et al., "Purification of Human Anti-TF (Thomsen-Friedenreich) and Anti-Tn Antibodies by Affinity Chromatography on Glycophorin A Derivatives and Characterization of the Antibodies by Microtiter Plate ELISA," Archivum Immunologiae et Therapiae Experimentalis, vol. 46, pp. 69-77 (1998).
Elbashir, S. et al., "Duplexes of 21-Nucleotide RNAs Mediate RNA Interference in Cultured Mammalian Cells," Nature, vol. 411, pp. 494-498 (2001).
Feng, H. et al., "Stressed Apoptotic Tumor Cells Express Heat Shock Proteins and Elicit Tumor-Specificity Immunity," Blood, vol. 97, No. 11, pp. 3505-3512 (2001).
Ferencik, M., Handbook of Immunochemistry, First Edition, Chapman & Hall, London, pp. 115-116 (1993).
Fiebig, H. et al., "Clonogenic Assay with Established Human Tumour Xenografts: Correlation of In Vitro to In Vivo Activity as a Basis for Anticancer Drug Discovery," European Journal of Cancer, vol. 40, Issue 6, pp. 802-820 (2004).
Freshney, R., Culture of Animal Cells: A Manual of Basic Technique and Specialized Applications, Alan R. Liss Inc., New York, p. 4 (1983).
Fujiwara, H. et al., "Establishment of a Tumor-Specific Immunotherapy Model Utilizing TNP-Reactive Helper T Cell Activity and its Application to the Autochthonous Tumor System," The Journal of Immunology, vol. 133, No. 1, pp. 509-514 (1984).
Gallucci, S. et al., "Natural Adjuvants: Endogenous Activators of Dendritic Cells," Nature Medicine, vol. 5, No. 11, pp. 1249-1255 (1999).
Gallucci, S. et al., "Danger Signals: SOS to the Immune System," Current Opinion in Immunology, vol. 13, pp. 114-119 (2001).
Giovanella, B. et al., "Effects of Elevated Temperatures and Drugs on the Viability of L1210 Leukemia Cells," Cancer Research, vol. 30, pp. 1623-1631 (1970).
Gollasch, H. et al., "Identification of Immunogenic Peptide-Mimics for the Thomsen-Friedenreich-Glycoantigen," Annals of Hematology, vol. 77, No. Supp. 2, p. S84 XP-000960533 (1998).
Green, D. et al., "Activation-Induced Cell Death in T Cells," Immunological Reviews, vol. 193, Issue 1, pp. 70-81 (2003).
Gura, T., "Systems for Identifying New Drugs are Often Faulty," Science, vol. 278, pp. 1041-1042 (1997).
Herrera, A. et al., "Efficiency of Erythropoietin's Signal Peptide for $HIV_{MN}$-1 gp 120 Expression," Biochemical and Biophysical Research Communications, vol. 273, Issue 2, pp. 557-559 (2000).
Hinoda, Y. et al., "Circulating Tumor-Associated Antigens Detected by Monoclonal Antibodies Against the Polypeptide Core of Mucin-Comparison of Antigen MUSE11 with CA15-3," Gastroenterologia Japonica, vol. 27, No. 3, pp. 390-395 (1992).
Holm, P. et al., "Functional Mapping and Single Chain Construction of the Anti-Cytokeratin 8 Monoclonal Antibody TS1," Molecular Immunology, vol. 44, Issue 6, pp. 1075-1084 (2007).
Hosse, R. et al., "A New Generation of Protein Display Scaffolds for Molecular Recognition," Protein Science, vol. 15, Issue 1, pp. 14-27 (2006).
Hseih, L. et al., "Controlling Chemical Reactivity with Antibodies," Science, vol. 260, pp. 337-339 (1993).
Hufton, S. et al., "Development and Application of Cytotoxic T Lymphocyte-Associated Antigen 4 as a Protein Scaffold for the Generation of Novel Binding Ligands," FEBS Letters, vol. 475, Issue 3, pp. 225-231 (2000).
Ichiyama, "Induction of Non-HLA Restricted Anti-Tumor Effector Cells with Strong Cytoxic Activity Using MUC1/B7 Cotransfected K562 Cells," Cell Resource Center for Biomedical Research, Institute of Development, Aging, and Cancer, Tohoku University, Sendai, Japan, vol. 51, No. 3-4, pp. 93-110, XP-001182213 (2000).
International Search Report for PCT/DE2003/003994 (WO2004/050707) dated Aug. 10, 2004, 8 pages.
International Search Report for PCT Application No. PCT/EP2003/009140 (WO2004/018659) dated Feb. 9, 2004, 8 pages.
International Search Report for PCT Application No. PCT/EP2004/009281 (WO2005/017130) dated Apr. 14, 2005, 6 pages.
Isner, J. et al., "Clinical Evidence of Angiogenesis After Arterial Gene Transfer of $phVEGF_{165}$ in Patient with Ischaemic Limb," The Lancet, vol. 348, pp. 370-374 (1996).
Jäger, G. et al., "Treatment of Extranodal Marginal Zone B-Cell Lymphoma of Mucosa-Associated Lymphoid Tissue TYpe with Cladribine: A Phase II Study," Journal of Clinical Oncology, vol. 20, Issue 18, pp. 3872-3877 (2002).
Jensen, K. et al., "Functional Improvement of Antibody Fragments Using a Novel Phage Coat Protein III Fusion System," Biochemical and Biophysical Research Communications, vol. 298, Issue 4, pp. 566-573 (2002).
Jeschke, U. et al., "Expression of the Thomsen-Friedenreich Antigen and of its Putative Carrier Protein Mucin 1 in the Human Placenta and in Trophoblast Cells In Vitro," Histochemistry and Cell Biology, vol. 117, No. 3, pp. 219-226 (2002).
Kalka-Moll, W. et al., "Zwitterionic Polysaccharides Stimluate T Cells by MHC Class II-Dependent Interactions," The Journal of Immunology, vol. 169, pp. 6149-6153 (2002).
Karsten, U. et al., "A New Monoclonal Antibody (A78-G/A7) to the Thomsen-Friedenreich Pan-Tumor Antigen," Hybridoma, vol. 14, No. 1, pp. 37-44 (1995).
Karsten, U. et al., "Enhanced Binding of Antibodies to the DTR Motif of MUC1 Tandem Repeat Peptide is Mediated by Site-Specific Glycosylation," Cancer Research, vol. 48, pp. 2541-2549 (1998).
Kotera, Y. et al., "Comparative Analysis of Necrotic and Apoptotic Tumor Cells as a Source of Antigen(s) in Dendritic Cell-Based Immunization," Cancer Research, vol. 51, pp. 8105-8109 (2001).
Kozak, R. et al., "Nature of the Bifunctional Chelating Agent Used for Radioimmunotherapy with Yttrium-90 Monoclonal Antibodies: Critical Factors in Determining In Vivo Survival and Organ Toxicity," Cancer Research, vol. 49, pp. 2639-2644 (1989).
Kunz, H., "Synthetic Glycopeptides for the Development of Tumor-Selective Vaccines," Journal of Peptide Science, vol. 9, pp. 563-573 (2003).
Lazar, E. et al., "Transforming Growth Factor Alpha: Mutation of Aspartic Acid 47 and Leucine 48 Results in Different Biological Activities," Molecular and Cellular Biology, vol. 8, pp. 1247-1252 (1988).
Leffell, M., "An Overview of the Immune System: The Molecular Basis for Immune Responses," Human Immunology Handbook, Chapter 1, pp. 1-45 (1997).
Liao, K-W. et al., "Design of Transgenes for Efficient expression of Active Chimeric Proteins on Mammalian Cells," Biotechnology and Bioengineering, vol. 73, Issue 4, pp. 313-323 (2001).

(56) References Cited

OTHER PUBLICATIONS

Libyh, M. et al., "A Recombinant Human scFv Anti-Rh(D) Antibody with Multiple Valences Using a C-Terminal Fragment of C4-Binding Protein," Blood, vol. 90, No. 10, pp. 3978-3983 (1997).
Lozzio, C. et al., "Human Chronic Myelogenous Leukemia Cell-Line with Positive Philadelphia Chromosome," Blood, vol. 45, No. 3, pp. 321-334 (1975).
Luftig, R., Microbiology and Immunology, Lippincott-Raven Publishers, Philadelphia, pp. 228-229 (1998).
MacCallum, R. et al., "Antibody-Antigen Interactions: Contact Analysis and Binding Site Topography," Journal of Molecular Biology, vol. 262, Issue 5, pp. 732-745 (1996).
Mach, N. et al., "Cytokine-Secreting Tumor Cell Vaccines," Current Opinion Immunology, vol. 12, pp. 571-575 (2000).
Martin, A. et al., "Structural Families in Loops of Homologous Proteins: Automatic Classification, Modelling and Application to Antibodies," Journal of Molecular Biology, vol. 263, Issue 5, pp. 800-815 (1996).
Matzinger, P., "Tolerance, Danger, and the Extended Family," Annual Review in Immunology, vol. 12, pp. 991-1045 (1994).
Mazmanian, S. et al., "The Love-Hate Relationship Between Bacterial Polysaccharides and the Host Immune System," Nature Reviews, vol. 6, pp. 849-858 (2006).
Mise, K. et al., "Effect of Heat Treatment on Tumor Cells and Antitumor Effector Cells," Cancer Research, vol. 59, pp. 6199-6202 (1990).
Mitchell, M. et al., "Active Specific Immunotherapy for Melanoma: Phase I Trial of Allogeneic Lysates and a Novel Adjuvant," Cancer Research, vol. 48, pp. 5883-5893 (1988).
Mivechi, N., "Heat Sensitivity, Thermotolerance, and Profile of Heat Shock Protein Synthesis of Human Myelogenous Leukemias," Cancer Research, vol. 49, pp. 1954-1958 (1989).
Morrison, S. et al., "Complement Activation and Fc Receptor Binding by IgG," Protein Engineering of Antibody Molecules for Prophylactic and Therapeutic Applications in Man, Clark, M., Ed., pp. 101-113 (1993).
Natali, P. et al., "Heterogeneity in the Expression of HLA and Tumor Associated Antigens by Surgically Removed and Cultured Breast Carcinoma Cells," Cancer Research, vol. 43, pp. 660-668 (1983).
Nicaise, M. et al., "Affinity Transfer by CDR Grafting on a Nonimmunoglobulin Scaffold," Protein Science, vol. 13, Issue 7, pp. 1882-1891 (2004).
Novina, C. et al., "siRNA-Directed Inhibition of HIV-1 Infection," Nature Medicine, vol. 8, No. 7, pp. 681-686 (2002).
Nuttall, S. et al., "Design and Expression of Soluble CTLA-4 Variable Domain as a Scaffold for the Display of Functional Polypeptides," Proteins: Structure, Function, and Genetics, vol. 36, Issue 2, pp. 217-227 (1999).
Nygren, P-A. et al., "Scaffolds for Engineering Novel Binding Sites in Proteins," Current Opinion in Structural Biology, vol. 7, Issue 4, pp. 463-469 (1997).
Ohyama, C. et al., "Dual Roles of Sialyl Lewis X Oligosaccharides in Tumor Metastasis and Rejection by Natural Killer Cells," The EMBO Journal, vol. 18, No. 6, pp. 1516-1525 (1999).
Ohyama, C. et al., "Natural Killer Cells Attack Tumor Cells Expressing High Levels of Sialyl Lewis X Oligosaccharides," PNAS, vol. 99, No. 21, pp. 13789-13794 (2002).
Ouagari, K. et al., "Glycophorin A Protects K562 Cells from Natural Killer Cell Attack," The Journal of Biological Chemistry, vol. 270, No. 45, pp. 26970-26975 (1994).
Owens, G. et al., "Identification of Two Short Internal Ribosome Entry Sites Selected from Libraries of Random Oligonucleotides," PNAS, vol. 98, No. 4, pp. 1471-1476 (2001).
Paddison, P. et al., "Short Hairpin RNAs (shRNAs) Induce Sequence-Specific Silencing in Mammalian Cells," Genes & Development, vol. 16, pp. 948-958 (2002).
Pahlsson, P. et al., "Biochemical Characterization of the O-Glycans on Recombinant Glycophorin A Expressed in Chinese Hamster Ovary Cells," Glycoconjugate Journal, vol. 11, pp. 43-50 (1994).
Panka, D. et al., "Variable Region Framework Differences Result in Decreased or Increased Affinity of Variant Anti-Digoxin Antibodies," PNAS, vol. 85, No. 9, pp. 3080-3084 (1988).
Pascalis, R. et al., "Grafting of 'Abbreviated' Complementarity-Determining Regions Containing Specificity-Determining Residues Essential for Ligand Contact to Engineer a Less Immunogenic Humanized Monoclonal Antibody," The Journal of Immunology, vol. 169, pp. 3076-3084 (2002).
Paul, W., Ed., Fundamental Immunology, Second Edition, Raven Press, New York, pp. 1007-1009 (1989).
Peach, R. et al., "Complementarity Determining Region 1 (CDR1)- and CDR3-Analogous Regions in CTLA-4 and CD28 Determine the Binding to B7-1," Journal of Experimental Medicine, vol. 180, No. 6, pp. 2049-2058 (1994).
Peters, L. et al., "Preparation of Immuno-Therapeutic Autologous Tumor Cell Vaccines from Solid Tumors," Cancer Research, vol. 39, pp. 1353-1360 (1979).
Phillips, T., Analytical Techniques in Immunochemistry, Marcel Dekker, New York, pp. 307-310 (1992).
Price, M. et al., "Effect of Heat and Glutaraldehyde Upon the Immunogenicity of Meth A Sarcoma Cells," The British Journal of Cancer, vol. 40, pp. 663-665 (1979).
Price, M. et al., "Summary Report on the ISOBM TD-4 Workshop: Analysis of 56 Monoclonal Antibodies Against the MUC1 Mucin," Tumor Biology, vol. 19, Suppl. 1, pp. 1-20 (1998).
Restifo, N., "Building Better Vaccines: How Apoptotic Cell Death Can Induce Inflammation and Activate Innate and Adaptive Immunity," Current Opinion in Immunology, vol. 12, pp. 597-603 (2000).
Romani, N. et al., "Proliferating Dendritic Cell Progenitors in Human Blood," Journal of Experimental Medicine, vol. 180, pp. 83-93 (1994).
Rooman, M. et al., "Amino Acid Sequence Templates Derived from Recurrent Turn Motifs in Proteins: Critical Evaluation of Their Predictive Power," Protein Engineering, vol. 3, No. 1, pp. 23-27 (1989).
Rudikoff, S. et al., "Single Amino Acid Substitution Altering Antigen-Binding Specificity," PNAS, vol. 79, No. 6, pp. 1979-1983 (1982).
Saerens, D. et al., "Identification of a Universal VHH Framework to Graft Non-Canonical Antigen-Binding Loops of Camel Single-Domain Antibodies," Journal of Molecular Biology, vol. 352, Issue 3, pp. 597-607 (2005).
Samali, A. et al., "Thermotolerance and Cell Death are Distinct Cellular Responses to Stress: Dependence on Heat Shock Proteins," FEBS Letters, vol. 461, pp. 306-310 (1999).
Santegoets, S. et al., "In Vitro Priming of Tumor-Specific Cytotoxic T Lymphocytes Using Allogeneic Dendritic Cells Derived from the Human MUTZ-3 Cell Line," Cancer Immunology Immunotherapy, vol. 55, No. 12, pp. 1480-1490 (2006).
Sauter, B. et al., "Consequences of Cell Death: Exposure to Necrotic Tumor Cells, but Not Primary Tissue Cells or Apoptotic Cells, Induces the Maturation of Immunostimulatory Dendritic Cells," Journal of Experimental Medicine, vol. 191, No. 3, pp. 423-433 (2000).
Scheibel, T. et al., "Contribution of N- and C-Terminal Domains to the Function of Hsp90 in *Saccharomyces cerevisiae*," Molecular Microbiology, vol. 34, No. 4, pp. 701-713 (1999).
Schild, H. et al., "gp96—The Immune System's Swiss Army Knife," Nature Immunology, vol. 1, No. 2, pp. 100-101 (2000).
Schlom, J., "Monoclonal Antibodies: They're More and Less Than you Think," Molecular Foundations of Oncology, Broder, S., Ed., Chapter 6, pp. 95-134 (1991).
Schneider, F. et al., "Overexpression of Sialyltransferase CMP-Sialic Acid: Galβ1,3BalNAc-R α6-Sialyltransferase is Related to Poor Patient Survival in Human Colorectal Carcinomas," Cancer Research, vol. 61, No. 11, pp. 4605-4611 (2001).
Schneider, D. et al., "Thermostability of Membrane Protein Helix-Helix Interaction Elucidated by Statistical Analysis," FEBS Letters, vol. 532, No. 1-2, pp. 231-236 (2002).
Selawry, O. et al., "Hyperthermia Tissue-Cultured Cells of Malignant Origin," Cancer Research, vol. 17, pp. 785-791 (1957).

(56) References Cited

OTHER PUBLICATIONS

Sensi, M. et al., "Clonal Expansion of Lymphocytes in Human Melanoma Metastases After Treatment with a Hapten-Modified Autologous Tumor Vaccine," Journal of Clinical Investigation, vol. 99, No. 4, pp. 710-717 (1997).

Shaif-Muthana, M. et al., "Dead or Alive: Immunogenicity of Human Melanoma Cells When Presented by Dendritic Cells," Cancer Research, vol. 60, pp. 6441-6447 (2000).

Sivanandham, M. et al., "Cancer Vaccines: Clinical Applications," Principles and Practice of the Biologic Therapy of Cancer, Third Edition, Lippincott Williams & Wilkins, Philadelphia, Pennsylvania, pp. 632-647 (2000).

Skerra, A., "Engineered Protein Scaffolds for Molecular Recognition," Journal of Molecular Recognition, vol. 13, Issue 4, pp. 167-187 (2000).

Skerra, A., "Alternative Non-Antibody Scaffolds for Molecular Recognition," Current Opinion in Biotechnology, vol. 18, Issue 4, pp. 295-304 (2007).

Snippe, H. et al., "Adjuvant Directed Immune Specificity at the Epitope Level: Implications for Vaccine Development, A Model for Using Semliki Forest Virus Infection of Mice," Vaccine Design: The Role of Cytokine Networks, Gregoriadis, G. et al., Eds., Plenum Press, New York pp. 155-166 (1997).

Somersan, S. et al., "Primary Tumor Tissue Lysates are Enriched in Heat Shock Proteins and Induce the Maturation of Human Dendritic Cells," The Journal of Immunology, vol. 167, pp. 4844-4852 (2001).

Springer, G., "Immunoreactive T and Tn Epitopes in Cancer Diagnosis, Prognosis and Immunotherapy," Journal of Molecular Medicine, vol. 75, pp. 594-602 (1997).

Stimmel, J. et al., "Yttrium-90 Chelation Properties of Tetraazatetraacetic Acid Macrocycles, Diethylenetriaminepentaacetic Acid Analogs, and a Novel Terpyridine Acyclic," Bioconjugate Chemistry, vol. 6, Issue 2, pp. 219-225 (1995).

Todryk, S. et al., "Heat Shock Protein 70 Induced During Tumor Cell Killing Induces Th1 Cytokines and Targets Immature Dendritic Cell Precursors to Enhance Antigen Uptake," The Journal of Immunology, vol. 163, pp. 1398-1408 (1999).

Vajdos, F. et al., "Comprehensive Functional Maps of the Antigen-Binding Site of an Anti-ErbB2 Antibody Obtained with Shotgun Scanning Mutagenesis," Journal of Molecular Biology, vol. 320, Issue 2, pp. 415-428 (2002).

Van Rinsum, J. et al., "Specific Inhibition of Human Natural Killer Cell-Mediated Cytotoxicity by Sialic Acid and Sialo-Oligosaccharides," International Journal of Cancer, vol. 38, pp. 915-922 (1986).

Verma, I. et al., "Gene Therapy—Promises, Problems and Prospects," Nature, vol. 389, pp. 239-242 (1997).

Vermes, I. et al., "A Novel Assay for Apoptosis Flow Cytometric Detection of Phosphatidylserine Expression on Early Apoptotic Cells Using Fluorescein Labelled Annexin V," Journal of Immunological Methods, vol. 184, pp. 39-51 (1995).

Wells, A. et al., "Heat Shock Proteins, Tumor Immunogenicity and Antigen Presentation: An Integrated View," Immunology Today, vol. 21, No. 3, pp. 129-132 (2000).

Wu, S. et al., "Conformation of Complementarity Determining Region L1 Loop in Murine IgG λ Light Chain Extends the Repertoire of Canonical Forms," Journal of Molecular Biology, vol. 229, Issue 3, pp. 597-601 (1993).

Wu, H. et al., "Humanization of a Murine Monoclonal Antibody by Simultaneous Optimization of Framework and CDR Residues," Journal of Molecular Biology, vol. 294, Issue 1, pp. 151-162 (1999).

Yoshima, T. et al., "Heat Shock Factor 1 Mediates Hemin-Induced *hsp70* Gene Transcription in K562 Erythroleukemia Cells," The Journal of Biological Chemistry, vol. 273, No. 39, pp. 25466-25471 (1998).

Office Action (Restriction Restriction) dated Oct. 5, 2006 in U.S. Appl. No. 10/524,738.
Office Action dated Dec. 14, 2006 in U.S. Appl. No. 10/524,738.
Office Action dated Aug. 10, 2007 in U.S. Appl. No. 10/524,738.
Office Action dated Feb. 6, 2008 in U.S. Appl. No. 10/524,738.
Office Action dated Aug. 4, 2008 in U.S. Appl. No. 10/524,738.
Advisory Action dated Jan. 29, 2009 in U.S. Appl. No. 10/524,738.
Notice of Allowance dated May 19, 2009 in U.S. Appl. No. 10/524,738.
Office Action (Restriction Requirement) dated May 9, 2008 in U.S. Appl. No. 10/568,098.
Office Action dated Jan. 27, 2009 in U.S. Appl. No. 10/568,098.
Office Action dated Jul. 23, 2009 in U.S. Appl. No. 10/568,098.
Advisory Action dated Oct. 7, 2009 in U.S. Appl. No. 10/568,098.
Advisory Action dated Jan. 14, 2010 in U.S. Appl. No. 10/568,098.
Pre-Appeal Brief Conference Decision dated Feb. 25, 2010 in U.S. Appl. No. 10/568,098.
Office Action dated Sep. 29, 2010 in U.S. Appl. No. 10/568,098.
Examiner Interview Summary Record dated Apr. 28, 2011 in U.S. Appl. No. 10/568,098.
Examiner Interview Summary Record dated May 5, 2011 in U.S. Appl. No. 10/568,098.
Notice of Allowance dated May 12, 2011 in U.S. Appl. No. 10/568,098.
Office Action (Restriction Requirement) dated Jun. 23, 2008 in U.S. Appl. No. 10/536,834.
Office Action dated Feb. 19, 2009 in U.S. Appl. No. 10/536,834.
Office Action dated Nov. 10, 2009 in U.S. Appl. No. 10/536,834.
Office Action dated Aug. 5, 2010 in U.S. Appl. No. 10/536,834.
Office Action dated Feb. 2, 2011 in U.S. Appl. No. 10/536,834.
Notice of Allowance dated Aug. 25, 2011 in U.S. Appl. No. 10/536,834.

Raska, Milan et al., "Glycosylation Patterns of HIV-1 gp120 Depends on the Type of Expressing Cells and Affect Antibody Recognition," The Journal of Biological Chemistry, vol. 285(27):20860-20869 (2010).

Figure 1
```
+MU1
|
|       +Bacteroides thetaiotaomicron strain 17.4 AY319392
|       |
|       |   +Bacteroides thetaiotaomicron strain 0633 AY895186
|       +-7
|     +-11  +-8 +Bacteroides thetaiotaomicron strain 8713 AY895202
|     | |   ||
|     | |   +-9 +Bacteroides thetaiotaomicron BNRRR16SB M58763
|     | |   ||
|     | |   +-10 +Bacteroides thetaiotaomicron strain 3751 AY895192
|     | |    |
+-20  |     +Bacteroides thetaiotaomicron ATCC 29148 BNRRR16SAF L16489
|     |
|     |       +Bacteroides acidifaciens AB021156
|     |   +-18   +-2
|     |   |   | +Bacteroides acidifaciens strain A1 AB021158
|     |   | +-5
|     |   | | +Bacteroides acidifaciens strain A32 AB021162
|     |   | +-4
|     |   +-12 | +Bacteroides acidifaciens strain A29 AB021160
|     |     +-3
|     |       +Bacteroides acidifaciens strain A40 AB021164
|     |
|     | +-13 +Bacteroides caccae ATCC 43185T BC16S X83951
|  +-19  |
|  |  | +Bacteroides fragilis BNRRGDA M11656
+-22 |  +-6
|    |   +—Bacteroides distasonis BNRRR16S M86695
|    +—1
|        +————Escherichia coli ATCC 11755T ECAT1177T X80725
|
|      +Bacteroides ovatus AB050108
|    +-14
|  +-15 +Bacteroides ovatus ATCC 8438T BO16S X83952
|  | |
|  +-17 +Bacteroides ovatus NCTC 11153 L16484 BNRRR16SAA
|  |
|  |  +Bacteroides ovatus strain 3941 AY895193
|  +-16
|    +Bacteroides ovatus strain 4140 AY895197
|
+Bacteroideaceae bacterium Smarlab AY538687
|
|+Bacteroides sp. WH302 AY895184
23-21
|+Bacteroides sp. WH305 AY895185
|
+AG6
```

Figure 5
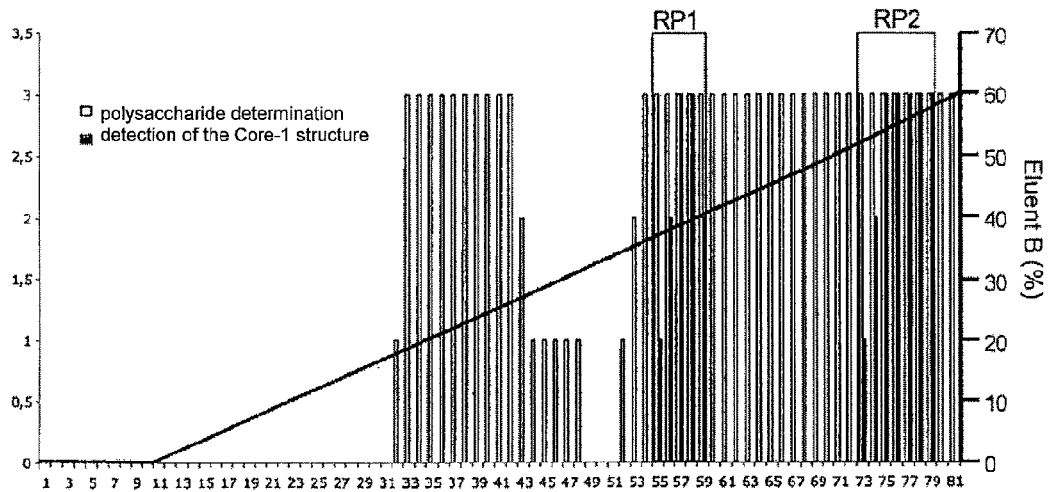
Figure 6
-desHex-desHex-desHexM-HexNAc(HexNAc-Hex)-Hex-
Figure 7
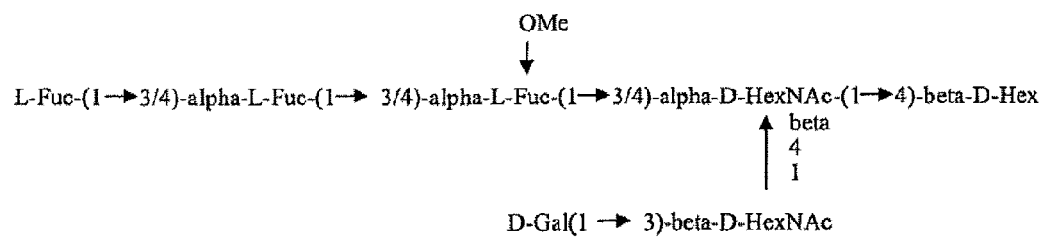

Figure 10
A)
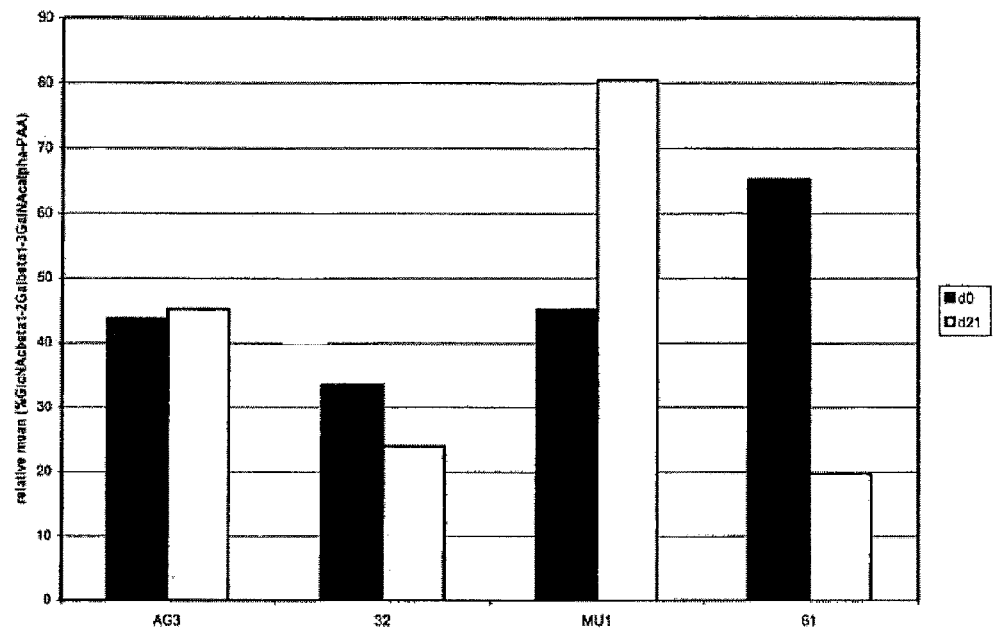
B)
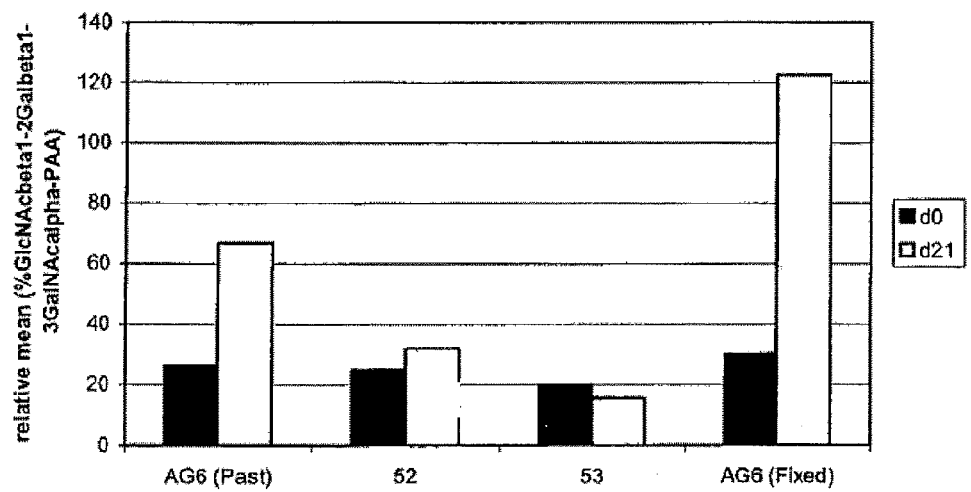

A)

Figure 11B)
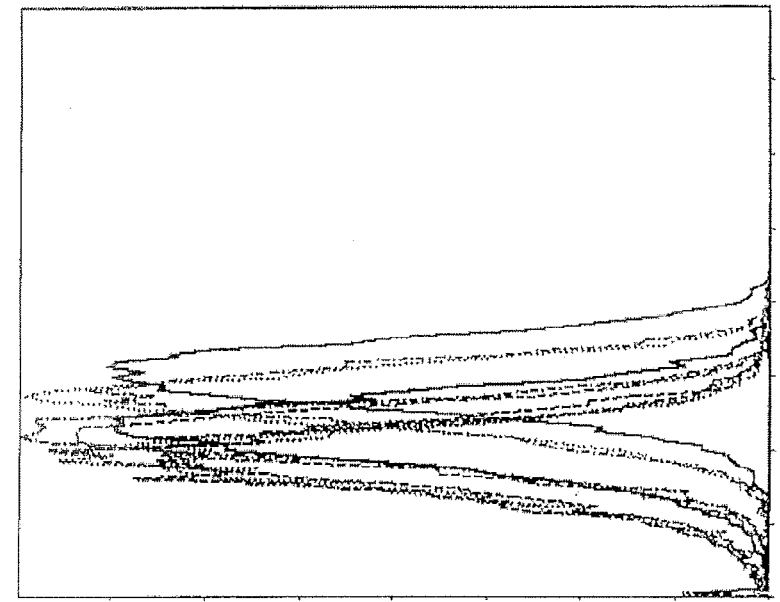
NM-D4
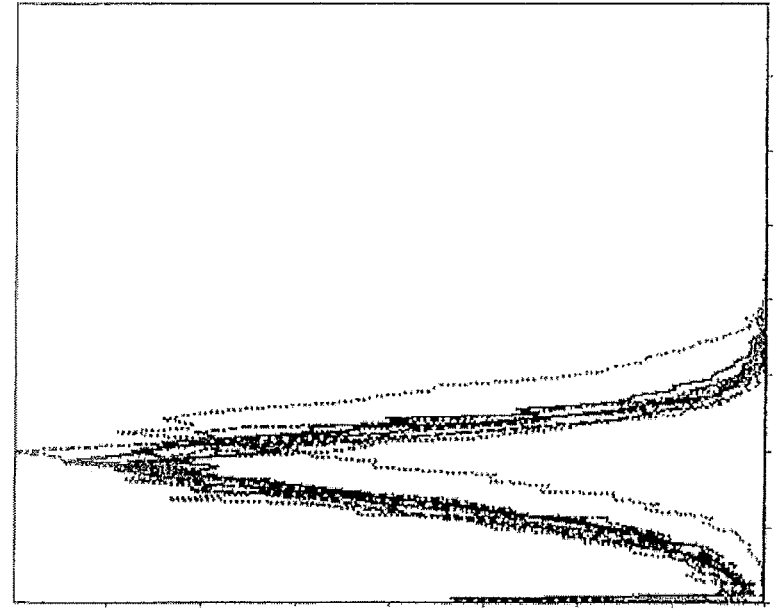
NM-wt
Anti-Maus-IgM

Figure 13
A)
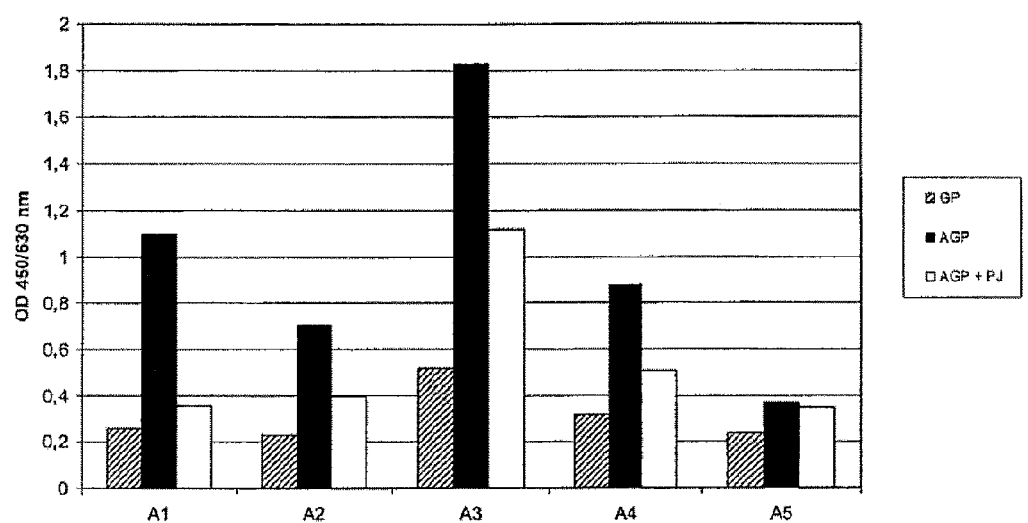
B)
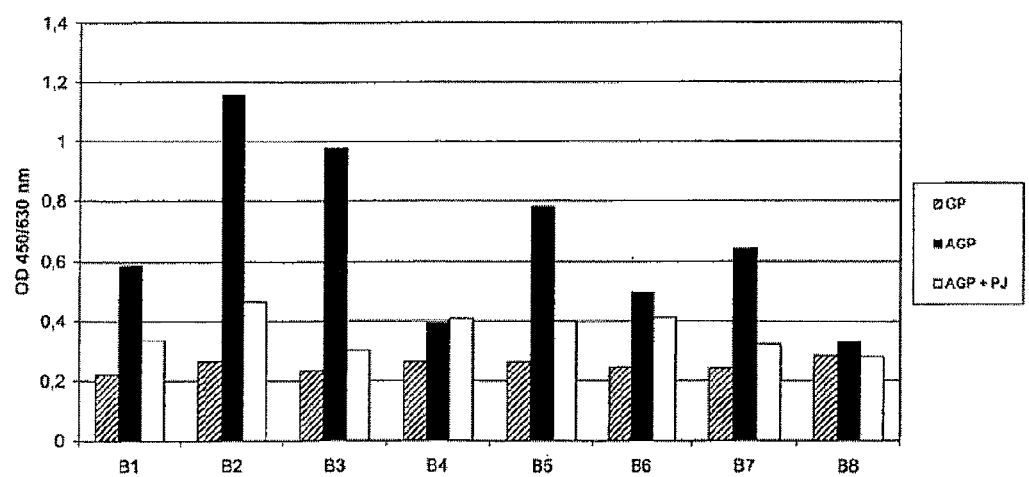

Figure 19
1
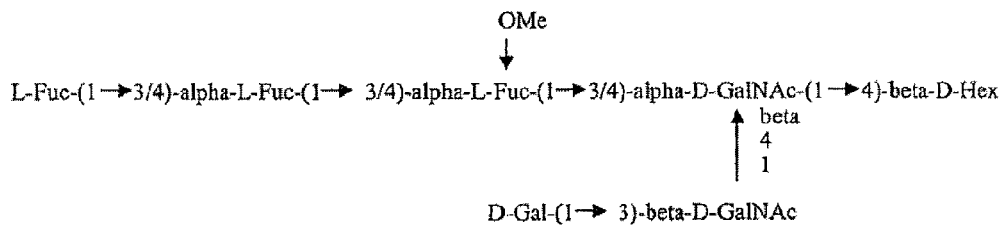
2
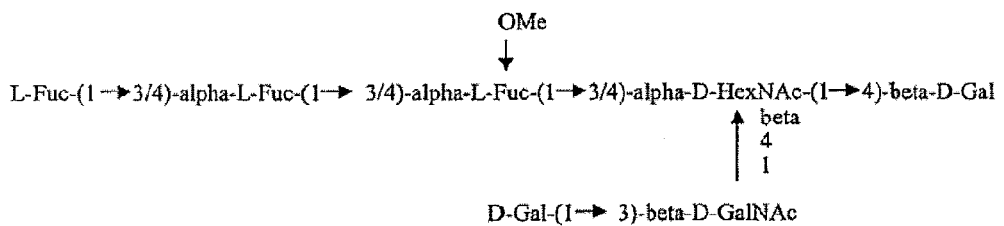
3
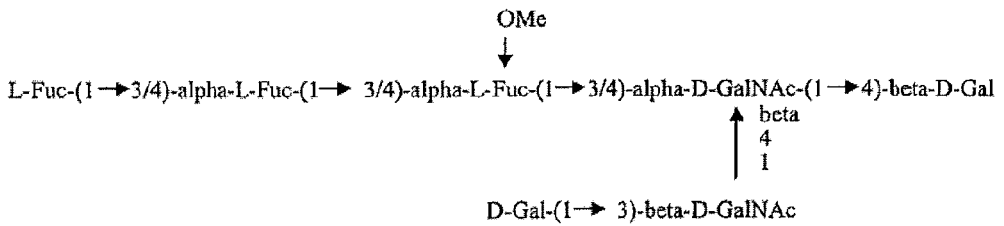
4
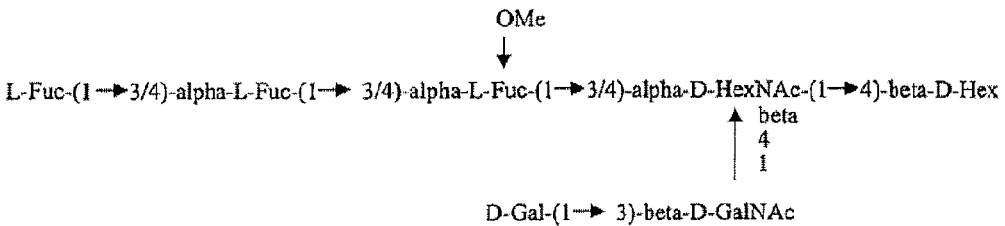

Figure 19 - continued
5
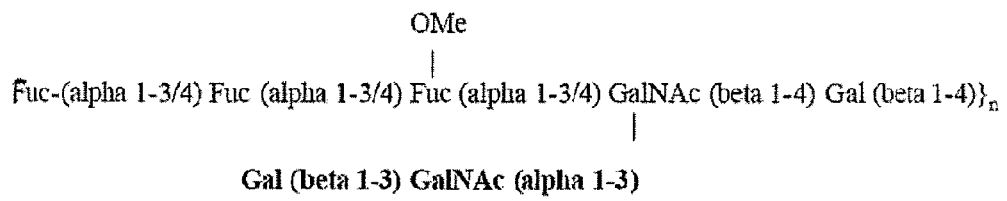
Fig. 20
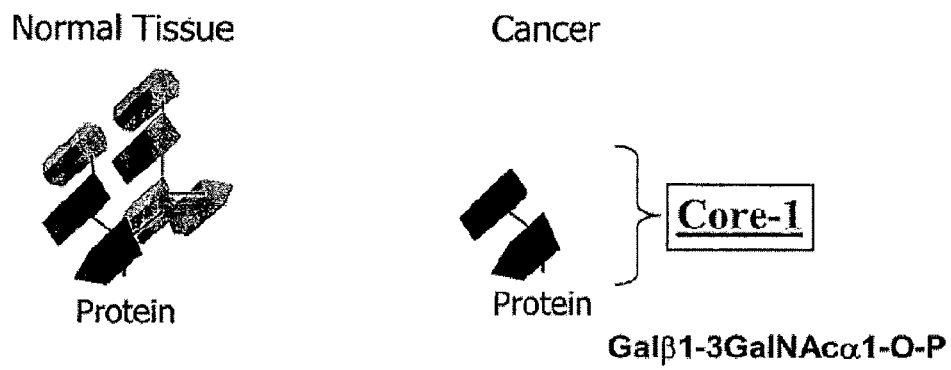
Fig. 21
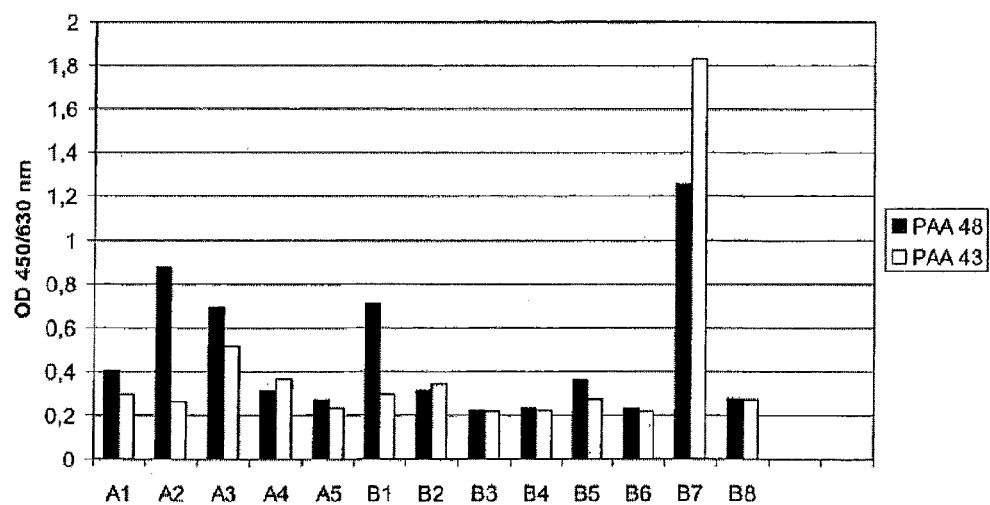

Figure 22

| Antibiotic/Strain | 53 | 52 | AG6 | MU1 | lac Ø | lac + | AG3 | LH2 | 32 |
|---|---|---|---|---|---|---|---|---|---|
| Species | B. ovatus | B. thetaiotaomicron | B. ovatus | B. ovatus | E. coli | E. coli | E. coli | E. coli | E. coli |
| Strain | DSMZ 1896 | DSMZ 2079 | AG6 | MU1 | lac Ø | lac + | AG3 | LH2 | DSMZ 8697 |
| Penicillin | R | R | R | MS | R | R | R | R | R |
| Mezlocillin | R | R | MS | MS | HS | S | HS | HS | S |
| Ampicillin | R | R | R | R | S | S | S | S | S |
| Ampicillin +Sulbactam | HS | HS | HS | HS | HS | HS | HS | HS | HS |
| Piperacillin + Tazobactam | S | MS | S | S | HS | HS | HS | HS | HS |
| Meropenem | HS | HS | HS | HS | HS | HS | HS | HS | HS |
| Clindamycin | HS | MS | S | R | R | R | R | HS | HS |
| Metronidazol | S | S | HS | HS | R | R | R | R | R |

| Antibiotic/Strain | lac Ø | lac + | AG3 | LH2 | 32 | 53 | 52 | AG6 | MU1 |
|---|---|---|---|---|---|---|---|---|---|
| Species | E. coli | E. coli | E. coli | E. coli | E. coli | B. ovatus | B. thetaiotaomicron | B. ovatus | B. ovatus |
| Strain | lac Ø | lac + | AG3 | LH2 | DSMZ 8697 | DSMZ 1896 | DSMZ 2079 | AG6 | MU1 |
| Ampicillin sulfamethoxazole + trimethoprim | S | S | S | S | S | R | R | R | R |
| Gentamycin | HS | HS | HS | HS | HS |  |  |  |  |
| Tobramycin | S | S | S | S | S |  |  |  |  |
| Mezlocillin | HS | HS | HS | HS | HS |  |  | MS | MS |
| Cefotiam | HS | HS | HS | HS | HS |  |  |  |  |
| Cefotaxin | HS | HS | HS | HS | HS | HS | HS |  |  |
| Meropenem | HS | HS | HS | HS | HS |  |  |  | HS |
| Ceftriaxon | HS | HS | HS | HS | HS |  |  |  |  |

Figure 22 - continued

| | | | | | | | |
|---|---|---|---|---|---|---|---|
| Cefuroxim | MS | MS | MS | MS | | | |
| Cefixim | HS | HS | HS | HS | | | |
| Tetracyclin | MS | MS | MS | MS | | | |
| Oxacillin | R | R | R | R | | | |
| Erythromycin | R | R | R | R | | | |
| Vancomycin | R | R | R | R | | | |
| Ampicillin + Sulbactam | HS | HS | HS | HS | HS | HS | HS |
| Linezolid | R | R | R | R | | | |
| Piperacillin | HS | HS | HS | HS | | | |
| Piperacillin + Tazobactam | HS | HS | HS | HS | MS | S | S |
| Amikacin | S | S | S | S | | | |
| Ceftazidim | HS | HS | HS | HS | | | |
| Imipenem | HS | HS | HS | HS | | | |
| Rifampicin | R | R | MS | R | | | |
| Ciprofloxacin | HS | HS | HS | HS | R | R | |
| Fosfomycin | HS | HS | S | HS | | | |
| Penicillin | R | R | R | R | R | R | MS |
| Teicoplanin | R | R | R | R | HS | MS | |
| Clindamycin | R | R | R | R | MS | S | R |
| Bacitracin | R | R | R | R | | | |
| Neomycin | S | S | S | S | | | |
| Colistin | S | S | S | S | | | |
| Fucidinsäure | R | R | R | R | S | HS | HS |
| Metronidazol | | | | | | | |

R = resistent    S=sensitive
MS= medium sensitivity    HS = high sensitivity

CARBOHYDRATE SPECIFIC CELLULAR IMMUNITY INDUCING MICROORGANISMS AND FRACTIONS THEREOF

CROSS REFERENCE TO RELATED APPLICATIONS

This application is a national stage filing under 35 U.S.C. §371 of International Application No. PCT/EP2007/009765, filed on Nov. 12, 2007, and claims the benefit of priority of European Application No. 06090208.7, filed on Nov. 10, 2006, and European Application No. 06090209.5, filed on Nov. 10, 2006. All of these applications, including International Application No. PCT/EP2007/009765, are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Dec. 17, 2012, is named Sequence Listing_904980028.txt and is 34,558 bytes in size.

FIELD OF THE INVENTION

The present invention relates to the field of prevention and treatment of diseases that are characterized by the occurrence of certain carbohydrate epitopes. The invention provides nutraceuticals and pharmaceutical compositions comprising a microorganism positive for the carbohydrate epitope and fractions thereof which induce an effective carbohydrate-specific cellular immune response against carbohydrate-positive cells and diseases. Furthermore it provides methods for the selection, isolation and identification of carbohydrate-positive microorganisms which are suitable as an effective part of the nutraceutical or pharmaceutical composition. It provides methods for the generation of carbohydrate specific dendritic cells and cell lines and carbohydrate specific T cells, T cell clones and T cell lines. The invention further provides formulations and methods for prophylaxis and treatment of diseases associated with certain carbohydrate epitopes.

BACKGROUND OF THE INVENTION

Carbohydrate antigens often occur in combination with human diseases. For instance, aberrant glycosylation is a typical hallmark of cancer cells, thereby creating new carbohydrate structure that are absent from or rarely present on normal human cells. Those carbohydrate structures were believed to be suitable candidates for the generation of tumor vaccines, but the carbohydrate itself are poorly immunogenic structures classified as T cell independent antigens. Therefore, vaccine development focused on the generation of synthetic carbohydrate based anti-tumor vaccines, whereby carbohydrate epitopes are coupled to immune potentiating carrier structures or natural proteins or oligopeptides (such as MUC1) and combined with additional adjuvances for the induction of an immune response especially for the induction of a cellular immune response. Polysaccharide are linked to immunogenic polypeptides such as tetanus or diphtheria toxoid or KLH or T helper epitopes in order to alter the immune response from T cell independent to T cell dependent in order to generate immunological memory. The production of such vaccines is extraordinarily difficult and expensive. Furthermore, such vaccines represent non-natural or artificial antigens with unknown or adverse side effects.

Until recently it was believed that carbohydrates are not presented by antigen presenting cells (e.g. dendritic cells) to immune effector cells and do not mediate a T cell immune response.

Now few reports show that complex carbohydrate are not removed during processing of glycoproteins by antigen presenting cells and can be presented to major histocompatibility complex II restricted T cells together with the peptid.

In the case of the MUC1 antigen, internalization, processing and presentation of glycopeptides on dendritic cells could be shown. MUC1 bearing short sialylated carbohydrates induced activation and maturation of dendritic cells phenotypically similar to that induced by bacterial LPS thereby lacking specificity, but these DCs were not capable of inducting a Th1 type immune response after coculture with allogenic CD4+ T cells or cytotoxic CD8 responses (Carlos et al. (2005) J Immunol 175: 1628-1635).

MUC1-derived peptides O-glycosylated with a Tn epitope induce cellular immunogenicity in mice, but immunization with glycopeptide-loaded dendritic cells showed no immunotherapeutic effect, no selective lysis of human MUC1 expressing murine cell lines and the elicited CTLs showed cross-reactivity between glycosylated and non-glycosylated forms of the same peptides, so the immune response was not effective and not CH-specific (Stepensky et al. (2005) Clin Exp Immunol 143:139-149).

Cancer associated MUC1 carrying short sugar moieties from mono- to tetrasaccharides (such as the tumor antigens Tn, TF, S-Tn, and S-TF) can even induce suppression of human T cell responses (Agrawal et al. Nat Med 1998 January; 4(1):43-9).

Bacterial glycosylation is completely different from eukaryotic glycosylation due to a different profile of enzymes involved in the glycosylation machinery. The majority of the polysaccharides of bacteria are negatively charged polysaccharides which clearly fail to activate T cells and hence are generally classified as T cell independent type 2 antigens. More recently it was described that zwitterionic capsular polysaccharides from certain bacteria have the ability to activate CD4+ T cells. However, MHCII restriction for zwitterionic polysaccharide antigens is not clear, and the T cells are activated in a polyclonal non-antigen specific fashion which is not antigen or epitope specific but show a broad Vβ usage and cross-reactivity apparently resembling the broad activation induced by mitogens (Cobb and Kasper, Cell Microbiol 2005; Eyon, Zenewicz, Flavell, Cell, 2005).

Furthermore, carbohydrates and carbohydrate antigens are generally known as weak immunogens.

Th1 type immunity is considered to be important and necessary in tumor rejection and in elicitation of potent immune responses in various diseases (Kobayashi et al., 1998, J. Immunol. 160: 5869-5873). It was shown that some short tumor carbohydrates may be presented and recognized together with certain aminoacids as combined necessary binding motifs. However, this does not lead to a Th1 type immune response. In contrast, in case of MUC1 desialylated MUC1 (presenting short sugar moieties such as Tn or TF) fails to induce T cell cytokine production and hence no T cell activation or in case of sialylated sugars induction of the secretion of cytokines such as TNFalpha together with IL-6 which are connected with tumor metastasis, tumor progression and bad prognosis, occur and hence fail to activate the necessary TH1 response and is even thought to be connected with tumor escape from immune responses (Carlos et al., J. Immunol,).

This state of the art teaches that natural molecules comprising human carbohydrate tumor antigens can not induce a potent cellular Th1 and cytotoxic immunity directed against carbohydrate epitopes, and that polysaccharides from bacteria, in particular the capsular polysaccharides, can not induce an antigen specific immune response.

Hence, the use of these carbohydrate molecules would not be suitable for tumor vaccine approaches using (i) dendritic cells for presentation of the carbohydrate antigens which would not induce a potent cytotoxic immune response when administered in humans and not be suitable for tumor vaccine approaches using (ii) APC such as DC for presentation of the carbohydrate antigens for generation of antigen specific T cells in a Th1 response for a adoptive T cell therapy in patients.

However, due to the importance of carbohydrate antigens in the development of pathologic diseases such as cancer, it would be advantageous to obtain means for inducing an effective carbohydrate-specific cellular immune response.

It is the object of the present invention to provide respective means.

DESCRIPTION

In order to overcome the above mentioned drawbacks in the art, the present invention provides the means for the induction of an effective carbohydrate-specific cellular immune response against a carbohydrate epitope or epitopes present on a molecule from a human or animal cell associated with a disease of said human or animal.

To our knowledge this surprising finding is the first report on the induction of a carbohydrate specific Th1 type immune response induced by a natural molecule.

Even further surprisingly we show for the first time that an effective carbohydrate-specific cellular Th1 type and a cytotoxic T cell immune response can be induced by the administration of suitable amounts of at least one microorganism that expresses a human or animal disease-associated carbohydrate epitope or at least one fraction thereof.

The usage of bacteria that usually inhabit the gastro-intestinal tract of humans results in a prophylactic and therapeutic agent that does not cause undesired side effects. The carbohydrate nature is responsible for the lack of relevant tolerogencity and shows no relevant allergic reactions.

As glycosylation in microorganisms is completely different from glycosylation in humans or animals, it was surprising that the microorganisms provided and obtainable by the present invention express a "human" carbohydrate epitope or part of it as it occurs on a human cell surface or is produced from a human cell and that this human antigen or part of it is presented by dendritic cells after loading with said microorganisms and induces an effective cellular immune response against said carbohydrate antigen which can in sense of the invention also be or comprise an effective cellular immune response against carbohydrate structures, carbohydrate conjugates or a mammalian cell comprising said carbohydrate epitope. Those loaded dendritic cells are functionally active and stimulate and activate T cells.

Most surprisingly this immune response is also carbohydrate specific and is e.g. not predominantly triggered by the underlying peptide sequence.

One important aspect of the present invention is that the carbohydrate positive microorganism is recognized by at least one carbohydrate binding molecule such as e.g. a carbohydrate epitope specific antibody. Hence, the carbohydrate positive microorganism is specifically bound by a carbohydrate epitope specific antibody when contacted with said antibody. The Carbohydrate structure is thus accessible for said carbohydrate epitope specific antibody in the carbohydrate positive microorganism of the present invention and not "hidden" by other structures. This important characteristic which can be determined upon testing—suitable tests are described below—ensures that the carbohydrate positive microorganism and/or the carbohydrate positive fraction or lysate thereof carries the carbohydrate epitope of interest and is thus at least immunochemically virtually identical to the carbohydrate epitope of interest and not an epitope that is merely similar to the carbohydrate epitope of interest. This feature is important to ensure that an immune response is triggered by said carbohydrate positive microorganism that is sufficiently specific for the carbohydrate epitope of interest. Such carbohydrate epitope specific antibodies, that can be used to determine that a microorganism carries the carbohydrate epitope of interest, specifically recognize the carbohydrate epitope e.g. in a tumor-relevant surrounding and hence as naturally occurring. This further ensures that the microorganism carries the carbohydrate epitope of interest in a form that triggers the desired immune response.

The carbohydrate epitope specific antibodies can accordingly be used to determine that the carbohydrate positive microorganisms of the present invention carry Carbohydrate structures mimicking the carbohydrate epitope of interest e.g. as present on tumors. This characteristic—carbohydrate epitope specificity—is decisive for the ability of the microorganism of the present invention to trigger the desired immune response.

Due to the fact that the microorganisms of the present invention are truly carbohydrate positive and are respectively selected—what can be determined/done by the use of carbohydrate epitope specific antibodies—the invention provides carbohydrate positive microorganisms which induce or enhance a specific and thus potent immune response against the carbohydrate epitope of interest. As indicated above, said carbohydrate epitope is preferably a human carbohydrate epitope and hence a carbohydrate epitope found on or presented by a human cell. The formulation of the present invention activates the immune system in a tumor-specific manner by inducing high anti-carbohydrate epitope antibody levels which are specific. To our knowledge, the present invention is the first antigen-specific food additive/nutraceutical or pharmaceutical which is able to activate a specific immune shield against tumors and the first food-additive which is able to induce a carbohydrate and in particular Core-1 tumor antigen-specific immune response.

According to one embodiment, the invention provides a method of identifying a carbohydrate positive microorganism according to the present invention which microorganism is thus capable of triggering a specific immune response.

Hence, a method for isolating a carbohydrate positive microorganism carrying a preferably human carbohydrate epitope of interest from a mixture of microorganisms is provided, comprising (a) bringing a carbohydrate binding molecule specific for the carbohydrate epitope of interest into contact with a mixture of microorganisms, and (b) isolating at least one microorganism bound to said carbohydrate binding molecule from said mixture, (c) optionally testing that the isolated microorganism is a carbohydrate positive microorganism by testing the isolated microorganism for specific binding to said carbohydrate binding molecule.

This selection method allows the identification of microorganisms which carry the carbohydrate epitope of interest and are thus suitable components for the formulations according to the present invention. As outlined above, said carbohydrate epitope is preferably a human carbohydrate epitope such as e.g. a tumor marker.

As becomes apparent from the examples, several carbohydrate epitopes exist which are associated with diseases and in particular cancer (see e.g. table 1). Furthermore, there are also binding molecules known which specifically bind said human carbohydrate epitopes of interest (see table 2). Furthermore, methods for generating carbohydrate binding molecules specific for the carbohydrate epitope of interest are also described herein.

According to a preferred embodiment, said method additionally comprises testing the induction of an effective carbohydrate specific cellular immune response and/or humoral immune response against said carbohydrate epitope by said microorganism and/or fraction and/or lysate thereof in vivo or in vitro. According to this preferred embodiment said carbohydrate positive microorganism induces or enhances an immune response against the carbohydrate epitope of interest in at least one human or animal recognizing the carbohydrate epitope of interest and/or tumor cell positive for said carbohydrate epitope. Due to the fact that the microorganism is positive for the carbohydrate epitope of interest, an immune response against the carbohydrate epitope of interest is induced/enhanced upon administration of the identified microorganism. Thereby an immunosurveillance mechanism is established that may e.g. eliminate newly arising tumor cells carrying the carbohydrate epitope of interest, thereby preventing primary tumor growth and/or which strengthens the immune system and/or improves an immune response.

Therefore, according to a preferred embodiment, step (d) comprises testing the induction of an effective carbohydrate specific cellular immune response against said carbohydrate epitope by said carbohydrate positive microorganism and/or fraction and/or lysate thereof for the activation of CD4 positive Th1 type T cells and/or for the activation of cytotoxic CD8 positive T cells, preferably in at least one animal or human and/or in vitro.

According to one embodiment, said cellular immune response test performed in step (d) comprises
  i.) Loading at least one dendritic cell with the carbohydrate positive cell identified in steps (a) to (c);
  ii.) bringing into contact a suitable amount of said at least one dendritic cell loaded with said carbohydrate positive microorganism with a suitable amount of immune cells which can be activated or inhibited by a dendritic cell;
  iii.) cultivation in order to allow interaction of said immune cells with said loaded dendritic cells;
  iv.) adding a suitable amount of antigen presenting cells (APC) loaded with a suitable amount of at least one second compound carrying the same carbohydrate epitope as the carbohydrate positive microorganism, wherein said second compound is different from said carbohydrate positive microorganism;
  v.) cultivation for restimulation of said immune cells
  vi.) determining whether restimulation of the immune cells occurred.

By performing this cellular response test it can be determined whether a certain carbohydrate epitope present of said carbohydrate positive microorganism is capable of triggering a cellular immune response. So far the prior art assumed that carbohydrates are unable to trigger a cellular immune response. However, it has now been found that certain carbohydrate epitopes are able to elicit a cellular immune response. It is thus important to provide test systems for determining whether a carbohydrate positive microorganism identified by the method of the present invention is indeed able to trigger a respective cellular response, thereby determining whether said microorganism is suitable e.g. for therapy. Said test uses dendritic cells as dendritic cells are able to prime and thus stimulate immune cells such as T-cells. Dendritic cells process compounds they are encountering and present the processed compounds/antigens on their surface. However, MHC cells such as dendritic cells can only present certain kinds of antigens and it is important to determine whether the antigen/epitope of interest can be presented by dendritic cells as only such antigens/epitopes are able to elicit a cellular immune response.

Therefore, dendritic cells are loaded with the Carbohydrate-positive microorganism identified in steps (a) to (c). Suitable conditions for loading are described herein.

Said loaded dendritic cells are then contacted with immune cells, in particular lymphocytes such as T-cells. The immune cells can be obtained e.g. from human donors. Dendritic cells presenting antigens matching the receptors of the immune cells activate and thus stimulate the lymphocytes thereby allowing them to proliferate and survive. Lymphocytes which do not match the antigens presented by the dendritic cells are not activated and die.

This first round of stimulation provides activated lymphocytes which are specific for any corresponding antigen presented by said loaded dendritic cells. However, the aim of the present step is to identify whether the carbohydrate positive microorganism can stimulate a cellular response specific for the carbohydrate epitope.

Therefore, a selection step is performed wherein the lymphocytes are restimulated in order to determine whether the carbohydrate epitope of the carbohydrate positive microorganism stimulates the lymphocytes and thus triggers a cellular response. In said selection step antigen presenting cells such as e.g. dendritic cells are loaded with a second compound which also carries the carbohydrate of interest. However, said second compound is different from the carbohydrate positive microorganism. This second compound is also processed by the APCs and the antigens are presented by said APCs. As the second compound is different from the carbohydrate positive microorganism, most presented antigens, preferably all antigens are—besides the Carbohydrate of interest—different from the antigens presented in the first round. This has the effect that only those lymphocytes survive the second round of restimulation which find a matching antigen presented by said APCs. In case the dendritic cells of the first round as well as the APCs of the second round both present an antigen comprising or consisting of the carbohydrate epitope of interest, lymphocytes recognizing said antigen are stimulated and thus survive as they are also restimulated. Those lymphocytes which do not find a matching partner when contacting with said APCs loaded with said second compound carrying the carbohydrate epitope of interest die due to a lack of restimulation. This selection step ensures that a cellular response against the Carbohydrate of interest is detected.

Further embodiments regarding the provided test systems that can be used in conjunction with the present invention are described in the claims and subsequently.

The carbohydrate positive microorganisms identified by said method which have the described characteristics and advantages and can be used in the formulation according to the present invention. The formulation according to the present invention can be used for prophylactic and/or therapeutic purposes and/or in supporting immunological activities.

The invention also provides formulations which can be used as pharmaceutical composition and as nutraceuticals and can induce the immune responses against the carbohydrate epitopes on human or animal cells or against a disease by a series of different administration routes including the systemic administration such as but not limited to intra peritoneal, intravenous, intradermal, subcutaneous but even more surprisingly via oral administration mediating a systemic immune response even when administering the microorganisms or fractions thereof via the oral route.

A formulation of the invention is a nutraceutical or a pharmaceutical composition which comprises at least one microorganism specifically bound by at least one carbohydrate binding molecule binding a carbohydrate epitope present on a molecule from a human or animal cell, or a fraction or a lysate thereof, whereby said microorganism or a fraction or a lysate thereof, or said formulation, said nutraceutical, or said pharmaceutical composition induce an effective carbohydrate-specific cellular immune response against said carbohydrate antigen in at least one animal or human, preferably a cytotoxic T cell response.

In one embodiment of the invention the formulation of the present invention can be a nutraceutical and provides the means for the induction of a specific immune shield against diseases associated with certain carbohydrate epitopes or antigens. This is in contrast to conventional probiotics and prebiotics which result not in an antigen specific immune response but in an overall unspecific induction of the immune system. Use of the formulation of the present invention as a nutraceutical has several advantages compared to conventional vaccination strategies. One of it is the important convenience for the patient or the person who is using it. The immunostimulation is carbohydrate epitope or antigen specific and can even be induced well prior to the establishment of a disease or tumor building a specific immune shield in order to prevent, inhibit or reduce the development of such diseases or to be used in combination with other therapies of the disease or a therapy. Therefore, aggressive therapies (such as chemotherapy, radiotherapy or surgery) with severe side effects can be avoided. In a preferred embodiment the individual does not necessarily have to visit a physician in order to actively pursue disease prophylaxis, but can obtain the necessary formulation incorporated in a food, thereby decreasing the psychological barrier against other prevention possibilities.

Pharmaceutical compositions of the invention have also the advantage that they can target diseases with high medical need where carbohydrates or carbohydrate markers play an important role.

Without intending to be limiting, examples of such diseases and the associated human carbohydrate epitopes are listed in table 1.

TABLE 1

| Disease: | Carbohydrate epitope: |
| --- | --- |
| Melanoma | GM2, GD2, GD3L, GD3, 9-O-acetyl GD2, 9-O-acetyl GD3 |
| B cell lymphoma | GM2, GD2 |
| Small-cell lung cancer | GM2, Fucosyl GM1, Globo H, polysialic acid, sLe a (sialyl-Lewis a) |
| Breast cancer | GM2, Globo H, TF, Core-1, Galbeta1-3GalNAc-, Le y (Lewis-Y) |
| Prostate cancer | GM2, Globo H, Tn, sTn, TF, Le y, sLe a, Core-1 |
| Lung cancer | GM2 Globo H, Le y, Core-1 |
| Colon cancer | GM2, sTn, TF, Le y, Core-1, |
| Ovarian cancer | GM2, Globo H, sTn, TF, Le y, Core-1 |
| Stomach cancer | GM2, Le y, Le a, sLe a, Core-1 |
| Neuroblastoma, | GM2, GD2, GD3L, polysialic acid |

TABLE 1-continued

| Disease: | Carbohydrate epitope: |
| --- | --- |
| Sarcoma | GM2, GD2, GD3L, GD3 |
| Pancreas cancer | sLe a, sLe x (sialyl Lewis x) |
| Gastrointestinal cancers | sLe a, sLe x |
| CD4+CD56+ neoplasia | sLe x (CD15) |

However, the carbohydrate epitope can also be suitable for other indications such as but not limited to TF for lung cancer, liver cancer, stomach cancer, kidney cancer, prostate cancer, and Core-1 for kidney and liver cancer.

Surprisingly, the formulation of the present invention acts as an immunosurveillance mechanism against carbohydrate-positive diseases or tumor cells after administration in a human or an animal. It induces or enhances a carbohydrate-specific immune response in humans or animals that prevents or reduces the occurrence of disease or tumor cells characterized by the expression of the carbohydrate antigen that was applied to the human or animal.

The formulation of the present invention induces high specific anti-carbohydrate antibody titers and/or even more surprisingly an effective carbohydrate-specific cellular immune response recognizing the carbohydrate antigen or carbohydrate structures, carbohydrate conjugates or a mammalian cell comprising said carbohydrate epitope. Suitable carbohydrate positive microorganism can be identified with the screening methods and test systems described herein.

Due to the biologic nature of the formulation, its production is less expensive and time consuming as the production of conventional immunotherapeutic formulations.

Surprisingly, the formulation of the present invention has internal adjuvant properties, therefore additional adjuvances or immune-potentiating carriers are not necessary in all cases.

A) Nutraceuticals and Pharmaceutical Composition

The present invention provides a formulation selected from the group comprising nutraceutical and pharmaceutical compositions, comprising at least one carbohydrate positive microorganism which is recognized and thus bound upon contact by at least one carbohydrate binding molecule specifically recognizing a carbohydrate epitope present on a molecule from a human or animal cell, or a fraction or a lysate thereof, whereby said microorganism, said fraction or said lysate or said formulation comprising those induces an effective carbohydrate-specific cellular immune response against said carbohydrate epitope, and/or a carbohydrate structure, carbohydrate conjugate or a mammalian cell comprising said carbohydrate epitope.

One important aspect of the present invention is that the carbohydrate positive microorganism and/or the carbohydrate positive lysate or fraction thereof is recognized by at least one carbohydrate binding molecule, preferably a carbohydrate epitope specific antibody. Hence, the carbohydrate positive microorganism and/or the carbohydrate positive lysate or fraction thereof is specifically bound by carbohydrate binding molecule when contacted with said carbohydrate binding molecule. Hence, a carbohydrate structure similar or identical to the carbohydrate epitope of interest, which is preferably a human carbohydrate epitope, is thus accessible for said carbohydrate binding molecule in the carbohydrate positive microorganism of the present invention and not "hidden" by other structures. This important characteristic which can be determined upon testing—suitable tests are described below—ensures that the carbohydrate positive microorganism and/or the carbohydrate positive fraction or lysate thereof carries the carbohydrate epitope of interest and is thus at least immunochemically virtually identical to the carbohydrate epitope of interest and not an epitope that is merely similar to the carbohydrate epitope of interest. This feature is important to ensure that an immune response is triggered by said carbohydrate positive microorganism that is sufficiently specific for the carbohydrate epitope of interest. Such carbohydrate binding molecule, that can be used to determine that a microorganism carries the carbohydrate epitope of interest, specifically recognize the carbohydrate epitope e.g. in a tumor-relevant surrounding. Also comprised are microorganisms which are not naturally carbohydrate positive but may be converted to a carbohydrate positive microorganism by a chemical treatment such as e.g. a periodate treatment. Respective microorganisms can be e.g. used after periodate treatment (uncovering Core-1) as components of the formulations of the present invention if they are due to the chemical treatment then recognized by the carbohydrate binding molecules and are hence converted to a carbohydrate positive microorganism.

In a preferred embodiment of the invention, said induction of said effective carbohydrate specific cellular immune response occurs in at least one human or animal.

In another preferred embodiment of the invention, said induction of said effective carbohydrate specific cellular immune response is performed in vitro.

In a preferred embodiment of the invention said effective carbohydrate-specific cellular immune response comprises activation of CD4 positive T cells of Th1 type and/or activation of CD8 positive cytotoxic T cells directed against said carbohydrate epitope, and/or a carbohydrate structure, carbohydrate conjugate or a mammalian cell comprising said carbohydrate epitope.

In a preferred embodiment of the invention said effective carbohydrate-specific cellular immune response comprises activation of CD4 positive T cells of Th1 type and activation of CD8 positive cytotoxic T cells directed against said carbohydrate epitope, and/or a carbohydrate structure, carbohydrate conjugate or a mammalian cell comprising said carbohydrate epitope.

The present invention provides formulations comprising microorganisms presenting human or animal carbohydrate epitopes, and/or lysates and/or fractions thereof which induce an effective carbohydrate-specific immune response, more preferably an effective carbohydrate-specific cellular immune response, even more preferably said cellular immune response comprises activation of Th1 helper T-cells and cytotoxic T cells.

In a preferred embodiment the present invention provides a formulation selected from the group comprising a nutraceutical and a pharmaceutical composition which comprises at least one microorganism specifically bound by at least one carbohydrate binding molecule binding a carbohydrate epitope present on a molecule from a human or animal cell or a fraction or a lysate thereof, whereby said microorganism or a fraction or a lysate thereof, or said formulation, said nutraceutical, or said pharmaceutical composition induce an effective carbohydrate-specific cellular immune response against said carbohydrate epitope, and/or a carbohydrate structure, carbohydrate conjugate or a mammalian cell comprising said carbohydrate epitope.

In another preferred embodiment, the invention provides a nutraceutical comprising at least one microorganism carrying or presenting at least one human or animal carbohydrate epitope, and/or lysates and/or fractions thereof which induce an effective carbohydrate-specific immune response, more preferably an effective carbohydrate-specific cellular immune response against said carbohydrate epitope, or a carbohydrate structure, carbohydrate conjugate or a mammalian cell comprising said carbohydrate epitope, even more preferably said cellular immune response comprises activation of Th1 helper T-cells and cytotoxic T cells.

In a preferred embodiment, the invention provides a pharmaceutical composition comprising at least one microorganism carrying or presenting at least one human or animal carbohydrate epitope, and/or a lysate and/or fraction thereof which induce an effective carbohydrate-specific immune response against said carbohydrate epitope, or a carbohydrate structure, carbohydrate conjugate or a mammalian cell comprising said carbohydrate epitope, more preferably an effective carbohydrate-specific cellular immune response, even more preferably said cellular immune response comprises activation of Th1 helper T-cells and cytotoxic T cells.

Preferably the pharmaceutical composition of the present invention is used to prevent or reduce the occurrence of disease cells that are expressing the human or animal carbohydrate epitope and/or to prevent or reduce the spread or metastasis of said cells, such as but not limited to tumor cells or cancer cells expressing or comprising the human or animal carbohydrate epitope.

In another embodiment of the invention the pharmaceutical composition is used to treat a disease or a tumor expressing the human or animal carbohydrate epitope.

In a preferred embodiment of the invention the nutraceutical or the pharmaceutical composition of the present invention is used as a vaccine against cells or disease characterized by the occurrence of the carbohydrate epitope or a part thereof which mediates the specificity.

Said diseases or tumors associated with or expressing the carbohydrate epitope are listed elsewhere herein.

The pharmaceutical formulation of the invention comprises at least one carbohydrate-positive microorganism and a pharmaceutically acceptable carrier. The preparation and administration of a formulation of this invention (e.g. drug comprising carbohydrate-positive microorganism) is in accordance with known techniques. For example, the formulation can be combined with conventional galenic adjuvants to form a composition suitable for the desired method of application. For example, the compounds of this invention can be employed in mixture with conventional excipients, i.e., pharmaceutically acceptable organic or inorganic carrier substances suitable for parenteral or enteral application which do not deleteriously react with the active compounds. Suitable pharmaceutically acceptable carriers include but are not limited to water, salt solutions, alcohols, vegetable oils, polyethylene glycols, gelatin, lactose, amylose, magnesium stearate, viscous paraffin, perfume oil, fatty acid monoglycerides and diglycerides, pentaeyritol fatty acid esters, hydroxy methylcellulose, polyvinyl pyrrolidone, talc, etc.

The nutraceutical or the pharmaceutical composition of the present invention can be administered to a human or an animal via different routes of application or administration. Preferred routes of administration in the sense of the invention are described elsewhere herein.

In a preferred embodiment of the invention the nutraceutical or the pharmaceutical composition are orally applied to a human or an animal.

The invention provides a formulation selected from the group comprising a nutraceutical and a pharmaceutical composition comprising at least one microorganism bound by at least one carbohydrate binding molecule specifically recognizing a carbohydrate epitope present on a molecule from a human or animal cell, or a fraction or a lysate thereof, whereby said microorganism, said fraction or said lysate or said formulation comprising those induces an effective carbohydrate-specific cellular immune response against said carbohydrate epitope in at least one animal or human. Thereby and anywhere else herein an immune response against a carbohydrate epitope also means an immune response against a carbohydrate structure, carbohydrate conjugate or a mammalian cell comprising said carbohydrate epitope.

In a preferred embodiment said formulation induces or enhances a specific immune response against said carbohydrate epitope in a human or animal.

In a preferred embodiment said formulation induces or enhances a specific immune response against said carbohydrate epitope in a human or animal whereby said carbohydrate epitope is associated with a disease in humans or animals.

In another preferred embodiment said specific immune response against said carbohydrate epitope comprises a humoral immune response against said carbohydrate epitope.

Said humoral immune response against said carbohydrate epitope results in the production of carbohydrate specific antibodies in the human or animal and can be determined by the humoral immune response tests as described below. Enhancing of the humoral immune response means the increase of an already present antibody titre against said carbohydrate epitope after administration of the formulation of the invention In another preferred embodiment said specific immune response against said carbohydrate epitope comprises an effective carbohydrate-specific cellular immune response against said carbohydrate epitope.

In another preferred embodiment said effective carbohydrate-specific cellular immune response comprises activation of CD4 positive T cells of Th1 type and activation of CD8 positive cytotoxic T cells directed against said carbohydrate epitope.

In another preferred embodiment said specific immune response against said carbohydrate epitope comprises an effective carbohydrate-specific cellular immune response and a humoral immune response against said carbohydrate epitope.

In a preferred embodiment of the invention the carbohydrate epitope is selected from the group comprising TF, Core-1, Tn, sialyl-Tn, sialyl-TF, Globo-H, Lewis-Y, sialyl-Lewis-A, sialyl-Lewis-X, polysialic acid, Lewis-X, GM2, GD2, GD3, 9-O-acetyl GD3, 9-O-acetyl GD2, GD3L, fucosyl GM1, Fucosyl GM1, Lewis-A, Lewis B, sLac, sialylated type 1 chain, CA 19-9 antigen, CA 72-4 antigen and CA-50 antigen.

In a preferred embodiment of the invention the carbohydrate binding molecule is selected from the group comprising at least one lectin, at least one selectin, and/or at least one antibody and/or at least one molecule derived therefrom which bind to TF, Core-1, Tn, sialyl-Tn, sialyl-TF, Globo-H, Lewis-Y, sialyl-Lewis-A, sialyl-Lewis-X, polysialic acid, Lewis-X, GM2, GD2, GD3, 9-O-acetyl GD3, 9-O-acetyl GD2, GD3L, fucosyl GM1, Lewis-A, Lewis-B, sLac, sialylated type 1 chain, CA 19-9 antigen, CA 72-4 antigen or CA-50 or to an epitope comprising any of these carbohydrate structures or parts thereof.

In a preferred embodiment the the invention provides a formulation selected from the group comprising nutraceutical and pharmaceutical compositions, comprising at least one carbohydrate positive microorganism bound by at least one carbohydrate binding molecule specifically recognizing a carbohydrate epitope present on a molecule from a human or animal cell, or a fraction or a lysate thereof, whereby said microorganism, said fraction or said lysate or said formulation comprising those induces an effective carbohydrate-specific cellular immune response against said carbohydrate epitope, and/or a carbohydrate structure, carbohydrate conjugate or a mammalian cell comprising said carbohydrate epitope, in at least one animal or human; wherein (i) said effective carbohydrate-specific cellular immune response comprises activation of CD4 positive T cells of Th1 type and/or activation of CD8 positive cytotoxic T cells directed against said carbohydrate epitope, and/or a carbohydrate structure, carbohydrate conjugate or a mammalian cell comprising said carbohydrate epitope, and (ii) the carbohydrate epitope is selected from the group comprising TF, Core-1, Tn, sialyl-Tn, sialyl-TF, Globo-H, Lewis-Y, sialyl-Lewis-A, sialyl-Lewis-X, polysialic acid, Lewis-X, GM2, GD2, GD3, 9-O-acetyl GD3, GD3L, fucosyl GM1, Fucosyl GM1, Lewis-A, Lewis-B, sLac, sialylated type 1 chain, CA 19-9 antigen, CA 72-4 antigen and CA-50 antigen, and (iii) the carbohydrate binding molecule is selected from the group comprising lectins, selectins, and/or antibodies and/or molecules derived therefrom which bind to TF, Core-1, Tn, sialyl-Tn, sialyl-TF, Globo-H, Lewis-Y, sialyl-Lewis-A, sialyl-Lewis-X, polysialic acid, Lewis-X, GM2, GD2, GD3, 9-O-acetyl GD3, GD3L, fucosyl GM1, Fucosyl GM1, Lewis-A, Lewis-B, sLac, sialylated type 1 chain, CA 19-9 antigen, CA 72-4 antigen or CA-50 antigen or to a carbohydrate structure comprising any of these carbohydrate epitopes or parts thereof.

Without intending to be limiting, examples of carbohydrate structures and corresponding carbohydrate binding molecules are listed in table 2.

TABLE 2

| Carbohydrate | carbohydrate binding molecule | |
|---|---|---|
| epitope | lectin | monoclonal antibody |
| TF or Core-1 | galectin, C-type lectins from macrophages, sialoadhesin, PNA [3], Jacalin [3], MAL [3], EEL [3], ECL [3] | Nemod-TF1 [2], Nemod-TF2 [2], A78-G/A7 [2], HB-T1 [11], HH8 [14], A68-B/A11 [2] |
| Tn | C-type lectins from macrophages, sialoadhesin, BPL [3], DBA [3], GSL I [3], MPL [3], RCA [3], SJS [3], SBA [3] | HB-Tn1 [11] |
| sialyl-Tn | | CA 72-4 [1], TKH2 [1], HB-STn1 [11] |
| Globo-H | | A69-A/E8 [2], VK9 [13] |
| Lewis-Y | | A46-B/B10 [2], A63-D/B12 [2], A51-B/A6 [2], A70-C/C8 [2], A70-A/A9 [2] |
| sialyl-Lewis-A | E-selectin | CA 195 [1], CA 50 [1], 121SLE [12] |
| sialyl-Lewis-X | E-selectin | CA19-9 [1], KM931 [10], T174 [10] |
| Lewis-X | | 73-30 [4], BG-7 (P12) [4] |
| Lewis-A | | CA 195 [1], MAB2108 (7LE) [4], BG-5 (T174) [4], PR5C5 [12] |
| Lewis-B | | MAB2102 (2.25LE) [4], BG-6 (T218) [4] |
| sialylated type 1 chain | | CA 242 [1] |
| sLac | | CA 50 [1], DU-PAN-2 [1] |
| polysialic acid | MAL II [3], SNA [3] | Mab735 [9], 5A5 [13] |
| fucosyl GM1 | | F12 [13] |
| GM2 | | BP283 [5], PGNX [13] |
| GD2 | | Mab 126 [1], 3F8 [8], ME 36.1 [1] |
| GD3 | | R24 [6], MAB2053 [7], ME 36.1 [1] |

TABLE 2-continued

| Carbohydrate epitope | carbohydrate binding molecule | |
|---|---|---|
| | lectin | monoclonal antibody |
| 9-O-acetyl GD2 | | 3F8 [8] |
| 9-O-acetyl GD3 | | ME3.11 [1] |

[1] Orntoft et al. Electrophoresis 1999, 20, 362-371
[2] Glycotope GmbH Berlin, www.glycotope.com
[3] vector laboratories, www.vectorlabs.com
[4] Amano et al. Clin Diagn Lab Immunol 1997(September), 540-544
[5] Acris Antibodies GmbH, www.acris-antibodies.com
[6] Reaman et al. Cancer Res 1990 50 (1): 202-5
[7] CHEMICON International, Inc. www.chemicon.com
[8] Ye et al. 1992; 50 (2): 197-201
[9] Husmann et al. J Histochem Cytochem 1990; 38 (2): 209-15
[10] Calbiochem www.Calbiochem.com
[11] DakoCytomation Dako Deutschland GmbH, Germany, www.dakogmbh.de
[12] Dianova, Hamburg, Germany
[13] Livingston et al. Cancer Immunol Immunother (2005) 54: 1018-1025
[14] Clausen et al. Mol Immunol(1988) 25: 199-204

Said carbohydrate positive microorganism and fractions and lysates of the carbohydrate positive microorganism and combinations thereof are described in detail under Definitions and elsewhere herein, as well as methods for identifying and isolating said microorganisms or fractions thereof.

In a further preferred embodiment the invention provides a nutraceutical or a pharmaceutical composition comprising at least one carbohydrate positive microorganism or fraction or lysate thereof which induces or enhances a carbohydrate specific immune response against the carbohydrate epitope in at least one human or animal functioning as a shield against carbohydrate epitope positive cancer cells by having the potential to destroy cancer cells which carry or comprise said carbohydrate epitope.

Carbohydrate epitope positive cancer cells in sense of the invention means cancer cells which express, carry or comprise said carbohydrate epitope or which produce said carbohydrate epitope or which are associated with the carbohydrate epitope.

In a further preferred embodiment the invention provides a nutraceutical or a pharmaceutical formulation comprising at least one carbohydrate positive microorganism or fraction or lysate thereof which induces or enhances a carbohydrate specific immune response in at least one human or animal functioning as a shield against cells from a disease associated with said carbohydrate epitope by having the potential to destroy said cells.

In a further preferred embodiment of the invention the nutraceutical is used in order to build said carbohydrate specific immune response which functions as a shield against carbohydrate cells which has the potential to destroy those cells as described above by orally administering the nutraceutical in (at least one) healthy individuals.

In a further preferred embodiment the nutraceutical of the invention is used in order to reduce or even further preferred to prevent the occurrence of a carbohydrate positive disease or tumor by orally administering the nutraceutical in at least one healthy individual.

In a preferred embodiment of the invention the pharmaceutical composition comprising at least one carbohydrate positive microorganism or fraction or lysate thereof is used to build a carbohydrate specific immune response which functions as a shield against carbohydrate epitope positive cancer cells by having the potential to destroy those cells as shown herein for example by the induction of the carbohydrate epitope specific antibodies, the carbohydrate epitope specific complement dependent cytotoxicity of carbohydrate epitope antibodies against carbohydrate epitope positive tumor cells killing those effectively, or by secretion of TNFalpha and/or INFgamma by carbohydrate epitope specific T cell responses which are scientifically recognized surrogate markers by those skilled in the art for a specific cytotoxic T cell mediated tumor cell killing for those tumor cells carrying the carbohydrate epitope, as shown in the examples and described herein.

The nutraceutical or the pharmaceutical composition of the invention is used to treat a carbohydrate positive disease or tumor in at least one human or animal.

In a preferred embodiment of the invention the nutraceutical comprising at least one carbohydrate positive microorganism or fraction thereof is used in order to treat a carbohydrate positive disease or tumor by orally administering the nutraceutical in patients suffering from this disease.

In a preferred embodiment of the invention the pharmaceutical composition comprising at least one carbohydrate positive microorganism or fraction thereof is used in order to treat a carbohydrate positive disease or tumor in patients suffering from this disease.

In a further preferred embodiment the nutraceutical or pharmaceutical composition of the invention is used in order to reduce or even more preferred to prevent the occurrence of a carbohydrate positive disease or tumor or metastasis.

In a further preferred embodiment the invention provides a nutraceutical or a pharmaceutical composition comprising at least one carbohydrate positive microorganism or fraction thereof which reduces or prevents the spread or metastasis of a carbohydrate positive disease or tumor in at least one human or animal when administered.

In a further preferred embodiment the invention provides a formulation selected from the group comprising a nutraceutical or a pharmaceutical composition comprising at least one carbohydrate positive microorganism or fraction thereof which is used for prophylaxis and treatment of a human or animal disease associated with a carbohydrate epitope.

In a further preferred embodiment the invention provides a pharmaceutical composition which is used to prevent or reduce the spread of the tumor or metastasis or spread of metastasis or time to relapse of a carbohydrate epitope positive tumor or tumor cells, to improve quality of life or median survival or rate of time to relapse, or to treat a tumor patient which has or had a carbohydrate epitope positive tumor by administering the pharmaceutical composition in patients suffering from this disease.

In a further preferred embodiment of the invention the nutraceutical or the pharmaceutical composition comprises at least two different carbohydrate positive microorganism or fractions thereof.

In another preferred embodiment of the invention the nutraceutical or the pharmaceutical composition comprises at least two different carbohydrate positive microorganism or fractions thereof wherein the carbohydrate positive microorganisms or fractions are positive for the same carbohydrate.

In another preferred embodiment of the invention the nutraceutical or the pharmaceutical composition comprises at least two different carbohydrate positive microorganism or fractions thereof wherein the carbohydrate positive microorganisms or fractions are positive for different carbohydrates.

In another preferred embodiment of the invention the aforementioned nutraceutical or pharmaceutical composition of the invention comprise at least one carbohydrate positive microorganism and at least one fraction of a carbohydrate positive microorganism, preferentially from more than one carbohydrate positive microorganism whereby the carbohydrate positive microorganism and the fraction of a carbohydrate positive microorganism are positive for the same or different carbohydrates.

In a further preferred embodiment of the invention the nutraceutical or pharmaceutical formulation comprises at least one carbohydrate positive microorganism or fraction thereof combined with at least one other beneficial microorganism.

Said beneficial microorganism is preferably a selected from the group comprising *Lactobacillus* and *Bifidobacterium*.

In another preferred embodiment the nutraceutical or pharmaceutical composition of the invention comprises at least one fraction of the carbohydrate positive microorganism and at least one carbohydrate positive microorganism.

In a further preferred embodiment the nutraceutical or pharmaceutical composition of the invention comprises at least one fraction of the carbohydrate positive microorganism combined with at least one other beneficial microorganism, such as but not limited to a *lactobacillus* and/or *bifidobacterium*, even more preferred a combination of fractions of carbohydrate positive microorganisms of different strains combined with other beneficial microorganisms.

The formulation of the present invention selected from the group comprising a nutraceutical and a pharmaceutical composition can consist of a microorganism or fraction thereof alone or can comprise further ingredients or components such as but not limited to more than one microorganism or fraction thereof or other microorganisms or fractions thereof or buffer solutions or carriers or pharmaceutically acceptable carriers or food as described elsewhere herein.

Said nutraceutical of the invention can consist of at least one carbohydrate positive microorganism or fraction thereof alone, such as but not limited to a microorganism that is living or dead, lyophilized, or pasteurized, or lysates, or components, or fractions thereof, or in an at least partially solubilized form in a liquid, or it can consist of additional components such as but not limited to other nutrients, nutrition additives or food or drink additives, solutions or emulsions known to those skilled in the art. Said nutraceutical can be applied orally in different forms, such as capsules, tablets, emulsions, powder, liquids. The nutraceutical can be given by itself or mixed into food or drinks. Said nutraceutical can also be any food, drink, component of a drink or food, a food additive, or a stand alone nutraceutical.

In a preferred embodiment the nutraceutical is used as a capsule or a tablet. In another preferred embodiment the nutraceutical is mixed into food or drinks such as but not limited to those listed elsewhere in that invention.

The present invention refers also to a nutraceutical comprising at least one microorganism bound by at least one carbohydrate binding molecule specifically recognizing a carbohydrate epitope present on a molecule from a human or animal cell, or a fraction or a lysate thereof, whereby said microorganism, said fraction or said lysate or said formulation comprising those induces an effective carbohydrate-specific cellular immune response against said carbohydrate epitope in at least one animal or human.

In a preferred embodiment of the invention said nutraceutical is applied to a human or an animal as food or food additive.

Food in the context of invention is any substance consumed by living organisms, including liquid drinks. Food is the main source of energy and of nutrition for animals/humans, and is usually of animal or plant origin. The food is preferred vegan food which comprises generally all types of food that are free of animal products, like meat, milk or eggs. The food in the context of the invention is also preferred non-vegan food containing animal products. Food in the context of the invention is:

(i) any substance or product, whether processed, partially processed or unprocessed, intended to be, or reasonably expected to be ingested by humans whether of nutritional value or not; (ii) water and other drinks;

(iii) chewing gum or candy products; and/or (iv) articles and substances used as an ingredient or component in the preparation of food.

Food in the context of the invention is traditionally obtained through farming, ranching, and fishing, with hunting, foraging and other methods of subsistence locally important for some populations, but minor for others. In the modern era, in developed nations, food supply is increasingly dependent upon agriculture, industrial farming, aquaculture and fish farming techniques which aim to maximise the amount of food produced, whilst minimising the cost. These include a reliance on mechanised tools which have been developed, from the threshing machine, seed drill, through to the tractor and combine, etc. These have been combined with the use of pesticides to promote high crop yields and combat those insects or mammals which reduce yield. More recently, there has been a growing trend towards more sustainable agricultural practices. This approach—which is partly fueled by consumer demand—encourages biodiversity, local self-reliance and organic farming methods.

Types of manufactured food (food which contains at least one carbohydrate positive microorganism or fraction thereof) in the context of the invention are:

drinks: beer, juice, soft drink, squash, wine, drinks containing milk, milk products or other alcoholic or non-alcoholic beverages, e.g. water, including just carbonated water, fruit juices and vegetable juices, soft drinks, aguas frescas, lemonade, cola, ginger ale, irn bru, root beer, sarsaparilla, cream soda, dandelion and burdock, squash, a fruit-flavoured syrup diluted with water, sports drinks, infusions, coffee, tea, dairy drinks, for example milk, yogurt drink, chocolate milk, milkshake, egg nog, almond milk, horchata, alcoholic beverages, cocktails—mixed drinks, hot beverages, for example hot chocolate, hot cider, cappuccino or pearl milk tea bread is a staple food for many nations, being made of risen dough of wheat or other cereals e.g. rye-wheat, toastbread (white bread), whole-grain, wheat-rye, white bread, multigrain, rye, sunflower seed, pumpkin seed, pizza, chapatis, tortillas, baguettes, pitas, lavash, biscuits, pretzels, naan, bagels, puris, cake, pumpernickel, wholemeal bread, wheatgerm bread, wholegrain, granary bread and many other variations cakes and cookies e.g. angelfood cake, apple cake, babka, buccellato, bundt cake, butter cake, butterfly cake, carrot cake, cheesecake, chocolate cake, christmas cake, chiffon cake, croquembouche, cupcake, devil's food cake, eccles cake, fairy cake, fruit cake, german chocolate cake, génoise cake, gingerbread, gob, gooey butter cake, hot milk cake, ice cream cake, jaffa cakes, leavened cake, mooncake, panettone, pineapple cake, pound cake, Queen Elisabeth cake, red bean cake, red velvet cake, sachertorte, simnel cake, spice cake, sponge cake, suncake, teacake, tarte tatin, vanilla slice or wedding cake cheese is a curdled milk product, of which many varieties exist e.g. sardo cheese, testouri cheese, bokmakiri cheese, kwaito cheese, wookie cheese, ackawi cheese, basket cheese, labneh, jibneh arabieh cheese, kenafa cheese, naboulsi cheese, paneer, affineur, bergkäse, brimsen, dachsteiner, tyrolean grey cheese, luneberg, beauvoorde cheese, brussels' cheese, herve cheese, limburger cheese, maredsous cheese, passendale cheese, plateau de herve cheese, postel cheese, remedou cheese, danish blue cheese, danish tilsit or tilsit havarti, allgäu emmental cheese, cambozola cheese, harzer cheese. limburger cheese. spundekäs cheese, feta cheese, halloumi cheese or mozzarella cheese dessert is a course, usually sweet, and generally served after the main course, e.g. ice cream e.g. biscuits or cookies, cakes, crumbles, custards, fruit, gelatin desserts, ice creams, meringues, pastries, pies or tarts, puddings, sorbets, soufflés or trifles french fries, chips, e.g. potato chips or "crisps", tortilla chips or corn chips functional food (functional foods are called nutraceuticals, a portmanteau of nutrition and pharmaceutical, and can include food that has been genetically modified; the general category includes processed food made from functional food ingredients, or fortified with health-promoting additives, like "vitamin-enriched" products, and also, fresh foods (e g vegetables) that have specific claims attached)

jam and Jelly e.g. gooseberries-, redcurrants-, blackcurrants-, citrus fruits-, apples-, raspberries-, strawberries- and ripe blackberries-jam or royal jelly pasta e.g. shaped pasta, campanelle, casarecci, cavatelli, conchiglie, conchiglioni, farfalle, fiori, fusilli, fusilli bucati, gemelli, gigli, gramigna, lumache, lumaconi, maltagliati, orecchiette, pipe, quadrefiore, radiatori, ricciolini, rotelle, rotini, spiralini, strozzapreti, torchio or trofie pie e.g. bacon and egg pie, chicken and mushroom pie, corned beef pie, cornish pasty, fish pie, kalakukko, kulebjaka, pizza pie, pork pie, pot pie, scotch pie, shepherd's pie, stargazy pie, steak pie, steak and kidney pie, apple pie, banana cream pie, blackberry pie, blueberry pie, boston cream pie, bumbleberry pie, cherry pie, chocolate cream pie, coconut cream pie, custard pie, dutch apple pie, grape pie, key lime pie, lemon meringue pie, lemon pie, mixed berry pie, orange pie, peach pie, rhubarb pie, strawberry-rhubarb pie, strawberry pie or vinegar pie pizza e.g. the classic types and their respective toppings include: marinara or napoletana: tomato, olive oil, oregano, and garlic; margherita: tomato, olive oil, fresh basil leaves, and fior-di-latte (mozzarella made from cow's milk) or mozzarella di bufala; formaggio e pomodoro: tomato, olive oil, and grated parmesan cheese, basil leaves are optional; ripieno or calzone: fior-di-latte or mozzarella di bufala, sometimes also ricotta cheese, olive oil, and salami, other meats, vegetables, etc or stromboli: mozzarella, meat, vegetables, etc.

processed meats e.g. meat form amphibians, toad, artificial meat, imitation meat, in vitro meat, beef (bovines), buffalo, cattle, steak, veal (calves), yak, poultry (birds), chicken, duck, game birds, turkey, canids, seafood, fish, shark, crustaceans, crab, rabbit, mutton (sheep), lamb, pork (pigs), ham (haunch), bacon (cured strips of meat) or insects sandwiches e.g. aram sandwich, filled baguette, bacon butty, bun, burger, burrito, chip butty, club sandwich, grilled cheese, döner kebab, georgia hots, melt sandwich: tuna melt, etc., panini, steak sandwich, taco, tea sandwich, toasted sandwich, torta or wrap salad e.g. caesar salad, chef salad, cobb salad, greek salad, italian salad, mesclun salad, niçoise salad, bean salads like green bean salad, seven bean salad, chicken salad, egg salad, fruit salad (sliced, peeled fruits served in their own juices or with a dressing), larb, pasta salad, potato salad, somen salad, som tam, tabouli, waldorf salad or watergate salad sauce e.g. white sauces, mushroom sauce, sauce allemande, sauce américaine, sauce suprême, elouté brown sauces, bordelaise sauce, bourguignonne sauce, chateaubriand sauce, sauce africaine, sauce robert, béchamel sauce, mornay sauce, emulsified sauces, béarnaise sauce, hollandaise sauce, mayonnaise, tartar sauce, salad cream, butter sauces, beurre blanc, café de paris, sweet sauces, fish sauce, sambal, barbecue sauce, mole, tomato sauce or tzatziki sausage e.g. andouille, black pudding, blood sausage, boerewors, bratwurst, breakfast sausage, butifarra, chorizo, cumberland sausage, falukorv, fuet, haggis, kieska, kielbasa, kishka, kishke, knackwurst, kovbasa, landjäger, linguiça, liver sausage, lukanka, mettwurst, mincemeat, mortadella, salami, soujouk, thüringer, weißwurst or white pudding snack food: confectionery, potato chips, chocolate, hardtack, candy bars, junk food e.g. boiled peanuts, candy bars, cheetos, chex mix, cookies, crackers, combos, fudge rounds, hula hoops, ice cream, moon pies, pirate's booty, popcorn, pork rinds, potato chips, pretzels, smart puffs, soft drinks, snow balls, student food, swiss cake rolls, tings, twinkies, veggie booty or zebra cakes soup e.g. dessert soups (ginataan, filipino soup made from coconut milk, milk, fruits and tapioca pearls); oshiruko, a Japanese azuki bean soup or fruit soups, winter melon soup, miso soup, pho, ramen, saimin, romanian potato soup, avgolemono, borscht, bouillabaisse, callaloo, cock-a-leekie, fanesca, gazpacho, lentil soup, minestrone, mulligatawny soup, scotch broth, snert, solyanka, tarator or waterzooi.

sugar or sugar products e.g. golden syrup, candies or chocolates.

yoghurt, curds, sour cream, whipped cream e.g. lassi, kefir, ayran, doogh or tarator.

drink powders or tablets e.g. vitamin drinks or mineral drinks capsules or tablets therapeutic food (therapeutic foods are food designed for specific, usually nutritional, therapeutic purposes), functional food, medical food, enteral food, parenteral food, food of specified health use.

Examples are Ensure, a fortified milkshake drink designed primarily for the elderly, and Plumpy'nut, a peanut based food designed for emergency feeding of severely malnourished children.

In another preferred embodiment the formulation of the invention is manufactured as an over the counter drug.

Said humoral immune response against the carbohydrate epitope is an antibody response against the carbohydrate epitope which can be detected by at least one of the humoral immune response tests 1, 2, 3, 4, 5 or 6. Respective tests are also useful in conjunction with the method of identifying a suitable carbohydrate positive microorganism according to the present invention.

In a preferred embodiment the invention provides a humoral immune response test (humoral immune response test 1) against the carbohydrate epitope comprising, testing the binding of an antibody, antibodies in serum, or antibodies gained from serum, plasma or faeces, in an ELISA to compounds such as proteins or peptides carrying the carbohydrate epitope whereby a positive humoral immune response against the carbohydrate epitope shows a significantly higher binding of the antibodies to said carbohydrate epitope carrying compound such as a protein or peptide than to said compound such as e.g. a protein or peptide without the carbohydrate epitope or to said compound (e.g. a protein or peptide) after an enzymatical or chemical treatment that destroys the carbohydrate epitope. In a preferred embodiment, the binding of said antibody or antibodies is significantly higher after administration of the nutraceutical, the pharmaceutical composition, the carbohydrate positive microorganism or the fraction thereof or formulations comprising those than the binding of the corresponding antibody, antibodies in serum, or antibodies gained from serum, plasma or faeces, gained before said administration.

Said enzymatical or chemical treatment of the carbohydrate epitope destroys the carbohydrate structure of the carbohydrate epitope. Said enzymatical or chemical treatment of the carbohydrate epitope can be performed using techniques known to those skilled in the art such as but not limited to treatment with neuraminidase, sialidase, glucosidase, galactosidase, glycosidase, exoglycosidase, fucosidase, HexNAcase, or periodic acid (mild periodate oxidation/periodate treatment as described in the examples).

For example the carbohydrate epitopes Core-1 and Tn are destroyed by treatment with periodic acid as described in the examples.

An example of a preferred embodiment of the humoral immune response test 1 is described in detail in example 11. Example 11 describes the testing of the humoral immune response against the carbohydrate epitope Core-1 in ELISA against asialoglycophorin, a protein carrying the carbohydrate epitope, against glycophorin which is the same protein but with the Core-1 masked by sialic acid and against periodic acid treated asialoglycophorin, whereby the treatment with periodic acid destroys the Core-1 structure.

In another preferred embodiment the invention provides a humoral immune response test (humoral immune response test 2) against a carbohydrate epitope comprising, testing the binding of an antibody, antibodies in serum, or antibodies gained from serum, plasma or faeces, in an ELISA to carbohydrate structures coupled to polyacrylamid (PAA conjugates), whereby a positive humoral immune response against a carbohydrate epitope shows a significant higher binding of the antibody or antibodies to the PAA-conjugate comprising the carbohydrate epitope than to the same PAA-conjugate after enzymatical or chemical treatment destroying the carbohydrate epitope and/or a higher binding of the antibody or antibodies to a PAA-conjugate comprising the carbohydrate epitope compared to an PAA-conjugate not comprising the carbohydrate epitope, preferably both. In a preferred embodiment, the binding of said antibody or antibodies to a PAA-conjugate comprising the carbohydrate epitope is significantly higher after administration of the nutraceutical, the pharmaceutical composition, the carbohydrate positive microorganism or the fraction thereof or formulations comprising those than the binding of the corresponding antibody, antibodies in serum, or antibodies gained from serum, plasma or faeces, gained before said administration.

A preferred embodiment of the humoral immune response test 2 is described in detail in example 11.

In another preferred embodiment the invention provides a humoral immune response test (humoral immune response test 3) against the carbohydrate epitope comprising, testing the binding of an antibody, antibodies in serum, or antibodies gained from the serum, plasma or faeces, in a flow cytometry test for its binding to cells comprising the carbohydrate epitope and to cells not comprising the carbohydrate epitope whereby a positive humoral immune response against the carbohydrate epitope shows a significant higher binding of the antibodies to cells comprising the carbohydrate epitope than to cells negative for the carbohydrate epitope. In a preferred embodiment, the binding of said antibody or antibodies to cells comprising the carbohydrate epitope is significantly higher after administration of the nutraceutical, the pharmaceutical composition, the carbohydrate positive microorganism or the fraction thereof or formulations comprising those than the binding of the corresponding antibody, antibodies in serum, or antibodies gained from serum, plasma or faeces, gained before said administration. A preferred embodiment of the humoral immune response test 3 is described in detail in example 11.

In another preferred embodiment the invention provides a humoral immune response test (humoral immune response test 4) against the carbohydrate epitope comprising, testing the binding of an antibody, antibodies in serum, or antibodies gained from the serum, plasma or faeces, in an immune fluorescence test for its binding to cells comprising the carbohydrate epitope and to cells negative for the carbohydrate epitope whereby a positive humoral immune response against the carbohydrate epitope shows a significant higher binding of the antibody or antibodies to cells comprising the carbohydrate epitope than to cells not comprising the carbohydrate epitope and/or to cells comprising the carbohydrate epitope after emzymatical or chemical treatment that destroys the carbohydrate epitope. In a preferred embodiment, the binding to cells comprising the carbohydrate epitope is significantly higher after administration of the nutraceutical, the pharmaceutical composition, the carbohydrate positive microorganism or the fraction thereof or formulations comprising those than the binding of the corresponding antibody, antibodies in serum, or antibodies gained from serum, plasma or faeces, gained before said administration. The immunofluorescence test can be made more quantitative by serial dilutions of the antisera and/or by taking photographs under identical exposure conditions.

Those skilled in the art are able to identify suitable carrier molecules and to couple suitable structures to obtain the desired carbohydrate structure coupled to the carrier molecules with or without linker. Those skilled in the art are also able to select those cells or antigens, with or without enzymatical or chemical treatment, and to select and modify the suitable methods to test the humoral immune response for the carbohydrate epitope. However, the aforementioned humoral immune response tests 1 to 4 and especially the preferred combinations thereof provided by the present invention are clearly preferred and have clear advantages in respect to specificity as also seen from examples.

In another preferred embodiment the invention provides a humoral immune response test (humoral immune response test 5) against the carbohydrate epitope comprising,
 a) incubating a suitable amount of cells comprising the carbohydrate epitope, labeled with a suitable amount of a marker such as europium or chromium-51, with a suitable amount of an antibody, of antibodies in serum, or of antibodies gained from the serum, plasma or faeces, with a suitable amount of complement for a suitable time (typically between 3 to 5 hours or over night);
 b) measuring the lysis of the cells by determining the release of the marker such as europium or chromium-51 after the incubation under (a) whereby a positive humoral immune response against the carbohydrate epitope shows a significantly higher lysis of cells comprising the carbohydrate epitope than of cells not comprising the carbohydrate epitope and/or it shows a higher lysis of cells comprising the carbohydrate epitope, than a lysis without complement and/or than a lysis without the antibody and/or than a lysis with an antibody or antibodies which does not bind or which binds less to cells comprising the carbohydrate epitope.

Said humoral immune response test 5 tests the carbohydrate specific complement dependent cytotoxicity (CDC), an effector mechanism mediated by certain antibodies, of the induced humoral immune response or carbohydrate specific antibodies in a target cell lysis test. The test comprises incubating a suitable amount of cells comprising the carbohydrate epitope, labeled with a suitable amount of marker such as europium or chromium-51, with a suitable amount of an antibody, of antibodies in serum, or of antibodies gained from the serum, plasma or faeces, with a suitable amount of complement for a suitable time (typically between 3 to 5 hours or over night). The cells comprising the carbohydrate epitope are labeled with said marker such as europium or chromium-51 which allows the measurement of cells which are lysed. The amount of lysed cells is determined, preferably by measuring the release of the marker (e.g. europium or chromium-51) after incubation. A suitable control can be determined by those skilled in the art such as carbohydrate negative cells, an antibody or an antibody mixture not binding to the target cell, and/or without complement. The test can be optimized in respect to suitable amounts of antibodies, numbers of labeled tumor cells, concentration of complement, and incubation time by those skilled in the art for its use in the invention and as described.

The complement-dependent cytotoxicity (CDC) of the invention is preferably determined using an Europium Release Assay. The target cells are incubated for 10 minutes at 4° C. in 800 µl of europium buffer (50 mM HEPES, pH 7.4, 93 mM NaCl, 5 mM KCl, 2 mM $MgCl_2$, 10 mM diethylentriaminepentaacetic acid, 2 mM europium (III) acetate), electroporated (710V, 1 pulse, 30 µs) in a Multiporator (Eppendorf), and subsequently incubated on ice for another 10 minutes. Thereafter, the cells are washed 5 times in RPMI/5% FCS and seeded in a 96-well round-bottom plate (Nunc; $5 \times 10^3$/well). Following addition of 20 µl of antibody containing solution at varying dilutions or the corresponding controls (medium, isotype control human IgM), the samples are incubated 20 minutes at room temperature. 10 µl of 1:10 diluted complement (Baby rabbit complement) is added to correspondent wells. In the control wells 10 µl of RPMI/5% FCS are added instead of complement solution. For determination of spontaneous release target cells are incubated with media alone, and maximum release is determined by complete lysis of the target with ethanol. Following incubation at 37° C. for 4 hours, the plate is centrifuged at 500×g for 5 minutes, and 20 µl of cell-free supernatant from every well are pipetted in 200 µl per well of enhancement solution (Perkin-Elmer Wallac) on the previously prepared flat-bottom plate (Nunc-Immunoplate Maxisorp). Following incubation for 15 minutes at room temperature, the fluorescence is determined ($Victor^2$ Fluorometer, Perkin-Elmer Wallac). The specific cytotoxicity is obtained from the equation (experimental lysis−spontaneous lysis)/(maximum lysis−spontaneous lysis)×100%.

In another preferred embodiment the invention provides a humoral immune response test (humoral immune response test 6) against the carbohydrate epitope comprising,
a) incubating a suitable amount of cells comprising the carbohydrate epitope and/or of cells not comprising the carbohydrate epitope, labeled with a suitable amount of a marker such as europium or chromium-51, with a suitable amount of an antibody, of antibodies in serum, or of antibodies gained from the serum, plasma or faeces, with a suitable amount of at least one immune effector cell or mixture of cells comprising immune effector cells or peripheral blood mononuclear cells for a suitable time, typically between 3 to 5 hours or over night, and
b) measuring the lysis of the cells by determining the release of the marker such as europium or chromium-51 after the incubation under (a) whereby a positive humoral immune response against the carbohydrate epitope shows a significantly higher lysis of cells comprising the carbohydrate epitope than of carbohydrate epitope negative cells than a lysis without the antibody and/or than a lysis with an antibody or antibodies which does not bind or which binds less to cells comprising the carbohydrate epitope.

Said humoral immune response test 6 tests the antibody dependent cellular cytotoxicity (ADCC), an effector mechanism mediated by certain antibodies, of the induced humoral immune response or carbohydrate epitope specific antibodies in a target cell lysis test in combination with immune effector cells. The test comprises incubating suitable amounts of labeled carbohydrate epitope positive target cells, with suitable amounts of antibodies in serum or antibodies gained from the serum, or an isolated carbohydrate epitope antibody with suitable amounts of immune effector cells such as those present in PBMC (peripheral blood mononuclear cells) for a suitable time, typically between 3 to 5 hours or over night. The cells comprising the carbohydrate epitope are labeled with europium or chromium-51 which allows the measurement of cells which are lysed. The amount of lysed cells is determined, preferably by measuring the release of europium or chromium-51 after incubation. A suitable control can be determined by those skilled in the art such as carbohydrate epitope negative cells, an antibody or an antibody mixture not binding to the target cell, and/or without immune effector cells (e.g. PBMC). The test can be optimized in respect to suitable amounts of antibodies, numbers of labeled tumor cells, numbers of immune effector cells, and incubation time by those skilled in the art for its use in the invention.

The antibody dependent cellular cytotoxicity (ADCC) of the invention is preferably determined using an Europium Release Assay. The target cells are incubated for 10 minutes at 4° C. in 800 µl of europium buffer (50 mM HEPES, pH 7.4, 93 mM NaCl, 5 mM KCl, 2 mM $MgCl_2$, 10 mM diethylentriaminepentaacetic acid, 2 mM europium (III) acetate), electroporated (710V, 1 pulse, 30 µs) in a Multiporator (Eppendorf), and subsequently incubated on ice for another 10 minutes. Thereafter, the cells are washed 5 times in RPMI/5% FCS and seeded in a 96-well round-bottom plate (Nunc; $5 \times 10^3$/well). Following addition of 20 µl of Core1-specific antibodies at varying concentrations (0.05 to 50 µg/ml final concentration in 200 µl incubation volume) or the corresponding controls (medium, isotype control IgG), PBMC (human peripheral blood mononucleare cells, 80 µl) are added as effector cells, using different effector cell/target cell ratios from 100:1 to 10:1, preferably of 50:1. To determine spontaneous release, 80 µl RPMI/5% FCS without effector cells are added. Maximum release is determined after complete lysis of the target with ethanol.

Following incubation at 37° C. for 4 hours, the plate is centrifuged at 500×g for 5 minutes, and 20 µl of cell-free supernatant from every well is pipetted in 200 µl per well of enhancement solution (Perkin-Elmer Wallac) on the previously prepared flat-bottom plate (Nunc-Immunoplate Maxisorp). Following incubation for 15 minutes at room temperature, the fluorescence is determined ($Victor^2$ Fluorometer, Perkin-Elmer Wallac). The specific cytotoxicity is obtained from the equation (experimental lysis−spontaneous lysis)/(maximum lysis−spontaneous lysis)×100%.

In a preferred embodiment said humoral immune response tests 1 to 6 further comprise prior to the test
a. the administration of the nutraceutical, the pharmaceutical composition, the carbohydrate positive microorganism or the fraction or lysate thereof or the formulations comprising those to a human or animal
b. isolating the antibody, antibodies in serum, or antibodies gained from the serum, plasma or faeces.

In a further preferred embodiment of the invention a nutraceutical or a pharmaceutical formulation comprising at least one carbohydrate positive microorganism or fraction or lysate thereof induces a humoral immune response against the carbohydrate epitope which is positive for at least two humoral immune response tests out of the humoral immune response tests 1 to 6, preferably positive for humoral immune response tests 1 and 3, and more preferably for humoral immune response test 1, 2 and 3, and more preferably for humoral immune response test 1, 2, 3, and 4, and more preferably for humoral immune response test 1, 2, 3, 4, and 6, and even more preferably for humoral immune response test 1, 2, 3, 4, and 5, and most preferably positive for all 6 humoral immune response tests.

Also provided are cellular immune response tests. Said cellular immune response against the carbohydrate epitope is a T-cell response against the carbohydrate epitope which can be detected by at least one of the cellular immune response tests 1 to 5. More preferably is a cellular immune response against the carbohydrate epitope which is a cytotoxic T cell response or a Th1 type helper T cell response against the carbohydrate epitope. Most preferably is a cellular immune response against the carbohydrate epitope which is a cytotoxic T cell response and a Th1 type helper T cell response against the carbohydrate epitope which can be detected by cellular immune response tests 1, 2, 3, 4 and 5. Said tests can also be used in conjunction with the methods of identifying a suitable carbohydrate positive microorganism described herein in order to test/analyse which carbohydrate positive microorganisms are also able to trigger a cellular immune response.

Said cellular immune response tests comprise bringing into contact dendritic cells loaded with a carbohydrate positive microorganism together with immune cells and cultivation for appropriate times and under appropriate conditions and subsequently adding for restimulation dendritic cells loaded with at least one carbohydrate epitope carrying molecule and cultivation for appropriate times and conditions and subsequently measuring the amount of secreted GM-CSF, TNFalpha, or INFgamma, or measuring the proliferation of T cells, or the inhibition of the secretion of GM-CSF, TNFalpha, or INFgamma, or the proliferation by antibodies against the carbohydrate epitope or measuring the presentation of carbohydrate epitope on the dendritic cells or measuring the lysis of carbohydrate epitope positive cells by activated immune cells, preferably by activated T cells.

Said dendritic cells, herein also called DC, can be any dendritic cell or a mixture of dendritic cells or a mixture of cells comprising dendritic cells or at least one dendritic cell. They can be derived from human donors which are healthy or which have a disease, such as but not limited to tumor disease or Crohns disease or carbohydrate epitope positive disease or one of the diseases listed elsewhere herein, or from animals. Said DCs can be obtained and loaded as known by those skilled in the art and are typically obtained from CD34 positive precursor cells or CD14 positive monocytic cells from human blood or bone marrow which are differentiated to immature dendritic cells (iDC) using certain combination of suitable molecules known to those skilled in the art. The iDCs are loaded with the carbohydrate positive microorganism or with carbohydrate epitope carrying molecule, or appropriate controls, and are further matured using certain combination of suitable molecules known to those skilled in the art to obtain loaded dendritic cells which correspond to loaded mature dendritic cells (mDC) which are able to activate T-cells. Those DC can also be of the Langerhans cell type.

In a preferred embodiment, said DCs originate from a dendritic cell line such as but not limited to the human dendritic cell line NEMOD-DC (obtainable from Glycotope GmbH Berlin, Germany; www.glycotope.com) or Mutz-3.

Said loading of dendritic cells means that the dendritic cells are incubated in the appropriate differentiation and maturation state with suitable amounts of a carbohydrate positive microorganism, or fractions or lysates thereof or at least one carbohydrate epitope carrying-molecule for a suitable time, typically this occurs within the maturation step described above in combination with suitable molecules, typically for 24 to 48 hours, leading to loaded dendritic cells capable of activating immune cells, preferably T cells, comprising carbohydrate epitope specific T-cells.

Said immune cells can be PBMC (peripheral blood mononuclear cells) or other cell populations comprising CD4+ and/or CD8+ T-cells, preferably CD4+ and CD8+ T-cells. Those skilled in the art know how to gain those cells from a human or animal and generation of those cells can comprise preparations by ficoll gradient from human blood or from blood cells of leukapherases and can comprise in case further enrichment by T cell specific magnetic sorting technologies.

In a preferred embodiment the dendritic cells are matched in at least one MHC class molecule with the immune cells, preferably in an MHC class I molecule or MHC class II molecule, more preferable in at least one MHC class I and one MHC class II molecule, more preferably in more MHC molecules and most preferably in all MHC molecules. The latter can be achieved by obtaining the dendritic cells and the immune cells from the same individual.

Said appropriate times and conditions for cultivation of the immune cells with the loaded dendritic cells and for the subsequent adding of the loaded dendritic cells are known to those skilled in the art and can be optimized by him taking into consideration the conditions the cells are in. Typically the incubation time is 7 to 10 days for each of the two steps (primary activation and restimulation).

Said carbohydrate epitope carrying molecule in sense of the described cellular immune response tests means sufficient amounts of a cell or tumor cell carrying the carbohydrate epitope, a protein carrying the carbohydrate epitope, or a polypeptide carrying the carbohydrate epitope. Said cell or tumor cell carrying the carbohydrate epitope can be living or dead, or a lysate from those cells or a fraction thereof, more preferred is a lysate. A protein carrying the carbohydrate epitope can be any protein carrying the carbohydrate epitope such as carrier proteins whereon the carbohydrate epitope is bound on tumors. A polypeptide carrying the carbohydrate epitope can be any polypetide carrying the carbohydrate epitope, preferably those which can be presented with the carbohydrate epitope on the mDC.

Said carbohydrate positive microorganism in sense of the described cellular immune response tests means sufficient amounts of the particular carbohydrate positive microorganism which can be living or dead, or a lysate from those cells or a fraction thereof, more preferred is a lysate or a fraction thereof.

Controls are used to further confirm the positivity of the immune response. Those skilled in the art are able to use appropriate controls as such which are described in more detail below and in example 12. Examples are the use of controls which are loaded onto the DC as described for the carbohydrate epitope carrying molecules and used for restimulation and can comprise (i) cells which are negative for the carbohydrate epitope or do not comprise it, preferably those which are related to or resemble as closely as possible the carbohydrate epitope positive cells, in the corresponding format such as living or dead, or a lysate from those cells or a fraction thereof; (ii) a protein not carrying the carbohydrate epitope, preferably the same protein as used as the carbohydrate epitope carrying molecule but without the carbohydrate epitope, preferably without any glycosylation or with an elongated or shortened carbohydrate structure not comprising the carbohydrate epitope, (iii) a polypeptide not carrying the carbohydrate epitope, preferably the same polypeptide as used as the carbohydrate epitope carrying molecule but without the the carbohydrate epitope, preferably without any glycosylation or with an elongated or shortened carbohydrate structure not comprising the carbohydrate epitope. Additional controls may be (iv) non-loaded mDC treated in the same way as the mDC loaded with the carbohydrate epitope carrying molecules including the necessary molecules and conditions for maturation but without any additional molecule corresponding to the carbohydrate epitope carrying molecule or above mentioned controls (i-iii). The examples and the preferred embodiments describe in detail the most suitable controls, while other suitable ones might be selected by those skilled in the art.

In a preferred embodiment of the invention the dendritic cells are functional dendritic cells obtained from the leukemia cell line MUTZ-3 [as described in DE10139428 A1, WO2003/023023 A1, EP01419240, US20040265998, CA2457287, 10139428.4 (DE), PCT/EP02/09260, 02758474.7 (EP), U.S. Ser. No. 10/486,966, CA2,457,287)] or cells derived from MUTZ-3 such as NEMOD-DC (e.g. NMD-100 or NMD-200 obtainable from Glycotope GmbH Berlin, Germany [www.Glycotope.com]). Those dendritic cells are active dendritic cells which are fully capable to activate T cells and to process and/or present antigens on their surface including on MHC class molecules. In a further preferred embodiment of the invention the dendritic cells are functional dendritic cells obtained from MUTZ-3 or cells derived from MUTZ-3, such as NMD-100 or NMD-200, and the immune cells are matched in MHC class I molecule such as HLA-A2 or HLA-B44, preferably HLA-A2 and HLA-B44. In a further preferred embodiment a lysate of cells comprising the carbohydrate epitope is used as carbohydrate epitope carrying molecule Due to variances from experiments to experiments which is in particular typical for cellular immunological methods known to those skilled in the art, controls have to be set up in parallel to the test as known to those skilled in the art.

According to one embodiment, the invention provides an in vitro cellular immune response test against a carbohydrate epitope of interest comprising
  a.) Loading at least one dendritic cell with a first carbohydrate positive compound, wherein said carbohydrate positive compound carries the carbohydrate epitope of interest;
  b.) bringing into contact a suitable amount of said at least one dendritic cell loaded with said carbohydrate positive compound with a suitable amount of immune cells which can be activated or inhibited by a dendritic cell;
  c.) cultivation in order to allow interaction of said immune cells with said loaded dendritic cells;
  d.) adding a suitable amount of antigen presenting cells (APC) loaded with a suitable amount of at least one second compound carrying the same carbohydrate epitope as said first compound, wherein said second compound is different from said first carbohydrate positive compound;
  e.) cultivation for restimulation of said immune cells
  f.) determining the amount of restimulated immune cells.

The invention provides a method for determining whether certain carbohydrate epitope is capable of triggering a cellular immune response. So far the prior art assumed that carbohydrates are unable to trigger a cellular immune response. However, it has now been found that certain carbohydrate epitopes are able to elicit a cellular immune response. It is thus important to provide test systems for determining whether a certain carbohydrate epitope is indeed able to trigger a respective response, thereby determining whether said carbohydrate epitope is a suitable working point e.g. for therapy. The invention thus uses dendritic cells as dendritic cells are able to prime and thus stimulate immune cells such as T-cells. Dendritic cells process compounds they are encountering and present the processed compounds/antigens on their surface. However, MHC cells such as dendritic cells can only present certain kinds of antigens and it is important to determine whether the antigen/epitope of interest can be presented by dendritic cells as only such antigens/epitopes are able to elicit a cellular immune response. The principles of this cellular immune response test are also illustrated in FIG. 22.

Therefore, dendritic cells are loaded with the compound of interest which is assumed to or carries the carbohydrate structure/epitope of interest. Said compound can e.g. be a microorganism carrying the carbohydrate epitope of interest as described herein, a tumor cell or any other compound carrying the carbohydrate epitope of interest. Suitable conditions for loading and suitable compounds carrying carbohydrate structures are described herein.

Said loaded dendritic cells are then contacted with immune cells, in particular lymphocytes such as T-cells. The immune cells can be obtained e.g. from human donors. Dendritic cells presenting antigens matching the receptors of the immune cells activate and thus stimulate the lymphocytes thereby allowing them to proliferate and survive. Lymphocytes which do not match the antigens presented by the dendritic cells are not activated and die.

This first round of stimulation provides activated lymphocytes which are specific for any corresponding antigen presented by said loaded dendritic cells. However, the aim of the present method is to identify whether the carbohydrate epitope/antigen of interest can stimulate a cellular response.

Therefore, a selection step is performed wherein the lymphocytes are restimulated in order to determine whether the carbohydrate of interest stimulates the lymphocytes and thus triggers a cellular response. In said selection step antigen presenting cells such as e.g. dendritic cells are loaded with a second compound which also carries the carbohydrate of interest. However, said second compound is different from the first compound. This second compound is also processed by the APCs and the antigens are presented by said APCs. As the second compound is different from the first compound most presented antigens, preferably all antigens are—besides the carbohydrate epitope of interest—different from the antigens presented in the first round. This has the effect that only those lymphocytes survive the second round of restimulation which find a matching antigen presented by said APCs. In case the dendritic cells of the first round as well as the APCs of the second round both present an antigen comprising or consisting of the carbohydrate epitope of interest, lymphocytes recognizing said antigen are stimulated and thus survive as they are also restimulated. Those lymphocytes which do not find a matching partner when contacting with said APCs loaded with said second compound carrying the carbohydrate epitope of interest die due to a lack of restimulation. This selection step ensures that a cellular response against the carbohydrate of interest is detected.

In the last step it is determined whether the lymphocytes were indeed restimulated. This can be done e.g. by determining
- secretion products of the lymphocytes which are secreted if said lymphocytes are (re)stimulated such as interferon alpha, interferon gamma or GM-CSF
- the proliferation of the T-cells.

Suitable tests for determining whether restimulation occurs are described herein.

The specificity of said test can be enhanced by using a carbohydrate binding structure which specifically recognizes said carbohydrate epitope of interest when presented by the dendritic cells/APCs. According to said embodiment, at least a portion of said stimulated lymphocytes according to step c) are contacted with a suitable amount of antigen presenting cells (APC) loaded with a suitable amount of at least one second compound carrying the same carbohydrate epitope as said first compound, wherein said second compound is different from said carbohydrate positive compound, in the presence of a carbohydrate binding molecule recognizing said carbohydrate epitope of interest. Said carbohydrate binding molecule recognizing said carbohydrate epitope of interest blocks the interaction of the APCs with said lymphocytes thereby preventing restimulation and hence survival of the cells. This additional step further ensures that the carbohydrate of interest specifically stimulates lymphocytes and thus triggers a specific cellular immune response. This specificity enhancing/confirming step can be either done in parallel—by splitting the stimulated lymphocytes according to step c—or by performing said enhancing/confirming step additionally and thus afterwards.

According to a first embodiment (cellular immune response test 1) the amount/degree of restimulated lymphocytes is determined by measuring GM-CSF secretion. E.g. the amount of secreted GM-CSF can be measured by ELISA or ELISPOT.

According to a preferred embodiment, a cellular immune response test (embodiment of a cellular immune response test 1) against the carbohydrate epitope is provided comprising
a) bringing into contact a suitable amount of dendritic cells comprising at least one dendritic cell, dendritic cells, or a mixture of cells comprising at least one dendritic cell, loaded with a suitable amount of the carbohydrate positive microorganism, a lysate or a fraction thereof, formulations comprising those, the nutraceutical, or the pharmaceutical composition of the invention together with a suitable amount of immune cells comprising at least one immune cell, CD4+ T cell, CD8+ T cell, a mixture of cells comprising at least one T cell, or peripheral blood mononuclear cells, which can be activated or inhibited by a dendritic cell
b) cultivation for an appropriate time and under an appropriate condition
c) adding a suitable amount of dendritic cells comprising at least one dendritic cell, dendritic cells, or a mixture of cells comprising at least one dendritic cell, loaded with a suitable amount of at least one carbohydrate epitope carrying molecule
d) cultivation for an appropriate time and under an appropriate condition for restimulation
e) measuring the amount of secreted GM-CSF by ELISA or ELISPOT, whereby a positive cellular immune response against the carbohydrate epitope shows (i) a significantly higher GM-CSF secretion of said immune cells restimulated with said dendritic cells loaded with a carbohydrate epitope carrying molecule than the GM-CSF secretion of corresponding immune cells restimulated with corresponding unloaded dendritic cells and/or than the GM-CSF secretion of corresponding immune cells restimulated with corresponding dendritic cells loaded with a molecule not carrying or comprising the carbohydrate epitope, and/or (ii) a significantly higher GM-CSF secretion of said immune cells restimulated with said dendritic cells loaded with a protein, peptide, or molecule carrying or comprising the carbohydrate epitope than the GM-CSF secretion of corresponding immune cells restimulated with corresponding dendritic cells loaded with corresponding protein, peptide, or molecule not carrying or not comprising the carbohydrate epitope, and/or (iii) a significantly higher GM-CSF secretion of said immune cells restimulated with said dendritic cells loaded with a protein, peptide, or molecule carrying or comprising the carbohydrate epitope than the GM-CSF secretion of corresponding immune cells restimulated with corresponding dendritic cells loaded with corresponding protein, peptide, or molecule carrying or comprising the carbohydrate epitope but chemically or enzymatically treated for destruction of the carbohydrate epitope, and/or (iv) a significantly higher GM-CSF secretion of said immune cells restimulated with said dendritic cells loaded with a lysate or fractions of cells comprising the carbohydrate epitope than the GM-CSF secretion of corresponding immune cells restimulated with corresponding dendritic cells loaded with a lysate of cells negative for the carbohydrate epitope or not comprising it.

Corresponding immune cells means that the same immune cells, which are or comprise at least one immune cell, CD4+ T cell, CD8+ T cell, a mixture of cells comprising at least one T cell, or peripheral blood mononuclear cells, or other elsewhere described cells and mixtures of cells, which can be activated or inhibited by a dendritic cell, are used for the control or comparative test with a control or test molecule, mixture of molecules, cells, cell lysates or fractions, microorganism or fractions thereof than those which are used for said immune cells in order to allow a comparison.

Corresponding dendritic cells means that the same dendritic cells, which are or comprise at least one dendritic cell, dendritic cells, or a mixture of cells comprising at least one dendritic cell or other elsewhere described cells and mixtures of cells able to active T cells, loaded with a suitable amount of at least one carbohydrate epitope carrying molecule, are used for the control or comparative test with a control or test molecule, mixture of molecules, cells, cell lysates or fractions, microorganism or fractions thereof or without any, than those which are used for said dendritic cells in order to allow a comparison.

This is known to those skilled in the art and they can be selected by those skilled in the art. This is shown in more detail in the examples. For clarification: For example, the same amount of immune cells from the same preparation are brought into contact with the same amount of dendritic cells from the same preparation loaded with the same amount of asialoglycophorin and in parallel with the same amount of glycophorin or periodate treated asialoglycophorin and used in the test in order to allow optimal comparability.

Variations are known to those skilled in the art and can be determined by those or are described in more detail in examples.

Said cellular immune response test 1 tests the activation of CD4+ and/or CD8+ T-cells specific for the carbohydrate epitope by a carbohydrate positive microorganism by measuring the specific induced secretion of GM-CSF comprising bringing into contact dendritic cells loaded with a carbohydrate positive microorganism, lysate or fraction thereof and immune cells and cultivation for appropriate times and conditions and subsequently adding dendritic cells loaded with a carbohydrate epitope carrying molecule for restimulation and cultivation for appropriate times and conditions and subsequently measuring the amount of secreted GM-CSF in response to this restimulation. Said measuring of the amount of secreted GM-CSF is preferably done by ELISA or ELISPOT, more preferably ELISA, and is known to those skilled in the art. In the most preferred embodiment of the invention the cellular immune response test 1 comprises bringing into contact functional dendritic cells obtained from cells derived from MUTZ-3, NMD-100 or NMD-200 loaded with a carbohydrate positive microorganism together with PBMC (peripheral blood mononuclear cells) matched at least in MHC class I (HLA-A2) and (HLA-B44) and cultivation of these cells for appropriate times and conditions, typically 7 to 10 days, and subsequently adding for restimulation functional dendritic cells obtained from cells derived from MUTZ-3 loaded with lysate of cells comprising the carbohydrate epitope, or with a carbohydrate carrying molecule and cultivation for appropriate times and conditions, typically 7 to 9 days, and subsequently measuring the amount of secreted GM-CSF in an ELISA or ELISPOT analysis. ELISA and ELISPOT analysis of GM-CSF-release is known to those skilled in the art and described in detail in examples. A positive cellular immune response against the carbohydrate epitope shows a higher GM-CSF secretion of the immune cells restimulated with DC loaded with a lysate of cells comprising the carbohydrate epitope than the secretion of the immune cells restimulated with DC loaded with a lysate of carbohydrate epitope negative cells and/or it shows a higher GM-CSF secretion of the immune cells restimulated with DC loaded with a carbohydrate epitope carrying molecule than the immune cells restimulated with DC loaded with a carbohydrate epitope negative molecule. A preferred embodiment of the cellular immune response test 1 is described in detail in example 12.

According to a second embodiment (cellular immune response test 2) the amount/degree of restimulated lymphocytes is determined by measuring the amount of INFgamma or TNFalpha secretion. In a preferred embodiment said cellular immune response test 2 against the carbohydrate epitope comprises
  a. bringing into contact a suitable amount of dendritic cells comprising at least one dendritic cell, dendritic cells, or a mixture of cells comprising at least one dendritic cell, loaded with a suitable amount of the carbohydrate positive microorganism, a lysate or a fraction thereof, formulations comprising those, the nutraceutical, or the pharmaceutical composition of the invention together with a suitable amount of immune cells comprising at least one immune cell, CD4+ T cell, CD8+ T cell, a mixture of cells comprising at least one T cell, or peripheral blood mononuclear cells, which can be activated or inhibited by a dendritic cell
  b. cultivation for an appropriate time and under an appropriate condition
  c. adding a suitable amount of dendritic cells comprising at least one dendritic cell, dendritic cells, or a mixture of cells comprising at least one dendritic cell, loaded with a suitable amount of at least one carbohydrate epitope carrying molecule
  d. cultivation for an appropriate time and under an appropriate condition for restimulation and
  e. measuring the amount of secreted IFNgamma and/or secreted TNFalpha by ELISA or ELISPOT, whereby a positive cellular immune response against the carbohydrate epitope shows (i) a significantly higher IFNgamma and/or TNFalpha secretion of said immune cells restimulated with said dendritic cells loaded with a carbohydrate epitope carrying or comprising molecule than the IFNgamma and/or TNFalpha secretion of corresponding immune cells restimulated with corresponding unloaded dendritic cells and/or a higher IFNgamma and/or TNFalpha secretion of said immune cells restimulated with said dendritic cells loaded with a carbohydrate epitope carrying or comprising molecule than the IFNgamma and/or TNFalpha secretion of corresponding immune cells restimulated with corresponding dendritic cells loaded with a molecule not carrying or not comprising the carbohydrate epitope, and/or (ii) a significantly higher IFNgamma and/or TNFalpha secretion of said immune cells restimulated with said dendritic cells loaded with a protein, peptide, or molecule carrying or comprising the carbohydrate epitope than the IFNgamma and/or TNFalpha secretion of corresponding immune cells restimulated with corresponding dendritic cells loaded with corresponding protein, peptide, or molecule not carrying or not comprising the carbohydrate epitope, and/or (iii) a significantly higher IFNgamma and/or TNFalpha secretion of said immune cells restimulated with said dendritic cells loaded with a protein, peptide, or molecule carrying or comprising the carbohydrate epitope than the IFNgamma and/or TNFalpha secretion of corresponding immune cells restimulated with corresponding dendritic cells loaded with corresponding protein, peptide, or molecule carrying or comprising the carbohydrate epitope but enzymatically or chemically treated for destruction of the carbohydrate epitope, and/or (iv) a significantly higher IFNgamma and/or TNFalpha secretion of said immune cells restimulated with said dendritic cells loaded with a lysate or fractions of cells comprising the carbohydrate epitope than the IFNgamma and/or TNFalpha secretion of corresponding immune cells restimulated with corresponding dendritic cells loaded with a lysate of cells negative for the carbohydrate epitope or not comprising it.

Said cellular immune response test 2 tests the activation of cytotoxic T-cells such as CTL (cytotoxic T lymphocytes) and or Th1 type cytotoxic T helper cells to carbohydrate epitope specific activated cytotoxic T-cells by a carbohydrate positive microorganism. Said measuring of the amount of secreted IFNgamma and/or TNFalpha is preferably done by ELISA or ELISPOT, more preferably ELISPOT and is known to those skilled in the art. In the most preferred embodiment of the invention the cellular immune response test 2 comprises bringing into contact functional dendritic cells obtained from cells derived from MUTZ-3 or NMD-100 OR NMD-200 loaded with a carbohydrate positive microorganism together with PBMC (peripheral blood mononuclear cells) matched at least in MHC class I (HLA-A2 and HLA-B44) and cultivation of these cells for appropriate times and conditions, typically 7 to 10 days, and subsequently adding for restimulation functional dendritic cells obtained from cells derived from MUTZ-3, NMD-100 or NMD-200 loaded with lysate of cells comprising the carbohydrate epitope or a carbohydrate epitope carrying molecule and cultivation for appropriate times and conditions, typically 7 to 9 days, and subsequently measuring the amount of secreted IFNgamma by ELISPOT analysis and/or secreted TNFalpha by ELISA analysis. ELISA and ELISPOT analysis of TNFalpha and IFNgamma is known to those skilled in the art and described in detail in examples. A preferred embodiment of the cellular immune response test 2 is described in detail in example 12.

According to a third embodiment (cellular immune response test 3) the amount/degree of restimulated lymphocytes is determined by measuring the proliferation and/or proliferation induction. In a preferred embodiment said cellular immune response test 3 against the carbohydrate epitope comprises a) bringing into contact a suitable amount of dendritic cells comprising at least one dendritic cell, dendritic cells, or a mixture of cells comprising at least one dendritic cell, loaded with a suitable amount of the carbohydrate positive microorganism, a lysate or a fraction thereof, formulations comprising those, the nutraceutical, or the pharmaceutical composition of the invention together with a suitable amount of immune cells comprising at least one immune cell, CD4+ T cell, CD8+ T cell, a mixture of cells comprising at least one T cell, or peripheral blood mononuclear cells, which can be activated or inhibited by a dendritic cell b) cultivation for an appropriate time and under an appropriate condition c) adding a suitable amount of dendritic cells comprising at least one dendritic cell, dendritic cells, or a mixture of cells comprising at least one dendritic cell, loaded with a suitable amount of at least one carbohydrate epitope carrying molecule d) cultivation for an appropriate time and under an appropriate condition for restimulation and e) measuring the proliferation and/or proliferation induction, preferably by using the WST reaction in combination with a colorimetric measurement (as described in the examples), whereby a positive cellular immune response against the carbohydrate epitope shows (i) a significantly higher proliferation of immune cells or a significantly higher number of T cells after a certain time of cultivation when restimulated with said dendritic cells loaded with a carbohydrate epitope carrying or comprising molecule than the proliferation or number when restimulated with corresponding unloaded dendritic cells and/or than the proliferation or number when restimulated with corresponding dendritic cells loaded with a molecule not carrying or comprising the carbohydrate epitope, and/or (ii) a significantly higher proliferation of immune cells or a significantly higher number of T cells after a certain time of cultivation when restimulated with said dendritic cells loaded with a protein, peptide, or molecule carrying or comprising the carbohydrate epitope than the proliferation or number when restimulated with corresponding dendritic cells loaded with corresponding protein, peptide, or molecule not carrying or not comprising the carbohydrate epitope, and/or (iii) a significantly higher proliferation of immune cells or a significantly higher number of T cells after a certain time of cultivation when restimulated with said dendritic cells loaded with a protein, peptide, or molecule carrying or comprising the carbohydrate epitope than the proliferation or number of corresponding immune cells restimulated with corresponding dendritic cells loaded with corresponding protein, peptide, or molecule carrying or comprising the carbohydrate epitope but enzymatically or chemically treated for destruction of the carbohydrate epitope, and/or (iv) a significantly higher proliferation of immune cells or a significantly higher number of T cells after a certain time of cultivation when restimulated with said dendritic cells loaded with a lysate or fractions of cells carrying or comprising the carbohydrate epitope than the proliferation or number of corresponding immune cells restimulated with corresponding dendritic cells loaded with a lysate of cells negative for the carbohydrate epitope or not comprising it.

Said cellular immune response test 3 tests the activation of CD4+ and CD8+ T-cells to carbohydrate epitope specific activated T-cells by a carbohydrate positive microorganism or a fraction or lysate thereof by measuring the induction of the proliferation of T-cells comprising bringing into contact dendritic cells loaded with a carbohydrate positive microorganism and immune cells and cultivation for appropriate times and conditions and subsequently adding dendritic cells loaded with a carbohydrate epitope carrying molecule for restimulation and cultivation for appropriate times and conditions and subsequently measuring the proliferation. Said measuring of the proliferation induction is preferably done using the WST reaction in combination with a colorimetric measurement and deduction of the DC alone and the non-restimulated immune cells alone which is known to those skilled in the art and is described in example 12. In the most preferred embodiment of the invention the cellular immune response test 3 comprises bringing into contact functional dendritic cells obtained from cells derived from MUTZ-3 or NMD-100 or NMD-200 loaded with a carbohydrate positive microorganism or a lysate or fraction thereof together with PBMC (peripheral blood mononuclear cells) matched at least in MHC class I (HLA-A2 and HLA-44) and cultivation of these cells for appropriate times and conditions, typically 7 to 10 days, and subsequently adding for restimulation functional dendritic cells obtained from cells derived from MUTZ-3 NMD-100 or NMD-200 loaded with lysate of cells comprising the carbohydrate epitope or the carbohydrate epitope carrying molecule and cultivation for appropriate times and conditions, typically 7 to 9 days, and subsequently measuring the proliferation rate as described above and in more detail in example 12. A positive cellular immune response against the carbohydrate epitope shows a higher proliferation of T cells restimulated with DC loaded with the carbohydrate epitope carrying molecule than the proliferation rate of the DC alone and the T cells put into contact with mDC unloaded or with DC loaded with the corresponding control. A preferred embodiment of the cellular immune response test 3 is described in detail in example 12.

In another preferred embodiment the invention provides a cellular immune response test (cellular immune response test 4) against the carbohydrate epitope comprising (a) bringing into contact a suitable amount of a dendritic cell, dendritic cells, or a mixture of cells comprising at least one dendritic cell, loaded with a suitable amount of
  (i) the carbohydrate positive microorganism, a lysate or a fraction thereof,
  (ii) formulations comprising those,
  (iii) the nutraceutical, or the pharmaceutical composition of the invention or
  (iv) a carbohydrate epitope carrying or comprising molecule,
  (v) a mixture comprising a carbohydrate epitope carrying molecule,
  (vi) a cell positive for or comprising the carbohydrate epitope, a lysate or fraction thereof,
  together with a suitable amount of at least one carbohydrate binding molecule;

(b) testing binding of said carbohydrate binding molecule.

A positive presentation of the carbohydrate epitope on said dendritic cell or cells is present when the binding of the carbohydrate binding molecule is higher to said dendritic cell or cells loaded with a carbohydrate epitope carrying molecule than its binding to an corresponding unloaded dendritic cell or cells and/or to a corresponding dendritic cell or cells loaded with a molecule not carrying or comprising the carbohydrate epitope or a carbohydrate epitope carrying or comprising molecule after an enzymatical or chemical treatment that destroys the carbohydrate epitope and/or when the binding of the carbohydrate binding molecule is higher to said dendritic cell or cells loaded with the carbohydrate positive microorganism, lysate or fraction thereof, the nutraceutical, the pharmaceutical composition or formulations thereof, than to a corresponding dendritic cell or cells unloaded or than to the a corresponding dendritic cell or cells loaded with a microorganism which is not bound by a carbohydrate binding molecule or than to a corresponding dendritic cell or cells loaded with the carbohydrate positive microorganism after enzymatical or chemical treatment that destroys the carbohydrate epitope.

Said cellular immune response test 4 tests the ability of dendritic cells to present the carbohydrate epitope on its surface after loading with a carbohydrate positive microorganism or a fraction or lysate thereof showing the potential of the loaded dendritic cells to process and present the microorganism-derived carbohydrate epitope to immune cells such as T cells comprising bringing suitable amounts of a carbohydrate positive microorganism or a fraction or lysate thereof and dendritic cells in a suitable differentiation and maturation state together, preferably immature DC which are then maturated to mDC using an appropriate cocktail of molecules known to those skilled in the art and measure the presentation of the carbohydrate epitope by the loaded DC by testing the binding of a carbohydrate binding molecule of the invention to said loaded DC. Said testing of the binding is performed by appropriate methods, preferably immunocytochemistry, immunofluorescence or flow cytometry, and more preferably by immunocytochemistry which are known by those skilled in the art and are described in the examples.

The test shows a positive presentation of loaded DC when the binding of the carbohydrate binding molecule is higher to the DC loaded with the carbohydrate positive microorganism than to DC unloaded, or more preferably to DC loaded with a microorganism which is not bound by a carbohydrate binding molecule or to DC loaded with the carbohydrate positive microorganism after enzymatical or chemical treatment that destroys the carbohydrate epitope. In a preferred embodiment of the invention the cellular immune response test 4 comprises bringing into contact suitable amounts of functional immature dendritic cells obtained from cells derived from MUTZ-3 or NMD-100 OR NMD-200 with lysates of a carbohydrate positive microorganism and subsequent culturing and maturation for 24 h-48 hours using a suitable molecule cocktail such as described in example 12 and testing the presentation of the carbohydrate epitope via immunofluorescence microscopy (immunocytochemistry) using carbohydrate epitope specific antibodies.

A preferred embodiment of the cellular immune response test 4 is described in detail in example 12.

The invention also provides a cellular immune response test (cellular immune response test 5) against the carbohydrate epitope comprising
  a) incubating a suitable amount of target cells from a cell line comprising the carbohydrate epitope labelled with a suitable amount of a marker such as europium or chromium-51 with at least one immune cell directed against the carbohydrate epitope or a mixture of cells comprising at least one immune cell directed against the carbohydrate epitope for a suitable time (typically between 3-6 hours or over night) and under suitable conditions, and
  b) measuring the lysis of the target cells by determining the release of the marker such as europium or chromium-51 whereby a positive cellular immune response against the carbohydrate epitope shows a significantly higher lysis of cells comprising the carbohydrate epitope than of carbohydrate epitope negative cells and/or it shows a significantly higher lysis of cells comprising the carbohydrate epitope incubated with carbohydrate epitope directed immune cells, than a lysis of cells comprising the carbohydrate epitope incubated with corresponding control immune cells not directed against the carbohydrate epitope.

Said CIRT 5 tests the carbohydrate epitope specific cytotoxicity of immune effector cells directed against the carbohydrate epitope such as but not limited to T cell, T cells, T cell clone, T cell line, CD4 positive T cells, CD8 positive T cells, NK cells and/or PBMCs.

The generation of carbohydrate epitope directed immune cells is described elsewhere herein.

In a preferred embodiment of the invention the carbohydrate epitope directed immune cells are obtained by the administration of the formulation of the invention, the carbohydrate positive microorganism or the fraction or lysate thereof to a human or animal, more preferred by the administration of the formulation of the invention, the carbohydrate positive microorganism or the fraction or lysate thereof to a human or animal and subsequent isolation of the immune cells from the human or animal.

In another preferred embodiment of the invention the carbohydrate epitope directed immune cells are restimulated at least once with dendritic cells loaded with the formulation of the invention, the carbohydrate positive microorganism or the fraction or lysate thereof or a carbohydrate epitope carrying molecule or tumor cell prior to their use in CIRT 5.

In a more preferred embodiment of the invention the carbohydrate epitope directed immune cells are restimulated more than once with dendritic cells loaded with the formulation of the invention, the carbohydrate positive microorganism or the fraction or lysate thereof or a carbohydrate epitope carrying molecule or tumor cell prior to their use in CIRT 5, whereby carbohydrate epitope on different carriers (such as but not limited to carbohydrate epitope on or from microorganism, molecule, protein or tumor cell) is used for different rounds of restimulation.

The test comprises incubating suitable amounts of labeled carbohydrate epitope positive target cells, with suitable amounts of immune cells directed against the carbohydrate epitope for a suitable time, typically between 3 and 6 hours or over night. The carbohydrate epitope positive cells are labeled with europium or chromium-51 which allows the measurement of cells which are lysed. The amount of lysed cells is determined, preferably by measuring the release of europium or chromium-51 after incubation. A suitable control can be determined by those skilled in the art such as carbohydrate epitope negative cells or corresponding control immune cells not directed against the carbohydrate epitope. The test can be optimized in respect to suitable numbers of labeled tumor cells, numbers of immune effector cells, and incubation time by those skilled in the art for its use in the invention.

In a preferred embodiment the CIRT 5 is performed using an Europium Release Assay. The target cells are incubated for 10 minutes at 4° C. in 800 µl of europium buffer (50 mM HEPES, pH 7.4, 93 mM NaCl, 5 mM KCl, 2 mM $MgCl_2$, 10 mM diethylentriaminepentaacetic acid, 2 mM europium (III) acetate), electroporated (710V, 1 pulse, 30 µs) in a Multiporator (Eppendorf), and subsequently incubated on ice for another 10 minutes. Thereafter, the cells are washed 5 times in RPMI/5% FCS and seeded in a 96-well round-bottom plate (Nunc; $5\times10^3$/well). Thereafter carbohydrate epitope directed immune cells or corresponding immune cells are added as effector cells (100 µl/well), using different effector cell/target cell ratios from 100:1 to 5:1, preferably effector cell/target cell ratios from 50:1 to 20:1. To determine spontaneous release, 100 µl RPMI/5% FCS without effector cells are added. Maximum release is determined after complete lysis of the target with ethanol.

Following incubation at 37° C. for 4 hours, the plate is centrifuged at 500×g for 5 minutes, and 20 µl of cell-free supernatant from every well is pipetted in 200 µl per well of enhancement solution (Perkin-Elmer Wallac) on the previously prepared flat-bottom plate (Nunc-Immunoplate Maxisorp). Following incubation for 15 minutes at room temperature, the fluorescence is determined (Victor$^2$ Fluorometer, Perkin-Elmer Wallac). The specific cytotoxicity is obtained from the equation (experimental lysis–spontaneous lysis)/(maximum lysis–spontaneous lysis)×100%.

In a further preferred embodiment of the invention a nutraceutical or a pharmaceutical composition comprising at least one carbohydrate positive microorganism or lysate or fraction thereof induces an effective carbohydrate specific cellular immune response against the carbohydrate epitope which is positive for at least two cellular immune response tests out of the cellular immune response tests 1 to 5.

In an even further preferred embodiment of the invention a nutraceutical or a pharmaceutical formulation comprising at least one carbohydrate positive microorganism or lysate or fraction thereof induces a humoral and a cellular immune response against the carbohydrate epitope which is positive for at least one humoral immune response test and at least one cellular immune response tests.

In an even further preferred embodiment of the invention a nutraceutical or a pharmaceutical formulation comprising at least one carbohydrate positive microorganism or lysate or fraction thereof induces a humoral and a cellular immune response against the carbohydrate epitope which is positive for at least two humoral immune response test and two cellular immune response tests, preferably positive for humoral immune response tests 1 and 3 and cellular immune response test 1 and 3, and more preferably for humoral immune response tests 1, 2 and 3 and cellular immune test 1, 2 and 3, and even more preferably for humoral immune response test 1, 2, 3 and 4 and cellular immune response test 1, 2, 3 and 4, and even more preferably for humoral immune response test 1, 2, 3, 4, and 6, and all 5 cellular immune response test, and even more preferably for humoral immune response test 1, 2, 3, 4, and 5, and all 5 cellular immune response test, and most preferably positive for all 6 humoral immune response tests and all 5 cellular immune response tests.

In another preferred embodiment the invention provides the cellular immune response tests 1 to 5 wherein the dendritic cell, dendritic cells or a mixture of cells comprising dendritic cell comprises at least one dendritic cell which is a mature dendritic cells when bringing into contact with said immune cells.

In another preferred embodiment the invention provides the cellular immune response tests 1 to 5 wherein the dendritic cell, dendritic cells or a mixture of cells comprise functional dendritic cells obtained from cells derived from MUTZ-3.

In another preferred embodiment the invention provides the cellular immune response tests 1 to 5 wherein said immune cells are matched with said dendritic cells at least in one MHC class I molecule.

In another preferred embodiment the invention provides the cellular immune response tests 1 to 5 wherein the carbohydrate epitope carrying molecule is a lysate or fraction of cells comprising the carbohydrate epitope.

In another preferred embodiment the invention refers to the use of any of the immune response tests as described above for determining the immune response against the carbohydrate epitope induced or enhanced by the nutraceutical, the pharmaceutical composition, the carbohydrate positive microorganism or the fraction thereof, or formulations comprising those according to this invention in at least one human or animal.

In another preferred embodiment the invention refers to the use of any of the immune response tests as described above for testing the natural existing immune response in a human or animal without or before administration of the nutraceutical, the pharmaceutical composition, the carbohydrate positive microorganism or the fraction thereof or formulations comprising those in at least one human or animal.

In another preferred embodiment the invention refers to use of any of the immune response tests as described above for determining and optimizing the effective amount, maximal effective amount, dose, dose regimen, administration route, composition, formulation, carriers and other molecules used therewith of the nutraceutical, the pharmaceutical composition, the carbohydrate positive microorganism or the fraction thereof, or formulations comprising those according to the invention.

B) Provision of Carbohydrate Positive Microorganisms and Methods for Testing the Potential of a Carbohydrate Positive Microorganism to Induce Immune Responses, Methods for Isolating a Carbohydrate Positive Microorganism, Methods for Identifying Suitable Carbohydrate Positive Microorganism for Nutraceuticals and Pharmaceutical Compositions The invention provides a carbohydrate positive microorganism which is recognized/bound by at least one carbohydrate binding molecule which also specifically recognizes a carbohydrate epitope present on a molecule from a human or animal cell, whereby said microorganism induces an effective carbohydrate-specific cellular immune response against said carbohydrate epitope in at least one animal or human.

The characteristics and advantages of respective carbohydrate positive microorganisms and methods for obtaining them are described above and below. As the carbohydrate positive microorganism is bound and thus recognized by at least one carbohydrate binding molecule which also specifically recognizes the carbohydrate epitope of interest in its "natural" environment (e.g. on a human or animal cell, as e.g. a tumor cell) it is ensured that the carbohydrate positive microorganism and/or the carbohydrate positive fraction or lysate thereof carries a carbohydrate structure which is at least immunochemically virtually identical to the carbohydrate epitope of interest This feature is important to ensure that an immune response is triggered by said carbohydrate positive microorganism that is sufficiently specific for the carbohydrate epitope of interest. Such carbohydrate binding molecules, preferably antibodies, that can be used to determine that a microorganism carries the carbohydrate epitope of interest, specifically recognize the carbohydrate epitope e.g. in a tumor-relevant surrounding.

The invention provides a carbohydrate positive microorganism or fraction or lysate thereof which is recognized and thus bound upon contact by at least one carbohydrate binding molecule specifically recognizing a carbohydrate epitope present on a molecule from a human or animal cell, which induces an effective carbohydrate specific cellular immune response and/or a humoral immune response against said carbohydrate epitope, and/or a carbohydrate structure, carbohydrate conjugate or a mammalian cell comprising said carbohydrate epitope, in at least one animal or human.

In a preferred embodiment the carbohydrate positive microorganism induces an effective carbohydrate specific cellular immune response against said carbohydrate epitope, and/or a carbohydrate structure, carbohydrate conjugate or a mammalian cell comprising said carbohydrate epitope, in at least one animal or human preferably comprising activation of CD4 positive T cells of Th1 type and/or activation of CD8 positive cytotoxic T cells.

The invention provides a suitable carbohydrate positive microorganism for use in a formulation according to the invention selected from the group comprising a nutraceutical and a pharmaceutical composition of the invention wherein the carbohydrate positive microorganism is bound by at least one carbohydrate binding molecule specifically recognizing a carbohydrate epitope present on a molecule from a human or animal cell, whereby said microorganism induces an effective carbohydrate-specific cellular immune response against said carbohydrate epitope, preferably in at least one animal or human.

In another preferred embodiment said immune response is induced in vitro.

The invention provides a carbohydrate positive microorganism which induces an effective carbohydrate-specific cellular immune response against said carbohydrate epitope, carbohydrate epitope positive tumor cells or carbohydrate epitope positive diseases, preferably in at least one human or animal and/or in vitro.

In a preferred embodiment the invention provides or uses the
(i) carbohydrate positive microorganism of the invention, or
(ii) the nutraceutical or the pharmaceutical formulation comprising a carbohydrate positive microorganism
which is selected from the group comprising
*Escherichia coli, Streptococcus, Bacteroides, Rhuminococcus, Lactobacillus, Bifidobacterium, Peptostreptococcus, Fusobacterium, Johnsonella, Atopobium, Staphylococcus, Eubacterium, Finegoldia, Clostridium, Eggerthella, Butyribacterium, Citrobacter, Helicobacter, Propionibacterium* and *Corynebacterium;*
and more preferably selected from the group comprising *Escherichia coli*, Bacteroises, such as *Bacteroides ovatus, Bacteroides thetaiotaomicron, Bacteroides acidophilus, Bacteroides caccae;*
and even more preferred selected from the group comprising the new strain *Bacteroides ovatus* AG6(DSM 18726), the new strain *Bacteroides ovatus* MU1(DSM 18728) and the new strain *Escherichia coli* LH2(DSM 18727) deposited at the "DSMZ-Deutsche Sammlung von Mikroorganismen and Zellkulturen GmbH" in Braunschweig (Germany), by Glycotope GmbH, Robert-Rössle-Str. 10, 13125 Berlin (Germany) at the Oct. 20, 2006, and most preferably the new strains AG6 or MU1.

In a further preferred embodiment of the invention the carbohydrate positive microorganism of the nutraceutical or the pharmaceutical formulation is a combination of carbohydrate positive microorganisms of different strains.

In a further preferred embodiment, the carbohydrate positive microorganism of the formulation according to the invention is a combination of carbohydrate positive microorganisms of different strains selected from the strains AG6, MU1 and LH2.

In a further preferred embodiment the nutraceutical or pharmaceutical composition of the invention comprises at least one carbohydrate positive microorganism combined with at least one other beneficial microorganism, such as but not limited to a *lactobacillus* and/or *bifidobacterium*, even more preferred a combination of carbohydrate positive microorganisms of different strains combined with other beneficial microorganisms.

In a preferred embodiment of the invention the carbohydrate positive microorganism is a non-pathogenic microorganism.

In a further preferred embodiment of the invention the carbohydrate positive microorganism is isolated from a healthy donor.

In a further preferred embodiment of the invention the carbohydrate positive microorganism can be isolated from a healthy donor.

In a further preferred embodiment of the invention the carbohydrate positive microorganism is used in the nutraceutical or pharmaceutical composition as a living organism.

In a further preferred embodiment of the invention the carbohydrate positive microorganism is used as a living organism and is administered orally.

In a further preferred embodiment of the invention the carbohydrate positive microorganism used in the nutraceutical or pharmaceutical composition is sensitive to at least one antibiotic.

In a further preferred embodiment of the invention the carbohydrate positive microorganism used in the nutraceutical can colonize the gut.

In another preferred embodiment of the invention the carbohydrate positive microorganism used in the nutraceutical or pharmaceutical composition is dead.

In an even further preferred embodiment of the invention the carbohydrate positive microorganism used in the nutraceutical or pharmaceutical composition is pasteurized.

In an even more preferred embodiment of the invention the carbohydrate positive microorganism is used in the nutraceutical or pharmaceutical composition as a living organism and was isolated from a healthy human donor and can colonize the human gut and is antibiotic sensitive.

In an even more preferred embodiment of the invention the carbohydrate positive microorganism is used in the nutraceutical in a pasteurized form and was isolated from the gut of a healthy human donor and is antibiotic sensitive.

In another preferred embodiment of the invention the carbohydrate positive microorganism used in the pharmaceutical composition is dead or lysed.

In a further preferred embodiment of the invention the carbohydrate positive microorganism used in the nutraceutical or pharmaceutical composition is lyophilized.

The invention further provides a method for testing the potential of a carbohydrate positive microorganism or fraction thereof to induce a humoral immune response against the carbohydrate epitope comprising
a) administration of a suitable amount of the carbohydrate positive microorganism or fraction thereof to at least one human or animal
b) test of the immune response in at least one of humoral immune response tests 1-6 against the carbohydrate epitope.

The invention further provides a method for testing the potential of a carbohydrate positive microorganism or fraction thereof to induce an effective carbohydrate-specific cellular immune response against the carbohydrate epitope comprising
- a) administration of a suitable amount of the carbohydrate positive microorganism or fraction thereof to at least one human or animal and
- b) test of the immune response in at least one cellular immune response test against the carbohydrate epitope.

In a preferred embodiment the invention provides a method for testing the potential of any of the nutraceuticals, the pharmaceutical compositions, the carbohydrate positive microorganisms or the fractions thereof, or formulation comprising those, to induce an immune response and to determine which immune response is induced.

In another preferred embodiment the invention provides a method to determine the dose, the dosing regimen, the route of administration, the formulation, the carriers or other components used in or with the nutraceuticals, the pharmaceutical compositions, the carbohydrate positive microorganisms or the fractions thereof, or formulation comprising those.

The invention further provides a method for testing the potential of a carbohydrate positive microorganism to induce a humoral immune response comprising at least one of the humoral immune response test 1 to 6, preferably at least two, more preferably three, more preferably 4, more preferably 5, and most preferably all 6 humoral immune response tests, whereby at least one animal or human was given suitable amounts of the microorganism to be tested either orally or systemically (with or without additional adjuvants) and the antibodies in serum or antibodies gained from the serum, plasma or faeces are tested preferably in comparison to the antibodies in serum or antibodies gained from the blood, plasma or faeces before the microorganisms were given. Those skilled in the art are able to determine suitable amounts of the microorganism and ways to gain the antibodies from blood and suitable controls. The tests are described in detail herein and/or in example 11.

The invention further provides a method for testing the potential of a carbohydrate positive microorganism to induce a cellular immune response comprising at least one of the cellular immune response tests 1 to 5, preferably at least two, more preferably three, and most preferably all 5 cellular immune response tests.

The invention further provides a method for testing the potential of a carbohydrate positive microorganism to induce a cytotoxic cellular immune response comprising at least the cellular immune response test 2, preferably 2 and 1, more preferably 2, 3, and, and most preferably all 5 cellular immune response tests.

In both embodiments of the invention the tests are either performed as described above in vitro or the cellular immune response tests 1 to 3 and 5 were performed by giving at least one animal or human suitable amounts of the microorganism to be tested either orally or systemically (with or without additional adjuvants) and the immune cells were gained from the blood and (i) tested according to the cellular tests 1 to 3 or 5 as described above or (ii) tested according to the cellular tests 1 to 3 or 5 as described above with the difference that the immune cells are not brought into contact with dendritic cells loaded with a carbohydrate positive microorganism and only dendritic cells loaded with the carbohydrate epitope carrying molecule were added for restimulation. The (i) is preferably used to enhance the in vivo effect and to improve the read out with weaker responses and (ii) is preferably used for strong responses. Those skilled in the art are able to determine suitable amounts of the microorganism and suitable controls. The tests are described in detail in example 12.

The invention further provides in a preferred embodiment a method for testing the potential of a carbohydrate positive microorganism to induce a humoral and a cellular immune response which corresponds to a combination of the above described methods, comprising at least one of the humoral immune response test 1 to 6 and at least one of the cellular immune response tests 1 to 5, preferably at least two of the humoral immune response tests 1 to 6 and at least one, more preferred at least two of the cellular immune response tests 1 to 5, more preferably at least three of the humoral immune response test 1 to 6, more preferably at least 4 of the humoral immune response tests 1 to 6 and all of the cellular immune response tests 1 to 5, more preferably at least 5 of the humoral immune response tests 1 to 6 and all of the cellular immune response tests 1 to 5, and most preferably all 6 humoral immune response tests 1 to 6 and all 5 cellular immune response tests 1 to 5.

The invention also provides methods to identify a carbohydrate positive microorganism in sense of the invention and methods to isolate a carbohydrate positive microorganism out of a mixture of carbohydrate epitope positive and negative microorganisms.

The invention further provides a method for isolating a carbohydrate positive microorganism carrying the carbohydrate structure of interest from a mixture of microorganisms, comprising
- (a) bringing a carbohydrate binding molecule specific for the carbohydrate structure of interest into contact with a mixture of microorganisms, and
- (b) isolating at least one microorganism bound to said carbohydrate binding molecule from said mixture,
- (c) testing that the isolated microorganism is a carbohydrate positive microorganism and carries the carbohydrate structure of interest.

The details of the respective method were also described above.

In a preferred embodiment the invention further provides a method for isolating a carbohydrate positive microorganism from a mixture of microorganisms wherein under step (b) magnetic particles are used for separation/enrichment of microorganisms bound to said carbohydrate binding molecule.

In a preferred embodiment the invention relates to a method for isolating the microorganism as described elsewhere herein, comprising:
- (a) bringing said carbohydrate binding molecule into contact with a mixture of microorganisms; and
- (b) isolating at least one microorganism bound to said carbohydrate binding molecule; and
- (c) testing the isolated microorganism for specific binding to said carbohydrate binding molecule and
- (d) testing the induction of an effective carbohydrate specific cellular immune response and/or humoral immune response against said carbohydrate epitope.

Said carbohydrate epitope can e.g. be a part of a carbohydrate structure, carbohydrate conjugate or a mammalian cell comprising said carbohydrate epitope. Preferably a respective humoral or cellular response is triggered in at least one animal or human by said microorganism and/or fraction and/or lysate thereof.

In a preferred embodiment the invention relates to a method for isolating the microorganism as described elsewhere herein, comprising:
- (a) bringing said carbohydrate binding molecule into contact with a mixture of microorganisms; and
- (b) isolating at least one microorganism bound by said carbohydrate binding molecule; and (c) testing the isolated microorganism for specific binding to said carbohydrate binding molecule and (d) testing the induction of an effective carbohydrate specific cellular immune response against said carbohydrate epitope, and/or a carbohydrate structure, carbohydrate conjugate or a mammalian cell comprising said carbohydrate epitope, by said microorganism and/or fraction and/or lysate thereof, preferably for the activation of CD4 positive Th1 type T cells and/or for the activation of cytotoxic CD8 positive T cells, preferably in at least one animal or human and/or in vitro.

In a preferred embodiment the invention further provides a method for isolating a carbohydrate positive microorganism from a mixture of microorganisms wherein said mixture of microorganisms is a mixture of at least two microorganisms selected from the group comprising microorganisms from a healthy human and/or patient, an animal, soil, food, and/or plants.

In a preferred embodiment the invention further provides a method for isolating a carbohydrate positive microorganism from a mixture of microorganisms wherein said mixture of microorganisms is a mixture comprising microorganisms from the human gastrointestinal tract, human stool, human blood, human tissue, or human body fluids of healthy individuals or patients.

In a preferred embodiment the invention further provides a method for isolating a carbohydrate positive microorganism from a mixture of microorganisms which is performed under anaerob conditions which allow the isolation of anaerob carbohydrate positive microorganisms.

Said mixture of microorganisms can be any mixture of at least two different microorganism, such as but not limited to those occurring in nature, such as but not limited to in soil, food, plants, animals, human gastrointestinal tract, human blood, human tissue, human body fluids of healthy individuals or patients, most preferred is a mixture of microorganisms from a healthy individual. The microorganisms are preferably brought into a suitable solution before bringing the mixture into contact with a carbohydrate binding molecule. The carbohydrate binding molecule is preferably coupled to a carrier, such as magnetic beads, which allow the separation of the microorganism bound to said carrier. And after bringing the carbohydrate binding molecule together with the mixture of microorganism those microorganisms bound to the carbohydrate binding molecule are separated from those not bound to the antibody. In an alternative embodiment the carbohydrate binding molecule is not coupled to a carrier and the carbohydrate positive microorganism is isolated together with the carbohydrate binding molecule by using methods specifically isolating the antibody, such as Protein A, Protein G, Protein L or anti-IgM antibodies or anti-IgG antibodies which are itself coupled to a carrier such as a magnetic bead chromatographic bed material. In a preferred embodiment of the invention carbohydrate positive microorganisms bound to the carbohydrate binding molecule are thoroughly washed with a suitable buffer (such as PBS-a) and plated on selective and non-selective media such as but not limited to MRS, BSM, KF, N, S, WC, BHI, CBA and ST (for details see table 3). Resulting colonies are scraped from the plates and applied to additional rounds of affinity enrichment with carbohydrate specific molecules. Colonies are picked, re-streaked and analysed for carbohydrate expression in ELISA and immunofluorescence (more details under examples 1-9). From these descriptions and from the examples someone skilled in the art is able to adjust or optimize the methods for various bacteria from various sources.

In a preferred special embodiment the method is performed under anaerob conditions which allow the isolation of anaerob carbohydrate positive microorganism, which is for example important for the majority of microorganism from the human gut.

The method is described in detail in examples 1 to 9.

In another preferred embodiment the microorganisms are isolated from food. In an even more preferred embodiment the microorganisms are isolated from the gastrointestinal system, and even more preferred from human stool.

The method is described in detail in examples 1 to 9.

The invention further provides a method for identifying a suitable carbohydrate positive microorganism for use as a component for nutraceuticals and pharmaceutical compositions of the invention comprising a) testing a microorganism for its binding to at least one carbohydrate binding molecule and b) identifying this carbohydrate positive microorganism which is bound by at least one carbohydrate binding molecule as described herein.

In a preferred embodiment of the invention the testing of a microorganism for its binding to at least one carbohydrate binding molecule is done by ELISA, whereby a carbohydrate positive microorganism show an ELISA signal with at least one carbohydrate binding molecule of at least 3 times, more preferred 5 times and even more preferred of at least 10 times of the background signal.

Preferred are carbohydrate positive microorganisms which show a reduced binding of the carbohydrate binding molecule after treatment of the carbohydrate positive microorganism with enzymes or chemicals destroying the carbohydrate epitope as described elsewhere herein.

In a preferred embodiment the invention relates to a method for identifying the carbohydrate positive microorganism as described elsewhere herein, comprising:

a) bringing said carbohydrate binding molecule into contact with a microorganism or a mixture of microorganisms; and b) identifying the microorganism which is specifically bound by said carbohydrate binding molecule; and c) testing the induction of a cellular and/or humoral immune response by said microorganism and/or fractions and or lysates thereof, whereby said microorganism induces an effective carbohydrate specific cellular and/or humoral immune response against against said carbohydrate epitope, and/or a carbohydrate structure, carbohydrate conjugate or a mammalian cell comprising said carbohydrate epitope, preferably in at least one animal or human and/or in vitro.

In another preferred embodiment the invention relates to a method for identifying the microorganism as described elsewhere herein, comprising:

a) bringing said carbohydrate binding molecule into contact with a microorganism or a mixture of microorganisms; and b) identifying the microorganism which is specifically bound by said carbohydrate binding molecule; and c) testing the induction of an effective carbohydrate specific cellular immune response by said microorganism and/or fractions and or lysates thereof, whereby said microorganism induces an effective carbohydrate specific cellular immune response against against said carbohydrate epitope, and/or a carbohydrate structure, carbohydrate conjugate or a mammalian cell comprising said carbohydrate epitope, preferably in at least one animal or human and/or in vitro.

The induction of said effective carbohydrate specific cellular immune response against said carbohydrate epitope, and/or a carbohydrate structure, carbohydrate conjugate or a mammalian cell comprising said carbohydrate epitope can be measured by the cellular immune response tests as disclosed herein or by methods known to those skilled in the art.

In a preferred embodiment the invention relates to a method for identifying a suitable carbohydrate positive microorganism for use in nutraceuticals and pharmaceutical compositions of the invention comprising
 a) testing a carbohydrate positive microorganism for its binding to at least one carbohydrate binding molecule and
 b) testing for its ability to induce an immune response in humans or animals recognizing the carbohydrate epitope and/or a carbohydrate epitope positive cell or tumor cell and
 c) identifying this microorganism which is bound by at least one carbohydrate binding molecule as described herein and induces an immune response in humans or animals recognizing the carbohydrate epitope and/or a carbohydrate epitope positive cell or tumor cell by being positive for at least one humoral immune response test out of 1-6 or at least one cellular immune response test out of 1-5 as described herein.

In a preferred embodiment the invention relates to a method for identifying a suitable carbohydrate positive microorganism for use as a component for nutraceuticals and pharmaceutical compositions of the invention wherein the induced immune response after administration of a formulation according to the present invention in a human or an animal is an immune response positive for at least one humoral immune response test against carbohydrate epitope and at least one cellular immune response test against the carbohydrate epitope as described elsewhere herein.

The methods for identifying a suitable carbohydrate positive microorganism for use as a component for nutraceuticals and pharmaceutical compositions of the invention can be used to identify a suitable microorganisms from existing strains such as found at DSMZ or other collections of microorganisms or from the carbohydrate positive microorganism isolated by a method for isolating a carbohydrate positive microorganism from a mixture of microorganism according to the invention.

The invention relates also to a method for isolating and identifying carbohydrate positive bacteria comprising
 a) isolating whole bacteria from faeces samples,
 b) performing affinity enrichments of carbohydrate epitope positive bacteria using one or more carbohydrate binding molecules under aerobic or anaerobic conditions,
 c) plating the enriched bacteria on different selective media and screening of the bacteria for binding to carbohydrate binding molecules.

In another preferred embodiment the invention refers to a method for isolating and identifying a carbohydrate positive bacteria comprising
 a) isolating a mixture of microorganisms comprising whole bacteria from faeces samples
 b) bringing a carbohydrate binding molecule into contact with a mixture of microorganisms
 c) isolate the microorganism which bind the carbohydrate binding molecule under aerobic or anaerobic conditions using magnetic particle separation,
 d) plating the enriched bacteria on at least one selective medium
 e) identifying the microorganism which is bound by at least one carbohydrate binding molecule.

In another preferred embodiment the invention refers to a method for isolating and identifying carbohydrate positive bacteria comprising
 a) generation of a pure bacterial strain which is bound by at least one carbohydrate binding molecule; and/or
 b) testing for the ability of said pure bacterial strain to induce or enhance an immune response against the carbohydrate epitope in at least one human or animal.

In another preferred embodiment, the invention provides a method for testing the potential of a carbohydrate positive microorganism to induce a carbohydrate epitope specific immune response comprising the following steps:
 1) identification of carbohydrate positive microorganisms and production in pure cultures;
 2) identification of immune effective bacterial strains of the gut;
 3) generation of an effective, immunologically and toxicologically tested carbohydrate positive preparation as a nutrition additive ready for human tests;
 4) induction or enhancement of a carbohydrate specific immune responses in humans; and if necessary
 5) isolation, identification and testing of an immune effective defined carbohydrate epitope positive fraction or component of said microorganism.

In a preferred embodiment of the invention, the carbohydrate binding molecule of the above described methods is selected from the group comprising monoclonal antibodies, polyclonal antibodies, lectins and/or selectins and/or molecules derived therefrom.

In a preferred embodiment of the invention, the carbohydrate epitope of the above described methods is selected from the group comprising TF, Core-1, Tn, sialyl-Tn, sialyl-TF, Globo-H, Lewis-Y, sialyl-Lewis-A, sialyl-Lewis-X, polysialic acid, Lewis-X, GM2, GD2, GD3, 9-O-acetyl GD3, 9-O-acetyl GD2, GD3L, fucosyl GM1, Fucosyl GM1, Lewis-A, Lewis B, sLac, sialylated type 1 chain, CA 19-9 antigen, CA 72-4 antigen and/or CA-50 antigen.

The method is described in detail in examples 1-10.

The invention relates also to a method for generating carbohydrate positive microorganisms comprising
 a) contacting a microorganism with an agens for induction of mutations by chemical and/or physical mutagens such as but not limited to EMS, UV, methotrexat, microwave, cancerogenic substances, carcinogen, mutagen or radiation under conditions killing the majority of microorganisms and
 b) cultivating surviving microorganisms under suitable conditions
 c) enriching, isolating and/or identifying carbohydrate positive microorganisms as described elsewhere herein
 d) testing for the ability of said microorganism to induce or enhance an immune response against the carbohydrate epitope in at least one human or animal.

The invention relates also to a method for generating carbohydrate positive microorganisms by genetical engineering comprising
 a) introduction, knock out and/or silencing of genes, part of genes, DNA, RNA, antisense RNA, oligonucleotides, oligopeptides or proteins into a microorganism thereby affecting carbohydrate epitope biosynthesis, carbohydrate epitope degradation or biosynthesis or degradation of flanking carbohydrates and
 b) enriching, isolating, identifying and/or testing of carbohydrate positive microorganisms as described elsewhere herein.

In a preferred embodiment said microorganism is a carbohydrate epitope negative microorganism.

In a further preferred embodiment said microorganism is a beneficial microorganism for the intestinal tract such as but not limited to *Lactobacillus* or *Bifidobacterium*.

In a further preferred embodiment said microorganism is a microorganism used for production of conventional food such as but not limited to *Lactobacillus* or *Bifidobacterium*.

In another embodiment said microorganism is already carbohydrate epitope positive and the method is used in order to increase the amount of carbohydrate epitope expressed on the cell surface.

In a preferred embodiment, the carbohydrate positive microorganism isolated or identified by any of the above mentioned methods or a fraction or a lysate thereof is used for manufacturing a medicament or a nutraceutical for prohylaxis and/or therapy of a disease associated with said carbohydrate epitope whereby said microorganism and/or fraction and/or lysate induces an effective carbohydrate specific cellular and/or humoral immune response against said carbohydrate epitope, and/or a carbohydrate structure, carbohydrate conjugate or a mammalian cell comprising said carbohydrate epitope, in at least one animal or human.

In another preferred embodiment, the carbohydrate positive microorganism isolated or identified by any of the above mentioned methods or a fraction or a lysate thereof is used for manufacturing a medicament or a nutraceutical for prohylaxis and/or therapy of a disease associated with said carbohydrate epitope whereby said microorganism and/or fraction and/or lysate induces an effective carbohydrate specific cellular immune response against said carbohydrate epitope, and/or a carbohydrate structure, carbohydrate conjugate or a mammalian cell comprising said carbohydrate epitope, in at least one animal or human, preferably the immune response comprises activation of CD4 positive Th1 type T cells and/or activation of CD8 positive cytotoxic T cells.

Suitable manufacturing procedures and conditions are known to those skilled in the art or can be adjusted by those skilled in the art.

C) Provision of Fractions of the Carbohydrate Positive Microorganism

The invention provides a fraction of the carbohydrate positive microorganism of the invention whereby the carbohydrate positive microorganism epitope present on a molecule from a human or animal cell, whereby said fraction of the carbohydrate positive microorganism induces an effective carbohydrate-specific cellular immune response against said carbohydrate epitope in at least one animal or human is bound by at least one carbohydrate binding molecule specifically recognizing a carbohydrate The invention provides a suitable fraction of the carbohydrate positive microorganism of the invention for use in a formulation of the invention selected from the group comprising a nutraceutical or a pharmaceutical composition.

The invention provides a fraction of the carbohydrate positive microorganism of the invention which induces a carbohydrate specific immune response against the carbohydrate epitope or carbohydrate epitope positive cells or tumor cells in humans or animals.

Said fraction of a carbohydrate positive microorganism means preparations or purifications of smaller parts of said microorganisms such as cell wall preparation, envelope preparation, lysates, lipopolysaccharid preparation, preparation of capsules, or capsule polysaccharide preparation, which are described in the examples (example 10) or someone skilled in the art is able to optimize and select one suitable method or a combination of suitable methods. They preferably comprise at least one carbohydrate positive component of said carbohydrate positive microorganism. They can be obtained by preparations or purifications from at least one carbohydrate positive microorganism. Said preparations and purifications can be obtained by methods known to those skilled in the art such as those described above, or single or sequential cell fractionation, phenol water extractions, ether extractions, lysozyme digestions or chromatographic methods. The carbohydrate positive component or the fraction containing the carbohydrate positive component is detected by binding of the fraction to at least one carbohydrate binding molecule in test systems such as but not limited to ELISA or Dot blots which are known to those skilled in the art. In a preferred embodiment of the invention the fraction comprising a carbohydrate positive component is obtained by affinity chromatography using at least one carbohydrate binding molecule.

In a preferred embodiment a single preparation or purification step is used. In another preferred embodiment a combination of at least preparation and purification steps are used.

In a further preferred embodiment the carbohydrate positive component is enriched in said fraction when compared to the whole microorganism as can be determined by an increased binding of at least one carbohydrate binding molecule to the fraction in comparison to the microorganism, for example by ELISA, and preferably then when the weight of the contained biological material in the same volume is equal.

Said carbohydrate positive component means any component of a carbohydrate positive microorganism which is bound by at least one carbohydrate binding molecule. Said carbohydrate positive component comprises at least one carbohydrate structure or carbohydrate mimicking structure which can be available in form of its natural molecule where it is part of on the microorganism, such as a peptide, oligopeptide, polypeptide, lipid, ceramide, carbohydrate, lipoprotein, polysaccharide, oligosaccharide, polysaccharide, proteoglycan, lipopolysaccharide or glycoprotein, or as a part of said natural molecule, or alone. The carbohydrate positive component can be used in sense of the invention as a fraction of the carbohydrate positive microorganism as such or coupled to other non-natural carrier structures such as proteins, lipids, chemical molecules such as polyacrylamide. Preferably it is used in its natural form. The carbohydrate positive component can comprise a single carbohydrate epitopestructure or carbohydrate mimicking structure or repeating units of said structures and can contain additional carbohydrate structures or units or other biomolecule structures. Said carbohydrate mimicking structure is a structure which is bound by at least one carbohydrate binding molecule and induces an immune response against the carbohydrate epitope, preferably an effective carbohydrate specific cellular immune response or humoral immune response against said carbohydrate epitope and more preferably an effective carbohydrate specific cellular immune response and a humoral immune response against said carbohydrate epitope and/or cells associated with said carbohydrate epitope.

The carbohydrate positive microorganism wherefrom the carbohydrate positive fraction is derived is described elsewhere in that invention.

In a further preferred embodiment of the invention the fraction of the carbohydrate positive microorganism (active component) of the nutraceutical or the pharmaceutical formulation comprises a combination of fractions from one carbohydrate positive microorganism or preferentially from different carbohydrate positive microorganisms of different strains. The fractions can be of the same or a different preparation or purification type, preferably is a combination of carbohydrate positive components which have different molecular carrier or mimikry structures such as but not limited to a peptide, oligopeptide, polypeptide, lipid, ceramide, carbohydrate, lipoprotein, polysaccharide, oligosaccharide, polysaccharide, proteoglycan or glycoprotein, or as a part of another natural or synthetic molecule.

In another preferred embodiment of the invention the carbohydrate positive component is not part of the bacterial lipopolysaccharide.

In a further preferred embodiment said fraction of the carbohydrate positive microorganism comprises a combination of carbohydrate positive components of carbohydrate positive microorganisms of at least two different strains.

In another preferred embodiment of the invention said carbohydrate structure or said repeating units thereof are obtained by enrichment and/or purification and/or isolation from a carbohydrate positive microorganism.

In a further preferred embodiment of the invention said carbohydrate structure or said repeating units thereof are obtained by chemical synthesis, technique therefore are known to those skilled in the art.

In a further preferred embodiment of the invention said carbohydrate structure or said repeating units thereof are obtained by enrichment and/or purification and or isolation from strain AG6.

Details are shown in example 10.

In a further preferred embodiment of the invention said carbohydrate structure or said repeating units thereof are obtained by chemical synthesis.

Those skilled in the art are able to determine suitable conditions and methods for chemically synthesizing the carbohydrate structure according to FIG. 8 or repeating units thereof.

D) Methods for the Generation of Immune Cells Directed Against the Carbohydrate Epitope The invention provides a method for generation of a functional dendritic cell against said carbohydrate epitope comprising bringing into contact a suitable amount of a dendritic cell or a mixture of dendritic cells or a mixture of cells comprising at least one dendritic cell with a suitable amount of the formulation as described elsewhere herein for a suitable time under suitable conditions to generate at least one functional dendritic cell against said carbohydrate epitope and/or a carbohydrate structure, carbohydrate conjugate or a mammalian cell comprising said carbohydrate epitope. As outlines above, said carbohydrate epitope is preferably a human epitope and preferably uncharged. Preferably, said dendritic cells are not loaded with peptides carrying the carbohydrate epitope of interest.

The invention provides a method for generation of a functional dendritic cell against the carbohydrate epitope comprising bringing into contact a suitable amount of a dendritic cell or a mixture of dendritic cells or a mixture of cells comprising at least one dendritic cell with a suitable amount of at least one carbohydrate positive microorganism, lysate, or fraction thereof, as described elsewhere herein for a suitable time under suitable conditions to generate at least one functional dendritic cell loaded with the carbohydrate epitope.

The invention provides a method for generation of a functional dendritic cell against the carbohydrate epitope comprising bringing into contact a suitable amount of a dendritic cell or a mixture of dendritic cells or a mixture of cells comprising at least one dendritic cell with a suitable amount of at least one carbohydrate epitope carrying molecule or at least one disease cell associated with the carbohydrate epitope or of at least one carbohydrate epitope positive tumor cell or a lysate or a fraction thereof, as described elsewhere herein, for a suitable time under suitable conditions to generate at least one functional dendritic cell loaded with the carbohydrate epitope.

Said functional dendritic cell against the carbohydrate epitope is a dendritic cell or a mixture of dendritic cells which activates at least one T cell against the carbohydrate epitope which can preferentially be tested by a cellular immune response test of the invention and is positive against the carbohydrate epitope in at least one of the cellular immune response tests described elsewhere herein. In a preferred embodiment the functional dendritic cell is presenting the carbohydrate epitope on its surface and can be detected by a carbohydrate epitope specific antibody or a carbohydrate binding molecule as described for example in the cellular immune response test 4. In a preferred embodiment of the invention the functional dendritic cell against the carbohydrate epitope is obtained by bringing into contact an immature dendritic cell or a mixture of immature dendritic cells or a mixture of dendritic cells comprising at least one immature dendritic cell with a suitable amount of at least one carbohydrate positive microorganism, lysate, or fraction thereof, as described elsewhere herein for a suitable time and under suitable conditions to mature said dendritic cell using suitable conditions as described elsewhere herein and as known to those skilled in the art, comprising for example the molecules TNFalpha (tumor necrosis factor alpha), LPS (Lipopolysaccharide) or BCG (Bacille Calmette Guerin), INFgamma (interferon gamma), dexamethasone, and/or TGFbeta (transforming growth factor beta), to a functional dendritic cell loaded with the carbohydrate epitope. In a preferred embodiment of the invention the dendritic cell is derived from MUTZ-3 or NemodDC (obtainable from Glycotope GmbH Berlin, Germamy; www.glycotope. corn), and further preferred immature dendritic cells were generated from MUTZ-3 cells or NemodDC under suitable conditions comprising using IL-4 and GM-CSF typically for about one week, the resulting immature dendritic cells or iNMDC are brought into contact with said suitable amount of at least one carbohydrate positive microorganism, lysate, or fraction thereof, the cells are matured using a suitable condition comprising for example TNFalpha, LPS, BCG, INFgamma, dexamethasone, or TGFbeta, preferably TNFalpha, typically for about one to two days resulting in mature dendritic cells loaded with the carbohydrate epitope corresponding to said functional dendritic cell against carbohydrate epitope.

In a preferred embodiment the invention provides a functional dendritic cell produced by the above described methods, wherein the functional dendritic cell is directed against the carbohydrate epitope an/or a carbohydrate structure, carbohydrate conjugate or a mammalian cell comprising said carbohydrate epitope.

In another preferred embodiment the invention provides a functional dendritic cell produced by the above described methods, wherein the functional dendritic cell is directed against said carbohydrate antigen or a mammalian cell comprising said and induces an effective carbohydrate specific cellular immune response and/or humoral immune response against cells and/or diseases expressing said carbohydrate epitope.

In a preferred embodiment the invention provides a method for generation of an activated T cell, T cells, T cell clone or T cell line against the carbohydrate epitope and/or a carbohydrate structure, carbohydrate conjugate or a mammalian cell comprising said carbohydrate epitope comprising
(a) bringing into contact a suitable amount of at least one functional dendritic cell as described above, with a suitable amount of at least one T cell or a mixture of T cells or a mixture of cells comprising at least one T cell, cultivation of said T cell or mixture of T cells together with said loaded functional dendritic cells for a suitable time under a suitable condition to activate or prime a T cell or T cells against said carbohydrate epitope, and (b) restimulating of said T cells with a suitable amount of at least one functional dendritic cell loaded with a human or animal cell or molecule carrying said carbohydrate epitope.

The invention provides a method for generation of an activated T cell or T cells against the carbohydrate epitope comprising (a) bringing into contact a suitable amount of at least one functional dendritic cell or a mixture of cells containing at least one functional dendritic cell, loaded with suitable amounts of the carbohydrate positive microorganism, lysate or fraction thereof with at least one T cell or T cells (b) cultivation of said T cell or T cells together with said loaded functional dendritic cells for a suitable time under suitable conditions to activate or prime a T cell or T cells against the carbohydrate epitope.

The invention provides a method for generation of an activated T cell or T cells against the carbohydrate epitope comprising (a) bringing into contact a suitable amount of functional dendritic cells or a mixture of cells containing at least one functional dendritic cell loaded with suitable amounts of a carbohydrate epitope carrying molecule, a carbohydrate epitope positive tumor cell or a cell comprising the carbohydrate epitope, or a lysate or fraction thereof with a T cell or T cells or a mixture of cells containing at least one T cell (b) cultivation of said T cell or T cells or mixture of cells containing at least one T cell together with said loaded functional dendritic cells for a suitable time under suitable conditions to activate or prime a T cell or T cells against the carbohydrate epitope.

In a preferred embodiment the invention provides a method for generation of an activated T cell or T cells against the carbohydrate epitope comprising (a) bringing into contact suitable amounts of functional dendritic cells loaded with suitable amounts of the carbohydrate positive microorganism or a lysate or fraction thereof with a T cell or T cells (b) cultivation of said T cell or T cells together with said loaded functional dendritic cells for a suitable time under suitable conditions to activate or prime a T cell or T cells against the carbohydrate epitope (c) adding functional dendritic cells loaded with a carbohydrate epitope carrying molecule or carbohydrate epitope positive tumor cell or a cell comprising the carbohydrate epitope or a lysate or fraction thereof for restimulation (d) cultivation for appropriate times and conditions.

In a preferred embodiment the invention provides a method for generation of an activated T cell or T cells against carbohydrate epitope comprising a) bringing into contact a suitable amount of at least one functional dendritic cell loaded with a suitable amount of at least one carbohydrate positive microorganism or a lysate or fraction thereof with a suitable amount of at least one T cell or a mixture of T cells or a mixture of cells comprising at least one T cell b) cultivating said T cell or mixture of T cells or mixture of cells comprising at least one T cell with said loaded functional dendritic cells for a suitable time under suitable conditions to activate or prime a T cell or T cells against the carbohydrate epitope.

In a preferred embodiment the invention provides a method for generation of an activated T cell or T cells against the carbohydrate epitope comprising a) bringing into contact a suitable amount of at least one functional dendritic cell loaded with a suitable amount of at least one carbohydrate epitope carrying molecule or carbohydrate epitope positive tumor cell, or a cell comprising the carbohydrate epitope or a lysate or fraction thereof with a suitable amount of at least one T cell or a mixture of T cells or a mixture of cells comprising at least one T cell b) cultivating said T cell or mixture of T cells or mixture of cells comprising at least one T cell with said loaded functional dendritic cells for a suitable time under suitable conditions to activate or prime a T cell or T cells against the carbohydrate epitope.

In another preferred embodiment the invention provides a method for generation of an activated T cell or T cells against the carbohydrate epitope comprising the steps (a) and (b) of the preceding methods and subsequently comprising, (c) adding a suitable amount of at least one functional dendritic cell loaded with a suitable amount of at least one carbohydrate epitope carrying molecule or carbohydrate epitope positive tumor cell, or a cell comprising the carbohydrate epitope or a lysate or fraction thereof for restimulation;

or adding a suitable amount of at least one functional dendritic cell loaded with a suitable amount of at least one carbohydrate positive microorganism, lysate or fraction thereof for restimulation; and (d) cultivation for an appropriate time and under an appropriate condition.

In another preferred embodiment the invention provides a method for generation of a T cell line against the carbohydrate epitope comprising the steps (a), (b), (c) and (d) of the preceding method and subsequently comprising at least one further round of restimulation whereby one round of restimulation comprises either steps (e) and (f) or steps (g) and (h), with (e) adding a suitable amount of at least one functional dendritic cell loaded with a suitable amount of at least one carbohydrate epitope carrying molecule or carbohydrate epitope positive tumor cell, or cell comprising the carbohydrate epitope or lysate or fraction thereof for restimulation;

(f) cultivation for an appropriate time and under an appropriate condition (g) adding a suitable amount of at least one functional dendritic cell loaded with a suitable amount of at least one carbohydrate positive microorganism, or lysate or fraction thereof for restimulation (h) cultivation for an appropriate time and under an appropriate condition.

In a further preferred embodiment the invention provides a method for generation of a T cell line against the carbohydrate epitope additionally comprising two further rounds of said round of restimulation.

In a more preferred embodiment the invention provides a method for generation of a T cell line against the carbohydrate epitope comprising three further rounds of said round of restimulation.

In an even more preferred embodiment the invention provides a method for generation of a T cell line against the carbohydrate epitope comprising five further rounds of of said round of restimulation.

In a further preferred embodiment the invention provides a method for generation of a T cell clone against carbohydrate epitope wherein an additional step of cloning the cells before one round of said rounds of restimulation is performed at least once.

In a preferred embodiment the activated T cell or T cells is a T cell line against the carbohydrate epitope, whereby preferably (c) and (d) which correspond to one round of restimulation is performed two times, more preferably three times, more preferably 4 times, and most preferably a T cell line for which more than 4 rounds of restimulation are performed.

In a preferred embodiment the activated T cell or T cells is a T cell clone against the carbohydrate epitope, whereby preferably (c) and (d) which correspond to one round of restimulation is performed two times, more preferably three times, more preferably 4 times, and most preferably a T cell line for which more than 4 rounds of restimulation are performed, and the cells are cloned at least once, for example by single cell dilution, before restimulation.

In a further preferred embodiment the invention provides a method for generation of a T cell clone against the carbohydrate epitope wherein said functional dendritic cell is a mature dendritic cell.

In a further preferred embodiment the invention provides a method for generation of a T cell clone against the carbohydrate epitope wherein said functional dendritic cell and the T cell or T cells are human cells.

In a further preferred embodiment the invention provides a method for generation of an activated T cell, a T cell clone or a T cell line against the carbohydrate epitope wherein said functional dendritic cell is derived from MUTZ-3 [patent applications 10139428.4 (DE), PCT/EP02/09260, 02758474.7 (EP), U.S. Ser. No. 10/486,966, CA2,457,287, DE10139428A1, WO2003/023023A1, EP01419240, US20040265998, CA2457287] such as but not limited to Nemod-DC (obtainable from Glycotope GmbH Berlin, Germany, www.glycotope.com).

In a further preferred embodiment the invention provides a method for generation of an activated T cell, a T cell clone or a T cell line against the carbohydrate epitope wherein said functional dendritic cell and the T cell or T cells are matched in at least one MHC class molecule.

In a preferred embodiment the invention provides an activated T cell, T cells, T cell clone or T cell line produced by any of the above described methods wherein the activated T cell, T cells, T cell clone or T cell line is directed against the carbohydrate epitope and/or a carbohydrate structure, carbohydrate conjugate or a mammalian cell comprising said carbohydrate epitope.

In a further preferred embodiment the invention provides an activated T cell, T cells, T cell clone or T cell line produced by any of the above described methods wherein the activated T cell, T cells, T cell clone or T cell line is directed against the carbohydrate epitope and/or a carbohydrate structure, carbohydrate conjugate or a mammalian cell comprising said carbohydrate epitope, and induces an effective carbohydrate specific cellular immune response against the carbohydrate epitope and/or cells and/or diseases associated with said carbohydrate epitope.

In a preferred embodiment of the invention, said induction of said effective carbohydrate specific cellular immune response occurs in at least one human or animal.

In another preferred embodiment of the invention, said induction of said effective carbohydrate specific cellular immune response is performed in vitro.

In a further preferred embodiment the invention provides the activated T cell or T cells against the carbohydrate epitope, the cell composition comprising T cells against the carbohydrate epitope, the T cell line against the carbohydrate epitope, or the T cell clone against the carbohydrate epitope obtained by a method as described above.

In a further preferred embodiment the invention provides the activated T cell or T cells against the carbohydrate epitope, the cell composition comprising T cells against the carbohydrate epitope, the T cell line against the carbohydrate epitope, or the T cell clone against the carbohydrate epitope as described above comprising at least one CD4+ helper cell against the carbohydrate epitope.

In a further preferred embodiment the invention provides the activated T cell or T cells against the carbohydrate epitope, the cell composition comprising T cells against the carbohydrate epitope, the T cell line against the carbohydrate epitope, or the T cell clone against the carbohydrate epitope as described above comprising at least one cytotoxic T cell against the carbohydrate epitope.

In a further preferred embodiment the invention provides the activated T cell or T cells against the carbohydrate epitope, the cell composition comprising at least one T cell against against the carbohydrate epitope, the T cell line against the carbohydrate epitope, or the T cell clone against the carbohydrate epitope as described above which kills at least one against the carbohydrate epitope positive tumor cell or a disease cell associated with the carbohydrate epitope or secretes molecules which mediate the killing of at least one tumor cell.

The activated T cell or T cells against the carbohydrate epitope, the cell composition comprising T cells against the carbohydrate epitope, the T cell line against the carbohydrate epitope, or the T cell clone against the carbohydrate epitope of the invention which kill at least one carbohydrate epitope positive tumor cell or disease cell or secrete molecules which mediate the killing of at least one tumor cell or disease cell means that said cytotoxic T cell or cells against against the carbohydrate epitope kill a carbohydrate epitope positive tumor cell or disease cell which can be determined either by using the according cellular immune response test described elsewhere herein measuring the secretion of INFgamma or TNFalpha or by a cytotoxicity test (such as cellular immune response test 5) wherein at least one labelled carbohydrate epitope positive tumor cell or disease cell is lysed by said T cells as principally known to those skilled in the art by using the T cells of the invention, for example CTL or Th1 cells or by inducing a specific CD4 T helper response which mediates the activation of according humoral and cellular immune responses which result in the killing of at least one carbohydrate epitope positive tumor cell.

Those skilled in the art are able to perform the described task by using the herein disclosed methods and material. They can determine the best conditions to obtain those functional dendritic cells or T cells, the best route of administration, and/or suitable compositions comprising those and/or and are further described in preferred embodiments for generation and use in patent applications DE10139428A1, WO2003/023023A1, EP01419240, US20040265998, CA2457287.

Said activated T cell or T cells against carbohydrate epitope means that the generated T cell, T cells or cell composition comprising T cells is positive for at least one of the cellular immune tests of the invention, preferably for two, more preferably for three and most preferably for all 4. Preferably they comprise at least one CD4+ helper cell, and even more preferably at least one cytotoxic T cell able to kill at least one carbohydrate epitope positive tumor cell.

Said T cell or T cells used for bringing into contact is either at least one CD4+ and/or CD8+ T-cell which was isolated or enriched before by standard methods known to those skilled in the art or is a cell composition which comprises at least one CD4+ and/or CD8+ T-cells.

Said lysate can be any lysate from a carbohydrate epitope positive microorganism or from a carbohydrate epitope positive tumor cell, respectively, such as but not limited to a lysate generated by repetitive freeze-thawing, by sonication, by mechanical force or by temperature induction.

For details on generation of the carbohydrate epitope specific T cells see example 12.

A functional dendritic cell is a cell which can activate a T cell.

Activation of a T cell means stimulation of proliferation and/or the conversion from a naïve to an active T cell. An active T cell secretes molecules which induce or help an immune response against the target the carbohydrate epitope or tumor cells or disease cells carrying the carbohydrate epitope, preferably those cytotoxic T cells which mediate the killing of a carbohydrate epitope positive tumor cell or disease cell.

In a preferred embodiment said functional dendritic cell is a mature dendritic cell. More preferred the dendritic cell precursor from which the mature cell is derived from is obtained from a human, more preferably from a human from which the T cell or T cells were also obtained or which are matched in at least one MHC class molecule. In a more preferred embodiment the functional dendritic cell is derived from MUTZ-3, and even further preferred the MUTZ-3 cells or cells derived therefrom were differentiated using Il-4 and GM-CSF, loaded with appropriate amounts of the carbohydrate positive microorganism, lysate or fraction thereof or the carbohydrate epitope carrying molecule or carbohydrate epitope positive tumor cell, lysate or fraction thereof, and further matured using for example suitable amounts of TNF-alpha to mature dendritic cells which correspond to the functional dendritic cells of the invention. In an even more preferred embodiment loaded functional dendritic cells are used together with PBMC (peripheral blood mononuclear cells) matched at least in MHC class I (HLA-A2) and (HLA-B44).

Those skilled in the art are able to determine the suitable conditions for generating functional dendritic cells loaded with the carbohydrate positive microorganism, lysate or fraction thereof or the carbohydrate epitope carrying molecule or the carbohydrate epitope positive tumor cell or disease cell, or the lysate or fraction thereof, as well as suitable amounts and enrichment or purification procedures of a T cell or T cells and suitable conditions for culturing both cells together, such as comprising times, media, culture conditions and additional factors needed. Functional dendritic cells are typically differentiated from precursor cells within 6-10 days and loaded and matured for another 1 to 2 days. Cultivation of said T cell or T cells together with said loaded functional dendritic cells is typically performed for 7 to 10 days, and the addition and cultivation of loaded functional dendritic cells for restimulation typically for 7 to 9 days for each round of restimulation. Further details are shown in the example 12.

In another preferred embodiment different dendritic cells or functional dendritic cells from different sources, such as MUTZ-3 derived and donor derived dendritic cells from a human, are used for the different steps of priming and restimulation. Those skilled in the art are able to select the best combination details.

The successful generation of a T cell, T cells or cell compositions comprising a T cell, T cells, CD4+ and/or CD8+ T cells against the carbohydrate epitope can be tested by using at least one cellular immune response test of the invention. Further details are described elsewhere herein. Preferably at least two cellular immune response tests are positive, more preferably three, more preferably four and most preferably all five.

Description used here for the dendritic cells, their usage and suitable conditions and molecules for its use is also valid for the cellular immune response tests described elsewhere herein and vice versa and will be valid for all other parts of the invention.

In another embodiment the invention provides an activated T cell against the carbohydrate epitope.

In another embodiment the invention provides T cells comprising at least one activated T cell against the carbohydrate epitope.

In another embodiment the invention provides a T cell line against the carbohydrate epitope. In another embodiment the invention provides a T cell clone against the carbohydrate epitope.

In a preferred embodiment the T cell line or T cell clone was generated using MUTZ-3 derived functional dendritic cells (such as Nemod-DC) loaded with the carbohydrate positive microorganism, the lysate or fraction thereof in combination with at least one round of restimulation with MUTZ-3 derived functional dendritic cells loaded with at least one carbohydrate epitope carrying molecule or carbohydrate epitope positive tumor cell or disease cell, or lysate or fraction thereof from a healthy donor, and even more preferred from a patient, and even more preferred from a patient whose disease or tumor is positive for binding with a carbohydrate binding molecule, preferably with a carbohydrate epitope specific antibody.

The invention further provides a method for generating at least one activated T cell for use as a tumor therapy comprising administering the activated T cells against the carbohydrate epitope positive tumor cells into a patient.

E) Methods for Inducing an Immune Shield Against Diseases Associated with the Carbohydrate Epitope and Methods for Preventing and/or Treating Diseases Associated with the Carbohydrate Epitope The invention provides a method for inducing or enhancing an effective carbohydrate specific cellular immune response and/or specific humoral immune response against said carbohydrate epitope, and/or a carbohydrate structure, carbohydrate conjugate or a mammalian cell comprising said carbohydrate epitope, in at least one animal or human. comprising administering in a human or an animal an effective amount of the formulation as described elsewhere herein.

In a preferred embodiment, the invention provides a method for inducing or enhancing an effective carbohydrate specific cellular immune response against said carbohydrate epitope, and/or a carbohydrate structure, carbohydrate conjugate or a mammalian cell comprising said carbohydrate epitope, in at least one animal or human. comprising administering in a human or an animal an effective amount of the formulation as described elsewhere herein, preferably said effective carbohydrate specific cellular immune response comprises activation of CD4 positive T cells of Th1 type and/or of CD8 positive cytotoxic T cells, more preferably said effective carbohydrate specific cellular immune response comprises activation of CD4 positive T cells of Th1 type and activation of CD8 positive cytotoxic T cells.

The induction of said effective carbohydrate specific cellular immune response is preferably measured by the cellular immune response tests as described elsewhere herein.

In a preferred embodiment the invention provides a method to treat a cancer patient or a patient suffering from a disease associated with the carbohydrate epitope comprising the administration of any of the activated T cell or T cells against the carbohydrate epitope, the cell composition comprising at least one T cell against the carbohydrate epitope, the T cell line against the carbohydrate epitope, or the T cell clone against the carbohydrate epitope as described above or a composition comprising those.

In a preferred embodiment the invention provides a method to treat a cancer patient or a patient suffering from a disease associated with the carbohydrate epitope comprising the administration of a suitable amount of at least one of the functional dendritic cells against the carbohydrate epitope as described above or a composition comprising those.

In a preferred embodiment the invention provides a method to treat a cancer patient wherein the patient has or had a cancer cell positive for the carbohydrate epitope.

In a more preferred embodiment the invention provides a method to treat a cancer patient or a patient suffering from a disease associated with the carbohydrate epitope wherein the functional dendritic cell is autologous In another preferred embodiment the invention provides a method to treat a cancer patient or a patient suffering from a disease associated with the carbohydrate epitope wherein the functional dendritic cell is allogeneic originating from a donor In a preferred embodiment the invention provides a method to treat a cancer patient or a patient suffering from a disease associated with the carbohydrate epitope wherein the functional dendritic cell is derived from MUTZ-3.

In a preferred embodiment the invention provides a method to treat a cancer patient or a patient suffering from a disease associated with the carbohydrate epitope wherein the functional dendritic cell shares at least one MHC class molecule with said patient.

The invention further provides a method to treat a cancer patient or a patient suffering from a disease associated with the carbohydrate epitope comprising the administration of any of the activated T cell or T cells against the carbohydrate epitope, the cell composition comprising at least one T cell against carbohydrate epitope, the T cell line against the carbohydrate epitope, or the T cell clone against the carbohydrate epitope described elsewhere herein or a composition comprising at least one of those.

The invention further provides a method to treat a cancer patient or a patient suffering from a disease associated with the carbohydrate epitope comprising the administration of a suitable amount of at least one of the functional dendritic cells against the carbohydrate epitope described elsewhere herein or a composition comprising those.

In a preferred embodiment of the invention at least one of said methods are used for a patient which has or had a cancer cell positive for the carbohydrate epitope which is detectable by at least one carbohydrate binding molecule or carbohydrate epitope specific antibody and in its preferred embodiment described elsewhere herein.

In a preferred embodiment of the invention at least one of said methods are used for a patient which has or had a disease associated with the carbohydrate epitope which is detectable by at least one carbohydrate binding molecule or carbohydrate epitope specific antibody as described elsewhere herein.

Further preferred are said methods wherein the functional dendritic cell is autologous, further preferred wherein the functional dendritic cell is allogeneic, further preferred when the functional dendritic cell originates from a donor, even more preferred when the functional dendritic cell is derived from MUTZ-3, even more preferred when any of the described functional dendritic cells shares at least one MHC class molecule with the individual it is administered to.

The invention provides a method for inducing or enhancing a specific humoral and/or cellular immune response against the carbohydrate epitope, the carbohydrate epitope carrying molecule or carbohydrate epitope positive tumor cells or carbohydrate epitope positive disease cells comprising administering in a human or an animal an effective amount of the nutraceutical, or the pharmaceutical composition, or the carbohydrate positive microorganism, or the fraction thereof which are described elsewhere herein, or formulations comprising those.

The invention provides a method for inducing an effective carbohydrate specific cellular immune response against the carbohydrate epitope, the carbohydrate epitope carrying molecule or carbohydrate epitope positive tumor cells or carbohydrate epitope positive disease cells comprising administering in a human or an animal an effective amount of the nutraceutical, or the pharmaceutical composition, or the carbohydrate positive microorganism, or the fraction thereof which are described elsewhere herein, or formulations comprising those.

In a preferred embodiment the invention provides a method for inducing an effective carbohydrate specific cellular immune response against the carbohydrate epitope in at least one individual comprising activation of Th1 type CD4 positive T helper cells and/or cytotoxic CD8 positive T cells against the carbohydrate epitope, detectable by at least one of the immune response tests described elsewhere herein.

In another preferred embodiment the invention provides a method for inducing an effective carbohydrate specific cellular immune response against the carbohydrate epitope in at least one individual comprising activation of Th1 type CD4 positive T helper cells and cytotoxic CD8 positive T cells against the carbohydrate epitope, detectable by at least one of the immune response tests described elsewhere herein.

The invention provides a method for inducing or enhancing a specific humoral and cellular immune response against the carbohydrate epitope, the carbohydrate epitope carrying molecule or carbohydrate epitope positive tumor cells or carbohydrate epitope positive disease cells comprising administering in a human or an animal an effective amount of the nutraceutical, or the pharmaceutical composition, or the carbohydrate positive microorganism, or the fraction thereof which are described elsewhere herein, or formulations comprising those.

The invention provides a method for inducing or enhancing a carbohydrate epitope specific immune response which functions as a shield against carbohydrate epitope positive cancer or disease cells by having the potential to destroy at least one carbohydrate epitope positive cancer or disease cell.

In a preferred embodiment the invention provides a method for inducing a carbohydrate epitope specific immune response which functions as a shield against carbohydrate epitope positive cancer cells by having the potential to destroy those cells as shown herein, for example by the induction of carbohydrate epitope specific antibodies, by the induction of a carbohydrate epitope specific complement dependent cytotoxicity of carbohydrate epitope specific antibodies against carbohydrate epitope positive tumor cells or disease cells killing those effectively, and/or by secretion of TNFalpha and/or INFgamma by carbohydrate epitope specific T cell responses which are scientifically recognized surrogate markers by those skilled in the art for a specific cytotoxic T cell mediated cell killing for those tumor cells or disease cells carrying the carbohydrate epitope, as shown in the examples and described herein, comprising administering in a human or an animal an effective amount of the nutraceutical, or the pharmaceutical formulation, or the carbohydrate positive microorganism, or the fraction thereof which are described elsewhere herein, or formulations comprising those.

The invention further provides a method for reducing or even further preferred for preventing the occurrence of a tumor, preferably a carbohydrate epitope positive tumor, comprising administering in a human or an animal an effective amount of the nutraceutical, or the pharmaceutical formulation, or the carbohydrate positive microorganism, or the fraction thereof which are described elsewhere herein, or formulations comprising those, preferably in a healthy individual.

The invention further provides a method for reducing or even further preferred for preventing the occurrence of a disease, preferably a carbohydrate epitope positive disease, comprising administering in a human or an animal an effective amount of the nutraceutical, or the pharmaceutical formulation, or the carbohydrate positive microorganism, or the fraction thereof which are described elsewhere herein, or formulations comprising those, preferably in a healthy individual.

The invention further provides a method for reducing or even further preferred for preventing the spread or metastasis of a tumor, preferably of a carbohydrate epitope positive tumor, comprising administering in a human or an animal an effective amount of the nutraceutical, or the pharmaceutical formulation, or the carbohydrate positive microorganism, or the fraction thereof which are described elsewhere herein, or formulations comprising those.

The invention provides a method to treat a tumor, preferably a carbohydrate epitope positive tumor, comprising administering in a human or an animal an effective amount of the nutraceutical, or the pharmaceutical formulation, or the carbohydrate positive microorganism, or the fraction thereof which are described elsewhere herein, or formulations comprising those.

The invention provides a method to treat a disease, preferably a disease associated with the carbohydrate epitope, comprising administering in a human or an animal an effective amount of the nutraceutical, or the pharmaceutical formulation, or the carbohydrate positive microorganism, or the fraction thereof which are described elsewhere herein, or formulations comprising those.

The invention provides a method for reducing or even further preferred for preventing the occurrence of a carbohydrate epitope positive disease or tumor comprising administering in a human or an animal an effective amount of the nutraceutical, or the pharmaceutical formulation, or the carbohydrate positive microorganism, or the fraction thereof which are described elsewhere herein, or formulations comprising those, preferably in a healthy individual.

In a preferred embodiment the present invention provides a method for the immunization or vaccination of a human or an animal against a carbohydrate epitope present on a molecule from a human or animal cell comprising (i) administration to a human or an animal of an effective amount of immune cells or a mixture of cells comprising at least one immune cell directed against the carbohydrate epitope as described elsewhere herein and induction of an immune response by said immune cell in the human or animal (priming) and ii) boostering of the immune response by the administration of an effective amount of a formulation as described elsewhere herein.

In a preferred embodiment the present invention provides a method for the immunization or vaccination of a human or an animal against a carbohydrate epitope present on a molecule from a human or animal cell comprising (i) administration to a human or an animal an effective amount of immune cells or a mixture of cells comprising at least one immune cell directed against the carbohydrate epitope a least once and induction of an immune response by said immune cell in the human or animal (priming) and ii) boostering of the immune response by the administration of an effective amount of a pharmaceutical composition comprising a carbohydrate-positive microorganism and/or a fraction thereof.

Said immune cell directed against the carbohydrate epitope can be selected from the group comprising dendritic cell or cells, dendritic cell line, T cell or cells, T cell line and or T cell clone or mixtures comprising those whereby said immune cell is directed against the carbohydrate epitope. Generation of said immune cells is described elsewhere herein.

In a preferred embodiment of the invention the administration of said immune cells and the priming is performed once.

In another preferred embodiment of the invention the administration of said immune cells and the priming is performed twice.

In another preferred embodiment of the invention the administration of said immune cells and the priming is performed at least three to five times.

In a preferred embodiment of the invention the boostering of the immune response by the administration of an effective amount of a pharmaceutical composition comprising a carbohydrate-positive microorganism and/or a fraction thereof is performed once.

In another preferred embodiment of the invention the boostering is performed 2-10 times, more preferably than 10 times, more preferably up to 20 times, most preferably boostering is performed continually at regular time intervals over a period of several month to several years.

In a preferred embodiment of the invention the boostering of the immune response is done 1-5 times close to the priming and thereafter at intervals from 3 month to 1 year or, 1 year to 10 years.

In a preferred embodiment the present invention provides a method for the induction of an effective carbohydrate-specific cellular and/or humoral immune response against a carbohydrate epitope, preferably a cytotoxic T cell response, present on a molecule from a human or animal cell comprising i) oral administration of a nutraceutical comprising a carbohydrate positive microorganism or a lysate or fraction thereof to a human or an animal ii) repeating the oral administration for the induction of an immune shield against the occurrence of a disease characterized by the presence of the carbohydrate epitope.

The nutraceutical of the present invention can be any food or food additive or dietary supplement or medical food or food of specified health use or food for special dietary use or functional food and can be applied in different forms as described elsewhere herein.

In a preferred embodiment of the invention the nutraceutical is administered at irregular intervals.

In a preferred embodiment of the invention the nutraceutical is administered at regular intervals from daily to weekly, more preferred is an initial regular application of at least weekly interval over a period of 1-6 month with subsequent irregular intervals of repeated administration.

In a preferred embodiment of the invention the nutraceutical is used as clinical food. In an even further preferred embodiment the nutraceutical is used before and/or after taking a biopsy, preferably a potential tumor. And even more preferably the nutraceutical is used before and/or after surgery of a tumor, preferably a tumor positive for the carbohydrate epitope. And even more preferably the nutraceutical is used in combination with other treatments.

In another preferred embodiment the present invention provides a method for the vaccination or immunization of a human or an animal against the carbohydrate epitope and/or carbohydrate epitope positive diseases or tumors comprising
- ii) administration to a human or an animal an effective amount of functional dendritic cells or a mixture of cells comprising at least one functional dendritic cell directed against the carbohydrate epitope at least once and induction of an immune response by said functional dendritic cells in the human or animal and
- iii) boostering of the immune response by the administration of an effective amount of a pharmaceutical composition comprising at least one carbohydrate positive microorganism and/or a fraction and/or a lysate thereof at least once.

In another preferred embodiment the present invention provides a method for the vaccination of a human or an animal against a carbohydrate epitope present on a molecule from a human or animal cell and/or carbohydrate epitope positive diseases or tumors comprising
- i) administration to a human or an animal an effective amount of activated T cells, T cell clone, T cell line or a mixture of cells comprising at least one activated T cell directed against the carbohydrate epitope a least once and induction of an immune response by said activated T cells in the human or animal and
- ii) boostering of the immune response by the administration of an effective amount of a pharmaceutical composition comprising the carbohydrate positive microorganism and/or a fraction and/or a lysate thereof at least once.

The generation of functional dendritic cells, activated T cells, T cell lines and T cell clones is described elsewhere herein.

In a preferred embodiment of the invention the administration according to the previous methods under (i) is performed once.

In another preferred embodiment of the invention the administration according to the previous methods under (i) is performed twice.

In another preferred embodiment of the invention the administration according to the previous methods under (i) is performed at least three to five times.

In a preferred embodiment of the invention the boostering of the immune response by the administration of an effective amount of a pharmaceutical composition according to (ii) of the previous methods is performed once, in another preferred embodiment of the invention the boostering is performed 2-10 times, more preferably more than 10 times, more preferably up to 20 times, most preferably boostering is performed continually at regular time intervals over a period of several month to several years.

In a preferred embodiment of the invention the boostering of the immune response is done 1-5 times close to the priming and thereafter at intervals from 3 month to 1 year or 1 year to 10 years.

In a preferred embodiment the invention provides a method for prophylaxis and/or treatment of a carbohydrate epitope positive tumor and/or disease comprising administration of a suitable amount of a formulation, a carbohydrate positive microorganism or fraction thereof, a functional dendritic cell or an activated T cell, T cell line or T cell clone against the carbohydrate epitope an/or a carbohydrate structure, carbohydrate conjugate or a mammalian cell comprising said carbohydrate epitope as described elsewhere herein to a human or an animal.

The invention provides a method for reducing or even further preferred for preventing the spread of a carbohydrate epitope positive disease comprising administering in a human or an animal an effective amount of the nutraceutical, or the pharmaceutical formulation, or the carbohydrate positive microorganism, or the fraction thereof which are described elsewhere herein, or formulations comprising those.

The invention provides a method to treat a carbohydrate epitope positive disease comprising administering in a human or an animal an effective amount of the nutraceutical, or the pharmaceutical formulation, or the carbohydrate positive microorganism, or the fraction thereof which are described elsewhere herein, or formulations comprising those.

The invention provides a method to strengthen the immune system or to improve an immune response comprising administering in a human or an animal an effective amount of the nutraceutical, or the pharmaceutical composition, or the carbohydrate positive microorganism, or the fraction thereof which are described elsewhere herein, or formulations comprising those. This can be for example but is not limited to a general improvement of the condition of the immune system for example against infectious diseases or tumors, an improvement of the activity of other immune stimulatory agents or probiotics or prebiotics, or an action as an adjuvans.

In a preferred embodiment the nutraceutical, or the pharmaceutical formulation, or the carbohydrate positive microorganism, or the fraction thereof which are described elsewhere herein, or formulations comprising those of above described methods comprises at least one mircoorganism, lysate or fraction selected from the group comprising the strain *Bacteroides ovatus* strain AG6 (DSM 18726), the strain *Bacteroides ovatus* MU1 (DSM 18728), and/or the strain *Escherichia coli* LH2 (DSM 18727), more preferably from the strain AG6 and/or MU1 deposited at the "DSMZ-Deutsche Sammlung von Mikroorganismen and Zellkulturen GmbH" in Braunschweig (Germany), by Glycotope GmbH, Robert-Rössle-Str. 10, 13125 Berlin (Germany) at the Oct. 20, 2006.

The term formulation means any substance or composition of substances in a suitable form for administration comprising at least one of the nutraceutical, the pharmaceutical composition, the carbohydrate positive microorganism or the fraction thereof which can comprise a pharmaceutically acceptable carrier or a carrier acceptable for food additives and/or nutraceutical or the nutraceutical, the pharmaceutical composition, the carbohydrate positive microorganism or the fraction thereof alone.

The term preventing the occurrence refers to using the nutraceutical, the pharmaceutical composition, the carbohydrate positive microorganism or the fraction thereof or formulations comprising those to a subject with the purpose to reduce the risk or the rate or the probability of developing a carbohydrate epitope positive cancer or a carbohydrate epitope positive disease.

The term reducing or preventing the spread of a tumor or carbohydrate epitope positive disease or metastasis of a tumor refers to using the nutraceutical, the pharmaceutical composition, the carbohydrate positive microorganism or the fraction thereof or formulations comprising those to a subject with the purpose to reduce the risk or the rate or the probability of metastasis or spread of the disease to other organs or other sites in the body or other individuals.

The term treating refers to using the nutraceutical, the pharmaceutical composition, the carbohydrate positive microorganism or the fraction thereof or formulations comprising those to an individual or subject with the purpose to cure, heal, alleviate, relieve, alter, remedy, ameliorate, improve, or affect cancer, the symptoms of cancer, the predisposition toward cancer, time of survival, or time to progression.

Said carbohydrate epitope positive disease or disease associated with said carbohydrate epitope or disease characterized by the presence of said carbohydrate epitope is any disease which is associated with a prion, virus, microorganism, bacterium or other biological material which can be bound by at least one of the carbohydrate binding molecules, preferably by at least one of the carbohydrate epitope specific antibodies or which is associated with a component of the body or occurring in the body of a human or animal such as but not limited to a cell, microorganism, virus or particle which is bound by at least one of the carbohydrate binding molecules, preferably bound by at least one of the carbohydrate epitope specific antibodies.

The "effective amount" of any of the nutraceutical, the pharmaceutical composition, the carbohydrate positive microorganism or the fraction thereof or formulations comprising those comprises living or dead microorganism, or lysates or fractions of these microorganisms which correspond to or are derived from about $1 \times 10^6$ to about $1 \times 10^{14}$ cfu per person per day (cfu/person/day) whereby cfu is a colony forming unit as a measure for one microorganism as such known to and can be determined by those skilled in the art.

In another embodiment of the invention the effective amount is the amount of the nutraceutical, the pharmaceutical composition, the carbohydrate positive microorganism or the fraction thereof or formulations comprising those which induces a humoral or cellular immune response against the carbohydrate epitope in at least one individual, preferably a humoral and a cellular immune response against the carbohydrate epitope, detectable by at least one of the immune response tests against the carbohydrate epitope described elsewhere herein. In another embodiment of the invention the effective amount is the amount of the nutraceutical, the pharmaceutical composition, the carbohydrate positive microorganism or the fraction thereof or formulations comprising those which induces an effective carbohydrate specific cellular immune response against the carbohydrate epitope in at least one individual, preferably comprising activation of Th1 type CD4 positive T helper cells and/or cytotoxic CD8 positive T cells against the carbohydrate epitope, detectable by at least one of the immune response tests described elsewhere herein.

In another embodiment of the invention the effective amount is the amount of the nutraceutical, the pharmaceutical composition, the carbohydrate positive microorganism or the fraction thereof or formulations comprising those which is required to confer an immune shield against carbohydrate epitope positive tumor cells, to have a prophylactic effect against cancer or to have a therapeutic effect against cancer, or to have a prophylactic or therapeutic effect against another carbohydrate epitope positive disease, each in at least one individual.

The effective amount for an individual or a group of individuals can be determined and/or optimized by those skilled in the art, preferably using at least one immune response test against the carbohydrate epitope described elsewhere herein and preferably those combinations of immune response tests against the carbohydrate epitope which are described elsewhere herein as preferred embodiments and/or clinical response tests known to those skilled in the art or described elsewhere herein.

These effective amounts can vary from above described amounts or dosages or preferred amounts or dosages described elsewhere herein for a person depending for example on the subject, on the number and time schedule of dosages, on the format or formulation of the nutraceutical, the pharmaceutical composition, the carbohydrate positive microorganism or fraction thereof, on the route and time scheme of administration, on the purpose it is used for such as prophylaxis or treatment, on the state of a carbohydrate epitope positive disease or cancer, and they can vary depending on the species, races and between an individual animal or individual human receiving the nutraceutical, the pharmaceutical composition, the carbohydrate positive microorganism or the fraction thereof or formulations comprising those. Those skilled in the art are able to determine the suitable and/or the optimal dosage, administration route and time scheme for an individual or for a group of individuals preferably by using the description and an embodiment of the invention described herein.

Preferred are those effective amounts and dosages of the nutraceutical, the pharmaceutical composition, the carbohydrate positive microorganism or the fraction thereof or formulations comprising those which induce or enhance said immune response against the carbohydrate epitope in more than one individual, more preferably in a significant number of individuals, more preferably in at least 10%, more preferably in at least 20%, more preferably in at least 30%, more preferably in at least 40%, more preferably in at least 50%, and most preferably in the majority of individuals In a preferred embodiment the effective amount is the amount of said nutraceutical, said pharmaceutical composition, said carbohydrate positive microorganism or said fraction thereof or said formulations comprising those which induces an immune response against the carbohydrate epitope in at least one individual.

In a preferred embodiment said induced or enhanced immune response is a humoral and a cellular immune response against the carbohydrate epitope, detectable by at least one of the humoral immune response tests 1 to 6 and one of the cellular immune response tests 1 to 5.

In a preferred embodiment, the effective amount is the amount of said nutraceutical, said pharmaceutical composition, said carbohydrate positive microorganism or said fraction thereof or said formulations comprising those which is required to confer an immune shield against carbohydrate epitope positive tumor cells, to have a prophylactic effect against cancer or to have a therapeutic effect against cancer, or to have a prophylactic or therapeutic effect against another carbohydrate epitope positive disease, each in at least one individual. In another preferred embodiment, the effective amount is the amount of said nutraceutical, said pharmaceutical composition, said carbohydrate positive microorganism or said fraction thereof or said formulations comprising those which induces the maximal or near to maximal immune response against the carbohydrate epitope in at least one individual.

In an even more preferred embodiment the preferred effective amount is the amount of the nutraceutical, the pharmaceutical composition, the carbohydrate positive microorganism or the fraction thereof or formulations comprising those which induces the maximal or near to maximal immune responses against carbohydrate epitope as detected in the immune response tests against the carbohydrate epitope by those skilled in the art, whereby this maximal immune response does not have to be such which is positive in all immune response tests but preferably such which gives the highest antibody responses or antibody titers against the the carbohydrate epitope and/or the highest T cell response against the carbohydrate epitope and more preferably against carbohydrate epitope positive tumor cells, more preferably both, and most preferably those which show at least in the humoral immune response tests 1 and 3 against the carbohydrate epitope the highest antibody titres and/or at least in the cellular immune response test 1 or 2 or 3 the highest T cell responses against the carbohydrate epitope.

In preferred embodiment, the effective amount of said nutraceutical, said pharmaceutical composition, said carbohydrate positive microorganism or said fraction thereof or said formulations comprising living or dead microorganism, or lysates or fractions of these microorganisms which correspond to or are derived from about $1 \times 10^6$ to about $1 \times 10^{14}$ cfu per individual per dose.

In a more preferred embodiment the effective amount of the nutraceutical, the pharmaceutical composition, the carbohydrate positive microorganism or the fraction thereof or formulations comprising those comprises living or dead microorganism, lysates or fractions of these microorganisms which correspond to or are derived from $1 \times 10^7$ to $1 \times 10^{13}$ cfu/person/day, more preferably to $2 \times 10^8$ to $1 \times 10^{12}$, and more preferably $1 \times 10^9$-$1 \times 10^{11}$ cfu/person/day.

The effective amounts or effective doses can also vary, as recognized by those skilled in the art, depending on the route of administration, excipient usage, and the possibility of co-usage with other agents, such as those for immune enhancement, for inducing an immune response, or building an immune shield, or preventing or treating cancer.

The effective amounts or effective doses can also vary, as recognized by those skilled in the art, depending on the format of use such as use as the nutraceutical, as the pharmaceutical composition, as the carbohydrate positive microorganism or as the fraction thereof or as the formulations comprising those as well as if they comprise living or dead microorganisms, lysates or fractions thereof, as well as on the number of doses as well as on the time intervals between doses. Those can be determined and optimized by those skilled in the art preferably by using the provided invention, tests and methods of the invention.

In a preferred embodiment, the nutraceutical is administered orally from more than one dose daily, to one dose daily, weekly, or monthly from a short term interval to a year long use, preferably daily or weekly use over 4 weeks to 2 years.

In another preferred embodiment, a single dose is administered to an individual.

In another preferred embodiment, multiple doses are administered to an individual.

In another preferred embodiment, the effective amount corresponds to a single dose.

In another preferred embodiment, the effective amount corresponds to multiple doses.

In a preferred embodiment, the pharmaceutical composition can be administered systemically for as little as only one dosage to many dosages, preferably weekly to monthly to 3 monthly or 6 monthly or a staggered combination thereof, and can be combined with a 6 monthly to yearly, to 5 yearly to ten yearly refreshment of the immunization.

In another preferred embodiment of the invention the effective dosage of the nutraceutical formulation comprising at least one carbohydrate positive microorganism or lysate or fraction thereof in humans is 0.1 mg/m$^2$-10 g/m$^2$, more preferred 10 mg/m$^2$-10 g/m$^2$, even more preferred 0.1 g/m$^2$-10 g/m$^2$.

In another preferred embodiment the formulation is administered first systemically with subsequent oral refreshments of the immunization.

The term administration means bringing into contact a human or an animal with an effective amount of the nutraceutical, the pharmaceutical composition, the carbohydrate positive microorganism or the fraction thereof or formulations comprising those for which additional carriers can be used. The routes of administration include any way to bring the human or animal into contact with the nutraceutical, the pharmaceutical composition, the carbohydrate positive microorganism or the fraction thereof or formulations comprising those. Preferred are those routes of administration, such as but not limited to oral administration, systemic administration, administration via inhalation or via bringing into contact with skin or another epidermis, which lead to an immune response against the carbohydrate epitope, to an immune shield against the carbohydrate epitope or carbohydrate epitope positive tumor cells, to a prophylactic effect against cancer or a therapeutic effect against cancer, which can be determined in its preferred forms as described above or elsewhere herein. Those skilled in the art can select the most suitable route of administration.

Examples for and preferred routes of administration and formulations are described in the following:

The nutraceuticals are preferably administered orally for example as either as capsules, tablets, emulsions, powder, liquids, in form of any food or drink, or as a component of a food or a drink such as a food additive. The nutraceutical can be given by itself or mixed with at least one other ingredient. The nutraceutical by itself or its mixture with at least one other ingredient can be given by itself or mixed into a food or a drink.

A formulation for oral administration of the nutraceutical, but also the pharmaceutical composition, the carbohydrate positive microorganism or the fraction thereof or formulations comprising those can be any orally acceptable dosage form or effective amount of the nutraceutical, the pharmaceutical composition, the carbohydrate positive microorganism or the fraction thereof or formulations comprising those including, but not limited to, tablets, capsules, nanoparticles, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

A formulation for oral administration can be any orally acceptable dosage form or effective amount of the nutraceutical, the pharmaceutical composition, the carbohydrate positive microorganism or the fraction thereof or formulations comprising those including, but not limited to, tablets, capsules, nanoparticles, emulsions and aqueous suspensions, dispersions and solutions. Commonly used carriers for tablets include lactose and corn starch. Lubricating agents, such as magnesium stearate, are also typically added to tablets. For oral administration in a capsule form, useful diluents include lactose and dried corn starch. When aqueous suspensions or emulsions are administered orally, the active ingredient can be suspended or dissolved in an oily phase combined with emulsifying or suspending agents. If desired, certain sweetening, flavoring, or coloring agents can be added.

The formulation of the present invention may be administered orally or parenterally. The parenteral administration includes injections such as drop infusion, hypodermic, intravenous or intramuscular injections, transdermal application with ointment or transdermal drug, and rectal application with suppository. Where the composition is administered orally, it may be prepared in the form of hard capsule, soft capsule, granule, powder, fine granule, pill, troche tablet, system of gradual active-ingredient delivery, liquid, and suspension. The preparation can be easily carried out by conventional methods in the pharmaceutical field.

The mode of administration and dosage forms will of course affect the therapeutic amounts of the compounds or compositions which are desirable and efficacious for the given treatment application. Where the formulation of the present invention is prepared in the form of oral administration, the composition may be prepared using conventional pharmaceutical ingredients in a normal medicine such as filler, extender, binder, disintegrator, surfactant, diluents such as lubricant and excipient. Particular example of the conventional ingredients includes recipients such as milk sugar, white sugar, sodium chloride, glucose, urea, starch, calcium carbonate, kaolin, crystal cellulose and silicic acid; binders such as water, ethanol, simple syrup, glucose liquid, starch liquid, gelatin solution, carboxymethyl cellulose, shellac, methyl cellulose, potassium phosphate and polyvinyl pyrrolidone; disintegrators such as dried starch, sodium alginate, agar powder, laminaran powder, sodium bicarbonate, calcium carbonate, polyoxyethylene sorbitan fatty acid esters, sodium lauryl sulfate, stearic acid monoglyceride, starch, and milk sugar; decay inhibitors such as white sugar, stearic acid, cacao butter and hydrogenated oil; absorbefacients such as quaternary ammonium salt and sodium lauryl sulfate; moisturizing agents such as glycerin and starch; absorbents such as starch, milk sugar, kaolin, bentonite and colloidal silicic acid; and lubricants such as purified talc and stearate. If necessary, the preparation further includes colorant, preservative, perfume, flavor agent and sweetening agent. Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid. In addition, pharmaceutically acceptable salts of compounds of the present invention may also be formed with a pharmaceutically acceptable cation, for instance, if a substituent group comprises a carboxy moiety. Suitable pharmaceutically acceptable cations are well known in the art and include alkaline, alkaline earth ammonium and quaternary ammonium cations.

In a preferred embodiment, the route of administration of the pharmaceutical composition is selected from the group consisting of intravenous injection, intraperitoneal injection, intramuscular injection, intracranial injection, intratumoral injection, intraepithelial injection, transcutaneous delivery, per oesophageal administration, intraabdominal administration, intraapendicular administration, intraarterial administration, intraarticular administration, intrabronchial administration, intrabuccal administration, intracapsular administration, intracardial administration, intracartilaginous administration, intracavitary administration, intracephalic administration, intracolic administration, intracutaneous administration, intracystic administration, intradermal administration, intraductal administration, intraduodenal administration, intrafascicular administration, intrafat administration, intrafilar administration, intrafissural administration, intragastric administration, intraglandular administration, intrahepatic administration, intraintestinal administration, intralamellar administration, intralesional administration, intraligamentous administration, intralingual administration, intramammary administration, intramedullary administration, intrameningeal administration, intramyocardial administration, intranasal administration, intraocular administration, intraoperative administration, intraoral administration, intraosseous administration, intraovarian administration, intrapancreatic administration, intraparietal administration, intrapelvic administration, intrapericardial administration, intraperineal administration, intraperitoneal administration, intraplacental administration, intrapleural administration, intrapontine administration, intraprostatic administration, intrapulmonary administration, intrarachidian administration, intrarectal administration, intrarenal administration, intrascleral administration, intrascrotal administration, intrasegmental administration, intrasellar administration, intraspinal administration, intrasplenic administration, intrasternal administration, intrastromal administration, intrasynovial administration, intratarsal administration, intratesticular administration, intrathoracic, administration, intratonsillar administration, intratracheal administration, intratubal administration, intratympanic administration, intraureteral administration, intraurethral administration, intrauterine administration, intravaginal administration, intravascular administration, intraventricular administration, intravertebral administration, intravesical administration, and intravitreous ad-ministration.

In a more preferred embodiment of the invention examples of routes of administration (=contacting) include parenteral, e.g., intravenous, intradermal, subcutaneous, oral, transdermal (topical), transmucosal, intraperitoneal, intranasal, rectal enteral and oral administration.

A formulation of the present invention can include pharmaceutically acceptable salts of the components therein. Pharmaceutically acceptable salts include the acid addition salts that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamino, 2-ethylamino ethanol, histidine, procaine and the like. Physiologically tolerable carriers are well known in the art. Exemplary of liquid carriers are sterile aqueous Solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium Chlorides, dextrose, propylene glycol, polyethylene glycol and other solutes. Liquid compositions can also contain liquid phases in addition to and to the exclusion of water. Exemplary of such additional liquid phases are glycerin, vegetable oils such as cottonseed oil, organic esters such as ethyl oleate, and water-oil emulsions. A formulation contains a carbohydrate positive microorganism, lysate or fraction thereof of the present invention, typically an amount of at least 0.1 weight percent of a carbohydrate positive microorganism, lysate or fraction thereof per weight of total composition. A weight percent is a ratio by weight of a carbohydrate positive microorganism, lysate or fraction thereof to total composition. Thus, for example, 0.1 weight percent is 0.1 grams of a carbohydrate positive microorganism carbohydrate positive microorganism, lysate or fraction thereof per 100 grams of total composition.

The term "pharmaceutically acceptable salt" refers to those salts of compounds which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, ptoluenesulfonic acid, salicylic acid and the like. Pharmaceutically acceptable salts include, for example, alkali metal salts, such as sodium and potassium, alkaline earth salts and ammonium salts.

The formulation comprising as the active ingredient carbohydrate positive microorganism, lysate or fraction thereof) may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874, to form osmotic therapeutic tablets for control release. A formulation according to the present invention may also, or alternatively, contain one or more drugs, which may be linked to a modulating agent or may be free within the composition. Virtually, any drug may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g. taxol or mitomycin C), antiinflammatories (e.g. ibuprofen and indomethacin), anthelmintics, antidepressants, antidotes, antiemetics, antihistamines, antihypertensives, antimalarials, antimicrotubule agents (e.g. colchicine or vinca alkaloids), antimigraine agents, antimicrobials, antiphsychotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g. cholera toxin), tranquilizers and urinary antiinfectives.

Formulations for oral use may also be presented as hard gelatin capsules where in the active ingredient is mixed with an inert solid diluent, for example calcium carbonate, calciumphosphate or kaolin, or as soft gelatin capsules wherein the active ingredient is mixed with water or an oil medium, for example peanut oil, liquid paraffin or olive oil. Aqueous suspensions contain the active materials in admixture with excipients suitable for the manufacture of aqueous suspensions. Such excipients are suspending agents, for example sodium carboxymethylcellulose, methylcellulose, hydroxypropylmethylcellulose, sodium alginate polyvinyl-pyrrolidone, gum tragacanth and gum acacia; dispersing or wetting agents may be a naturally occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such a polyoxyethylene with partial esters derived from fatty acids and hexitol anhydrides, for example polyoxyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose or Saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous Suspension by the addition of water provide the active ingredient in admixture with a dispersing or wetting agent, suspending agent and one or more preservatives. Suitable dispersing or wetting agents and suspending agents are exemplified, for example sweetening, flavouring and colouring agents, may also be present.

The formulation of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soya bean, lecithin, and esters or partial esters derived from fatty acids and hexitol anhydrides, for example sorbitan monooleate and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous Suspension. This Suspension may be formulated according to the known art using those suitable dispersing or wetting agents and suspending agents which have been mentioned above. The sterile injectable preparation may also be in a sterile injectable solution or Suspension in a non-toxic parenterally-acceptable diluent or solvent, for example as absolution in 1,3-butane diol. Among the acceptable vehicles and solvents that may be employed are water, Ringer's solution and isotonic sodium Chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables. Dosage levels of the order of from about 0.01 mg to about 140 mg per kilogram of body weight per: day are useful in the treatment of the above-indicated conditions (about 2.5 mg to about 7 g per patient per day). For example, a carbohydrate epitope positive tumor may be effectively treated by the administration of from about 0.01 to 50 mg of the compound per kilogram of body weight per day (about 0.5 mg to about 3.5 g per patient per day). The amount of active ingredient that may be combined with the carrier materials to produce a single dosage form will vary depending upon the host treated and the particular mode of administration. For example, a formulation intended for the oral administration of humans may vary from about 5 to about 95% of the total composition. Dosage unit forms will generally contain between from about 1 mg to about 10 g of active ingredient. It will be understood, however, that the specific dose level for any particular patient will depend upon a variety of factors including the activity of the specific compound employed, the age, body weight, general health, sex, diet time of administration, route of administration, rate of excretion, drug combination and the severity of the particular disease undergoing therapy. The dosage effective amount of compounds according to the invention will vary depending upon factors including the particular compound, toxicity, and inhibitory activity, the condition treated, and whether the compound is administered alone or with other therapies. Typically a dosage effective amount will range from about 0.0001 mg/kg to 1500 mg/kg, more preferably 1 to 1000 mg/kg, more preferably from about 1 to 150 mg/kg of body weight, and most preferably about 50 to 100 mg/kg of body weight. The invention relates also to a process or a method for the treatment of the abovementioned pathological conditions. The compounds of the present invention can be administered prophylactically or therapeutically, preferably in an amount that is effective against the mentioned disorders, to a warm-blooded animal, for example a human, requiring such treatment, the compounds are preferably being used in the form of pharmaceutical compositions or nutraceuticals.

Formulation of pharmaceutically-acceptable excipients and carrier Solutions is well-known to those of skill in the art, as is the development of suitable dosing and treatment regimens for using the particular compositions described herein in a variety of treatment regimens, including e.g., oral, parenteral, intravenous, intranasal, and intra-muscular administration and formulation.

A. Oral Delivery

In certain applications, the formulations disclosed herein may be delivered via oral administration to a human or an animal. As such, these compositions may be formulated with an inert diluent or with an assimilable edible carrier, or they may be enclosed in hard- or soft-shell gelatin capsule, or they may be compressed into tablets, or they may be incorporated directly with the food of the diet.

The active compounds may even be incorporated with excipients and used in the form of ingestible tablets, buccal tables, troches, capsules, elixirs, suspensions, syrups, wafers, and the like. The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or Saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. A syrup of elixir may contain the active compound sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

Typically, these formulations may contain at least about 0.1% of the active compound or more, although the percentage of the active ingredient (s) may, of course, be varied and may conveniently be between about 1 or 2% and about 60% or 70% or more of the weight or volume of the total formulation. Naturally, the amount of active compound(s) in each therapeutically useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

For oral administration the compositions of the present invention may alternatively be incorporated with one or more excipients in the form of a mouthwash, dentifrice, buccal tablet, oral spray, or sublingual orally-administered formulation. For example, a mouthwash may be prepared incorporating the active ingredient in the required amount in an appropriate solvent, such as a sodium borate solution (Dobell's Solution). Alternatively, the active ingredient may be incorporated into an oral solution such as one containing sodium borate, glycerin and potassium bicarbonate, or dispersed in a dentifrice, or added in a therapeutically-effective amount/ effective dose to a composition that may include water, binders, abrasives, flavoring agents, foaming agents, and humectants. Alternatively the compositions may be fashioned into a tablet or solution form that may be placed under the tongue or otherwise dissolved in the mouth.

B. Injectable Delivery

In certain circumstances it will be desirable to deliver the formulations disclosed herein parenterally, intravenously, intramuscularly, or even intraperitoneally. Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous Solutions or dispersions and sterile powders for the extemporaneous preparation of sterile injectable Solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g. glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be facilitated by various antibacterial and antifungal agents, for example, parabens, chlorobutanol, phenol, sorbic acid, thimerosal, and the like. In many cases, it will be preferable to include isotonic agents, for example, sugars or sodium Chloride. Prolonged absorption of the injectable compositions can be brought about by the use in the compositions of agents delaying absorption, for example, aluminum monostearate and gelatin.

For parenteral administration in an aqueous solution, for example, the solution should be suitably buffered if necessary and the liquid diluent first rendered isotonic with sufficient saline or glucose. These particular aqueous Solutions are especially suitable for intravenous, intramuscular, subcutaneous and intraperitoneal administration. In this connection, a sterile aqueous medium that can be employed will be known to those of skill in the art in light of the present disclosure. For example, one dosage may be dissolved in 1 ml of isotonic NaCl solution and either added to 1000 ml of hypodermoclysis fluid or injected at the proposed site of infusion. Some Variation in dosage will necessarily occur depending on the condition of the subject being treated. The person responsible for administration will, in any event, determine the appropriate dose for the individual subject. Moreover, for human administration, preparations should meet sterility, pyrogenicity, and the general safety and purity Standards as required by national or regional Offices of biologics Standards.

Sterile injectable Solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable Solutions, the preferred methods of preparation are vacuum-drying and freeze-drying techniques which yield a powder of the active ingredient plus any additional desired ingredient from a previously sterile-filtered solution thereof.

The compositions disclosed herein may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, Solutions will be administered in a manner compatible with the dosage formulation and in such amount as is therapeutically effective. The formulations are easily administered in a variety of dosage forms such as injectable Solutions, drug-release capsules, and the like.

As used herein, "carrier" includes any and all solvents, dispersion media, vehicles, coatings, diluents, antibacterial and antifungal agents, isotonic and absorption delaying agents, buffers, carrier Solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically-acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid Solutions or suspensions; solid forms suitable for solution in, or Suspension in, liquid prior to injection can also be prepared. The preparation can also be emulsified.

In another preferred embodiment the invention provides a method to induce or enhance a carbohydrate epitope specific immune response and/or to prevent or treat a carbohydrate epitope positive disease wherein said nutraceutical, said pharmaceutical composition, said carbohydrate positive microorganism or said fraction thereof or said formulations comprising those is administered to a healthy individual In another preferred embodiment the invention provides a method to induce or enhance a carbohydrate epitope specific immune response and/or to prevent or treat a carbohydrate epitope positive disease wherein said nutraceutical, said pharmaceutical composition, said carbohydrate positive microorganism or said fraction thereof or formulations comprising those is administered to an individual with disease associated with the carbohydrate epitope, a cancer, a tumor, at least one tumor or cancer cell, or at least one metastasis.

In particular, the nutraceutical, the pharmaceutical composition, the carbohydrate positive microorganism or the fraction thereof or formulations comprising those can be used to induce an immune response against a cancer, tumor, cancer cell, or cancer cells or the metastasis derived therefrom, to induce an immune response which functions as an immune shield against tumor cells, a cancer, tumor, cancer cell, or cancer cells or the metastasis derived therefrom, to treat a tumor or cancer, metastases and/or metastasis, and/or to reduce or to prevent the occurrence, spread or metastasis of a cancer, tumor, cancer cell, or cancer cells or the metastasis derived therefrom in healthy individuals or patients, respectively, each preferably comprising at least one carbohydrate epitope positive tumor cell, selected from a cancers, tumor or cancerous or tumorous diseases as described below or elsewhere herein. For example, the treatment is directed against primary tumors or cancers, minimal residual tumor or cancer diseases, relapses and/or metastases or parts thereof. The treatment of the tumors or cancers can also be effected as an adjuvant treatment. The nutraceutical, the pharmaceutical composition, the carbohydrate positive microorganism or the fraction thereof or formulations comprising those can also be used in the prophylaxis of carbohydrate positive positive tumor diseases, tumors or tumor cells. For example, prophylactic use is directed to the prophylaxis of tumors and metastases. These anti-tumor agents are administered in a suitable form according to well-known methods or as described elsewhere herein. A preferred variant is injection or administration of these anti-tumor agents or drugs orally, intravenously, locally in body cavities, e.g. intraperitoneal, intrarectal, intragastrointestinal routes, locally, e.g. directly in a tumor, in organs or lymphatic vessels (intranodal), but also subcutaneously, intradermally or on the skin, and intramuscularly. In a preferred fashion, types of administration can also be combined, in which case administration can be effected on different days of treatment or on one day of treatment as described in detail elsewhere herein. According to the invention, it is also possible to combine two or more of the inventive nutraceuticals, pharmaceutical compositions, carbohydrate positive microorganism s or the fractions thereof or formulations comprising those as well as combine one or a combination of those with one or more drugs or tumor treatments, such as antibody therapies, chemotherapies or radiotherapies, suitably administered or applied at the same time or separately in time.

The cancer, tumor, tumor cells, cancer cells or the metastasis derived therefrom is selected from the group of cancerous diseases or tumor diseases of the ear-nose-throat region, of the lungs, mediastinum, gastrointestinal tract, urogenital system, gynecological system, breast, endocrine system, skin, bone and soft-tissue sarcomas, mesotheliomas, melanomas, neoplasms of the central nervous system, cancerous diseases or tumor diseases during infancy, lymphomas, leukemias, paraneoplastic syndromes, metastases with unknown primary tumor (CUP syndrome), peritoneal carcinomatoses, immunosuppression-related malignancies and/or tumor metastases.

More specifically, the cancer, tumor, tumor cells, cancer cells or the metastasis derived therefrom may comprise the following types of cancer: adenocarcinoma of breast, prostate and colon; all forms of lung cancer starting in the bronchial tube; bone marrow cancer, melanoma, hepatoma, neuroblastoma; papilloma; apudoma, choristoma, branchioma; malignant carcinoid syndrome; carcinoid heart disease, carcinoma (for example, Walker carcinoma, basal cell carcinoma, squamobasal carcinoma, Brown-Pearce carcinoma, ductal carcinoma, Ehrlich tumor, in situ carcinoma, cancer-2 carcinoma, Merkel cell carcinoma, mucous cancer, non-parvicellular bronchial carcinoma, oat-cell carcinoma, papillary carcinoma, scirrhus carcinoma, bronchio-alveolar carcinoma, bronchial carcinoma, squamous cell carcinoma and transitional cell carcinoma); histiocytic functional disorder; leukemia (e.g. in connection with B cell leukemia, mixed-cell leukemia, null cell leukemia, T cell leukemia, chronic T cell leukemia, HTLV-II-associated leukemia, acute lymphocytic leukemia, chronic lymphocytic leukemia, mast cell leukemia, and myeloid leukemia); malignant histiocytosis, Hodgkin disease, non-Hodgkin lymphoma, solitary plasma cell tumor; reticuloendotheliosis, chondroblastoma; chondroma, chondrosarcoma; fibroma; fibrosarcoma; giant cell tumors; histiocytoma; lipoma; liposarcoma; leukosarcoma; mesothelioma; myxoma; myxosarcoma; osteoma; osteosarcoma; Ewing sarcoma; synovioma; adenofibroma; adenolymphoma; carcinosarcoma, chordoma, craniopharyngioma, dysgerminoma, hamartoma; mesenchymoma; mesonephroma, myosarcoma, ameloblastoma, cementoma; odontoma; teratoma; thymoma, chorioblastoma; adenocarcinoma, adenoma; cholangioma; cholesteatoma; cylindroma; cystadenocarcinoma, cystadenoma; granulosa cell tumor; gynadroblastoma; hidradenoma; islet-cell tumor; Leydig cell tumor; papilloma; Sertoli cell tumor, theca cell tumor, leiomyoma; leiomyosarcoma; myoblastoma; myoma; myosarcoma; rhabdomyoma; rhabdomyosarcoma; ependymoma; ganglioneuroma, glioma; medulloblastoma, meningioma; neurilemmoma; neuroblastoma; neuroepithelioma, neurofibroma, neuroma, paraganglioma, non-chromaffin paraganglioma, angiokeratoma, angiolymphoid hyperplasia with eosinophilia; sclerotizing angioma; angiomatosis; glomangioma; hemangioendothelioma; hemangioma; hemangiopericytoma, hemangiosarcoma; lymphangioma, lymphangiomyoma, lymphangiosarcoma; pinealoma; cystosarcoma phylloides; hemangiosarcoma; lymphangiosarcoma; myxosarcoma, ovarian carcinoma; sarcoma (for example, Ewing sarcoma, experimentally, Kaposi sarcoma and mast cell sarcoma); neoplasms (for example, bone neoplasms, breast neoplasms, neoplasms of the digestive system, colorectal neoplasms, liver neoplasms, pancreas neoplasms, hypophysis neoplasms, testicle neoplasms, orbital neoplasms, neoplasms of the head and neck, of the central nervous system, neoplasms of the hearing organ, pelvis, respiratory tract and urogenital tract); neurofibromatosis and cervical squamous cell dysplasia, and/or metastases derived from anyone of these.

In a preferred embodiment the cancer, tumor, tumor cells, cancer cells or the metastasis derived therefrom is selected from the group of cancerous diseases or tumor diseases comprising at least one cell or preferably a significant number of cells or more preferably a majority of tumor cells which are positive for carbohydrate epitope in the definition according to the invention, selected from the group of: tumors of the ear-nose-throat region, comprising tumors of the inner nose, nasal sinus, nasopharynx, lips, oral cavity, oropharynx, larynx, hypopharynx, ear, salivary glands, and paragangliomas, tumors of the lungs, comprising non-parvicellular bronchial carcinomas, parvicellular bronchial carcinomas, tumors of the mediastinum, tumors of the gastrointestinal tract, comprising tumors of the esophagus, stomach, pancreas, liver, gallbladder and biliary tract, small intestine, colon and rectal carcinomas and anal carcinomas, urogenital tumors comprising tumors of the kidneys, ureter, bladder, prostate gland, urethra, penis and testicles, gynecological tumors comprising tumors of the cervix, vagina, vulva, uterine cancer, malignant trophoblast disease, ovarian carcinoma, tumors of the uterine tube (Tuba Faloppii), tumors of the abdominal cavity, mammary carcinomas, tumors of the endocrine organs, comprising tumors of the thyroid, parathyroid, adrenal cortex, endocrine pancreas tumors, carcinoid tumors and carcinoid syndrome, multiple endocrine neoplasias, bone and soft-tissue sarcomas, mesotheliomas, skin tumors, melanomas comprising cutaneous and intraocular melanomas, tumors of the central nervous system, tumors during infancy, comprising retinoblastoma, Wilms tumor, neurofibromatosis, neuroblastoma, Ewing sarcoma tumor family, rhabdomyosarcoma, lymphomas comprising non-Hodgkin lymphomas, cutaneous T cell lymphomas, primary lymphomas of the central nervous system, Hodgkin's disease, leukemias comprising acute leukemias, chronic myeloid and lymphatic leukemias, plasma cell neoplasms, myelodysplasia syndromes, paraneoplastic syndromes, metastases with unknown primary tumor (CUP syndrome), peritoneal carcinomatosis, immunosuppression-related malignancy comprising AIDS-related malignancies such as Kaposi sarcoma, AIDS-associated lymphomas, AIDS-associated lymphomas of the central nervous system, AIDS-associated Hodgkin disease, and AIDS-associated anogenital tumors, transplantation-related malignancy, metastasized tumors comprising brain metastases, lung metastases, liver cancer, liver metastases, bone metastases, pleural and pericardial metastases, and malignant ascites, and/or metastases derived from anyone of these.

In another preferred embodiment the cancer, tumor, tumor cells, cancer cells or the metastasis derived therefrom is selected from the group comprising cancerous diseases or tumor diseases such as mammary carcinomas, gastrointestinal tumors, including colon carcinomas, stomach carcinomas, pancreas carcinomas, colon cancer, early gastric cancer, small intestine cancer, ovarian carcinomas, cervical carcinomas, lung cancer, prostate cancer, renal cell carcinomas, malignant melanoma, and/or liver cancer, and/or metastases derived from anyone of these.

In a further preferred embodiment the cancer, tumor, tumor cells, cancer cells or the metastasis derived therefrom is selected from the group of cancerous diseases or tumor diseases comprising at least one cell, preferably a significant number of cells, or more preferably a majority of tumor cells, which are positive for carbohydrate epitope in the definition according to the invention, selected from the group of mammary carcinomas, gastrointestinal tumors, including colon carcinomas, stomach carcinomas, pancreas carcinomas, colon cancer, early gastric cancer, small intestine cancer, ovarian carcinomas, cervical carcinomas, lung cancer, prostate cancer, renal cell carcinomas, malignant melanoma, and/or liver cancer, and/or metastases derived from anyone of these.

In another preferred embodiment the invention provides a method to induce or enhance a carbohydrate epitope specific immune response and/or to prevent or treat a carbohydrate epitope positive disease, the cancer, a tumor, at least one tumor or cancer cell, or at least one metastasis comprise at least one cell which is carbohydrate epitope positive.

In further preferred embodiment the invention provides a method to induce or enhance a carbohydrate epitope specific immune response and/or to prevent or treat a carbohydrate epitope positive disease wherein the individual has a cancer, a tumor, at least one tumor or cancer cell, or at least one metastasis selected from the group of cancerous diseases or tumor diseases comprising mammary carcinomas, gastrointestinal tumors, including colon carcinomas, stomach carcinomas, pancreas carcinomas, colon cancer, early gastric cancer, small intestine cancer, ovarian carcinomas, cervical carcinomas, lung cancer, prostate cancer, renal cell carcinomas, malignant melanoma, and/or liver cancer, and/or metastases derived from anyone of these.

In a preferred embodiment of the invention the disease associated with the carbohydrate epitope or carbohydrate epitope positive disease is selected from the group comprising gastrointestinal disorders, whipple's disease, arthritis, sarcoidosis, septicemia or osteoradionecrosis.

The gastrointestinal disorders are preferably selected from the group comprising functional bowel disorders and inflammatory bowel diseases; whereby the inflammatory bowel diseases are selected form the group comprising Crohn's disease, ileitis, and/or ulcerative colitis and the functional bowel disorders are selected form the group comprising gastroesophageal reflux, dyspepsia, irritable bowel syndrome and/or functional abdominal pain. The gastrointestinal tract in the context of the invention consists of the following components: mouth (buccal cavity; includes salivary glands, mucosa, teeth and tongue), pharynx, esophagus and cardia, stomach, which includes the antrum and pylorus, bowel or intestine: small intestine, which has three parts: duodenum, jejunum, ileum; large intestine, which has three parts: cecum (the vermiform appendix is attached to the cecum); colon (ascending colon, transverse colon, descending colon and sigmoid flexure); rectum and/or anus.

Diseases associated with the carbohydrate epitope in the meaning of the invention are also diseases entirely or partially due to the formation of autoantibodies and their damaging effect on the overall organism or organ systems, i.e., due to autoaggression. A classification into organ-specific, intermediary and/or systemic autoimmune diseases can be made. Preferred organ-specific autoimmune diseases are HASHIMOTO thyroiditis, primary myxedema, thyrotoxicosis (BASEDOW disease), pernicious anemia, ADDISON disease, myasthenia gravis and/or juvenile diabetes mellitus. Preferred intermediary autoimmune diseases are GOODPASTURE syndrome, autoimmune hemolytic anemia, autoimmune leukopenia, idiopathic thrombocytopenia, pemphigus vulgaris, sympathetic ophthalmia, primary bile cirrhosis, autoimmune hepatitis, colitis ulcerosa and/or SJÖGREN syndrome. Preferred systemic autoimmune diseases are rheumatoid arthritis, rheumatic fever, systemic lupus erythematodes, dermatomyositis/polymyositis, progressive systemic sclerosis, WEGENER granulomatosis, panarteritis nodosa and/or hypersensitivity angiitis. Typical autoimmune diseases are thyrotoxicosis, thyroid-caused myxedema, HASHIMOTO thyroiditis, generalized endocrinopathy, pernicious anemia, chronic gastritis type A, diseases of single or all corpuscular elements of the blood (for example, autoimmune hemolytic anemia, idiopathic thrombocytopenia or thrombocytopathy; idiopathic leukopenia or agranulocytosis), pemphigus vulgaris and pemphigoid, sympathetic ophthalmia, and numerous forms of uveitis, primarily biliary liver cirrhosis and chronic aggressive autoimmune hepatitis, diabetes mellitus type I, CROHN disease and colitis ulcerosa, SJÖGREN syndrome, ADDISON disease, lupus erythematodes disseminatus and discoid form of said disease, as dermatomyositis and scleroderma, rheumatoid arthritis (=primarily chronic polyarthritis), antiglomerular basement membrane nephritis. The basis is an aggressive immune reaction due to breakdown of the immune tolerance to self-determinants and a reduction of the activity of T suppressor cells (with lymphocyte marker T8) or an excess of T helper cells (with lymphocyte marker T4) over the suppressor cells; furthermore, formation of autoantigens is possible e.g. by coupling of host proteins to haptens (e.g. drugs), by ontogenetic tissue not developing until self-tolerance has developed, by protein components demasked as a result of conformational changes of proteins in connection with e.g. infection by viruses or bacteria; and by new proteins formed in connection with neoplasias.

Septicemic diseases in the meaning of the invention are diseases due to continuous or periodic invasion of pathogenic bacteria and/or their toxins from a focus of disease and their spreading on the lymph-blood route to form a general or local infection.

Septicemia in the meaning of the invention is preferably wound septicemia (phlegmon, thrombophlebitis, lymphangitis), puerperal septicemia (in case of puerperal fever), otogenic septicemia (in case of otitis media), tonsillogenic septicemia (in case of angina, peritonsillitis), cholangitic septicemia (in case of purulent cholecystitis, cholangitis), pylephiebitic septicemia (in case of pylephlebitis) umbilical septicemia (in case of omphalitis etc.), urosepticemia, as well as dental granuloma. Septicemia in the meaning of the invention can be acute to highly acute (foudroyant), subacute (e.g. as endocarditis lenta) or chronic, and of course, can also be neonatal septicemia.

Therefore, septicemias in the meaning of the invention are all pathogenic changes in a patient which can be associated with intermittent fever and cold chills, with spleen tumor, toxic reactions or damage of the bone marrow or blood (polynuclear leukocytosis, anemia, hemolysis, thrombocytopenia) or with pathogenic reactions in the heart and vasomotor nerve (tachycardia, centralization of the blood circulation, edemas, oliguria; possibly shock) or in the digestive tract (dry, coated tongue, diarrhea), or with septicopyemia (pyemia with formation of septic infarction and metastatic abscess).

In the meaning of the invention, preferred diseases include: AIDS, acne, albuminuria (proteinuria), alcohol withdrawal syndrome, allergies, alopecia (loss of hair), ALS (amyotrophic lateral sclerosis), Alzheimer's disease, retinal macula senile degeneration, anemia, thalassemia, anxiety syndrome, anthrax (milzbrand) aortic sclerosis, occlusive arterial disease, arteriosclerosis, arterial occlusion, arteriitis temporalis, arteriovenous fistula, asthma, respiratory insufficiency, autoimmune disease, prolapsed intervertebral disc, inflammation of the peritoneum, pancreatic cancer, Becker muscular dystrophy, benign prostate hyperplasia (BPH), bladder carcinoma, hemophilia, bronchial carcinoma, breast cancer, BSE, chlamydia infection, chronic pain, cirrhosis, commotio cerebri (brain concussion), Creutzfeld-Jacob disease, intestinal carcinoma, intestinal tuberculosis, depression, diabetes insipidus, diabetes mellitus, diabetes mellitus juvenilis, diabetic retinopathy, Duchenne muscular dystrophia, duodenal carcinoma, dystrophia musculorum progressiva, dystrophia, Ebola, eczema, erectile dysfunction, obesity, fibrosis, cervix cancer, uterine cancer, cerebral hemorrhage, encephalitis, loss of hair, hemiplegia, hemolytic anemia, hemophilia, urinary incontinence, pet allergy (animal hair allergy), skin cancer, herpes zoster, cardiac infarction, cardiac insufficiency, cardiovalvulitis, cerebral metastases, cerebral stroke, cerebral tumor, testicle cancer, ischemia, Kahler's disease (plasmocytoma), polio (poliomyelitis), rarefaction of bone, colon carcinoma, contact eczema, palsy, liver cirrhosis, leukemia, pulmonary fibrosis, lung cancer, pulmonary edema, lymph node cancer, (Morbus Hodgkin), lymphogranulomatosis, lymphoma, lyssa, gastric carcinoma, meningitis, mucoviscidosis (cystic fibrosis), multiple sclerosis (MS), myocardial infarction, neurodermitis, neurofibromatosis, neuronal tumors, kidney cancer (kidney cell carcinoma), osteoporosis, pancreas carcinoma, pneumonia, polyarthritis, polyneuropathies, potency disorders, progressive systemic sclerosi (PSS), prostate cancer, rectum carcinoma, pleurisy, craniocerebral trauma, vaginal carcinoma, sinusitis, esophagus cancer, tremor, tuberculosis, tumor pain, burns/scalds, intoxications, viral meningitis, menopause, soft-tissue sarcoma, soft-tissue tumor, cerebral blood circulation disorders, CNS tumors.

For testing, a study with healthy human volunteers should be performed, wherein serum antibody titers against Core-1 are determined by using at least one of the humoral immune response tests 1 to 6 determining the existing antibody response against Core-1 before first application of the nutraceutical and preferably volunteers with no or lower anti-Core-1 antibody levels are selected for the human trial. In those volunteers the nutraceutical comprising AG6 or MU1 or a placebo should be orally given over a period of 3 to 30 weeks. Oral application of at least two different dosages should be performed. Immune responses are followed by determination of the antibody and/or T cell response against Core-1 by using at least one of the humoral response tests 1 to 6 and/or cellular immune response tests 1 to 5 prior to and in suitable intervals after start of oral administration of the nutraceutical. If a formulation has the desired characteristics, there is a significant elevation of the antibody response against Core-1 and/or T cell response against Core-1 observed in a significant number of volunteers in the volunteer group that receives the nutraceutical in comparison to the titer before the study as positively tested by being positive in at least one of the humoral immune response tests 1 to 6 and/or in at least one of the cellular immune response tests 1 to 5. In the placebo group elevation of antibody or T-cell response against Core-1 should be less frequently observed or to a lesser extent.

This shows the effectiveness of the nutraceutical in humans for building an immune response against Core-1 which functions as a shield against Core-1 positive cancer cells for the prevention, reduction or spread of Core-1 positive tumors or metastasis or its treatment.

For testing the therapeutic potential, a study should be performed with human immuno competent cancer patients with Core-1 positive tumors which underwent surgery for removing the bulk tumor. Serum antibody titers against Core-1 are then determined by using at least one of the humoral immune response tests 1 to 6 for determining the existing antibody response against Core-1 before first application of the pharmaceutical composition. The pharmaceutical composition comprising AG6 or MU1 or a placebo are administered several times orally, intra peritoneally or intra venously over a period of 3 to 70 weeks. Administration of at least two different suitable dosages is performed. Immune responses are followed by determination of the antibody and/or T cell response against Core-1 by using at least one of the humoral response tests 1 to 6 and/or cellular immune response tests 1 to 5 and/or the clinical response are followed by determination of time to progression, tumor free survival and/or tumor volumes and/or sites, each prior to and in suitably intervals after start of the administration of the pharmaceutical composition. There is a significant elevation of the antibody response against Core-1 and/or of the T cell response against Core-1 observed in a significant number of volunteers in the group that receives the formulation of the invention in comparison to the titre before the study as positively tested by being positive in at least one of the humoral immune response tests 1 to 6 and/or in at least one of the cellular immune response tests 1 to 5 and/or a partial or complete clinical response or a elongated time to progression or time of survival in a significant number of the patients receiving the formulation. In the placebo group elevation of antibody or T-cell response against Core-1 is less frequently observed or to a lesser extend and/or no or a significantly lower clinical response is observed.

This may show the effectiveness of the pharmaceutical composition in humans for building an immune response against Core-1 which functions as a shield against Core-1 positive cancer cells for the prevention, reduction or spread of the occurrence of Core-1 positive tumors or metastasis or its treatment.

The contacting of the Core-1 positive microorganism or fraction thereof within the body of the living organism (human/animal) can initiate the production of antibodies binding Core-1, the Core-1 antigen, or Core-1 positive tumor cells in a significant number of humans or animals.

Surprisingly, antibodies against Core-1 can function as an immunosurveillance mechanism against newly arising cancer cells. Even more surprising, a Core-1 specific cellular immune response comprising activation of CD4 positive T cells of Th1 type and/or activation of CD8 positive cytotoxic T cells directed against Core-1, and/or a carbohydrate structure, carbohydrate conjugate or a mammalian cell comprising said carbohydrate epitope can be achieved in a significant number of humans or animals.

In a study with healthy human volunteers serum antibody titers against Tn or Lewis- or Lewis-Y can be determined by using at least one of the humoral immune response tests 1 to 6 determining the existing antibody response against Tn or Lewis Y before first application of the nutraceutical and preferably volunteers with no or lower Tn or Lewis Y antibody levels are selected for the human trial. In those volunteers the nutraceutical comprising a Tn positive microorganism, or a Lewis-Y positive microorganism or a placebo are orally given over a period of 3 to 30 weeks. Oral application of at least two different dosages is performed. Immune responses are followed by determination of the antibody and T cell response against Tn or Lewis Y by using at least one of the humoral response tests 1 to 6 and cellular immune response tests 1 to 5 prior to and in suitably intervals after start of oral administration of the nutraceutical. For suitable formulations a significant elevation of the antibody response against Tn or Lewis Y and/or T cell response against Tn or Lewis Y, respectively, should be observed in a significant number of volunteers in the volunteer group that receives the nutraceutical in comparison to the titre before the study as positively tested by being positive in at least one of the humoral immune response tests 1 to 6 and/or in at least one of the cellular immune response tests 1 to 5. In the placebo group elevation of antibody or T-cell response against Tn or Lewis Y is less frequently observed or to a lesser extend. The induction of the cellular immune response is characterized by the activation of Tn- or Lewis Y-specific T cells such as CD4 positive Th1 cells and/or CD8 positive cytotoxic T cells indicating the induction of an effective Tn- or Lewis Y-specific cellular immune response, respectively.

This may show the effectiveness of the nutraceutical in humans for building an immune response against Tn or Lewis-Y which functions as a shield against Tn or Lewis Y positive cancer cells for the prevention, reduction or spread of Tn or Lewis Y positive tumors or metastasis or its treatment.

Before first application of the pharmaceutical composition in a study with human immuno-competent cancer patients suffering from Lewis-Y positive tumors, serum antibody titres against Lewis-Y are determined by using at least one of the humoral immune response tests 1 to 6 determining the existing antibody response against Lewis-Y.

Patients are treated in the adjuvant setting after removing the bulk tumor. The pharmaceutical composition comprising a Lewis-Y positive bacteria strain or a placebo are administered several times orally, intra peritoneally or intra venously over a period of 3 to 70 weeks. Administration of at least two different suitable dosages is performed. Immune responses are followed by determination of the antibody and/or T cell response against Lewis-Y by using at least one of the humoral response tests 1 to 6 and/or cellular immune response tests 1 to 5. The clinical response is followed by determination of time to progression, tumor free survival and/or tumor volumes and/or sites, each prior to and in suitably intervals after start of the administration of the pharmaceutical composition. There is a significant elevation of the antibody response against Lewis-Y and/or of the T cell response against Lewis-Y observed in a significant number of volunteers in the group that receives the formulation of the invention in comparison to the titre before the study as positively tested by being positive in at least one of the humoral immune response tests 1 to 6 or in at least one of the cellular immune response tests 1 to 5 and/or a partial or complete clinical response or a elongated time to progression or time of survival in a significant number of the patients receiving the formulation.

The induced T cell response shows the features of an effective Lewis-Y specific cellular immune response comprising activation of CD4 positive Th1 T cells and/or CD8 positive cytotoxic T cells. In the placebo group elevation of antibody or T-cell response against Lewis-Y is less frequently observed or to a lesser extend and/or no or a significantly lower clinical response is observed.

This shows the effectiveness of the pharmaceutical composition in humans for building an immune response against Lewis-Y which functions as a shield against Lewis-Y positive cancer cells for the prevention, reduction or spread of the occurrence of Lewis-Y positive tumors or metastasis or its treatment.

The contacting of the Lewis-Y positive microorganism or fraction thereof within the body of the living organism (human/animal) can initiate the production of antibodies binding Lewis-Y, the Lewis-Y antigen, or Lewis-Y positive tumor cells in a significant number of humans or animals. Surprisingly, antibodies against Lewis-Y function as a immunosurveillance mechanism against newly arising cancer cells. The induction of an effective Lewis-Y specific cellular immune response can result in the killing of residual or newly arising Lewis-Y positive tumor cells in the patient.

F) Kits

The invention relates also to a kit for inducing a specific humoral and/or cellular immune response in a human or animal against the carbohydrate epitope or carbohydrate epitope positive tumor cells, as described elsewhere herein, comprising the nutraceutical, or the pharmaceutical formulation, or the carbohydrate positive microorganism, or the fraction thereof or or formulations comprising those, which are described elsewhere herein, and an information about the use of the kit.

The invention relates also to a kit for inducing an effective carbohydrate specific cellular immune response in a human or animal against the carbohydrate epitope or carbohydrate epitope positive tumor cells or disease cells, as described elsewhere herein, comprising the nutraceutical, or the pharmaceutical formulation, or the carbohydrate positive microorganism, or the fraction thereof or or formulations comprising those, which are described elsewhere herein, and an information about the use of the kit.

The invention relates also to a kit for reducing or preventing the occurrence of a carbohydrate epitope positive disease or a tumor, preferably a carbohydrate epitope positive tumor, comprising the nutraceutical, or the pharmaceutical formulation, or the carbohydrate positive microorganism, or the fraction thereof or formulations thereof which are described elsewhere herein, or formulations comprising those, and an information about the use of the kit.

The invention relates also to a kit for reducing or preventing the spread of a carbohydrate epitope positive disease or metastasis of a tumor, preferably of a carbohydrate epitope positive tumor, comprising the nutraceutical, or the pharmaceutical formulation, or the carbohydrate positive microorganism, or the fraction thereof or formulations thereof which are described elsewhere herein, or formulations comprising those, and an information about the use of the kit.

The invention relates also to a kit to treat a carbohydrate epitope positive disease or a tumor, preferably a carbohydrate epitope positive tumor, comprising the nutraceutical, or the pharmaceutical formulation, or the carbohydrate positive microorganism, or the fraction thereof or formulations thereof which are described elsewhere herein, or formulations comprising those, and an information about the use of the kit.

The invention relates also to a kit to strengthen the immune system or to improve an immune response as described elsewhere herein comprising the nutraceutical, or the pharmaceutical formulation, or the carbohydrate positive microorganism, or the fraction thereof or formulations thereof which are described elsewhere herein, or formulations comprising those, and an information about the use of the kit.

The kit may include information (instruction leaflet, internet address) explaining how to combine the components of the kit. Said information can also be related to a therapeutic scheme.

The invention relates also to a kit for the determination of the immune response against the carbohydrate epitope comprising at least one of the herein described immune response tests against carbohydrate epitope, preferably at least two, and more preferably at least one humoral and one cellular immune response test, comprising at least one of the material described under the according immune response test and an information about the use of the kit. In a preferred embodiment the kit additionally comprises according controls, and more preferably at least one of the nutraceutical, or the pharmaceutical formulation, or the carbohydrate positive microorganism, or the fraction thereof or formulations thereof which are described elsewhere herein, or formulations comprising those.

The invention relates also to a kit for generating at least one functional dendritic cell against the carbohydrate epitope, comprising the nutraceutical, or the pharmaceutical formulation, or the carbohydrate positive microorganism, or the fraction thereof or formulations comprising those, and an information about the use of the kit.

In preferred embodiment the kit for generating at least one functional dendritic cell against the carbohydrate epitope further comprises immature dendritic cells derived from a dendritic cell line such as but not limited to MUTZ-3 or Nemod-DC.

The invention relates also to a kit for generating at least one activated T cell, T cells, T cell clone or T cell line against the carbohydrate epitope, comprising the nutraceutical, or the pharmaceutical formulation, or the carbohydrate positive microorganism, or the fraction thereof or formulations thereof, or formulations comprising those, and an information about the use of the kit.

The invention relates also to a kit for isolating a carbohydrate positive microorganism or a fraction of a microorganism comprising at least one carbohydrate epitope carrying molecule or structure, comprising at least one carbohydrate epitope specific antibody or carbohydrate binding molecule and an information about the use of the kit.

The invention relates also to a kit for identifying a carbohydrate positive microorganism or a fraction of a microorganism comprising at least one carbohydrate epitope carrying molecule or structure, comprising at least one carbohydrate epitope specific antibody or carbohydrate binding molecule and an information about the use of the kit.

The invention relates also to a kit for identifying or isolating a carbohydrate positive microorganism or a fraction of a microorganism comprising at least one carbohydrate epitope positive molecule or structure or for identifying a suitable carbohydrate positive microorganism for use as a component for nutraceuticals and pharmaceutical compositions of the invention comprising at least one carbohydrate epitope specific antibody or carbohydrate binding molecule and an information about the use of the kit.

In a preferred embodiment the kit comprises at least one carbohydrate positive microorganism, lysate or fraction thereof as a positive control.

G) Methods for Antibody Generation

The invention also provides a method for generation of an antibody or antibody composition or polyclonal serum recognizing the carbohydrate epitope of interest, comprising
 (a) bringing into contact the nutraceutical, the pharmaceutical composition, the carbohydrate positive microorganism or fraction thereof with a human or an animal
 (b) inducing or enhancing a humoral immune response recognizing the carbohydrate epitope and/or a carbohydrate epitope positive tumor cell
 (c) isolating said anti carbohydrate epitope antibody or antibody composition.

According to one embodiment, in step (c) at least one cell is generated producing said anti carbohydrate epitope antibody or antibody composition. Said final step (c) can be done by various methods such as
 (i) by immortalization of at least one cell producing the anti carbohydrate epitope antibody, preferably by fusion with an immortal cell line as performed in the hybridoma technology, or preferably by infection with a suitable virus such as Epstein Barr Virus (EBV), or by recombinant transfection with at least one gene which causes immortalization of the cell such as E1 from EBV; or
 (ii) by analysis of the peptide sequence of at least the variable regions of the anti carbohydrate epitope antibody or at least the binding region of the anti carbohydrate epitope antibody responsible for the specificity of the antibody and transformation of cells with DNA encoding the anti-carbohydrate epitope antibody as a whole antibody of any isotype or a fragment thereof or a fusion protein of a fragment of the anti-carbohydrate epitope antibody or the whole antibody with at least one other amino acid or polypeptide sequence.

Preferred are cells which are able to stably produce the antibodies meaning that the cells can be passaged over a suitable amount of cycles for production of the antibodies such as but not limited to hybridoma cells and otherwise immortalised cells or by recombinantly stably transformed cells such as but not limited to CHO, NS0, SP2, Y0, PerC.6, Hec293. However, also transient expression such as the expression in COS or Hec293 cells or B cells are an embodiment of the invention. Said anti-carbohydrate epitope monoclonal antibody can be isolated from the culture supernatant. In a preferred embodiment of the invention said cell producing an anti-carbohydrate epitope monoclonal antibody is obtained by single cell cloning.

In a preferred embodiment the invention provides the nucleic acid such as DNA encoding the anti carbohydrate epitope antibody monoclonal antibody or a fragment thereof.

In a preferred embodiment the invention provides an anti carbohydrate epitope antibody or antibody composition or polyclonal serum, the anti carbohydrate epitope monoclonal antibody or at least one fragment thereof. In another embodiment the invention provides a cell producing an anti carbohydrate epitope antibody or antibody composition or at least one fragment thereof. In a further preferred embodiment the invention provides an anti carbohydrate epitope monoclonal antibody or the fragment thereof which is a humanized antibody or a human antibody from a transgenic mouse.

In a preferred embodiment the invention provides the cell producing an anti carbohydrate epitope antibody or antibody composition, the anti carbohydrate epitope monoclonal antibody or at least one fragment thereof as described above.

Said anti-carbohydrate epitope antibody in sense of the invention can be any inducible antibody in a human or an animal recognizing the carbohydrate epitope of interest and/or a tumor cell carrying a carbohydrate epitope of interest, preferably those antibodies which are carbohydrate epitope specific antibodies with the binding or specificity criteria described under definitions or elsewhere herein.

Said carbohydrate epitope antibody can have and format such as IgG, IgM, IgA, IgE, IgD or any fragment derived therefrom by technologies known to those skilled in the art such as but not limited to Fab, F(ab)2, single chain antibodies, single domain antibodies, multibodies, antibody fusion proteins, bispecific antibodies or antibody, and humanized or chimaerized antibodies.

Any animal or human can be brought into contact with the nutraceutical, the pharmaceutical composition, the carbohydrate positive microorganism and/or fraction thereof, preferred are humans and mice, rats, rabbits, goats, camels, chicken, hamster, guinea pig or monkeys, even further preferred are animals which are known to those skilled in the art to be particularly suitable for generating an antibody response such as but not limited to rabbits, goats, rats, humans, chimpanzees and mice for polyclonal antibody sera and those which are known to those skilled in the art to be particularly suitable for generating monoclonal antibodies such as but not limited to mice, rats, human, further preferred are transgenic mice which carry at least parts of the human antibody genes and humans.

Bringing into contact means any method or route of administration described elsewhere herein for administering the nutraceutical, the pharmaceutical composition, the carbohydrate positive microorganism and/or fraction thereof, which is able to induce a humoral response against the carbohydrate epitope of interest. Additional adjuvants may be used for increasing the immunogenicity which are known to those skilled in the art. Preferred is the oral and the systemic administration and within the latter the intra venous, the intra dermally, or the subcutaneous and even more the intra peritoneal administration.

The induction of the humoral immune response against the carbohydrate epitope of interest can be tested in the humoral immune response tests of the invention and at least one of the humoral immune response tests 1 to 6 has to be positive as described elsewhere herein, whereby in a preferred embodiment said antibodies gained from the serum, plasma or faeces also include those which are gained from cells producing antibodies against the carbohydrate epitope of interest, such as B-cells, or immortalized B-cells, or cells recombinantly expressing anti carbohydrate epitope antibodies. These antibodies can be gained in a variety of ways known to those skilled in the art, in a preferred embodiment sera from blood, or fractions of a sera, or a serum or a fraction of a serum which was preabsorbed against suitable antigens such as microbial antigens negative for the carbohydrate epitope of interest, preferably a microorganism negative for the carbohydrate epitope of interest, or antibodies from an antibody producing cell such as those described above in form of whole or fractionated cell supernatants or purified antibodies are used as said antibodies gained from the serum, plasma or faeces in at least one of the humoral immune test 1 to 6.

DEFINITIONS

Nutraceutical

In accordance with the present invention the term "nutraceutical" means any nutrient, composition of nutrients or formulation which can be taken orally by a human or animal such as but not limited to nutrients, nutrition additives, food additives, dietary supplements, clinical food or nutrition, medical food or nutrition, enteral food, enteral clinical nutrition, health care nutrition or food, food for special dietary use, food of specified health use or functional food that can be applied orally in different forms, such as but not limited to capsules, tablets, emulsions, powder, liquids, as well as in form of any food or drink or as a part of it. In special cases the nutraceutical can be given parenterally (parenteral food). The nutraceutical can be given by itself or mixed with at least one other ingredient. The nutraceutical by itself or its mixture with at least one other ingredient can be given by itself or mixed into a food or a drink. The term nutraceutical also means any food, beverage, capsule, tablet, emulsion, powder, or liquid.

Pharmaceutical Composition

In accordance with the present invention the term "pharmaceutical composition" means any composition which can be used as a drug, or a pharmaceutical, or a biological, or is a component of a drug or a pharmaceutical or a biological.

Carbohydrate-Positive Microorganism

In accordance with the present invention the term "carbohydrate positive microorganism" means any mircoorganism which is recognized and thus bound upon contact by at least one carbohydrate binding molecule specifically recognizing a carbohydrate epitope (as defined elsewhere herein) usually present on a molecule from a human or animal cell. Preferably this binding can be inhibited by mild periodate treatment, and/or by partial or complete chemical or enzymatic removal or alteration of the carbohydrate epitope or the carbohydrate structure comprising the carbohydrate epitope, and/or by inhibition of the binding of the carbohydrate binding molecule with suitable amounts of another carbohydrate binding molecule recognizing said carbohydrate epitope, and/or by inhibition of the binding of the carbohydrate binding molecule with suitable amounts of the carbohydrate epitope or a molecule, mixtures of molecules or cell comprising said carbohydrate epitope when incubated with the microorganism during binding studies with the carbohydrate binding molecule. Also comprised by the term "carbohydrate positive microorganism" are microorganisms wherein the carbohydrate epitope of interest is exposed only after a chemical or enzymatical treatment such as e.g. a periodate treatment. Hence, said microorganism is recognized and thus bound upon contact by at least a corresponding carbohydrate binding molecule after said treatment.

A carbohydrate positive microorganism can be any microorganism such as but not limited to bacteria, cyanobacteria, eubacteria, algae, fungi (mushrooms, yeasts, smuts, molds etc.), viruses and protozoa, preferred are bacterial microorganisms such as but not limited to microorganisms isolated from the soil, from plants, animals, humans or other higher living organisms such as cats, dogs, pigs, cows, goat, rabbit, mice, chimpanzees. In a preferred embodiment the carbohydrate positive microorganism is a microorganism which originates from the human gastrointestinal system.

Carbohydrate Binding Molecule

In accordance with the present invention the term carbohydrate binding molecule means a molecule that recognizes a certain carbohydrate structure or which binds to its epitope dependent of a certain carbohydrate such as but not limited to carbohydrate-specific monoclonal and polyclonal antibodies, lectins and selectins and/or molecules derived therefrom. Preferably, said carbohydrate binding molecule specifically recognizes a carbohydrate epitope present on a human or animal cell such as e.g. a tumor marker. By using respective carbohydrate binding molecules which are specific for a "human" carbohydrate epitope, one may isolate a carbohydrate positive microorganism carrying a structure that is identical to or mimics the carbohydrate epitope of interest as can be determined by binding of said carbohydrate binding molecule which is preferably an antibody. Examples of suitable carbohydrate binding molecules are described e.g. in Table 2.

Said carbohydrate-specific antibody can be a whole antibody from any animal or human such as murine, rat, human, camel, humanized or chimaeric IgM, IgG, IgG1, IgG2, IgG3, IgG4, IgA, IgE, IgD or any fragment of an antibody as long as it comprises the binding specificity or dependency against the carbohydrate, such as Fab, F(ab)2, single chain Fv, or single domain antibodies. Those antibodies can also contain at least one additional amino acid or mutations or polypeptide sequences, such as tags, linkers or multimerization domains and they can also originate from other sources than animals, such plants and such as selection from synthetic antibody libraries using for example phage display or ribosome display or by recombinant construction.

Carbohydrate Epitope

In accordance with the present invention the term "carbohydrate epitope" means the structure which is bound upon contact by a carbohydrate binding molecule:

Said carbohydrate epitope can thereby equal the carbohydrate part bound by said carbohydrate binding molecule or the carbohydrate epitope can comprise the carbohydrate part bound by the carbohydrate binding molecule. For further clarification, for example such as but not limited to (i) said carbohydrate epitope can equal the tetrasaccharide Lewis Y with all four carbohydrate units of which are necessary for the binding of the carbohydrate binding molecule the monoclonal antibody A70-C/C8, or said carbohydrate epitope is also Lewis Y comprising the trisaccharide H-type 2 which is the minimal binding specificity requirement for the carbohydrate binding molecule the monoclonal antibody A46-B/B10 and which also binds to the tetrasaccharide of Lewis Y, and/or (ii) said carbohydrate epitope equals the carbohydrate part bound by a carbohydrate molecule but it is linked differently, such as but not limited to a beta linkage instead of an alpha linkage or vice versa or linked via a different carbohydrate atom.

The term carbohydrate epitope can also mean the carbohydrate antigen which can be the same as the carbohydrate epitope or be any structure comprising a carbohydrate epitope described elsewhere herein in addition to e.g. a peptide part/portion.

The carbohydrate epitope can consist of carbohydrate structures or carbohydrate-mimicking structures such as polypeptides, peptides, lipids or carbohydrates or combinations thereof of a chemical structure different from the carbohydrate but which have a conformational structure which can be recognized by carbohydrate binding molecules of the invention and thus has immunochemically similar or identical properties.

The carbohydrate epitope can be linked to other biomolecules or be part of it such as but not limited to polysaccharides, peptidoglycans, glycoproteins, glycopeptides, glycolipids, lipopolysaccharides, glycosaminoglycans, capsular polysaccharides or O-antigens.

The carbohydrate epitope can also be linked via various linkers and various densities to natural or synthetic carriers, such as polyacrylamide (herein also called PAA), or other molecules such as chromatographic bed materials (e.g. sepharose), biotin or proteins, such as bovine serum albumin (BSA), ovalbumin (Ova), Keyhole limpet hemocyanin (KLH), toxins, toxoids, T helper epitopes.

The carbohydrate epitope originates or corresponds to (e.g. mimics) a carbohydrate epitope from a human or animal cell and can be present on the surface of the cell or intracellular or can be secreted by the human or animal cell. Preferably, said carbohydrate epitope is a disease marker, e.g. a tumor marker.

Effective Carbohydrate Specific Cellular Immune Response (ECSCIR)

In accordance with the present invention the term "effective carbohydrate specific cellular immune response" means a cellular immune response that is induced by the administration of an immunogen comprising a carbohydrate-epitope which preferably shows the following features:

(i) the immune response is against the carbohydrate epitope, meaning that the immune response is carbohydrate specific or dependent on the carbohydrate or the availability of the carbohydrate, whereby the immune response against the carbohydrate epitope can also be or comprise an immune response against at least one carbohydrate structure, carbohydrate conjugate and/or a mammalian cell comprising said carbohydrate epitope (ii) the immune response is MHC dependent (iii) the immune response comprises a Th1 type immune response comprising the activation of CD4 positive T cells of Th1 type and/or (iv) the induction of CD8 positive cytotoxic T cells, preferably the activation of CD4 positive T cells of Th1 type and the induction of CD8 positive cytotoxic T cells.

The Th1-type immunity is characterized by the proliferation of T cells and the secretion of the cytokines IFNgamma and/or TNFalpha and GM-CSF which can be measured by the cellular immune response tests as disclosed herein or by techniques known to those skilled in the art such as but not limited to proliferation assays, ELISA, ELISpot or flow cytometry.

Induction of CD8 positive cytotoxic T cells can be measured by the cellular immune response tests as disclosed herein or by techniques known to those skilled in the art.

Carbohydrate specificity of the cellular immune response can be determined by restimulation of activated T cells with the carbohydrate epitope, preferably with the carbohydrate epitope on a carrier different from the one used for the priming of the T cell response, such as but not limited to lysates or fractions from cells expressing the carbohydrate epitope or proteins or peptides carrying the carbohydrate epitope (in case of priming with the carbohydrate epitope on microorganisms) and/or by blockage of the proliferation and/or cytokine secretion with carbohydrate binding molecules and/or a MHC class specific antibody, preferably the carbohydrate specificity of the cellular immune response is determined by restimulation of activated T cells with the carbohydrate epitope on a carrier different from the one used for the priming of the T cell response and by blockage of the proliferation or cytokine secretion with carbohydrate binding molecules.

Fraction of a Carbohydrate-Positive Microorganism

In accordance with the present invention the term fraction of a carbohydrate-positive microorganism means a preparation or purification of a part or parts of said microorganism such as but not limited to cell wall preparation, envelope preparation, lysate, lipopolysaccharide preparation, preparation of capsules, or capsule polysaccharide preparation. They comprise at least one carbohydrate positive component of said carbohydrate positive microorganism which is bound by at least one of said carbohydrate binding molecules recognizing the carbohydrate epitope and/or antigen of choice. They can be obtained by preparation, purification, and/or preparation or purification steps from at least one carbohydrate positive microorganism. Said preparations and/or purifications can be obtained by methods known to those skilled in the art such as those described above, or such as but not limited to single or sequential cell fractionation, phenol water extractions, ether extractions, lysozyme digestions or chromatographic methods or combinations thereof. Furthermore, the term fraction of a carbohydrate positive microorganism also comprises artificially produced carbohydrate positive components which are also found on carbohydrate positive microorganisms of the present invention. FIG. 19 e.g. shows some Core-1 positive components and thus fractions of a Core-1 positive microorganism (here: AG6). These Core-1 positive components/fractions of the Core-1 positive microorganism AG6 could also be produced chemically. The carbohydrate positive component or the fraction containing the carbohydrate positive component is detected by binding of the fraction to at least one carbohydrate binding molecule in test systems such as but not limited to ELISA, flow cytometry, immuno fluorescence or Dot blots which are known to those skilled in the art. In a preferred embodiment of the invention the fraction comprising a carbohydrate positive component is obtained by affinity chromatography using at least one carbohydrate specific antibody. In a preferred embodiment a single preparation or purification step is used. In another preferred embodiment a combination of at least two preparations and/or purification steps are used.

Carbohydrate Positive Component

In accordance with the present invention the term carbohydrate positive component means any component of a carbohydrate positive microorganism which is bound upon contact by at least one carbohydrate specific antibody or carbohydrate binding molecule. Said carbohydrate positive component comprises at least one carbohydrate structure comprising the carbohydrate epitope as defined or described elsewhere herein which can be available in form of its natural molecule where it is part of the microorganism, such as a peptide, oligopeptide, polypeptide, lipid, ceramide, carbohydrate, lipoprotein, polysaccharide, oligosaccharide, polysaccharide, proteoglycan or glycoprotein, or as a part of said natural molecule, or alone. The carbohydrate positive component can be used in sense of the invention as a fraction of the carbohydrate positive microorganism as such or coupled to other non-natural carrier structures such as but not limited to proteins, lipids, chemical molecules such as polyacrylamide. Preferably it is used in its natural form or as a part of said natural molecule. The carbohydrate positive component can comprise one or different carbohydrate chain types with a single carbohydrate epitope or multiple carbohydrate epitopes or repeating units of said structures and can contain additional carbohydrate structures or units or other biomolecule structures. As described elsewhere herein the carbohydrate epitope can also be or comprise a carbohydrate mimicking structure which is a structure which can be bound by at least one carbohydrate specific antibody or binding molecule and/or can induce an immune response against the carbohydrate, preferentially a humoral immune response against the carbohydrate, and more preferably an effective cellular immune response against said carbohydrate, and even more preferentially a humoral immune response against the carbohydrate and an effective cellular immune response against the carbohydrate.

Natural Molecule

In accordance with the present invention the term "natural molecule" means any biomolecule or parts thereof that occur on at least one living or dead organism (such as but not limited to prion, virus, microorganism, protozoa, bacteria, algae, fungi, plant, animal, human) or is produced by that organism.

Natural molecules can be used as whole organisms (such as microorganisms or viruses) or can be isolated from natural sources or can be synthezised in exactly with the same structure as it occurs in nature.

Preferably, natural molecules are no combination of biomolecules or parts thereof that does not occur on an organism in that combination and are not coupled or conjugated to natural or synthetic carriers such as proteins, peptides, KLH, OVA, BSA, toxin, toxoid, T helper epitope, biotin, PAA, beads, nanoparticles or chromatographic bed material.

Without intending to be limiting, the invention will be explained in more detail with reference to the following examples.

FIGURE LEGENDS

FIG. 1

Unrooted tree based on the unambiguously aligned sequences (1248 base pairs) of the isolates AG6, MU1, their closest relatives and the *E. coli* type strain obtained with the Neighbor-Joining method (7).

FIG. 2

2a: LH *E. coli* strain PCR products obtained after amplification with the primer OPL07—lane 1—1 kb ladder; lanes 2-11—LH strains 2-5, 8, 13-16, 18; lane 12—strain 32 *E. coli* DSMZ 8697

2b: MU strains and AG6 obtained after amplification with the primer OPA18—lane 1—1 kb ladder; lanes 2-5—MU strains 1, 3-5; lane 6—AB12; lane 7—*B. thetaiotaomicron* DSMZ 2079; lane 8—*B. ovatus* DSMZ 1896; lane 9—*B. vulgatus* DSMZ 1447; lane 10—*B. acidifaciens* DSMZ 15896; lanes 11-13—AG6

FIG. 3

ELISA with coated bacterial strains AG6, LH2 and MU1 ($5 \times 10^6$ bacteria/ml) and the Core-1 specific monoclonal antibodies Nemod-TF1, Nemod-TF2 and less specific A68-B/A11 and control antibody A63-B/C2.

FIG. 3a

ELISA with coated bacterial strains *Helicobacter pylori* NCTC 11637, *E. coli* strain DSMZ 8697(strain 32) and *Bacteroides ovatus* strain MU1 (each at a density corresponding to $10 \times OD_{650\ nm}$ 0.1) and the monoclonal antibodies Nemod-TF1 Nemod-TF2 and A68-BA11 $OD_{450/630\ nm}$ minus $OD_{450/630\ nm}$ of control antibody A63-B/C2).

FIG. 4

SDS-PAGE and western blot analyses of capsule preparation of strain AG6

A) Alcian blue dye of SDS-polyacrylamide gel

B) DIG-glycan staining of western blot

C) staining of western blot with Nemod-TF2

FIG. 5

Enrichment of core-1-positive polysaccharides by reversed phase chromatography

FIG. 6

Sequence of repeating units of core-1-positive capsular polysaccharide of *B. ovatus* strain AG6

FIG. 7

Structure of repeating units of core-1-positive capsular polysaccharide of *B. ovatus* AG6 (L-Fuc: L-fucose, D-Gal: D-galactose, HexNAc: N-acetylhexosamin, D-Hex: D-hexose, OMe: O-methyl group)

FIG. 8

Structure of repeating units of core-1-positive capsular polysaccharide of *B. ovatus* AG6 (L-Fuc: L-fucose, D-Gal: D-galactose, HexNAc: N-acetylhexosamin, D-Hex: D-hexose, OMe: O-methyl group)

FIG. 9

Analysis of mouse sera by humoral immune response test 1

IgM antibodies against AGP and periodic acid treated AGP were determined by ELISA in sera from mice immunized with PBS (group L), Core-1 negative bacteria (group I) and Core-1 positive bacteria (group K)

Serum dilution 1:200, day 21

FIG. 10

ELISA signals of immune sera on carbohydrate-PAA conjugates: mean value of ELISA signals from 4 C3H mice against the PAA conjugate Gal beta1-3GalNAc alpha1-PAA relative to the ELISA signal against GloNAcβ1-2Galβ1-3GalNAcalpha-PAA (dilution of sera 1:100). FIG. 10A: mice immunized with strains AG3, 32, MU1 and 61: FIG. 10B: mice immunized with strains AG (pasteurized), 52, 53 and AG6 (fixed).

FIG. 12

Figure 2:
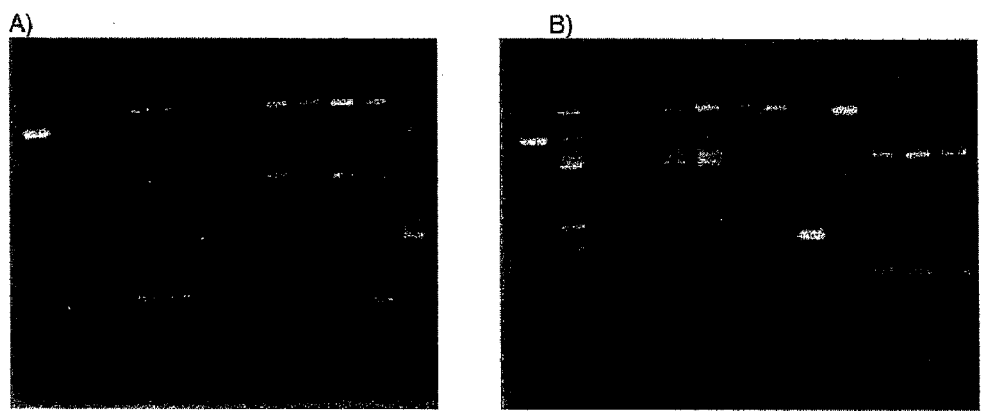

Humoral immune response test 1 of sera from germfree mice (control mouse and 3 different mice immunized with bacteria strain AG6)

FIG. 13

Humoral immune response test 1 of sera from C3H mice orally immunized with A) $2\times10^{11}$ (group A) or B) $2\times10^{10}$ (group B) pasteurized bacteria of strain AG6 daily at days 0 to 28. ELISA signals at day 21 against glycophorin (GP), asialoglycophorin (AGP) and periodate-treated AGP (AGP+PJ) of individual mice are shown

FIG. 14

Humoral immune response test 3 of sera from C3H mice orally immunized with pasteurized Core-1 positive bacteria (strain AG6). Sera from day 0 and day 28 were diluted 1:300 and analysed in flow cytometry for binding on the cell lines NM-wt and NM-D4.

FIG. 15

Cytokine production by T cells generated to Core1-positive bacteria lysates (AG6 and MU1) after restimulation with DC loaded with Core1-positive MN-D4 (DC/D4) or -negative NMwt (DC/wt) cell-lysates from human tumor cell lines. Inhibition of the cytokine production through pre-incubation of the lysate-loaded NM-DC with Core1-specific antibody (DC/D4+Ak).

A) GM-CSF production by T cells (CIRT 1)
B) TNF alpha production by T cells (CIRT 2)

FIG. 16

Cellular immune response test 2: Results of ELISpot assay for IFN-gamma production by responder T cells after restimulation with DC loaded with Core1-positive (DC/D4) or -negative (DC/wt) cell-lysates from human tumor cell lines and inhibition of the cytokine production through pre-incubation of the lysate-loaded NM-DC with Core1-specific antibody (DC/D4+Ak).

FIG. 17

Cellular immune response test 3: T cell proliferation assay (WST) on responder cells (R) after restimulation with DC loaded with Core1-positive (DC/D4) or -negative (DC/wt) cell-lysates from human tumor cell lines and inhibition of the proliferation through pre-incubation of the lysate-loaded NM-DC with Core1-specific antibody (DC/D4+Ak).

FIG. 18

Cellular immune response test 4: immunofluorescence analysis of mNM-DC loaded with Core-1 negative (AG3) or Core-1 positive (AG6) bacteria or Core-1 negative (NM-wt) or Core-1 positive (NM-D4) human cell line.

FIG. 19

Carbohydrate structures of Core-1 positive components L-Fuc: L-fucose, D-GalNAc: N-acetylgalactosamin, D-Gal: D-galactosamin, Hex: hexose, HexNAc: N-acetylhexosamin, OMe: O-methylation. Such structures are e.g. found on AG6.

FIG. 20

The hidden and exposed Core-1 antigen.

FIG. 21

FIG. 21 shows the ELISA signals against the PAA conjugate Galβ1-3 GalNAc a-PAA and the PAA conjugate Galβ1-3 GlcNAc a-PAA at day 21. Sera were considered as positive if the signal on PAA 48 was at least 30% higher then the signals on PAA 43. Considering this criteria, 5 (A1, A2, A3, B1 and B5) from the 6 mice developed a core-1 specific humoral immune response.

FIG. 22

Shows a table, wherein selected Core-1 positive strains as well as strains that were not Core-1 positive were characterized by their sensitivity against different antibiotics.

FIG. 23

Overview over a cellular response test according to the present invention.

EXAMPLES

Example 1

Anaerobic Culture Techniques and Media

Anaerobic techniques employed in the cultivation of bacteria were based on methods previously described which have been summarised by Breznak and Costilow. Media prepared with cysteine.HCl as a reducing agent were dispensed into anaerobic culture tubes (Ochs, Bovenden, Germany) or glass serum bottles, leaving approximately half to a third of the total vessel volume as gas head space, and sealed with butyl rubber stoppers. Solutions prepared without reducing agents (e.g. PBS-a) were boiled prior to dispensing. Before autoclaving, the gas phase was replaced with $N_2/CO_2$ (80/20, v/v). To achieve this, needles were thrust through the butyl rubber-stoppered bottles and the bottles were evacuated by means of a vacuum pump (Vacuubrand, Wertheim, Germany). Following evacuation, bottles, which were repeatedly shaken during the entire process, were gassed with $N_2/CO_2$ (80/20, v/v). This evacuation and gassing procedure was carried out three times in total. Prior to entering the vessels, the gas mixture was passed over a hot palladium catalyst to remove residual traces of oxygen present in the gas mixture. Resazurin (1 mg $l^{-1}$) was used as a redox indicator.

Media for plating were poured under a laminar flow hood and stored under anoxic conditions for at least 24 h before use. This was achieved in either pressurised ($1.5\times10^5$ Pa) anaerobic jars with a 3.5 l AnaeroGen (Oxoid, Basingstoke, England) or with a repeatedly flushed $N_2/CO_2/H_2$ (80/10/10, v/v/v) anaerobic chamber airlock (Don Whitley Scientific, Shipley, England). Manipulation of samples was carried out in an anaerobic chamber (MACS variable atmosphere workstation, Don Whitley Scientific, Shipley, England or Coy Laboratory Products, Grass Lake, USA).

Non-sterile solutions and materials were sterilised by autoclaving (121 C, $1.2\times10^5$ Pa, 15 min). Heat-labile compounds were made as concentrated stock solutions in milli-Q water, sterile-filtered (0.22 µm, mixed cellulose ester, Roth, Karlsruhe, Germany) and added to media at the concentrations required.

Example 2

Affinity Enrichment of Core-1 Positive Microorganisms 2.1 Preparation of TF1 and TF2 coated DYNABEADS® Magnetic Beads A volume of 100 µl DYNABEADS® Magnetic Beads (M-450 Rat Anti-Mouse IgM, Dynal Biotech ASA, Oslo, Norway) each was placed in 2 ml Safe-Lock Eppendorf tubes (Eppendorf, Hamburg, Germany), washed twice with 2 ml phosphate buffered saline a (PBS-a: 8.1 g $l^{-1}$ NaCl, 0.16 g $l^{-1}$ $NaH_2PO_4.H_2O$, 0.98 g $l^{-1}$ $Na_2HPO_4.2H_2O$, 1 g $l^{-1}$ BSA, pH 7.4) using the Dynal Magnetic Particle Concentrator—S (MPC®-S, Dynal Biotech, Oslo, Norway) and suspended in 25 µl of PBS-a. Lyophilised TF1 or TF2 cell culture supernatants were dissolved in 1 ml milli-Q synthesis grade water (Millipore, Billerica, Mass., USA). Dissolved TF1 or TF2 cell culture supernatants (1 ml) were added to the tubes with DYNABEADS® Magnetic Beads and incubated for 30 min at 4 C on a test tube rotator (model 34528, Snijders Scientific, Netherlands). Tubes were placed in the MPC®-S and left to stand for 3 min before removing the fluid with a pipette. The DYNABEADS® Magnetic Beads ere re-suspended in 2 ml PBS-a, placed in the MPC®-S and the fluid removed by pipetting. This washing step was performed three times. Washed DYNABEADS® Magnetic Beads were suspended in their original volume of 100 µl PBS-a. DYNABEADS® Magnetic Beads prepared in this manner were either used immediately or within two weeks of preparation after a repeated three-fold wash step with 2 ml PBS-a.

2.2 Collection and Processing of Faecal Samples for DYNABEADS® Magnetic Beads Enrichment Faecal samples of eight volunteers (Table 3) were collected in perforated plastic tubes, maintained under anoxic conditions using an AnaeroGen Compact (Oxoid, Basingstoke, England) and stored at 4° C. for a maximum of 4 h before processing. Volunteers were healthy adults who had not taken antibiotics for at least 3 months prior to the sampling date and consumed their usual diets.

TABLE 3

Individual parameters at the time of faecal sample collections

| Subject number | Age | Gender |
|---|---|---|
| 1 - G H | 24 | female |
| 2 - R M | 26 | female |
| 3 - T C | 25 | male |
| 4 - A G | 27 | female |
| 5 - A B | 37 | female |
| 6 - M U | 36 | female |
| 7 - L H | 24 | female |
| 8 - C A | 50 | male |

A tenfold (w/v) dilution of the faecal samples was prepared in PBS-b (PBS-b: 8.5 g l$^{-1}$ NaCl, 0.3 g l$^{-1}$ KH$_2$PO$_4$, 0.6 g l$^{-1}$ Na$_2$HPO$_4$, pH 7.0 containing 0.1 g l$^{-1}$ peptone and 0.25 g l$^{-1}$ cysteine.HCl). Six sterile 3 mm diameter glass beads were added and the diluted samples were homogenised by low speed vortexing. The homogenised sample was centrifuged (300×g, 1 min, 21 C) to sediment debris. A 200 µl portion of the resulting supernatant was added to 1.8 ml PBS-b resulting in an approximately 100-fold dilution of the original faecal sample. These dilutions were washed once with 2 ml PBS-b (8000×g, 5 min, 21 C) and the pellets suspended in 2 ml PBS-b.

2.3 DYNABEADS® Magnetic Beads Enrichment Procedure

A volume of 20 µl from the 100-fold dilution was added to a 2 ml tube containing 180 µl of PBS-a and 5 µl of either TF1 or TF2 antibody coated DYNABEADS® Magnetic Beads. The tubes were incubated for 30 min at 4 C on a test tube rotator. Tubes were placed in the MPC®-S and left to stand for 3 min before removing as much of the supernatant as possible by aspiration with a syringe and needle. The samples were washed three times with 2 ml PBS-a, again removing as much of the supernatant as possible.

2.4 Plating on Selective and Non-Selective Media

Washed samples were suspended in 1 ml PBS-b and 100 µl aliquots were spread-plated on various selective and non-selective media (Table 4) and incubated for 48 h at 37° C. in an anaerobic chamber.

TABLE 4

Media employed for spread-plating

| Media | Manufacturer | Selective for | Abbreviation |
|---|---|---|---|
| de Man, Rogosa and Sharpe | Merck, Darmstadt, Germany | lactobacilli, lactic acid bacteria | MRS |
| Bifidus Selective Medium | Fluka, St. Gallen, Switzerland | bifidobacteria | BSM |
| K-F Streptococcus Agar | Oxoid | streptococci | KF |
| Nutrient Agar | Oxoid | non-selective | N |
| Schaedler Anaerobe Agar | Oxoid | non-selective | S |
| Wilkins Chalgren Anaerobe Agar | Oxoid | non-selective | WC |
| Brain Heart Infusion Agar | Biomérieux, Marcy l'Etoile, France | non-selective | BHI |
| Columbia Agar with 5% sheep blood | Biomérieux | non-selective | CBA |
| Stamm Agar | | non-selective | ST |

Solid media were prepared according to the manufacturers' instructions. The composition of ST agar was as follows: 1 g l$^{-1}$ proteose peptone, 9 g l$^{-1}$ peptone from meat, 3 g l$^{-1}$ NaCl, 2 g l$^{-1}$ Na$_2$HPO$_4$.2H$_2$O, 3 g l$^{-1}$ meat extract, 4 g l$^{-1}$ yeast extract, 6 g l$^{-1}$ D (+)-glucose, 0.5 ml l$^{-1}$ TWEEN polysorbate 80, 0.25 g l$^{-1}$ cysteine.HCl, 1 mg l$^{-1}$ resazurin, 0.1 g l$^{-1}$ MgSO$_4$.7 H$_2$O, 5 mg l$^{-1}$ FeSO$_4$.7H$_2$O, 0.5 g l$^{-1}$, 3.4 mg l$^{-1}$ MnSO$_4$.2H$_2$O, 1.5 g l$^{-1}$ bacteriological agar, pH 7.0.

For subjects 1 to 4, colonies from one enrichment procedure were selected for ELISA-based screening. For subjects 5 to 8, the DYNABEADs® Magnetic Beads enrichment procedure was repeated twice as follows: Following 48 h incubation, colonies were scraped from the plates, suspended in PBS-b within the range of McFarland turbidity standards 3 to 5 (prepared as in (13)). As before, a 20 µl aliquot of this suspension was added to 180 µl of PBS-a. The enrichment and plating procedure was performed three times in total, as previously described.

The faecal samples of a further four subjects (5 AB, 6 MU, 7 LH and 8 CA) were enriched for Core 1 positive bacteria. The enrichment procedure was modified slightly in that the enrichment was carried out three times in total. I.e. colonies obtained after the initial isolation were scraped from the plates and subjected to a further enrichment. Sixty new isolates were obtained in this manner.

Example 3

Identification of Isolates 3.1 Biochemical

Bacteria were identified with the VITEK system (Biomerieux, Marcy l'Etoile, France). Bacteria were prepared according to the manufacturer's instructions and the identification cards used were as follows: ANI cards for anaerobic isolates and faculatively anaerobic Gram-positive rods able to grow in MRS broth (suspected *lactobacilli*), GPI cards for Gram-positive isolates and GNI+ cards for Gram negative aerobic isolates.

The biochemical identity of the isolates obtained using the VITEK system (Biomérieux, Marcy l'Etoile, France) is summarised in Table 5. The anaerobic isolates AG6, MU (1, 3-5) and AB12 all belong to the *Bacteroides fragilis* group, whereas the aerobic isolates are all members of the Enterobacteriaceae; both are Gram-negative.

TABLE 5

Identification of the isolated strains based upon biochemical characteristics (VITEK)

| Strain | Identification | Probability |
|---|---|---|
| AG6 MU (1, 3-5) AB12 | *Bacteroides ovatus* | 82-95% |
| AG3 LH (2-5, 8, 13-16, 18) | *Escherichia coli* | 89-99% |

3.2 Molecular (Sequencing)

DNA was extracted with the Invisorb Genomic DNA Kit III (Invitek, Berlin, Germany) following Manufacturer's instructions for protocol III B with washed cell pellets obtained from liquid cultures suspended in 1 ml of lysis buffer D. Primers 27f (5' AGA GTT TGA TCC TGG CTC AG) (SEQ ID NO: 1) and 1492r (5' TAC CTT GTT ACG ACT T) (10) (SEQ ID NO: 2) were used to amplify the bacterial 16S ribosomal RNA gene.

Each PCR was performed in triplicate and the reaction mixture (50 µl) contained: 50 mM KCl, 20 mM Tris-HCl, 1 mM MgCl$_2$, 0.25 mM each dNTP, 1 µM each primer, 2.5 units Taq DNA polymerase (Invitrogen, Karlsruhe, Germany) and 1 µl of the template DNA. The PCR program was: 94° C. for 5 min, 30 cycles of 94° C. for 1 min, 55° C. for 1 min and 72° C. for 1 min, and finally 72° C. for 10 min. PCR products were purified with the High Pure PCR Product Purification Kit (Roche, Ind., USA) following manufacturer's instructions. The products were analyzed by electrophoresis on a 1 agarose gel (w/v) in Tris-Acetate-EDTA buffer (4.84 g l$^{-1}$ Tris, 1.142 ml l$^{-1}$ glacial acetic acid 0.372 g l$^{-1}$ EDTA, pH 8.0). The DNA concentration was estimated using the Low DNA Mass Ladder (Invitrogen, Carlsbad, USA).

For sequencing, we used either primer 27f (SEQ ID NO: 1), 338f (5 GCT GCC TCC CGT AGG AGT) (2) (SEQ ID NO: 3), 338r (5' ACT CCT ACG GGA GGC AGC) (SEQ ID NO: 4), 968f (5' AAC GCG AAG AAC CTT AC) (14) (SEQ ID NO: 5), or 1492r (SEQ ID NO: 2). Sequencing reactions were performed with the DYEnamic™ ET Dye Terminator Cycle Sequencing Kit (Amersham Biosciences, Little Chalfont, England) following manufacturer's instructions. Sequencing products were analyzed with the MegaBACE 1000 System (Molecular Dynamics, Sunnyvale, USA). Sequences were assembled and manually adjusted using the ContigExpress function of the Vector NTI Suite 9.0.0 (Invitrogen, Carlsbad, USA). They were subsequently aligned with highly similar sequences (92% similarity or more) obtained with the BLAST function of the National Center for Biotechnology Information (NCBI) (1). Percentages of similarity were calculated from unambiguously aligned sequences using the Sequence Identity Matrix function of the Bioedit software version 5.0.9 or the Similarity Matrix version 1.1 of the Ribosomal Database Project. Sequencing results were confirmed by comparison with sequences obtained from a 16S rRNA gene sequencing service provider (AMODIA, Braunschweig, Germany).

The identity of the isolates is depicted in Table 6 and an unrooted phylogenetic tree based on the sequences of the isolates AG6, MU1, their closest relatives and the *E. coli* ATCC 11755 type strain is depicted in FIG. 1.

TABLE 6

Identification of the isolated strains based upon the unambiguously aligned sequences of the 16S rRNA genes using the similarity matrix function version 1.1 of the Ribosomal Database Project (5)

| Strain | Identity | Similarity (%) | to strain | Accession number | |
|---|---|---|---|---|---|
| AG6 | *Bacteroides ovatus* | 98.2 | ATCC 8483T | X83952 | (SEQ ID NO: 6) |
| | *Bacteroides thetaiotaomicron* | 97.1 | ATCC 29148T | L16489 | (SEQ ID NO: 7) |
| MU1 | *Bacteroides ovatus* | 98.0 | ATCC 8483T | X83952 | (SEQ ID NO: 6) |
| | *Bacteroides thetaiotaomicron* | 97.1 | ATCC 29148T | L16489 | (SEQ ID NO: 7) |
| AG3 | *Escherichia coli* | 99.5 | k12 MG1655 | AE000460 | (SEQ ID NO: 8) |
| GH1 | *Lactobacillus paracasei* sp. *paracasei* | 99.4 | JCM 8130T | D79212 | (SEQ ID NO: 9) |
| | *L. paracasei* sp. *tolerans* | 99.4 | JCM 1171T | D16550 | (SEQ ID NO: 10) |
| 96 | *Staphylococcus warneri* | 99.2 | ATCC 27836T | L37603 | (SEQ ID NO: 11) |
| | *Staphylococcus pasteuri* | 99.0 | ATCC 51129T | AF041361 | (SEQ ID NO: 12) |
| TC7 | *Lactobacillus rhamnosus* | 99.6 | JCM 1136T | D16552 | (SEQ ID NO: 13) |
| | *Lactobacillus zeae* | 98.7 | ATCC 15820 | D86516 | (SEQ ID NO: 14) |

3.3 Random Amplified Polymorphic DNA (RAPD)

Some Core 1 positive isolates obtained with the repeated Dynabead® enrichment procedure appeared very similar in their cell and colony morphology, despite having being isolated from different media. The strains were also very similar with regard to their biochemical profiles obtained with the VITEK system. The question arose, whether the isolated bacteria are identical strains. RAPD is a method that does not require sequence information, which can be applied to distinguish strains. Briefly, total genomic DNA is PCR amplified with a 10 base pair primer at low stringency so that random sequences of DNA are amplified based on homologous sequences to the primer being present in the target DNA. The resulting PCR products can be separated by agarose gel electrophoresis and the resulting pattern can be compared between strains. The resulting band patterns for all LH strains were analogous for the five RAPD primers (OPL07, M13, OPX14, OPA16, OPA18) employed. The pattern clearly differs from that of *E. coli* strain DSMZ 8697 (FIG. 2a), a strain that has been reported to have blood group B activity. The MU strains also appear very similar (FIG. 2b); however their band pattern clearly differs from that of other *Bacteroides* strains, including AG6. It would appear that one Core 1 positive strain was repeatedly enriched from each positive donor during the isolation process. The strains isolated differed between individuals.

Example 4

Growth and Fixation of Bacteria for the ELISA-Based Screening

Well separated colonies were randomly picked from selective and non-selective agar plates and re-streaked three times on non-selective media. Single colonies were picked and inoculated into ST (as above, omitting the agar), WC or MRS broth, depending on which afforded best growth, and grown overnight at 37° C. These cultures were inoculated (1%) into 300 ml fresh ST, WC or MRS broth and grown overnight at 37° C. Cells were pelleted (8000×g, 15 min, 4 C) and re-suspended in 10 ml PBS-c (8 g l$^{-1}$ NaCl, 0.2 g l$^{-1}$ KCl, 1.44 g l$^{-1}$ Na$_2$HPO$_4$, 0.24 g l$^{-1}$ KH$_2$PO$_4$) (12). This suspension was fixed 3 for to 4 h at 4 C by the addition of 30 ml of 4% paraformaldehyde (PFA) solution (prepared according to (8)) in PBS-c. Next, samples were washed with 40 ml PBS-c (8000×g, 15 min, 4 C) and the pellets suspended in 15 ml PBS-c, followed by addition of an equal volume of 96% ice-cold ethanol. Samples were stored at −20 C until analysis.

The purity of cultures was checked by comparing cell morphology, as well as Gram staining behaviour. Cultures were plated aerobically on CBA to determine their ability to grow in the presence of oxygen and to check for the absence of aerobic contaminants.

Example 5

Maintenance of Isolates

Cryo-stocks were maintained in Microbank tubes (MAST Diagnostica, Reinfeld, Germany) according to the manufacturer's instructions and stored at −80° C. Working stocks were maintained in WC, ST or MRS broth. These were sub-cultured every 14 days. The purity of the cultures was ascertained by observation of Gram-staining behaviour, cell morphology and periodic comparison of colony morphologies on CBA streak plates under both aerobic and anaerobic conditions.

Example 6

Growth, Fixation and Lyophilisation of Bacteria for Animal Experiments

For use in animal experiments the bacteria were grown and fixed as described in section 3 with the following modifications: The initial culture volume amounted to approximately 4 l. Before fixation, bacteria were washed once with 100 ml PBS-b (8000×g, 15 min, 4 C) and re-suspended in the minimal possible volume of PBS-b. This suspension was split into two equal portions, one for fixation (7.1), the other for lyophilisation (7.2).

6.1 Fixation

The portion for fixation was washed (8000×g, 15 min, 4 C) and re-suspended in 30 ml PBS-c. This suspension was added to 90 ml of the 4% PFA solution in PBS-c and fixed for 3 to 4 h at 4 C. To improve the removal of PFA, samples were washed three times with 120 ml PBS-c (8000×g, 15 min, 4 C). Cell pellets were suspended in 45 ml PBS-c, followed by addition of an equal volume of 96% ice-cold ethanol. Samples were stored at −20° C.

Before administration to the animals, fixed bacteria were lyophilised under sterile conditions in Lid$_{Bac}$ tubes (Eppendorf, Hamburg, Germany) to evaporate the ethanol. To ensure non-viability of the fixed bacteria, they were inoculated (1%) into WC broth and plated on CBA and monitored for absence of growth for the period of one week.

6.2 Pasteurization

Bacterial suspensions were washed twice in PBS and resuspended in a small volume of PBS. Bacterial suspensions were incubated at 72° C. for 30 min. As a control for successful inactivation bacteria were incubated in a suitable culture medium as described in example 4.

6.3 Lyophilisation

The portion for lyophilisation was added to an equal volume of 24% sterile-filtered sucrose and aliquoted in 300 µl portions into 2 ml Lid$_{Bac}$ tubes. These aliquots were snap-frozen in liquid nitrogen for 1 h and lyophilized (Alpha 2-4, Christ, Osterode, Germany) after placing them into racks pre-cooled to −80° C. Following lyophilisation, the lids of the tubes were closed and they were stored at 4° C. using the Anaerocult® C mini gas generator system (Merck, Darmstadt, Germany) with the addition of silica gel orange (Roth, Karlsruhe, Germany) as a desiccant.

6.4 Enumeration of Bacteria Preparations

Total cell numbers of fixed and lyophilised bacteria preparations were determined with a 0.01 mm depth Thoma-chamber (LO-Laboroptik, Friedrichsdorf, Germany). For lyophilised bacteria, the colony-forming units (CFU) were determined by plating 10-fold serial dilutions on WC agar of the overnight cultures and immediately before and after lyophilisation. For this purpose, the lyophilate was dissolved in 300 µl WC broth, left to stand for 15 min, re-suspended by low speed vortexing and serially diluted. The CFU of lyophilised preparations were enumerated before and after use in animal experiments to ensure viability. The purity of the preparations was checked as described in section 4.

Example 7

Serum Samples

Blood was collected with the S-monvette system (Sarstedt, Nümbrecht, Germany) and serum was prepared according to the manufacturer's instructions. Serum samples were stored in aliquots at −80° C. prior to analysis

Example 8

Faecal IgA Extraction

Faecal samples were collected, stored at −80° C. Faeces were lyophilised and net dry weights recorded. All manipulations were carried out on ice. Faecal IgA was extracted according to Grewal (6) with some modifications. Lyophilised samples (~30 mg) were suspended at a ratio of 15 µl/mg dry weight in IgA extraction buffer (PBS-Dulbecco (Biochrom, Berlin, Germany) with 1 g l$^{-1}$ BSA) with protease inhibitors (5 µg ml$^{-1}$ leupeptin (Calbiochem, Merck), 48 µg ml$^{-1}$ 4-(2-aminoethyl)benzenesulfonylfluoride (Merck), 1 µg ml$^{-1}$ aprotinin, 2 µg ml$^{-1}$ bestatin (Sigma, Steinheim, Germany) and homogenised. The samples were mixed by vortexing every 10 min. Following a 1 h incubation period, the samples were centrifuged (16000×g, 10 min, 4° C.) and the supernatant was collected in a new tube. The remaining pellet was suspended at a ratio of 10 µl/mg dry weight in IgA extraction buffer and homogenised. The extraction procedure was repeated and the resulting supernatant combined with the supernatant from the first extraction step. These supernatants were centrifuged (16000×g, 10 min, 4° C.) and the resulting supernatant was dispensed into new tubes, snap-frozen in liquid nitrogen and stored at −80° C. until analysis.

Example 9

Screening of Bacterial Strains by Enzyme-Linked Immunosorbent Assay

Fixed bacteria were diluted in PBS, cell numbers were adjusted to $1\times10^5$, $1\times10^6$, $5\times10^6$, $1\times10^7$, $1\times10^8$ or $5\times10^8$ cells/ml.

50 μl of bacterial solution were coated per well of a 96 well microtiterplate over night at 37° C. Plates were washed 3 times with PBS/0.02 TWEEN polysorbate 20 (Identical washing steps were performed after each incubation step.). After blocking of plates with PBS/2% BSA, ELISA plates were incubated with hybridoma culture supernatants containing different Core-1 recognizing monoclonal antibodies (Nemod-TF1, Nemod-TF2 or less specific A68/BA11,) or control antibody (A63-B/C2) in different dilutions. As secondary antibody served a peroxidase-.conjugated polyclonal goat-anti-mouse immunoglobulin (Dako P0260). The assay was developed with TMB as substrate, reaction was stopped by addition of 2.5 $NH_2SO_4$ and extinction was measured at 450/630 nm. For determination of periodate sensitivity of the antibody binding, coated ELISA plated were incubated with sodium periodate prior to the incubation with antibodies. Therefore, plates were washed with sodium acetate buffer (50 mM, pH 4,5) for 5 min and afterwards incubated with 10 mM periodic acid in sodium acetate buffer for 1 h in the dark. Plates were washed with sodium acetate buffer (5 min) and the reaction was stopped by addition of 50 mM sodium borohydrid in PBS (30 min).

Figure 3A:
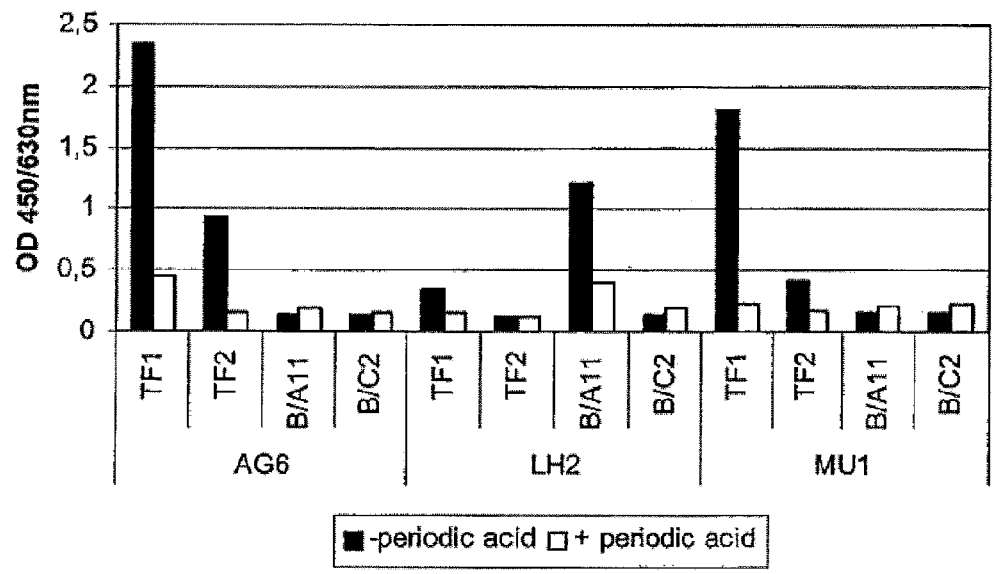
Figure 3B:
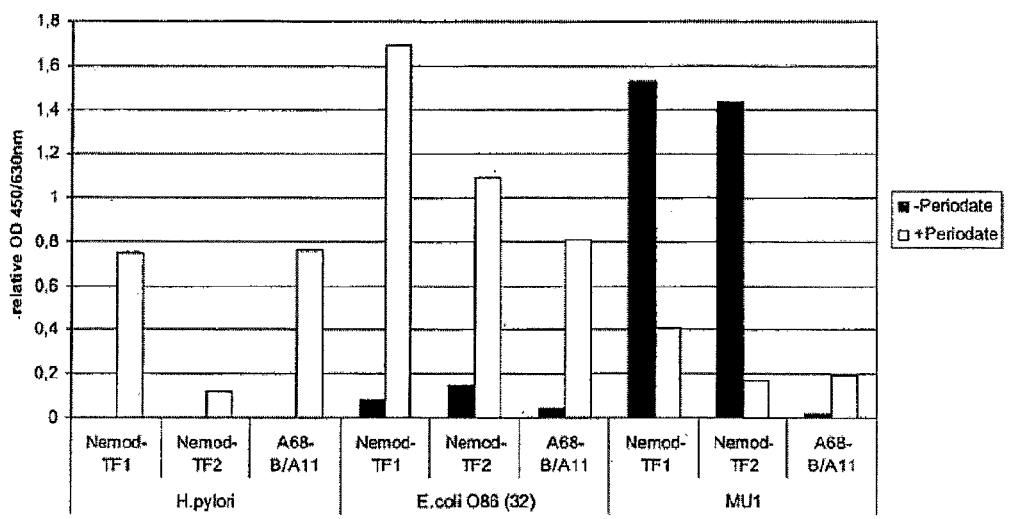

Example of such ELISA results is shown in FIGS. 3 and 3a.

Example 10

Preparation of Core-1-Containing Components of Bacteria 10.1. Analysis of Crude Capsule Preparations by SDS-PAGE and Western Blot Analyses Crude capsule preparations of strain AG6 were performed according to Pantosti et al. (1991, Infect. Immun. 59, 2075-2082).

Figure 4:
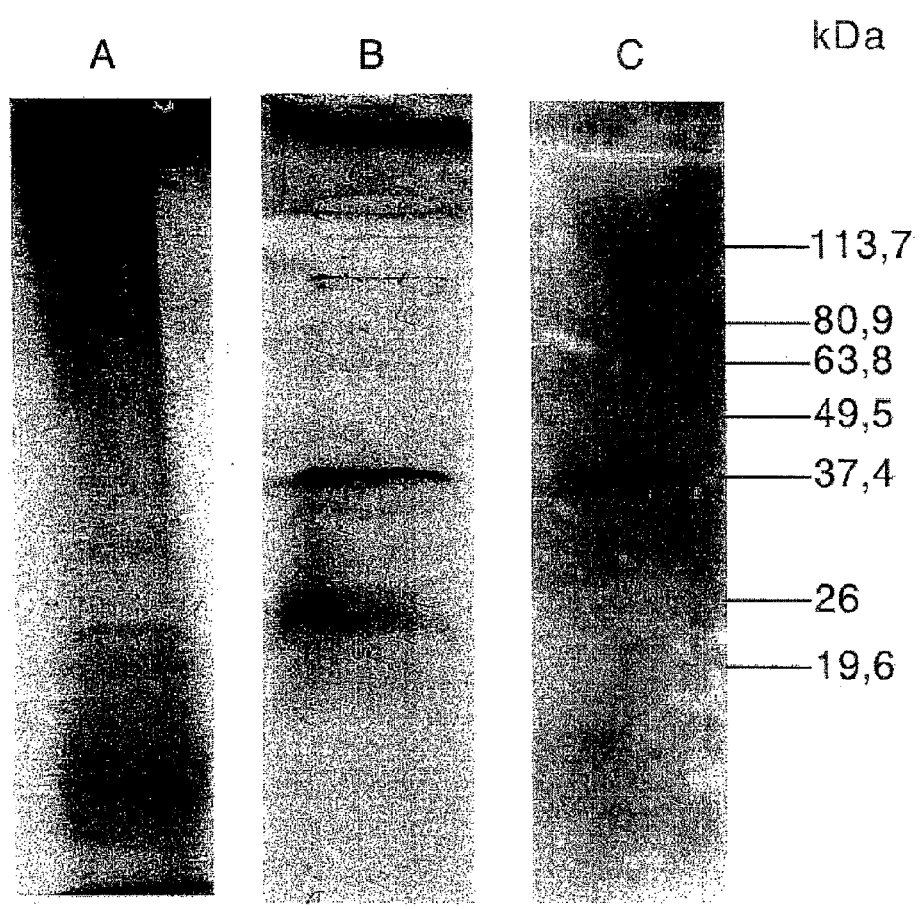

Capsule preparation was analysed by SDS-PAGE and polysaccharide in the preparation were detected by alcian blue staining after Karlyshev et al. (2001, J. Clin. Microbiol. 39, 279-284) showing a variety of carbohydrate containing bands and high percentage of high molecular weight carbohydrates within the preparation (FIG. 4A). After Western blot, polysaccharides were detected by the DIG-Glycan Detection Kit (LaRoche Diagnostics). Showing strong bands at 37 and 26 kDa. (FIG. 4B). Detection of core-1-containing polysaccharide on the western blot was performed using the core-1-specific antibody NEMOD-TF2 (culture supernatant) showing a core-1-positive band at 37 kDa (FIG. 4C).

10.2. Chromatographic Enrichment of Core-1 Positive Polysaccharides

Within the capsule preparation of strain AG6 there were still contaminants of lipopolysaccharides as shown by the measurement or KDO content of 11.2 μmol/μg after Haraet al. 1989, Anal. Biochem. 179, 162-166) and by SDS-PAGE.

Therefore capsule polysaccharides and lipopolysaccharides were separated by reversed phase chromatography on a C18 column using a propanol/methanol-gradient (see FIG. 5) according to Hashimoto et al. (2001, Eur. J. Biochem. 268, 3139-3144). Polysaccharides were eluted by a gradient of eluent B (72% propanol/8% methanol in 0.1M ammonium acetate pH 4.5). Detection of polysaccharides within the fractions was performed by dot blot and DIG-Glycan-Kit. Detection of core-1 was performed using the core-1 specific antibodies Nemod-TF1 and Nemod-TF2. Polysaccharides were eluted at propanol concentrations of 14-19% and 25-43%. Core-1 specific carbohydrate were only detected at 29-29.4% propanol (RP1) and 39-42% propanol (RP2), see FIG. 5 showing strong enrichment of core-1 positive polysaccharide by this method.

Core-1 positive fractions were used for additional chromatographic separations by mild acid hydrolysis followed by DEAE-chromatography using a 0-0.5M NaCl gradient according to Tzianabos et al. (1992, J. Biol. Chem. 267, 18230-18235). By this method the Core-1-positive polysaccharides were separated into three fractions eluted at 0 M NaCl (D1), 0.04 M NaCl (D2) and 0.9-0.17 M NaCl (D3), resulting in a further enrichment of core-1-positive polysaccharides.

In the process according to the instant invention, capsular polysaccharides of B. ovatus AG6 are purified and the structure is analysed by mass spectrometry. Preferable, the capsular polysaccharide of B. ovatus AG6 are accumulated by the phenol water extraction followed by ether extraction as already described by Pantosti et al. 1991. Thereafter, the core-1-positive polysaccharide is accumulated from rough capsular preparation (CPS) by reverse phase chromatography (C18 Synergi 4☐ Fusion-RP 80i, 250 mm×10 mm, Phenomenex). The monosaccharide contents of rough capsular polysaccharide extract and purified core-1-positive polysaccharide are determined by HPAEC-PAD analyses (high pH anion exchange chromatography, pulsed amperometric detection). Finally the structure of the core-1-positive capsular polysaccharide is analysed by mass spectrometry.

10.3 Monosaccharide Analyses of Rough Capsular Preparation Extract and Purified Capsular Extract of B. ovatus AG6

In the first step, the core-1-positive polysaccharide of the rough capsular preparation of B. ovatus AG6 was accumulated by reverse phase chromatography as already described before. Thereafter, the yield of purification as well as the monosaccharide content of accumulated core-1-positive polysaccharide was determined by HPAEC-PAD analyses.

Before monosaccharide analyses occurred, polysaccharide extracts was completely hydrolysed by 2 N trifluoroacetic acid (TFA) at 100° C. for 4 h. During the TFA hydrolyses the acetyl groups were lost. Therefore the monosaccharides glucosamin and galactosamin ($GlcNH_2$ and $GalNH_2$) could not distinguish from N-acetylglucosamine and N-acetylgalactosamin (GlcNAc and GalNAc). Monosaccharides were separated by high pH anion exchange chromatography and detected by pulsed amperometry as already described before. To identify the monosaccharides and to determine their concentrations, external and internal monosaccharide standards were used.

The proportional monosaccharide content of rough CPS extract, which was determined for LPS and CPS comparison (mentioned before), obviously vary from the proportional monosaccharide content of rough CPS extract determined for this comparison. Both rough CPS extracts were prepared from different cultures of B. ovatus AG6, which might be an explication for the mentioned variety of monosaccharide contents.

The yield of core-1-positive polysaccharides accumulated by reverse phase chromatography was 30%. Comparision of proportional monosaccharide contents of rough and purified capsular extracts revealed an increased amount of fucose, GalNAc/GalNH2, galactose and glucose, whereas glucose might be a contamination (table 7). The proportional content of rhamnose, GlcNH2/GlcNAc and mannose could be reduced by reverse phase chromatography (table 7). Galacturonic acid and glucuronic acid, which are characteristic components of capsular polysaccharides, could not be identified in the purified core-1-positive polysaccharide extract. These might indicate, that B. ovatus AG6 have more than one capsular polysaccharide. Both capsular polysaccharides might be separated from each other by reverse phase chromatography. Tzianabos et al. (1992) also described, that the capsule of B. fragilis consists of two different polysaccharides.

TABLE 7

Monosacchride analyses of rough capsular polysaccharide extract (CPS) and core-1-positive polysaccharide extract purified by reverse phase chromatography.

| Monosaccharides | Rough CPS-extract (%) | Purified CPS-extract (%) |
|---|---|---|
| Fucose | 9.5 | 11.4 |
| Rhamnose | 17.7 | 3.1 |

TABLE 7-continued

Monosacchride analyses of rough capsular polysaccharide extract (CPS) and core-1-positive polysaccharide extract purified by reverse phase chromatography.

| Monosaccharides | Rough CPS-extract (%) | Purified CPS-extract (%) |
|---|---|---|
| GalNH2/GalNAc | 5.2 | 14.9 |
| GlcNH2/GlcNAc | 14 | 3.5 |
| Galaktose | 4.6 | 6.9 |
| Glucose | 44.2 | 50 |
| Mannose | 18.2 | 6.9 |
| Galacturonic acid | 10 | 0 |
| Glucuronic acid | 0.5 | 0 |
| n.d. | 3 | 2 |

The proportional monosaccharide content is related to the total amount of monosaccharides.

The accumulation of fucose, GalNH2/GalNAc and galactose might be an indication, that these monosaccharides are components of the repeating units of the core-1-positive polysaccharide. Whereas the strongly reduced monosaccharides could be low contaminations.

10.4 Structure Analyses of the Core-1-Positive Polysaccharide by Mass Spectrometry The structure of core-1-positive polysaccharide was analysed by matrix-assisted laser time-off flight mass spectrometry (MALDI-TOF-MS) as already described above and by electrospray-Ion-Trap-mass spectrometry (ESI-Ion-Trap-MS).

For ESI-Ion-Trap mass spectrometry the accumulated core-1-positive polysaccharide was fragmentated either by hydrolysis with 1% acidic acid (1.5 h, at 100° C.) or enzymatic digestion with chondroitinase ABC (cleavage of beta1-4GalNAc/GlcNAc bounds) or with beta1-3 galactosidase. Furthermore, fragmentation by double digestion with chondroitinase ABC/alpha1-3,4 fucosidase or 1% acidic acid/beta1-3 galactosidase occurred (all enzyms were received from Glyko GmbH). All enzymatic digestions were incubated at 37° C. overnight. Mass spectrometric analyses (MS as well as MS/MS) were carried out in the positive and in the negative mode. Before analyses occurred, all samples were desalted by Carbograph SPE (Aalltech Associates Inc.) as described by manufacturers manual and diluted in 2.5 mM NH3/40% acetonitril.

The structure of core-1-positive glycan fragments, which was already identified by MALDI-MS analyses, could be verified by ESI-Ion-Trap determination. Additional fragments could also be identified by ESI-Ion-Trap mass spectrometry (table 8).

TABLE 8 structure analyses by ESI-Ion-Trap mass spectrometry (positive mode).

| MS | | MS/MS | |
|---|---|---|---|
| Determined masses ($M + H^+$/ $M + NH4^+$) | Identified sequence | Determined masses ($M + Na^+$) | Identified sequence |
| 425/442 | HexNAc-HexNAc | | |
| 573/590 | HexNAc(HexNAc)-Hex | 390 | HexNAc-Hex |
| 749/766 | HexNAc(HexNAc-Hex)-Hex | 595 | HexNAc-HexNAc-Hex |
| 529/545 | DesHex-desHexM-HexNAc | | |
| 690/706 | DesHex-desHexM-HexNAc-Hex | | |
| 733/750 | DesHex-HexNAc(HexNAc)-Hex | | |
| 674/591 | DesHex-desHex-desHexM-HexNAc | 493 | DesHex-desHex-desHexM |
| 633/650 | Hex-desHex-desHex-desHexM | | |

The purified core-1-positive polysaccharide was fragmentated by hydrolyses with 1% acidic acid for 1.5 h at 100° C.
HexNAc: N-acetylhexosamin, Hex: hexose, desHex: desoxyhexose, M: methyl-group The sequence of repeating units of core-1-positive capsular polysaccharide was determined by overlapping fragments (FIG. 6).

Mass spectrometric analyses of enzymatically digested core-1-positive polysaccharides gave indications of glycosidic bounds between the monosaccharides. Furthermore galactose (successful cleavage by beta1-3 galactosidase) and fucose (successful cleavage by alpha1-3,4 fucosidase) could be identified (FIG. 7).

This result is in accordance with the monosaccharide analyses mentioned before, which revealed an accumulation of fucose, galactose and GalNAc.

10.5 Verification of Core-1-Structure as Branching Disaccharide of Repeating Unit of Capsular Polysaccharide The branching core-1-structure, Galbeta1-3GalNAc, in the repeating unit should be identified by double digestion with the exoglycosidases beta1-3 galactosidase and HexNAcase (beta1-2,3,4,6 GalNAc/GlcNAc cleavage) followed by monosaccharide analyses as described above. Two samples containing equal amounts of core-1-positive polysaccharide were filtrated to purify them from free monosaccharides. Afterwards one of both samples was digested with beta1-3 galactosidase at 37° C. overnight. Both samples were filtrated once again to separate free galactose from the digested sample, whereas the undigested sample were used as negative control. Subsequently, the retentats were collected and digested with HexNAcase. Finally both samples were filtrated again. All eluates were analysed by HPAEC-PAD.

To control, if the core-1-structure was removed by double digestion but was untouched by HexNAcase digestion (negative control), the retentates were analysed by dot-blot using the DIG-Glykan Detection Kit (Roche Diagnostics) to detect polysaccharides and the core-1-specific antibody Nemod-TF1 to identify the core-1-structure.

In both eluates of double digested sample galactose (first eluat) and GalNAc (second eluat) could by identified by monosaccharide analyses. While in the eluat of negative control, which was only digested with the exoglycosidase HexNAcase, neither galactose nor GalNAc could be identified. This is a strong indication for the branching core-1-structure, Galbeta1-3GalNAc.

Dot-Blot analyses of double digested retentat and HexNAcase digested sample using the DIG-Glykan detection Kit revealed similar polysaccharide concentrations, which was applied on the nitrocellulose membrane. The core-1-structure could not detected in the double digested sample any more, whereas in the HexNAcase digested sample the core-1-structure was still identified by immunoblot using Nemod-TF1 antibody.

10.6 Verification of the Core-1-Positive Polysaccharide Structure by Analyses of its Separated Fragments.

For further verification of core-1-positive polysaccharide structure, the glykan was fragmentated by hydrolysis with 1% acidic acid (1.5 h, 100° C.). The glycan fragments were labeled by the fluorophore 2-amino benzamide (2-AB) as already described by J. C. Bigge et al. (1995). For this procedure, samples were rendered particle-free and salt-free by purification at Carbograph SPE column (Alltech Associates Inc.) and lyophilized. The pellet was dissolved in 5 µl 2-AB in DMSO/glacial acetic acid/sodium cyanoborohydride and incubated at 60° C. for 2 h. The 2-AB labeled fragments were separated from free 2-AB by paper chromatography. Finally 2-AB conjugated fragments were eluted by water. After lyophilization the pellet was dissolved in 50% acetonitril. Based on their size, fragments were separated by normal phase HPLC (column: Luna 3µ NH2 A100, Phenomenex, eluent A: 15 mM NH4-acetat, eluent B: acetonitril) with fluorescence detection. The sequence of fragments was analysed by ESI mass spectrometry. Finally, for verification of glycosidic bonds and better identification of monosaccharides being components of the fragments, the oligosaccharides were digested with the exoglykosidase beta1-3 galactosidase, alpha1-3, 4 fucosidase and HexNAcase as already described before. The success of digestion was controlled by ESI mass spectrometry and the removal of terminal monosaccharides was identified by HPAEC-PAD as already described before.

The already identified structure of repeating units of core-1-positive polysaccharide was confirmed by both analyses getting the expected oligosaccharide fragments and cleaved monosaccharides (table 9).

Figure 8:
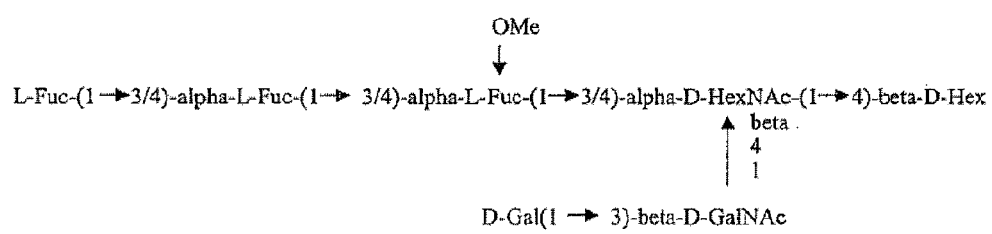

In conclusion, the structure of repeating units of core-1-positive capsular polysaccharide (FIG. 8) was confirmed by a variety of analyses.

Furthermore, the results revealed (please also see FIG. 19, in particular #5), that the glycosidic linkage between the Gal-GalNAc and the backbone GalNAc molecule is alpha-anomeric. This finding was supported by dot blot analyses with mAbs TF1, TF2 and HH8, which are specific for the alpha anomer of TF. The mAbs A68-E/A2 and A68-E/E3 which are specific for TFbeta were also used. Thereby, the tumour-specific Ag TFalpha was identified within the branching structure of capsular polysaccharide of B. ovatus AG6.

Example 11

Animal Model 11.1 Intra-Peritoneal Immunization of Mice with Dead Bacteria
11.1.1 Analysis of Mouse Sera by Humoral Immune Response Test 1

Female Balb/c mice (Charles River, 4 per group) were treated with Cyclophosphamid at a dose of 50 mg/kg body weight at day −1. At days 0, 7 and 14 mice were intra peritoneally injected with $5 \times 10^8$ bacteria (core-1 negative strains AG3 (group I), 32 or 53 or core-1 positive strain AG6 (group K)) in PBS or with PBS alone (group L). Serum samples were taken at days −4, 21, 27 and 30.

Mouse sera were analysed for binding to core-1 in ELISA. As Core-1 carrying antigen served asialoglycophorin. As a negative control periodic acid-treated asialoglycophorin was used. Periodate treatment destroys the outer carbohydrate ring of the core-1 thereby destroying the Core-1 epitope.

96-well flat-bottom microtiter plates were coated with asialoglycophorin A (AGP) at a concentration of 2 µg/ml. Plate was washed 3 times with PBS/TWEEN polysorbate. Half the plate was treated with periodate as follows:

Wells were incubated for 5 minutes with 50 mM sodium acetate buffer pH 4.5 followed by a 1 h incubation with 10 mM periodic acid in acetate buffer in the dark. Wells were incubated for 5 minutes with 50 mM sodium acetate buffer pH 4.5. Reaction was stopped by incubation with sodium borohydride (50 mM in PBS, 30 min). Next, plates were washed 5 times with PBS/TWEEN polysorbate.

Plates were then blocked by addition of 2% BSA for 30 min.

Incubation with different dilutions of mouse sera were performed for 1.5 h. Bound mouse immunoglobulin was detected with a peroxidase-conjugated goat anti-mouse IgM antibody (1:5000 in PBS/1% BSA). Assay was developed with TMB as substrate and reaction was stopped by addition of 2.5 N $H_2SO_4$.

TABLE 9

| Fragments of oligosaccharides | exoglycosidase | ESI-MS analyses | Monosaccharide analyses |
|---|---|---|---|
| HexNAc-Hex | beta1-3 galactosidase | HexNAc<br>Hex<br>HexNAc-Hex | GalNAc/GalNH2<br>galactose |
| DesHex-desHex-desHexM | alpha1-3,4 fucosidase | desHexM<br>DesHex-desHexM<br>DesHex-desHex | fucose |
| DesHex-desHex<br>DesHex-desHexM-<br>HexNAcM-HexNAc | alpha1-3,4 fucosidase<br>HexNAcase<br>(alpha1-2,3,4,6<br>GalNAc/GlcNAc) | desHex<br>HexNAc<br>DesHex-desHexM-<br>HexNAc | fucose<br>n.d |

Figure 9:
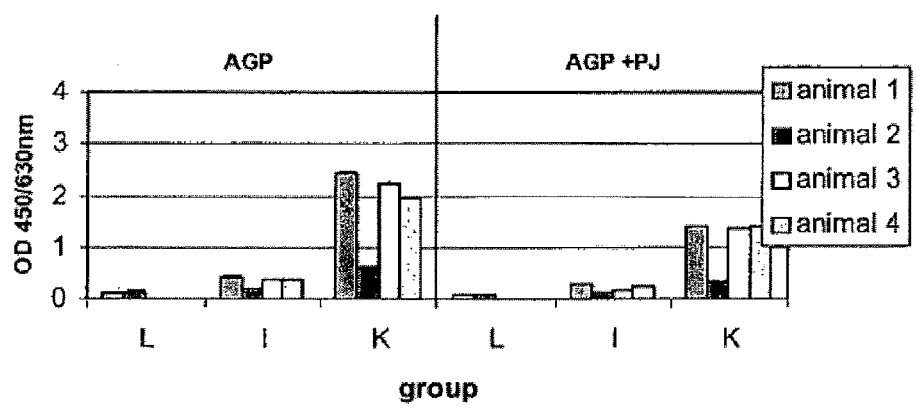

FIG. 9 shows the binding of serum IgM-antibodies to core-1 positive AGP and core-1 negative AGP (AGP+PJ). Only sera of three out of 4 mice immunized with Core-1-positive bacteria (group K) showed strong binding to AGP, whereas the signal is reduced after cleavage of Core-1 with PJ.

Therefore, core-1-positive bacteria are capable of inducing core-1-directed humoral immunity in mice.

11.1.2 Analysis of Mouse Sera by Humoral Immune Response Test 2

Male C3H mice (Charles River, 4 per group) were intraperitoneally immunized with 5×10$^8$ pasteurized bacteria from Core-1 positive and Core-1 negative strains in 200 µl PBS at days 0, 7 and 14. Sera were collected prior to immunization and at days, 13, 21 and 28 and analysed in humoral immune response test 2.

96-well flat-bottom microtiter plates were coated with different carbohydrate-PAA conjugates (GlcNAcβ1-2Galβ1-3GalNAcalpha-PAA, Fucalpha1-2Galβ1-3GalNAcalpha-PAA, GalNAcalpha1-3Galβ-PAA, Galalpha1-3-GalNAcβ-PAA, Gal beta1-3GalNAc alpha1-PAA) at 5 µg/ml in coating buffer (8.4 g/l NaHCO$_3$, 3.56 g/l Na$_2$CO$_3$, pH=9.49) and incubated over night at 4° C.

Plate was washed 3 times with PBS/TWEEN polysorbate. Plates were then blocked by addition of 2% BSA for 30 min.

Incubations with different dilutions of mouse sera were performed for 1.5 h. Bound mouse immunoglobulin was detected with a peroxidase-conjugated goat anti-mouse IgM antibody (1:5000 in PBS/1% BSA). Assay was developed with TMB as substrate and reaction was stopped by addition of 2.5 N H$_2$SO$_4$.

FIG. 10 shows the mean value of ELISA signals against the PAA conjugate Gal beta1-3GalNAc alpha1-PAA relative to the ELISA signal against GlcNAcβ1-2Galβ1-3GalNAcalpha-PAA, for sera from 4 mice per group at day 0 (pre-immune serum) and day 21 [relative ELISA signal is calculated after the equation: (ELISA signals against Gal beta1-3GalNAc alpha1-PAA)*100/(ELISA signal against GlcNAcβ1-2Galβ1-3GalNAcalpha-PAA)]. Sera were calculated as positive if immune serum showed an increase of at least 50% compared with the pre-immune serum. It could be shown that only the Core-1-positive strains AG6 and MU1 induced a Core-1 specific humoral immune response in mice.

11.1.3 Analysis of Mouse Sera by Humoral Immune Response Test 3

Female Balb/c mice (Charles River, 4 per group) were treated with Cyclophosphamid at a dose of 50 mg/kg body weight at day −1. At days 0, 7 and 14 mice were intra peritoneally injected with 5×10$^8$ bacteria (core-1 negative strains AG3 (group I), 32 or 53 or core-1 positive strain AG6 (group K)) in PBS or with PBS alone (group L). Serum samples were taken at days −4, 21, 27 and 30.

Flow cytometric analyses were performed in order to analyze binding of mouse sera to Core-1 positive and core-1 negative human tumour cell lines (NM-wt and NM-D4, respectively; NM-wt is the parental cell of NM-D4 as described in WO2005/017130 A2 and EP1654353, NM-D4 is deposited at the DSMZ under DSM ACC2605). 3×10$^5$ cells per tube were pelleted and the pellet was resuspended in 50 µl murine serum (diluted 1:50 in PBS/10% FCS), control antibody or PBS/10% FCS alone. Samples were incubated for 20 min at 4° C., washed with PBS and centrifuged. Next, cells were incubated with Cy3-conjugated goat anti-mouse-IgM antibody (Jackson Immuno Research, 1:200 in PBS/10% FCS) for 20 min at 4° C., washed with PBS and resuspended in 200 µl PBS for flow cytometric analysis.

Figure 11:
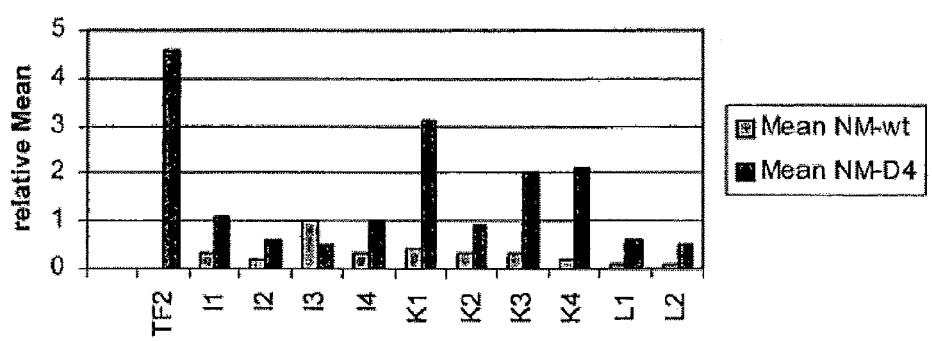
FIG. 11A shows mean fluorescence intensity of FACS analysis of mouse sera from mice immunized with PBS (group L), Core-1 negative bacteria (group I) and Core-1 positive bacteria (AG6, group K) at day 21.
FIG. 11B shows histogram overlay (black: group L, blue: group I, red: group K) of the FACS analysis.
FIG. 11c shows the results of the humoral immune response test 1 with sera of mice immunized with bacteria strains *Bacteroides ovatus* MU-1, *E. coli* LH2, *E. coli* AG3, *E. coli* O86 DSMZ 8697=32 (mean values of 4 mice per group are shown).
FIG. 11d shows the results of the humoral immune response test 2 with sera of mice immunized with bacteria strains *Bacteroides ovatus* MU-1, *E. coli* LH2, *E. coli* AG3, *E. coli* O86 DSMZ 8697=32 (mean values of 4 mice per group are shown).
FIG. 11e shows the results of the humoral immune response test 3 with sera of mice immunized with bacteria strains *Bacteroides ovatus* MU-1, *E. coli* LH2, *E. coli* AG3, *E. coli* O86 DSMZ 8697=32 (mean values of 4 mice per group are shown).

FIGS. 11a and b shows the binding of IgM antibodies from mouse sera to the human cell lines NM-wt (Core-1 negative) and NM-D4 (core-1 positive). Whereas binding to the Core-1 negative NM-wt line is comparable between mice immunized with Core-1 negative bacteria (group I) and Core-1 positive bacteria (group K), there is a significantly stronger binding of 3 out of 4 mice from group K to the Core-1 positive NM-D4 line. This is indicative of the core-1 specificity of the humoral immune response in mice immunized with Core-1 positive bacteria.

11.1.4 Analysis of Mouse Sera by Humoral Immune Response Tests 1, 2 and 3

C3H mice (Charles River, 4 mice per group) were intraperitoneally immunized with 1×10$^9$ pasteurized bacteria from Core-1 positive *Bacteroides ovatus* strain *Bacteroides ovatus* MU-1, A68-BA11-positive *E. coli* strain LH2 and Core-1 negative *E. coli* strains (AG3, *E. coli* O86 DSMZ 8697=32) in 200 µl PBS at days 0, 7 and 14. Sera were collected prior to immunization and at days 13, 21 and 28 and analysed in humoral immune response tests 1, 2 and 3 as described above.

While strain AG3 was negative for all humoral immune response tests, serum collected from mice after immunization with the strains *E. coli* O86 and LH2 showed AGP reactive antibodies in HIRT 1. Nevertheless, only the Core-1 positive strain MU-1 showed strong anti-Core 1 specific humoral immune responses against Core-1 on PAA conjugates (HIRT 2) and on human tumor cells (HIRT 3) in addition to the induction of AGP specific antibodies in HIRT. Therefore, we could induce a strong Core-1 specific humoral immune response only with a Core-1 positive microorganisms of the *Bacteroides ovatus* (MU-1).

Figure 11C:
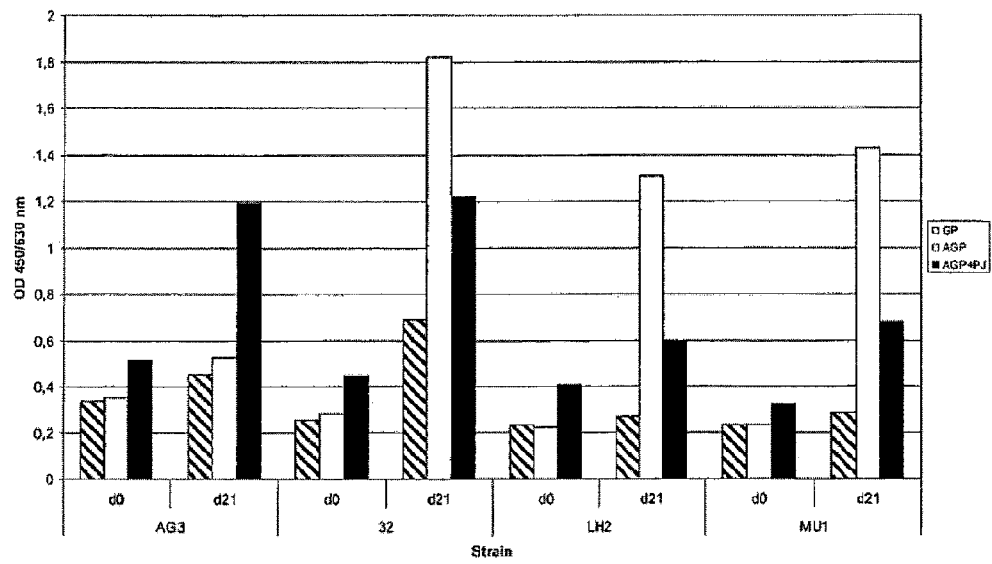
Figure 11D:
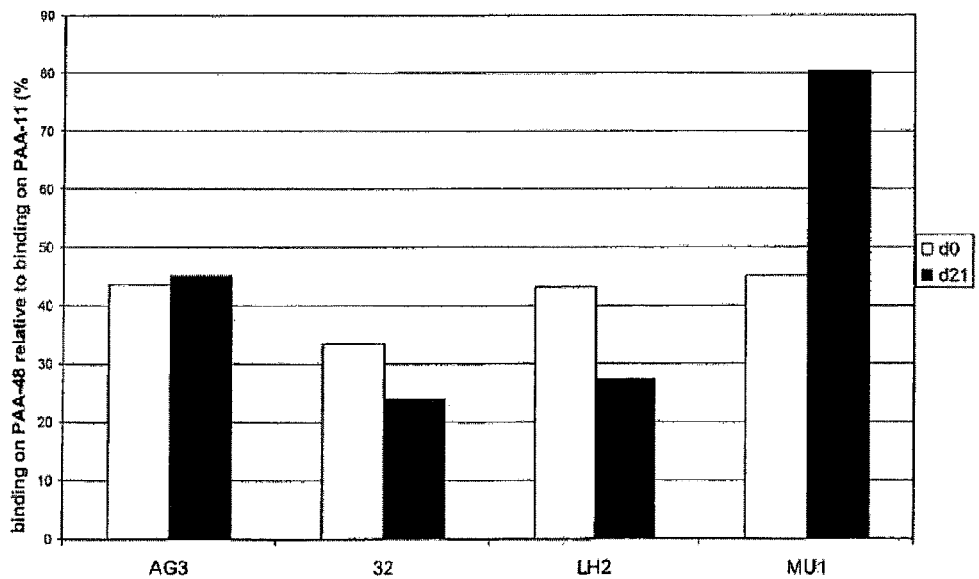
Figure 11E:
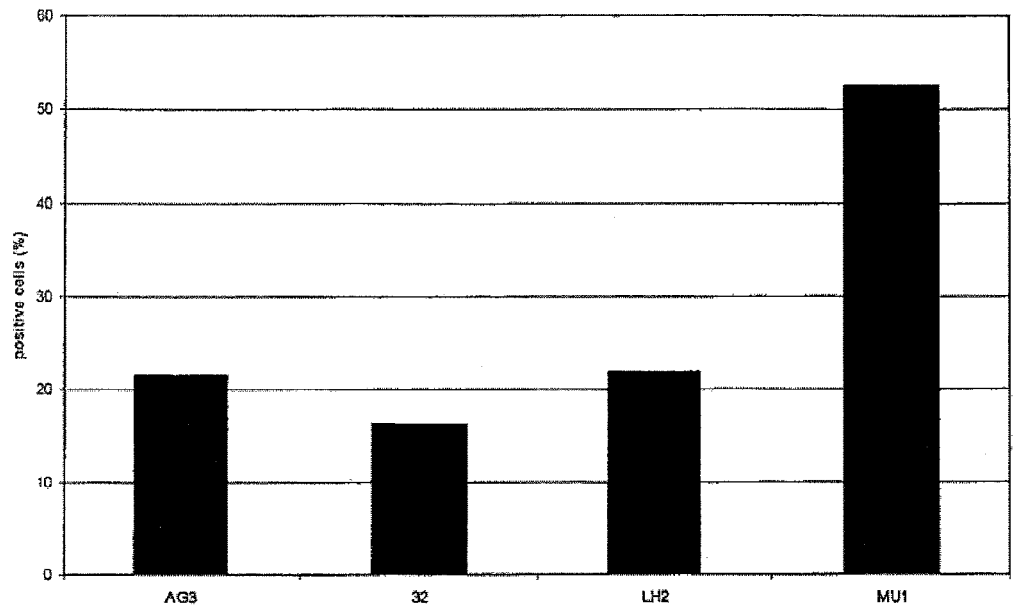

FIG. 11c to e show the results.

11.2. Oral Immunization of Germfree Mice with Live Core-1 Positive Bacteria

Germfree C3H-mice were orally immunized with 2×10$^9$ live bacteria of strain AG6 at days 2, 3, 4, 9, 10, 11, 16, 17 and 18. Serum samples were taken at day 0 (pre-immune sera) and at days 14 and 21 and analysed for AGP-specific IgM antibodies in humoral immune response test 1.

Figure 12:
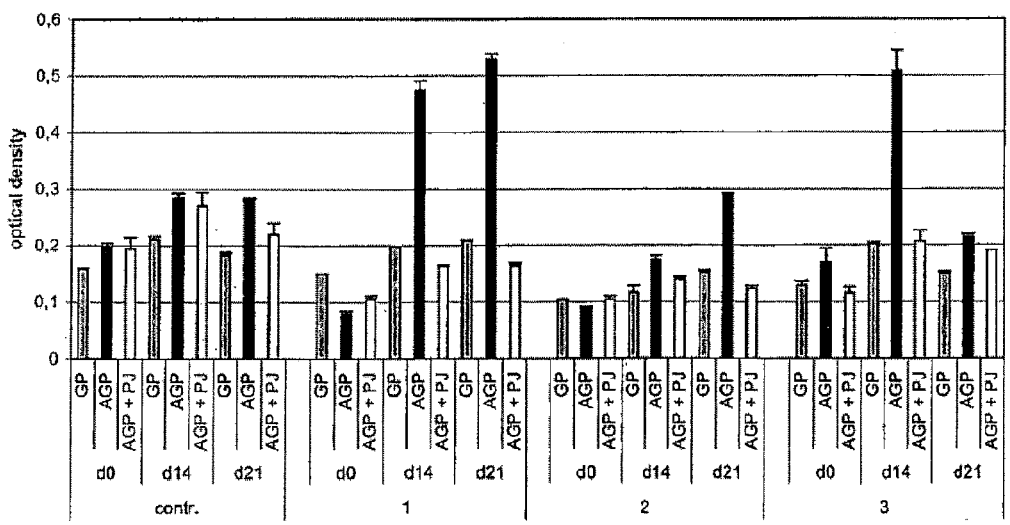

Immunized mice showed increased anti-core-1 titers compare to control mice as shown by binding of mouse sera to AGP coated microtiterplates. Detection of bound mouse IgM was performed with peroxidase-coupled anti-mouse-IgM antibodies. Specificity of the signal for core-1 was shown by the decrease of the ELISA signal after treatment with periodic acid (destroying the carbohydrate structure). After 14 or 21 days 3 out of 3 mice had elevated IgM-antibody levels to Core-1 whereas control mice showed no increase of ELISA signals to AGP in comparison to AGP+PJ as shown in FIG. 12.

11.3 Oral Immunization of Conventional Mice with Pasteurised and Living Core-1 Positive Bacteria C3H-mice were orally immunized with 1×10$^{11}$ (group A) or 1×10$^{10}$ (group B) pasteurized bacteria of strain AG6 daily at days 0 to 28. Serum samples were taken at day −1 (pre-immune sera) and at days 13, 21, 28 and 35 and analysed for AGP-specific IgM antibodies in humoral immune response test 1.

Serum collected from mice after immunization showed increased anti-Core-1 titers as shown by binding of mouse sera to microtiterplates coated with GP or AGP (with and without treatment with periodic acid). Detection of bound mouse IgM was performed with peroxidase-coupled anti-mouse-IgM antibodies. Specificity of the signal for core-1 was shown by the decrease of the ELISA signal after treatment with periodic acid (destroying the carbohydrate structure decrease of at least 30%) and by the lower signal against GP (increase of AGP signal of at least 50%).

It was shown that 5 out of 6 mice from group A and 5 out of 8 mice from group B had developed Core-1 specific antibodies by day 21 (FIG. 13).

In humoral immune response test 3 mouse sera were analysed for binding to the Core-1 positive tumor cell line NM-D4 in comparison to the Core-1 negative cell line NM-wt by flow cytometry. $3 \times 10^5$ cells per tube were pelleted and the pellet was resuspended in 50 µl murine serum (diluted 1:300 in PBS/1% BSA), control antibody or PBS/1% BSA alone. Samples were incubated for 60 min at 4° C., washed with PBS and centrifuged. Next, cells were incubated with biotin-conjugated goat anti-mouse-IgM antibody (Jackson Immuno Research; 1:200 in PBS/1% BSA) for 60 min at 4° C. and washed with PBS. Following cells were incubated with Cy3-conjugated streptavidin (Jackson Immuno Research, 1:200 in PBS/1% BSA) for 60 min at 4° C. and resuspended in 200 µl PBS for flow cytometric analysis.

Results were calculated after the following formula:

(% positive cells on $NM\text{-}D4_{immune\ serum}$ −% positive cells on $NM\text{-}D4_{pre\text{-}immune\ serum}$)/(% positive cells on $NM\text{-}wt_{immune\ serum}$ −% positive cells on $NM\text{-}wt_{pre\text{-}immune\ serum}$)=$X$ Mouse sera with a quotient $X \geq 10$ were seen as positive (with % positive cells on $NM\text{-}wt_{immune\ serum}$ −% positive cells on $NM\text{-}wt_{pre\text{-}immune\ serum} \geq 1$).

Figure 14:
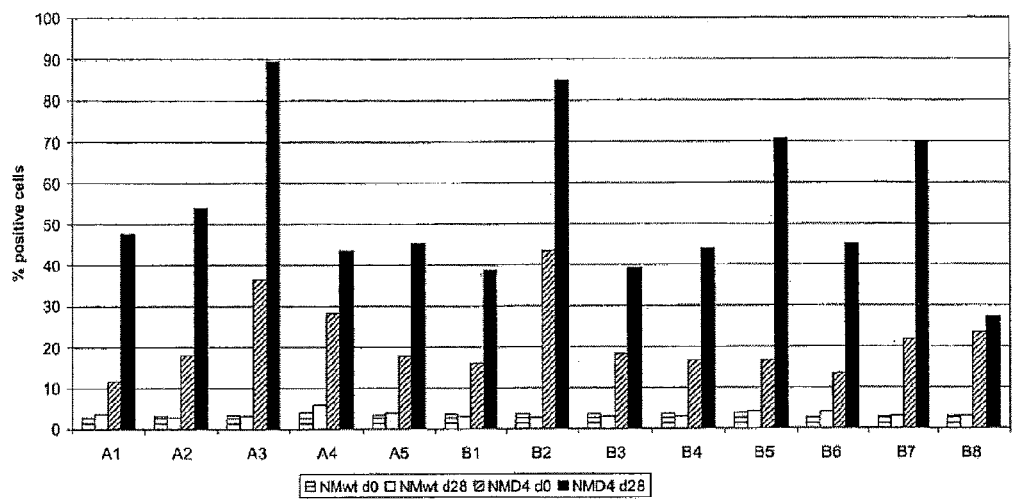

At day 28, 11 of 13 mice had developed a humoral immune response against the Core-1 positive human tumor cell line NM-D4 as shown in FIG. 14.

In humoral immune response test 2 mouse sera from day 28 were analysed for binding to Galβ1-3 GalNAc a-PAA (PAA 48) or Galβ1-3 GlcNAc a-PAA (PAA 43).

96-well flat-bottom microtiter plates were coated with either Galβ1-3 GalNAc a-PAA (PAA 48) or Galβ1-3 GlcNAc a-PAA (PAA 43) at 5 µg/ml in coating buffer (8.4 g/l NaHCO3, 3.56 g/l NA2CO3, pH=9.49) and incubated over night at 4° C. After blocking, incubations with sera were performed for 1.5 hour. Bound mouse immunoglobulin was detected with a peroxidase-conjugated goat anti-mouse IgM antibody (1:5000 in PBS 1% BSA). Assay was developed with TMB as substrate and reaction was stopped by addition of 2.5N H2SOP4.

The results are shown in FIG. 21. It was shown that 5 out of 13 mice had developed Core-1 specific antibodies by day 28.

Example 12

Potential of Core-1 Positive Bacteria for the Induction of a Cellular Immune Response (in Vitro)

12.1 Generation of Functional Dendritic Cells

Dendritic cell line NemodDC (pNM-DC) has been used as source for antigen presenting cells (APC). The pNM-DCs were differentiated into iNM-DC, followed by loading with bacterial lysates (BaLy) of following bacteria strains: AG6, MU1, 52 and 53. 50 µg/ml of every BaLy was added together with maturation cytokines to the culture media and iNM-DC were differentiated to their mature status (mNM-DC).

More detailed, in the first step pNM-DC ($1 \times 10^5$/ml) were differentiated into iNM-DC by 7 days incubation in NemodDC medium (70% MEM-alpha, 20% FCS, 10% CM5637) with addition of 1000 U/ml of GM-CSF, 100 U/ml IL-4 and 2.5 ng/ml TNF-alpha. Next, $1 \times 10^6$/ml of immature NM-DC (iNM-DC) were loaded either with bacteria lysates (50 µg/ml), tumor cell lysates ($1 \times 10^6$ lysed tumor cells for loading on $1 \times 10^6$ NM-DC) or AGP- and GP-proteins (20 µg/ml) and maturated for 2 days by addition of 75 ng/ml TNF-alphã.

The maturation phenotype of mNM-DC is very important for successful T-cell activation and was tested by means of flow cytometry for expression of CD1a, CD11c, CD14, CD40, CD35, CD80, CD83, CD86, CD116, HLA-ABC and HLA-DR. Only those DC which had phenotype correspondent to the phenotype of mature DCs were used for T-cell activation.

12.2 Generation of Activated T Cells Against Core-1 and Detection of GM-CSF (Cellular Immune Response Test 1) and TNF-Alpha (Cellular Immune Response Test 2) Production Using ELISA After 7-10 days of priming of T lymphocytes with NM-DC loaded with Core-1-positive bacterial lysates, resulting T cells (0.7-$1 \times 10^6$/ml) were restimulated with mNM-DC ($1 \times 10^5$/ml) loaded with Core1-positive tumor cell lysates (50 µg/ml). Following 48 hours of incubation supernatants were harvested and assayed using for evaluation of the cytokine production in response to human Core-1-positive tumor cell line NM-D4 the GM-CSF- and TNF-alpha-BD OptEIA™ Kits.

The 96-well plates were pre-coated with 50 µl of appropriate capture anti-human (GM-CSF or TNF-alpha) antibodies diluted 1:250 in coating buffer. After washing and blocking steps, 100 µl of supernatants or standards were added to microwells and incubated for 2 hours at room temperature. For standard curve the recombinant human GM-CSF in concentrations 0; 7.8; 15.6; 31.2; 62.5; 125; 250 pg/ml and the recombinant human TNF-alpha in concentrations 0; 4.7; 9.4; 18.8; 37.5; 75; 150; 300 pg/ml were used. After washing, 100 µl prepared Working Detector solution per well were added, and plate was incubated 1 hour at room temperature. In the next step 100 µl TMB One-Step Substrate Reagent were added per well. After final incubation for 30 minutes and addition of 50 µl of Stop Solution the extensions were read at 450 nm.

Figure 15:
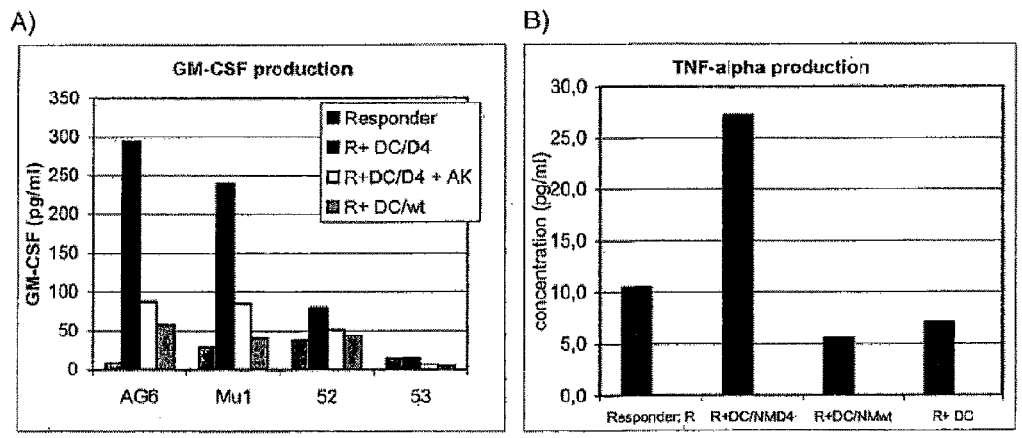

The results demonstrated in FIGS. 15A and B show clear evidence that T cells generated to Core1-positive bacteria lysates are able to recognise DC loaded with Core1-positive cell-lysate from human cell line NM-D4 by production of tumor-inhibitory cytokines such as TNF-alpha and GM-CSF. In contrast, very low level of cytokines was released in response to Core1-negative cell lysates. Moreover, this recognition was specifically inhibited through pre-incubation of lysate-loaded NM-DC with Core1-specific antibody.

12.3 ELISPOT Assay for Evaluation of the Secretion of IFN-Gamma by Activated T Lymphocytes Directed Against Core-1 (Cellular Immune Response Test 2)

ELISpot assay was used for evaluation of IFN-gamma secretion in response to antigen specific stimulation. This assay allows the quantification of functional ability of the pre-sensitised T cells to recognise Core1 antigens in an antigen specific manner.

The T lymphocytes were first activated in vitro by being co-cultured with DC loaded with bacterial lysates. After 7 to 10 days of priming, activated T cells were harvested and re-challenged with DC (in ratio T cell to DC 10:1) loaded with Core1-positive (NM-D4) and Core1-negative (NM-wt) human tumor cell lysates.

The wells of the ELISpot plate were pre-coated with mouse-anti-human-IFN-gamma-antibody (Mabtech-Kit) that binds to the nitrocellulose base of the ELISpot plate. The re-challenged T cells were transferred into the wells, and cytokines were released during the incubation period. IFN-gamma that is released locally around each T cell binds to, and is therefore 'captured' by the specific antibody. After 24 hours of incubation the cells were removed. A second anti-human-IFN-gamma antibody in concentration 1 µg/ml is added to the wells; this biotinylated antibody is coupled to an enzyme that is capable of converting a substrate into an insoluble coloured product. The plates are washed once more, and streptavidin conjugated with enzyme-AP in a concentration of 1 µg/ml is added. Finally a precipitating substrate BCIP+NBT is added and the plate is incubated until spots emerge at the side of the responding T cells. The coloured spots are counted and analysed using a digital-imaging system.

Figure 16:
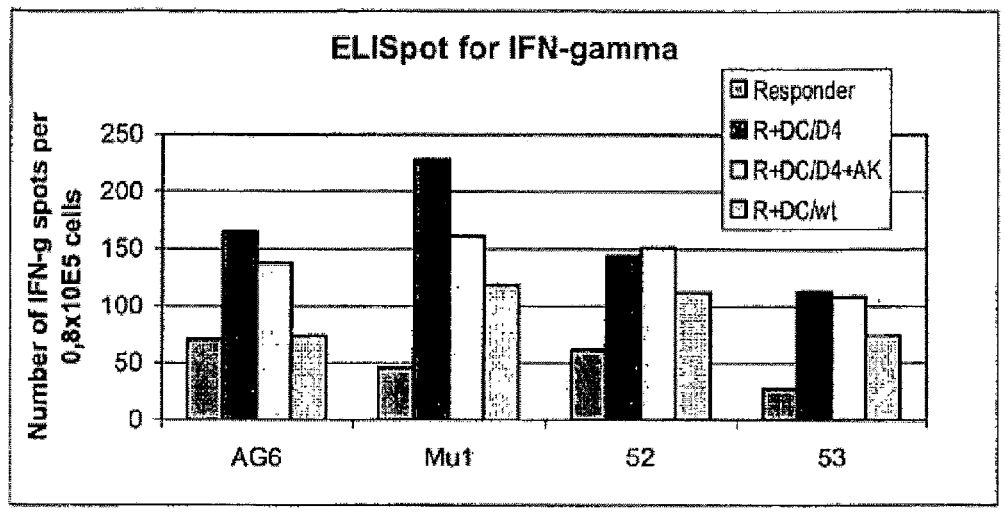

The results showed that T cells generated to Core1-positive bacterial lysates (AG6 and MU1) are able to recognise DC loaded with Core1-positive cell-lysate from human tumor cell line NM-D4 by production of tumor-inhibitory cytokine IFN-gamma (FIG. 16). Very low level of cytokines was released in response to Core1-negative cell lysates (R+DC/wt). Furthermore, the specificity of recognition of Core1-positive cell-lysate (R+DC/D4) was proved by blocking of cytokine release with the Core-1 specific antibody Nemod-TF1 (R+DC/D4+Ak).

12.4 Cellular Immune Response Test 3: T-Cell Proliferation Assay

The sensitised and re-stimulated T cells as described above for ELISpot analysis, were transferred after incubation from ELISpot plate into 96-well plate and were assayed using the colorimetric Cell Proliferation Reagent WST-1 (Roche Molecular Biochemicals), whose tetrazolium salt is cleaved by mitochondrial enzymes so that the amount of dye developed (read at 450 nm) directly correlates to the number of metabolically active cells in the culture. Absorbance of culture medium plus wst-1 in the absence of cells was the blank position for the enzyme-linked immunosorbent assay reader. The procedure consists of one-step-adding of 10 µl per well of WST-Proliferation reagent (Roche) and incubation for 3 hours at 37° C. following measurement at 450 nm.

Figure 17:
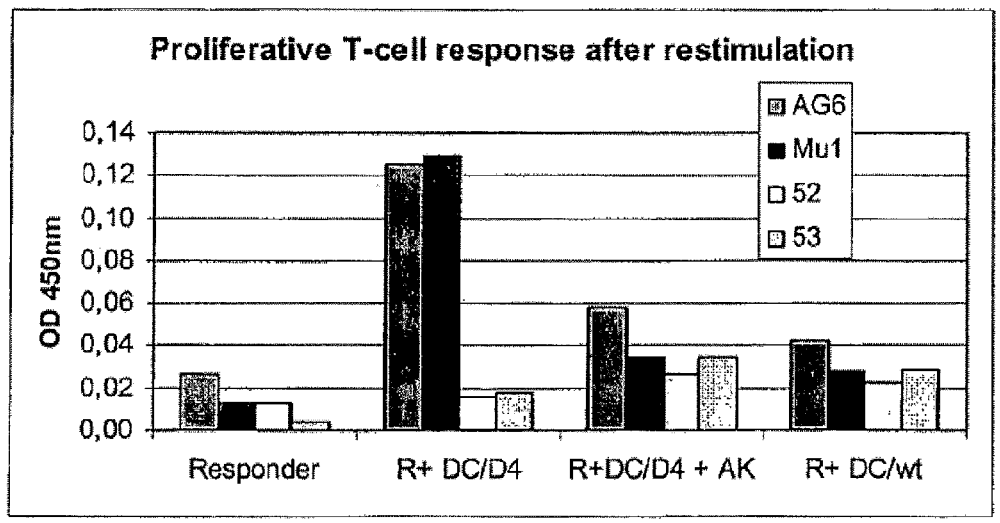

The results demonstrated in FIG. 17, show clear evidence that T cells generated to Core1-positive bacteria lysates, recognise DC loaded with Core1-positive cell-lysate from human tumor cell line NM-D4 as shown by specific proliferation. Moreover, this recognition was specifically inhibited through pre-incubation of lysate-loaded NM-DC with Core1-specific antibody.

12.5 Cellular Immune Response Test 4: Immunofluorescence Test for Core-1 Presentation on DCs Loaded with Bacterial Lysates In order to analyse the processing and presentation of Core-1 by bacterial lysate-loaded NM-DC, immunofluorescence analyses were performed using core-1 specific monoclonal antibodies (Nemod-TF1, NEMOD-TF2). The presentation of the processed Core1-antigen on the surface of the mature DC was demonstrated with help of Immunofluorescence. Immunofluorescence (IF) is a technique allowing the visualization of a specific antigen (Core1)) on cells by binding a specific Core-1 antibody following by addition of a secondary antibody labeled with fluorochrome, which is used to recognize a primary antibody.

In the first step pNM-DC ($1\times10^5$/ml) were differentiated into iNM-DC by 7 days incubation in NemodDC medium (70% MEM-alpha, 20% FCS, 10% CM5637) with addition of 1000 U/ml of GM-CSF, 100 U/ml IL-4 and 2.5 ng/ml TNF-alphaNext, $1\times10^6$/ml of immature NM-DC (iNM-DC) were loaded either with bacteria lysates (50 µg/ml), tumor cell lysates ($1\times10^6$ lysed tumor cells for loading on $1\times10^6$ NM-DC) or AGP- and GP-proteins (20 µg/ml) and maturated for 2 days by addition of 75 ng/ml TNF-alpha Matured and antigen loaded DC were washed and $1\times10^6$ cells per 50 µl were placed on the microtiterplate for immunofluorescence staining. 3 µg/ml of Core-1-specific antibody (Nemod-TF1) diluted in culture medium (10% FCS) was incubated with cell suspension for 1 hour at room temperature. After washing steps 50 µl 1:200 diluted secondary goat anti-mouse IgM, Cy3-labeled Ab (Jackson/Dianova) were added and incubated for 30 minutes. Following washing steps, 20 µl of cell suspension were placed into each well of a Multitest slide (10 wells, Roth). Immunofluorescence stained samples were examined with an Axioplan 2 fluorescence microscope equipped with the digital camera AxioCam (Zeiss).

Figure 18:
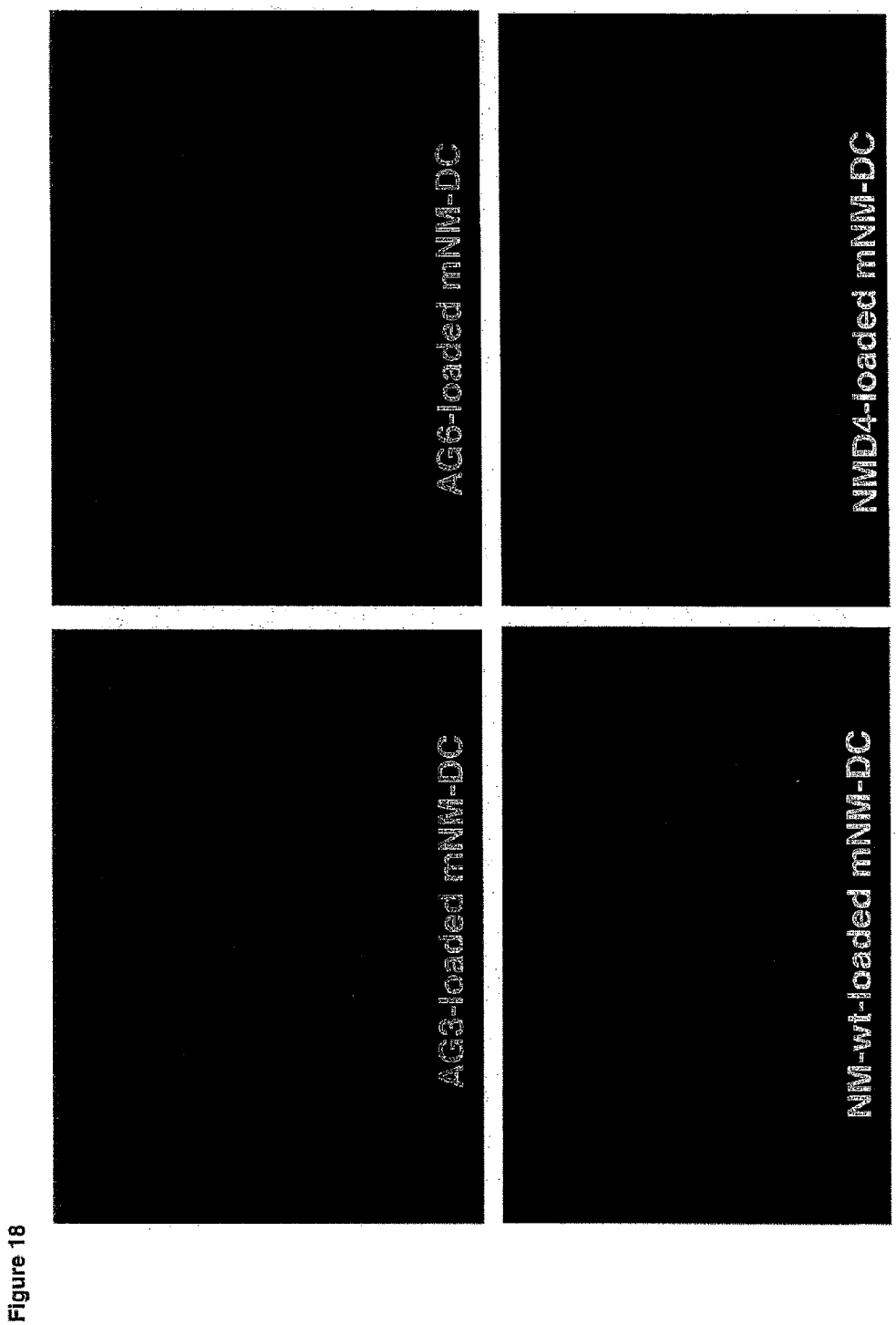
Figure 23:
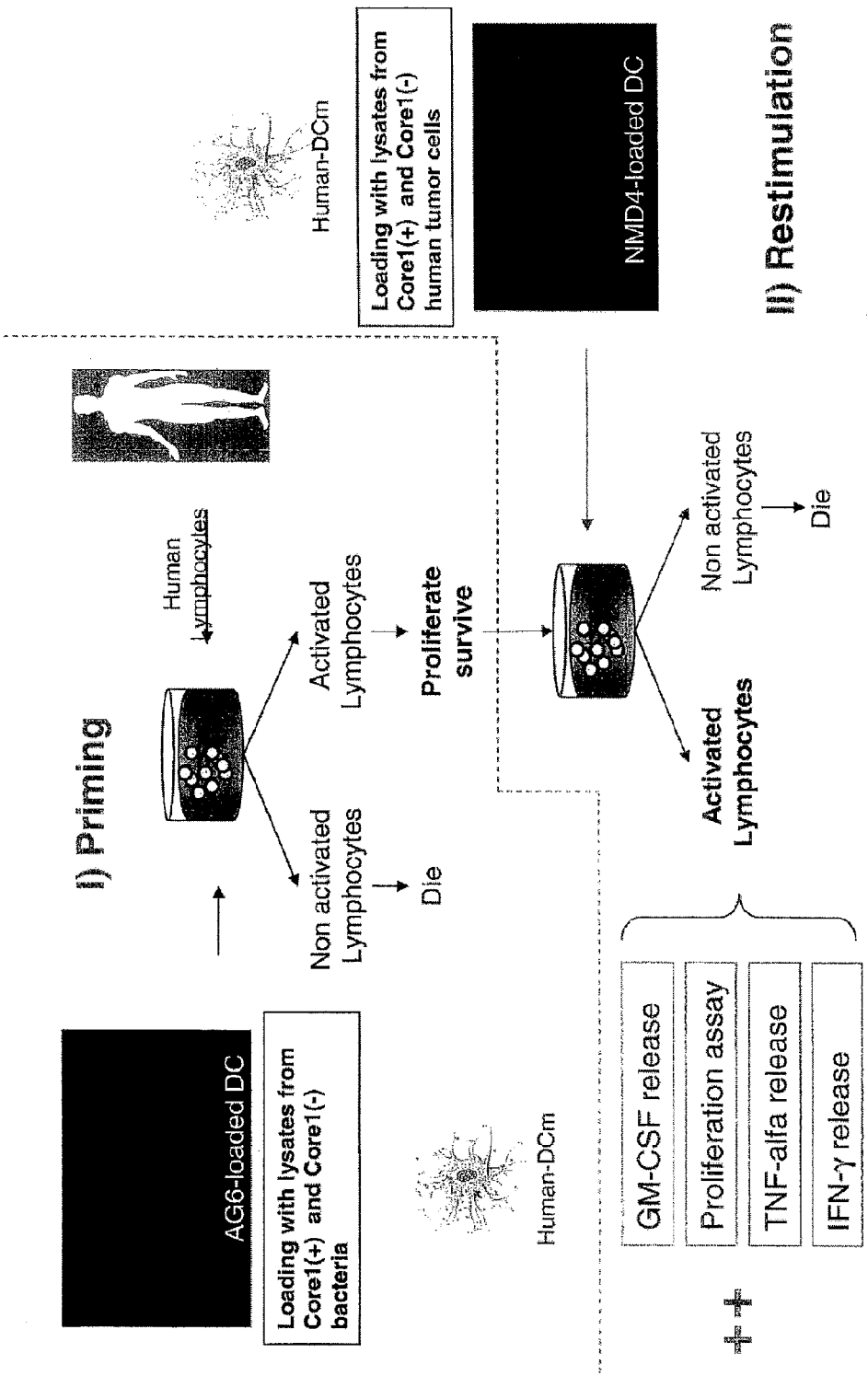

FIG. 18 shows positive Core-1-specific staining of the mature mNM-DC, which have processed AG6- and NM-D4-Core1-positive lysates; and negative immunofluorescence on mNM-DC loaded with Core1-negative lysates (AG3 and NM-wt)

While the invention has been described in terms of preferred embodiments, the skilled artisan will appreciate that various modifications, substitutions, omissions and changes may be made without departing from the spirit thereof. Accordingly, it is intended that the scope of the present invention be limited solely by the scope of the following claims, including equivalents thereof. Therefore, as will be apparent to those skilled in the art in which the invention is addressed, the present invention may be embodied in forms other than those specifically disclosed above without departing from the spirit or essential characteristics of the invention. The particular embodiments of the present invention, described above, are therefore to be considered in all respects as illustrative and not restrictive. The scope of the present invention is as set forth in the appended claims rather than being limited to the examples contained in the foregoing description. It should be understood that various alternatives to the embodiments of the invention described herein may be employed in practicing the invention. It is intended that the following claims define the scope of the invention and that the method and means within the scope of these claims and their equivalents be covered thereby.

Cell Lines:

NM-D4 (DSM ACC2605), NM-F9 (DSM ACC2606), ZR-75-1 (ATCC CRL-1500), CAMA-1 (ATCC HTB-21), KG-1 (DSM ACC 14), or A-204 (DSM ACC 250). NM-wt or NM-H9 (or NM-H9D8 DSM ACC2806). The NM-9 and NM-D4 cell lines have been deposited at the DSMZ by Nemod Biotherapeutics GmbH & Co. KG, Robert-Rossle-Strasse 10, 13125 Berlin, Germany (i. e. the depositor) who authorise the applicant of the present application to refer to the deposited biological material described herein and give their unreserved and irrevocable consent to the applicant of the present application that the deposited biological material described herein be made available to the public in accordance with Rule 28 (1) (d) of the European Patent Convention. The DSMZ is located at the Mascheroder Weg 1 b, D-38124 Braunschweig, Germany. The aforementioned DSMZ deposits were made pursuant to the terms of the Budapest treaty on the international recognition of the deposit of microorganisms for purposes of patent procedure.

AG6 (DSM 18726), MU1 (DSM 18728) and the new strain *Escherichia coli* LH2 (DSM 18727) deposited at the "DSMZ-Deutsche Sammlung von Mikroorganismen and Zellkulturen GmbH" in Braunschweig (Germany), by Glycotope GmbH, Robert-Rössle-Str. 10, 13125 Berlin (Germany) at the Oct. 20, 2006.

The invention claimed is:

1. A method for isolating a carbohydrate positive microorganism comprising a carbohydrate epitope of interest from a mixture of microorganisms, wherein the carbohydrate positive microorganism is capable of triggering a cellular immune response, comprising
    (a) bringing a carbohydrate binding molecule specific for the carbohydrate epitope of interest into contact with a mixture of microorganisms,
    (b) isolating at least one microorganism bound to said carbohydrate binding molecule from said mixture,
    (c) optionally testing that the isolated microorganism is a carbohydrate positive microorganism by testing the isolated microorganism for specific binding to said carbohydrate binding molecule, and
    (d) testing the induction of an effective carbohydrate specific cellular immune response against said carbohydrate epitope by said microorganism or a fraction or lysate thereof in vivo or in vitro, wherein step (d) comprises loading dendritic cells with said carbohydrate positive microorganism or fraction or lysate thereof and determining whether the carbohydrate epitope is presented by the dendritic cells, wherein presence of functional dendritic cells presenting the carbohydrate epitope is indicative for a carbohydrate microorganism capable of triggering a cellular immune response.

2. The method according to claim 1, wherein step (d) comprises testing the induction of an effective carbohydrate specific cellular immune response against said carbohydrate epitope by said carbohydrate positive microorganism and/or fraction and/or lysate thereof for the activation of CD4 positive Th1 type T cells and/or for the activation of cytotoxic CD8 positive T cells.

3. The method according to claim 1, wherein testing of the cellular immune response in step (d) comprises
    i) Loading at least one dendritic cell with the carbohydrate positive microorganism;
    ii) bringing into contact a suitable amount of said at least one dendritic cell loaded with said carbohydrate positive microorganism with a suitable amount of immune cells which can be activated or inhibited by a dendritic cell;
    iii) cultivating the resulting mixture in order to allow interaction of said immune cells with said loaded dendritic cells;
    iv) adding a suitable amount of antigen presenting cells (APC) loaded with a suitable amount of at least one second compound carrying the same carbohydrate epitope as the carbohydrate positive microorganism, wherein said second compound is different from said first carbohydrate positive microorganism;
    v) cultivating the mixture for restimulation of said immune cells; and
    vi) determining whether restimulation of the immune cells occurred.

4. The method according to claim 3, wherein at least a portion of the APCs loaded with a suitable amount of said second compound are contacted with the immune cells in the presence of a carbohydrate binding molecule recognizing said carbohydrate epitope of interest.

5. The method according to claim 3, wherein restimulation is determined by determining
    the secretion products of the immune cells which are secreted if said immune cells are (re)stimulated, wherein the secretion products are chosen from interferon alpha, interferon gamma and GM-CSF; and/or
    the proliferation of the immune cells, which occurs if said immune cells have been (re)stimulated.

6. The method according to claim 3, wherein testing of the cellular immune response is chosen from:
    (i) a cellular immune response test 1 wherein in step (d (vi)) restimulation of the immune cells is determined by measuring GM-CSF secretion;
    (ii) a cellular immune response test 2 wherein the immune cells are lymphocytes and in step (d (vi)) the amount/degree of restimulated lymphocytes is determined by measuring the amount of INFgamma and/or TNFalpha secretion;
    (iii) a cellular immune response test 3 wherein the immune cells are lymphocytes and in step (d (vi)) the amount/degree of restimulated lymphocytes is determined by measuring the proliferation and/or proliferation induction;
    (iv) a cellular immune response test 5 against the carbohydrate epitope of interest comprising
    a) incubating a suitable amount of target cells from a cell line comprising the carbohydrate epitope of interest labelled with a suitable amount of a marker with the immune cells directed against the carbohydrate epitope, and
    b) measuring the lysis of the target cells by determining the release of the marker whereby a positive cellular immune response against the carbohydrate epitope shows a significantly higher lysis of cells comprising the carbohydrate epitope than of carbohydrate epitope negative cells and/or it shows a significantly higher lysis of cells comprising the carbohydrate epitope incubated with the carbohydrate epitope directed immune cells, than a lysis of cells comprising the carbohydrate epitope incubated with corresponding control immune cells not directed against the carbohydrate epitope.

7. The method according to claim 1 wherein
    (i) the carbohydrate epitope is chosen from TF, Core-1, Tn, sialyl-Tn, sialyl-TF, Globo-H, Lewis-Y, sialyl-Lewis-A, sialyl-Lewis-X, polysialic acid, Lewis-X, GM2, GD2, GD3, 9-O-acetyl GD3, GD3L, fucosyl GM1, Lewis-A, Lewis-B, sLac, sialylated type 1 chain, CA 19-9 antigen, CA 72-4 antigen and CA-50 antigen, and
    (ii) the carbohydrate binding molecule is chosen from lectins, selectins, and/or antibodies and/or molecules derived therefrom which bind to TF, Core-1, Tn, sialyl-Tn, sialyl-TF, Globo-H, Lewis-Y, sialyl-Lewis-A, sialyl-Lewis-X, polysialic acid, Lewis-X, GM2, GD2, GD3, 9-O-acetyl GD3, GD3L, fucosyl GM1, Lewis-A, Lewis-B, sLac, sialylated type 1 chain, CA 19-9 antigen, CA 72-4 antigen or CA-50 antigen or to a carbohydrate structure comprising any of these carbohydrate epitopes or parts thereof.

8. A cellular immune response test method comprising
    a) Loading at least one dendritic cell with a microorganism carrying a carbohydrate epitope of interest or a fraction or lysate thereof;
    b) bringing into contact a suitable amount of said at least one dendritic cell loaded with said microorganism or fraction or lysate thereof with a suitable amount of immune cells which can be activated or inhibited by a dendritic cell;
    c) cultivation in order to allow interaction of said immune cells with said loaded dendritic cells;
    d) adding a suitable amount of antigen presenting cells (APC) loaded with a suitable amount of at least one compound carrying the same carbohydrate epitope as said microorganism or fraction or lysate thereof, wherein said compound is different from said microorganism or fraction or lysate thereof;

e) cultivation for restimulation of said immune cells; and
f) determining whether restimulation of the immune cells occurred.

9. The method according to claim 8, wherein at least a portion of the APCs loaded with a suitable amount of said compound are contacted with the immune cells in the presence of a carbohydrate binding molecule recognizing said carbohydrate of interest.

10. The method according to claim 8, wherein restimulation is determined by
the secretion products of the immune cells which are secreted if said immune cells are (re)stimulated, wherein the secretion products are chosen from interferon alpha, interferon gamma and GM-CSF and/or
the proliferation of the immune cells.

11. A method for generation of a functional dendritic cell against a carbohydrate epitope of interest comprising bringing into contact a suitable amount of dendritic cells with a suitable amount of a carbohydrate positive microorganism or fraction or lysate thereof comprising a carbohydrate epitope of interest for a suitable time under suitable conditions to generate at least one functional dendritic cell against said carbohydrate epitope, wherein said method is performed in vitro.

12. The method according to claim 11, wherein said dendritic cells are of human origin.

13. The method according to claim 11, wherein said carbohydrate epitope is not a dipolar carbohydrate epitope.

14. A method for generation of an activated T cell, T cells, T cell clone or T cell line against a carbohydrate epitope comprising
(a) bringing into contact a suitable amount of at least one functional dendritic cell obtained by the method according to claim 13 with a suitable amount of T cells,
(b) cultivating said T cells together with said loaded functional dendritic cells to activate or prime a T cell or T cells against said carbohydrate antigen, and
(c) restimulating said T cells with a suitable amount of antigen presenting cells (APC), wherein said method is performed in vitro.

15. The method according to claim 1, wherein testing of the cellular immune response is a cellular immune response test 4 against the carbohydrate epitope of interest comprising
(a) bringing into contact a suitable amount of dendritic cells loaded with a suitable amount of the carbohydrate positive microorganism, a lysate or a fraction thereof, together with a suitable amount of at least one carbohydrate binding molecule; and
(b) testing binding of said carbohydrate binding molecule to the dendritic cells.

16. The method according to claim 1, wherein step (d) further comprises testing the induction of an effective carbohydrate specific humoral immune response against said carbohydrate epitope by said microorganism or a fraction or lysate thereof in vivo or in vitro, wherein the induction of an effective carbohydrate specific humoral immune response against said carbohydrate epitope is tested by
(i) administering the carbohydrate positive microorganism or a fraction or lysate thereof to a human or animal;
(ii) isolating antibodies gained from the serum, plasma or faeces of said human or animal; and
(iii) performing a humoral immune response test chosen from
a) humoral immune response test 1 against the carbohydrate epitope comprising, testing the binding of the antibodies in an ELISA to compounds carrying the carbohydrate epitope, whereby a positive humoral immune response against the carbohydrate epitope shows a significantly higher binding of the antibodies to said carbohydrate epitope carrying compound than to said compound without the carbohydrate epitope or to said compound after an enzymatical or chemical treatment that destroys the carbohydrate epitope;
b) humoral immune response test 2 against the carbohydrate epitope comprising, testing the binding of the antibodies in an ELISA to carbohydrate structures coupled to polyacrylamid (PAA conjugates), whereby a positive humoral immune response against a carbohydrate epitope shows a significant higher binding of the antibodies to the PAA-conjugate comprising the carbohydrate epitope than to the same PAA-conjugate after enzymatical or chemical treatment destroying the carbohydrate epitope and/or a higher binding of the antibodies to a PAA-conjugate comprising the carbohydrate epitope compared to an PAA-conjugate not comprising the carbohydrate epitope;
c) humoral immune response test 3 against the carbohydrate epitope comprising, testing the binding of the antibodies in a flow cytometry test for its binding to cells comprising the carbohydrate epitope and to cells not comprising the carbohydrate epitope whereby a positive humoral immune response against the carbohydrate epitope shows a significant higher binding of the antibodies to cells comprising the carbohydrate epitope than to cells negative for the carbohydrate epitope;
d) humoral immune response test 4 against the carbohydrate epitope comprising, testing the binding of the antibodies in an immune fluorescence test for its binding to cells comprising the carbohydrate epitope and to cells negative for the carbohydrate epitope whereby a positive humoral immune response against the carbohydrate epitope shows a significant higher binding of the antibodies to cells comprising the carbohydrate epitope than to cells not comprising the carbohydrate epitope and/or to cells comprising the carbohydrate epitope after emzymatical or chemical treatment that destroys the carbohydrate epitope;
e) humoral immune response test 5 against the carbohydrate epitope comprising,
i) incubating a suitable amount of cells comprising the carbohydrate epitope, labeled with a suitable amount of a marker, with a suitable amount of the antibodies with a suitable amount of complement;
ii) measuring the lysis of the cells by determining the release of said marker after the incubation whereby a positive humoral immune response against the carbohydrate epitope shows a significantly higher lysis of cells comprising the carbohydrate epitope than of cells not comprising the carbohydrate epitope and/or it shows a higher lysis of cells comprising the carbohydrate epitope, than a lysis without complement and/or than a lysis without the antibody and/or than a lysis with an antibody or antibodies which does not bind or which binds less to cells comprising the carbohydrate epitope; and
f) humoral immune response test 6 against the carbohydrate epitope comprising
i) incubating a suitable amount of cells comprising the carbohydrate epitope, labeled with a suitable amount of a marker, with a suitable amount of the antibodies, with a suitable amount of immune effector cells or peripheral blood mononuclear cells, and ii) measuring the lysis of the cells by determining the release of the marker after the incubation, whereby a positive humoral immune response against the carbohydrate epitope shows a significantly higher lysis of cells comprising the carbohydrate epitope than of carbohydrate epitope negative cells than a lysis without the antibody and/or than a lysis with an antibody or antibodies which does not bind or which binds less to cells comparing the carbohydrate epitope.

17. The method according to claim 11, wherein said carbohydrate epitope is uncharged.

18. The method according to claim 11, wherein said carbohydrate epitope is linked to or part of a capsular polysaccharide.

19. The method according to claim 11, wherein the carbohydrate epitope is selected from the group consisting of TF, Core-1, Tn, sialyl-Tn, sialyl-TF, Globo-H, Lewis-Y, sialyl-Lewis-A, sialyl-Lewis-X, polysialic acid, Lewis-X, GM2, GD2, GD3, 9-O-acetyl GD3, 9-O-acetyl GD2, GD3L, fucosyl GM1, Lewis-A, Lewis-B, sLac, sialylated type 1 chain, CA 19-9 antigen, CA 72-4 antigen and CA-50 antigen.

* * * * *

UNITED STATES PATENT AND TRADEMARK OFFICE
CERTIFICATE OF CORRECTION

| | | |
|---|---|---|
| PATENT NO. | : 8,592,165 B2 | Page 1 of 1 |
| APPLICATION NO. | : 12/514200 | |
| DATED | : November 26, 2013 | |
| INVENTOR(S) | : Steffen Goletz et al. | |

It is certified that error appears in the above-identified patent and that said Letters Patent is hereby corrected as shown below:

On the title page, at Item (30) Foreign Application Priority Data, please change the first European application serial number from "06090208" to --06090208.7--.

On the title page, at Item (30) Foreign Application Priority Data, please change the second European application serial number from "06090209" to --06090209.5--.

Signed and Sealed this
Twenty-fifth Day of March, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,592,165 B2 | Page 1 of 1 |
| APPLICATION NO. | : 12/514200 | |
| DATED | : November 26, 2013 | |
| INVENTOR(S) | : Goletz et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 898 days.

Signed and Sealed this
Twenty-first Day of April, 2015

Michelle K. Lee
*Director of the United States Patent and Trademark Office*

SEQUENCE LISTING

<160> NUMBER OF SEQ ID NOS: 14

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer 27f

<400> SEQUENCE: 1
agagtttgat cctggctcag                                               20

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      primer 1492r

<400> SEQUENCE: 2
taccttgtta cgactt                                                   16

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer 338f

<400> SEQUENCE: 3
gctgcctccc gtaggagt                                                 18

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer 338r

<400> SEQUENCE: 4
actcctacgg gaggcagc                                                 18

<210> SEQ ID NO 5
<211> LENGTH: 17
<212> TYPE: DNA
<213> ORGANISM: Artificial Sequence
<220> FEATURE:
<223> OTHER INFORMATION: Description of Artificial Sequence: Synthetic
      primer 968f

<400> SEQUENCE: 5
aacgcgaaga accttac                                                  17

<210> SEQ ID NO 6
<211> LENGTH: 1395
<212> TYPE: DNA
<213> ORGANISM: Bacteroides ovatus
<220> FEATURE:
<221> NAME/KEY: modified_base
<222> LOCATION: (51)..(51)
<223> OTHER INFORMATION: a, c, t, g, unknown or other
<220> FEATURE:
<221> NAME/KEY: modified_base

```
<222> LOCATION: (125)..(125)
<223> OTHER INFORMATION: a, c, t, g, unknown or other
<220> FEATURE:
<221> NAME/KEY: modified_base
<222> LOCATION: (154)..(154)
<223> OTHER INFORMATION: a, c, t, g, unknown or other
<220> FEATURE:
<221> NAME/KEY: modified_base
<222> LOCATION: (168)..(168)
<223> OTHER INFORMATION: a, c, t, g, unknown or other
<220> FEATURE:
<221> NAME/KEY: modified_base
<222> LOCATION: (170)..(170)
<223> OTHER INFORMATION: a, c, t, g, unknown or other
<220> FEATURE:
<221> NAME/KEY: modified_base
<222> LOCATION: (177)..(177)
<223> OTHER INFORMATION: a, c, t, g, unknown or other
<220> FEATURE:
<221> NAME/KEY: modified_base
<222> LOCATION: (180)..(180)
<223> OTHER INFORMATION: a, c, t, g, unknown or other
<220> FEATURE:
<221> NAME/KEY: modified_base
<222> LOCATION: (393)..(393)
<223> OTHER INFORMATION: a, c, t, g, unknown or other
<220> FEATURE:
<221> NAME/KEY: modified_base
<222> LOCATION: (435)..(435)
<223> OTHER INFORMATION: a, c, t, g, unknown or other
<220> FEATURE:
<221> NAME/KEY: modified_base
<222> LOCATION: (720)..(721)
<223> OTHER INFORMATION: a, c, t, g, unknown or other
<220> FEATURE:
<221> NAME/KEY: modified_base
<222> LOCATION: (902)..(902)
<223> OTHER INFORMATION: a, c, t, g, unknown or other
<220> FEATURE:
<221> NAME/KEY: modified_base
<222> LOCATION: (973)..(973)
<223> OTHER INFORMATION: a, c, t, g, unknown or other
<220> FEATURE:
<221> NAME/KEY: modified_base
<222> LOCATION: (999)..(999)
<223> OTHER INFORMATION: a, c, t, g, unknown or other
<220> FEATURE:
<221> NAME/KEY: modified_base
<222> LOCATION: (1082)..(1082)
<223> OTHER INFORMATION: a, c, t, g, unknown or other
<220> FEATURE:
<221> NAME/KEY: modified_base
<222> LOCATION: (1232)..(1232)
<223> OTHER INFORMATION: a, c, t, g, unknown or other
<220> FEATURE:
<221> NAME/KEY: modified_base
<222> LOCATION: (1235)..(1235)
<223> OTHER INFORMATION: a, c, t, g, unknown or other

<400> SEQUENCE: 6
atgaacgcta gctacaggct taacacatgc aagtcgaggg gcagcatttt ngtttgcttg      60
caaactgaag atggcgaccg gcgcacgggt gagtaacacg tatccaacct gccgataact     120
ccggnatagc ctttcgaaag aaagattaat accngatagc atacgaanan cgcatgntan    180
ttttattaaa gaatttcggt tatcgatggg gatgcgttcc attagtttgt tggcggggta    240
acggcccacc aagactacga tggatagggg ttctgagagg aaggtccccc acattggaac    300
tgagacacgg tccaaactcc tacgggaggc agcagtgagg aatattggtc aatgggcgag    360
agcctgaacc agccaagtag cgtgaaggat ganggcccta tgggtcgtaa acttctttta    420
tatgggaata aagtnttcca cgtgtggaat tttgtatgta ccatatgaat aaggatcggc    480
taactccgtg ccagcagccg cggtaatacg gaggatccga gcgttatccg gatttattgg    540
gtttaaaggg agcgtaggtg gattgttaag tcagttgtga aagtttgcgg ctcaaccgta    600
```

```
aaattgcagt tgaaactggc agtcttgagt acagtagagg tgggcggaat tcgtggtgta      660
gcggtgaaat gcttagatat cacgaagaac tccgattgcg aaggcagctc actagactgn      720
nactgacact gatgctcgaa agtgtgggta tcaaacagga ttagataccc tggtagtcca      780
cacagtaaac gatgaatact cgctgtttgc gatatacagt aagcggccaa gcgaaagcat      840
taagtattcc acctggggag tacgccggca acggtgaaac tcaaaggaat tgacgggggc      900
cngcacaagc ggaggaacat gtggtttaat tcgatgatac gcgaggaacc ttacccgggc      960
ttaaattgca acngaatata ttggaaacag tatagccgna aggctgttgt gaaggtgctg     1020
catggttgtc gtcagctcgt gccgtgaggt gtcggcttaa gtgccataac gagcgcaacc     1080
cntatcttta gttactaaca ggttatgctg aggactctag agagactgcc gtcgtaagat     1140
gtgaggaagg tggggatgac gtcaaatcag cacggccctt acgtccgggg ctacacacgt     1200
gttacaatgg ggggtacaga aggcagctac cnggngacag gatgctaatc ccaaaaacct     1260
ctctcagttc ggatcgaagt ctgcaacccg acttcgtgaa gctggattcg ctagtaatcg     1320
cgcatcagcc atggcgcggt gaatacgttc ccgggccttg tacacaccgc ccgtcaagcc     1380
atgaaagccg ggggt                                                      1395
```

```
<210> SEQ ID NO 7
<211> LENGTH: 1475
<212> TYPE: DNA
<213> ORGANISM: Bacteroides thetaiotaomicron
<220> FEATURE:
<221> NAME/KEY: modified_base
<222> LOCATION: (3)..(3)
<223> OTHER INFORMATION: a, c, t, g, unknown or other
<220> FEATURE:
<221> NAME/KEY: modified_base
<222> LOCATION: (30)..(30)
<223> OTHER INFORMATION: a, c, t, g, unknown or other
<220> FEATURE:
<221> NAME/KEY: modified_base
<222> LOCATION: (78)..(79)
<223> OTHER INFORMATION: a, c, t, g, unknown or other
<220> FEATURE:
<221> NAME/KEY: modified_base
<222> LOCATION: (94)..(95)
<223> OTHER INFORMATION: a, c, t, g, unknown or other
<220> FEATURE:
<221> NAME/KEY: modified_base
<222> LOCATION: (195)..(195)
<223> OTHER INFORMATION: a, c, t, g, unknown or other
<220> FEATURE:
<221> NAME/KEY: modified_base
<222> LOCATION: (277)..(277)
<223> OTHER INFORMATION: a, c, t, g, unknown or other
<220> FEATURE:
<221> NAME/KEY: modified_base
<222> LOCATION: (341)..(341)
<223> OTHER INFORMATION: a, c, t, g, unknown or other
<220> FEATURE:
<221> NAME/KEY: modified_base
<222> LOCATION: (393)..(393)
<223> OTHER INFORMATION: a, c, t, g, unknown or other
<220> FEATURE:
<221> NAME/KEY: modified_base
<222> LOCATION: (441)..(441)
<223> OTHER INFORMATION: a, c, t, g, unknown or other
<220> FEATURE:
<221> NAME/KEY: modified_base
<222> LOCATION: (444)..(444)
<223> OTHER INFORMATION: a, c, t, g, unknown or other
<220> FEATURE:
<221> NAME/KEY: modified_base
<222> LOCATION: (462)..(462)
<223> OTHER INFORMATION: a, c, t, g, unknown or other
<220> FEATURE:
<221> NAME/KEY: modified_base
```

```
<222> LOCATION: (532)..(532)
<223> OTHER INFORMATION: a, c, t, g, unknown or other
<220> FEATURE:
<221> NAME/KEY: modified_base
<222> LOCATION: (1274)..(1274)
<223> OTHER INFORMATION: a, c, t, g, unknown or other
<220> FEATURE:
<221> NAME/KEY: modified_base
<222> LOCATION: (1405)..(1405)
<223> OTHER INFORMATION: a, c, t, g, unknown or other
<220> FEATURE:
<221> NAME/KEY: modified_base
<222> LOCATION: (1412)..(1412)
<223> OTHER INFORMATION: a, c, t, g, unknown or other

<400> SEQUENCE: 7
cantgaagag tttgatcctg gctcaggatn aacgctagct acaggcttaa cacatgcaag      60 tcgagggca gcatttcnnt ttgcttgcaa actnnagatg gcgaccggcg cacgggtgag     120
taacacgtat ccaacctgcc gataactcgg ggatagcctt tcgaaagaaa gattaatacc    180
cgatggcata atcanaccgc atggtcttat tattaaagaa tttcggttat cgatgggat     240 gcgttccatt aggcagttgg tgaggtaacg gctcacnaaa ccttcgatgg ataggggttc    300
tgagaggaag gtcccccaca ttggaactga gacacggtcc naactcctac gggaggcagc    360
agtgaggaat attggtcaat gggcgcaggc ctnaaccagc caagtagcgt gaaggatgac    420
tgccctatgg gttgtaaact nctnttatat gggaataaag tnttccacgt gtggaatttt    480
gtatgtacca tatgaataag gatcggctaa ctccgtgcca gcagccgcgg tnatacggag    540
gatccgagcg ttatccggat ttattgggtt taaagggagc gtaggtggac agttaagtca    600
gttgtgaaag tttgcggctc aaccgtaaaa ttgcagttga tactggctgt cttgagtaca    660
gtagaggtgg gcggaattcg tggtgtagcg gtgaaatgct tagatatcac gaagaactcc    720
gattgcgaag gcagctcact ggactgcaac tgacactgat gctcgaaagt gtgggtatca    780
aacaggatta gataccctgg tagtccacac agtaaacgat gaatactcgc tgtttgcgat    840
atacagtaag cggccaagcg aaagcattaa gtattccacc tggggagtac gccggcaacg    900
gtgaaactca aaggaattga cggggccg cacaagcgga ggaacatgtg gtttaattcg    960
atgatacgcg aggaaccta cccgggctta aattgcattt gaataatctg gaaacaggtt   1020
agccgcaagg caaatgtgaa ggtgctgcat ggttgtcgtc agctcgtgcc gtgaggtgtc   1080
ggcttaagtg ccataacgag cgcaacccctt atctttagtt actaacaggt catgctgagg   1140
actctagaga gactgccgtc gtaagatgtg aggaaggtgg ggatgacgtc aaatcagcac   1200
ggcccttacg tccggggcta cacacgtgtt acaatggggg gtacagaagg cagctacctg   1260
gtgacaggat gctnatccca aaagcctctc tcagttcgga tcgaagtctg caacccgact   1320
tcgtgaagct ggattcgcta gtaatcgcgc atcagccatg gcgcggtgaa tacgttcccg   1380
ggccttgtac acaccgcccg tcaanccatg anagccgggg gtacctgaag tacgtaaccg   1440
caaggagcgt cctagggtaa aactggtaat tgggg                              1475

<210> SEQ ID NO 8
<211> LENGTH: 10190
<212> TYPE: DNA
<213> ORGANISM: Escherichia coli

<400> SEQUENCE: 8
aagaacggca actaaactgt tattcagtgg catttagatc tatgacgtat ctggcaaacc      60
atgcccgatg cgacgctgtc gcgtcttatc gtgcctacaa atagtccgaa ccgtaggccg    120
gataaggcgt ttacgccgca tccggcaatt ggtgcatgat gcctgatgcg acgctgtcgc    180
```

```
gtcttatcgt gcctacaaat agtccgaacc gtaggccgga taaggcgttt acgccgcatc    240
cggcaattgg tgcatgatgc ctgatgcgac gctggcgcgt cttatcaggc ctacattggt    300
gccggatcgg tagaccggat aaggcgttca cgccgcatcc ggcaagtggt taaacccgct    360
caaacaccgt cgcaataccc tgacccagac cgatacacat cgtcgccaga ccaaactgaa    420
cgtctttgcg ttccatcaga ttcagcagcg tggtgctgat acgcgcaccg gaacaaccca    480
gcggatgacc cagcgcgatc gcgccaccgt tgaggttgat cttctcgtca atctgctcaa    540
ttagtcccag atctttaata catggcagga tctgcgcggc aaaggcttcg ttcatttcaa    600
acacgccgat atcgctggca gaaagccccg cttttttcag cgccagtttc gaggccggaa    660
ccgggccgta acccataatc gatgggtcac aaccaacgac cgccatcgaa cgcacgcgag    720
cgcgcggctt aagacctaat tcatgggcgc ggctttcact catcaccagc atggcagctg    780
cgccatcgga aagtgcagaa gatgtgcccg ccgttaccat accgtttact ggatcaaacg    840
ccggacgcag cgtggcgagg gcttccacgg tggtttccgg gcgaatcact tcgtcgtaat    900
taaactgctt caggacgccg tcggcatcgt gaccaccggt cgggatgatt tcattttaa     960 atgcggccga ctgcgtggcg gcccaggcgc gggcgtgtga ccgcgcggca aaggcatcct   1020
gcatttcacg gctgataccg tgcatacgcg ccagcatttc tgccgttaag cccatcatgc   1080
ccgccgcttt ggcgacattg cggctcaggc cggggtgaaa atcgacgccg tgactcatcg   1140
gcacatggcc catatgctcc acgccgccaa ccagacatgc ctgcgcatcg ccagtcatga   1200
tcattcgtgc tgcgtcatgc agtgcctgca tggatgaacc acacaagcga ttaacggtaa   1260
ccgccgggac agagtgtggt acttctgcca gcagcgccgc gttacgggcg atattaaaac   1320
cctgctccag cgtctgctgc acacaacccc agtaaatatc gtcgagggcc gccgcttcca   1380
gcgccgggtt acgcgccagc agcgtacgca ttaaatgagc ggagagatct tctgcacgca   1440
cgttacgaaa agcaccgccc ttcgaacggc ccatcggggt gcgaattgca tcgacaatga   1500
caacctgttc cattgtgact ccttaagccg ttttcaggtc gccaaccgga cgggctggct   1560
caaccggagt atagtacggt tcgttatgac gcgctttatt acgcagacct tccggcactt   1620
catacagcgg gccgaggtgc tgatattgct gtgccatatc gaggtatttt gcgctaccga   1680
gggtgtccag ccagcggaac gcgccgccgt ggaacggagg gaagcccagg ccgtagacca   1740
gcgccatatc cgcttccgcc ggagtggcga taatgccttc ctccagacag cgcaccactt   1800
cgttgaccat cgggatcatc atgcgggcga taatctcttc ttcgctgaaa tcgcgcttcg   1860
gctggctcac ttctgccagc aggtcttcaa cggcggcgtc ttcttctttc ttcggcttac   1920
ctttgctgtc ttctttataa cgccagaaac cgaggccgtt cttctgacca aagcggttgg   1980
catcaaacag cgcgtcgatg gcatcgcggt aatctttctg catccgctgc gggaagcctg   2040
ctgccatgac agcctgagcg tgatgcgcgg tatcaatgcc cacaacgtcc agcagatatg   2100
ccgggcccat cggccagcca aactgttttt ccatcacttt gtcgatcttg cggaaatccg   2160
cgccgtcgcg cagcagctgg ctgaaaccgg cgaaatacgg gaacagcacg cggttaacaa   2220
agaagccggg gcagtcgtta accacaatcg gcgtcttgcc catcttgctc gcccaggcga   2280
caactttcgc gatggtttcg tcggagcttt tctcgccgcg aataatttct accaacggca   2340
ttcggtggac cgggttaaag aagtgcatcc cgcagaagtt ttccgggcgt tccagcgcgt   2400
tggccagttc gctgatagga atggttgaag tgttagacgc cagcacggta tcctggcgta   2460
ctttttgttc ggtttctgcc agtacggctt ttttcacttt cgggttttca acaaccgctt   2520
ctaccacaat atccacgcgg tcaaatccgg cgtagtcgag cgttgggtgg attgtggaga   2580
```

```
tcacgccagc cagtttcaga ccatcgatct tgccgcgctc aagctgcttg ttcagcagtt    2640
tcgcggcttc ggtcatgccg agggttaacg acttgtcgtt gatatctttc atgacaaccg    2700
gcacgccttt ccacgcagac tggtaagcga tgccgccgcc cataatgcct gcacccagca    2760
ccgcggcctg tttcggggtt tcaacgtctt tggtgagttt cttcgctttg ccttttacat    2820
attgatcgtt aaggaaaatg ccgaccagtg cgcgggcttc gttggtatgc gccagcggga    2880
caaaactttt gttttccagg tttaaggctt cttcacgacc aaaacgggcc gcagcttcaa    2940 tggttttac tgcggtgatg ggggccggat aatgtttccc cgctgtttgt gcgaccatcc    3000
ctttagcgat ggtgaagctc atggtggctt caatcttgct cagttttagt ggttccagct    3060
tcggctgacg ttttgctttc cagtcgaggt cgccgttaat ggcctggcgt aaaaccgcct    3120
ttgcgccttc aaccagtttt tctgctttga ctacgccatc caccagaccg attttcagcg    3180
cctgatccgc gccgacatct ttaccggcgg caatgatttc cagcgcactg tcagcgccca    3240
gcatacgtgg catacgtaca gaaccgccaa agccaggcat gatgcccagt ttggtttccg    3300
gcagaccgat gcgcagatcc ggcgtcgcca gacgataatc ggtcgccagc acgcattcgc    3360
agccaccgcc cagcgcatag ccattgacgg cagcaatggt cggcaccggc agatcttcca    3420
ggcgattaaa cacgctattg gcaaagtgca gccactgact taactgttct tcaggaacga    3480
ggaacaggga caaaaattcg gtgatatcag caccgacgat aaaggctgct tgttcgaac    3540 gcagcagcag ccctttttaga tctgattgct gttccagcac gccgatggcc tcgccgaggc    3600
tggcgacggt cgcagtgtcg agtttattaa ctgaacctgg ggcatcaaat accagttcgg    3660
caatgccatc ttccagccag tcaaggtaca gggtgtcgcc tttgtaaagc atgtcagtct    3720
cctgaatccg caaggtgatc tggtcgtacc agatgagtcg aagtgtgtat tttgtgttaa    3780
aaatatgcaa acaaaagatt aaagaaatgc cgatctgatc acgctcggca gaaatcacgc    3840
tctggatgaa cgatgtgcta agatgcggag acttaaggtc aaaaaaacag aagggtaaaa    3900
aatggaatca ctggcctcgc tctataaaaa tcatatagct accttacaag aacggactcg    3960
cgatgcgctg gcgcgcttca agctggatgc gttacttatt cactccggcg agctgttcaa    4020
tgtttttctc gacgatcatc cctatccgtt taaagtgaac ccgcaattca aagcgtgggt    4080
gccggtaact caggtgccaa actgctggtt gctggtggat ggcgtgaaca agccgaaact    4140
gtggttctat ctgccggttg attactggca caacgtcgaa ccgctgccga cctctttctg    4200
gactgaagat gtgaagtga tcgcgctgcc gaaagccgat ggcattggta gcctgctgcc    4260
tgctgcgcgc ggcaatatcg gttatatcgg tccggtgccg gaacgtgcgc tgcaactggg    4320
tattgaggcc agcaacatca acccgaaagg ggttatcgac tacctgcatt actatcgctc    4380
cttcaaaact gagtacgaac tggcctgtat gcgtgaagcg cagaaaatgg cggtcaacgg    4440
tcaccgcgcg gcagaagaag cgttccgttc tggcatgagc gagttcgata tcaacattgc    4500
ctatctgacc gcgaccggtc atcgtgatac cgacgtacct tacagcaaca ttgtggcgct    4560
taacgaacac gctgcggtac tgcattacac caaactggac catcaggcac cggaagagat    4620
gcgcagcttc ctgctggatg ccggggcaga atataacggc tatgcggctg acctgacccg    4680
tacctggtcg gcaaaaagtg acaacgacta cgcgcagctg gtgaaggacg ttaatgatga    4740
acaactggcg ctgatcgcca ccatgaaagc aggcgtcagc tatgtggatt accacatcca    4800
gttccatcag cgcatcgcca aactgctgcg taaacatcaa atcatcaccg atatgagtga    4860
agaagcgatg gtcgaaaacg atcttaccgg gccgtttatg ccgcatggta tcggccatcc    4920
gctgggcctg caggtgcatg acgtcgctgg ttttatgcag gatgatagcg gtacgcacct    4980
```

```
cgcggcaccg gcaaaatatc cgtacctgcg ctgcacccgt attctccagc cgggcatggt   5040
gttaaccatc gaaccgggta tctacttcat cgaatcgcta ctggcaccgt ggcgtgaagg   5100
gcagttcagc aagcacttca actggcagaa aattgaagca ctgaaaccgt tcggcggcat   5160
tcgtatcgaa gacaacgtgg tgatccacga aaacaacgtg gaaaacatga cccgggatct   5220
gaaactggcg tgatggaaag ctggttaatt cctgcggcac cggtcacggt cgttgaagag   5280
atcaaaaaga gccgcttcat aacgatgttg gcgcataccg atggcgttga ggcggcgaaa   5340
gcgtttgttg aatcggtgcg ggcagaacac cccgatgccc ggcaccattg cgtggcgtgg   5400
gtcgcgggtg cgccggatga ttctcaacag ctgggtttct ctgacgacgg ggagccggcg   5460
ggaacggcag gtaaaccgat gctcgcccag ctaatgggca gcggcgtcgg ggaaattacc   5520
gctgtggtag tgcgctacta cggcggcata ttgcttggca ccggtgggtt agtgaaagcg   5580
tatggcggcg gcgtgaatca ggcgctgcgc cagctaacga cccaacgcaa gacgccatta   5640
accgaatata ctttgcaatg tgaatatcat cagttaaccg gcattgaagc gttgctgggg   5700
cagtgtgacg gcaaaattat caacagtgat tatcaggcat tcgttctgct gcgggtggcg   5760
cttccggcgg cgaaagtggc tgaattttcc gcaaagctgg cggattttag ccgtggttca   5820
ttgcaattgt tagcgattga agaataatcc ccacttcgtt ttgcagaact aaggaagcgg   5880
cagagatgca ttttcgcgcc attacccgaa tcgttggact actggtcatc ttatttttcag  5940 ggaccatgat tatccctggg ctggtagcac tcatctaccg ggatggagcg ggccgcgctt   6000
ttacccagac cttttttgtc gccctcgcca ttggctctat gctgtggtgg ccgaaccgca   6060
aagagaaagg cgaacttaaa tcccgtgagg ggtttctgat agtggtgctg ttctggaccg   6120
tgctgggtag cgtcggtgcg ctcccttta tcttctcgga aagcccgaac ctcacgatta   6180
ccgatgcgtt ttttgaatct ttctctggcc tgaccactac gggagccact acgctggtgg   6240
ggctggattc gctccctcac gccatcctct tttatcgcca gatgctgcaa tggtttggcg   6300
ggatggggat catcgtgttg gcggttgcga tactgcctat cctcggcgtg ggtgggatgc   6360
agctctatcg cgcagaaatg cccggcccgc tgaaagataa caaatgcgc ccgcgaattg    6420 cggaaacggc gaaaaccctg tggttgattt atgtcttgct gaccgtcgcc tgtgcgctgg   6480
cgttgtggtt tgccggaatg gatgcctttg atgccatcgg ccatagcttt gcgactatcg   6540
ctattggcgg cttctcgaca catgatgcca gtatcggtta tttcgatagc ccgactatta   6600
acactatcat tgctatcttc ctgctgatct ccggctgtaa ctacggtctg cactttcac    6660 tgttaagtgg gcgtagtctg aaggtttatt ggcgcgatcc ggaatttcgc atgtttatcg   6720
gcgtacagtt tacgctggtg gttatttgta ccctcgtact gtggtttcat aatgtctaca   6780
gttcggcgct gatgacaatt aaccaggcgt ttttccaggt ggtgtcgatg gcgacaaccg   6840
ccgggtttac aactgacagc attgcccgct ggccgctctt tttgccggta ctgcttttat   6900
gttcagcctt tatcggcggt tgcgccgggt caacgggcgg tggcctgaag gtgatccgca   6960
tcctgctgct gtttaagcag gggaaccgtg agctgaaacg actggtgcat ccgaacgccg   7020
tctatagcat taagctgggg aatcgcgcac tgccggaacg tatcctcgaa gccgtttggg   7080 gattttctc cgcctatgca ttggtgttta ttgtcagtat gctggcgatt atcgcacggg    7140
cgtggatgac ttttctgcct ttgcgtcggt tgttgcgaca ttgaataacc tggggccagg   7200
gcttggcgtg gttgctgata actttaccag tatgaacccg gtggctaaat ggatcctgat   7260
tgccaacatg ctgtttggtc gtctcgaggt ctttacattg ctggtgctct ttacccgac    7320 tttctggcgt gaatgatgga gtaatacgtg aaaacattaa ttcttttctc aacaagggac   7380
```

```
ggacaaacgc gcgagattgc ctcctacctg gcttcggaac tgaaagaact gggggatccag   7440 gcggatgtcg ccaatgtgca ccgcattgaa gaaccacagt gggaaaacta tgaccgtgtg   7500
gtcattggtg cttctattcg ctatggtcac taccattcag cgttccagga atttgtcaaa   7560
aaacatgcga cgcggctgaa ttcgatgccg agcgcctttt actccgtgaa tctggtggcg   7620
cgcaaaccgg agaagcgtac tccacagacc aacagctacg cgcgcaagtt tctgatgaac   7680
tcgcaatggc gtcccgatcg ctgcgcggtc attgccgggg cgctgcgtta cccacgttat   7740
cgctggtacg accgttttat gatcaagctg attatgaaga tgtcaggcgg tgaaacggat   7800
acgcgcaaag aagttgtcta taccgattgg gagcaggtgg cgaatttcgc ccgagaaatc   7860
gcccatttaa ccgacaaacc gacgctgaaa taagcataaa gaataaaaaa tgcgcggtca   7920
gaaaattatt ttaaatttcc tcttgtcagg ccggaataac tccctataat gcgccaccac   7980
tgacacggaa caacggcaaa cacgccgccg ggtcagcggg gttctcctga gaactccggc   8040
agagaaagca aaaataaatg cttgactctg tagcgggaag gcgtattatg cacaccccgc   8100
gccgctgaga aaagcgaag cggcactgct ctttaacaat ttatcagaca atctgtgtgg   8160
gcactcgaag atacgcgattc ttaacgtcgc aagacgaaaa atgaataccaa gtctcaaga   8220 gtgaacacgt aattcattac gaagtttaat tctttgagcg tcaaactttt aaattgaaga   8280
gtttgatcat ggctcagatt gaacgctggc ggcaggccta acacatgcaa gtcgaacggt   8340
aacaggaaga agcttgcttc tttgctgacg agtggcggac gggtgagtaa tgtctgggaa   8400
actgcctgat ggaggggat aactactgga aacggtagct aataccgcat aacgtcgcaa   8460
gaccaaagag ggggaccttc gggcctcttg ccatcggatg tgcccagatg gattagcta   8520 gtaggtgggg taacggctca cctaggcgac gatccctagc tggtctgaga ggatgaccag   8580
ccacactgga actgagacac ggtccagact cctacgggag gcagcagtgg ggaatattgc   8640
acaatgggcg caagcctgat gcagccatgc cgcgtgtatg aagaaggcct tcgggttgta   8700
aagtactttc agcggggagg aagggagtaa agttaatacc tttgctcatt gacgttaccc   8760
gcagaagaag caccggctaa ctccgtgcca gcagccgcgg taatacggag ggtgcaagcg   8820
ttaatcggaa ttactgggcg taaagcgcac gcaggcggtt tgttaagtca gatgtgaaat   8880
ccccgggctc aacctgggaa ctgcatctga tactggcaag cttgagtctc gtagagggg   8940 gtagaattcc aggtgtagcg gtgaaatgcg tagagatctg gaggaatacc ggtggcgaag   9000 gcggcccct ggacgaagac tgacgctcag gtgcgaaagc gtgggagca aacaggatta   9060 gataccctgg tagtccacgc cgtaaacgat gtcgacttgg aggttgtgcc cttgaggcgt   9120
ggcttccgga gctaacgcgt taagtcgacc gcctggggag tacggccgca aggttaaaac   9180
tcaaatgaat tgacgggggc ccgcacaagc ggtggagcat gtggtttaat tcgatgcaac   9240
gcgaagaacc ttacctggtc ttgacatcca cggaagtttt cagagatgag aatgtgcctt   9300
cgggaaccgt gagacaggtg ctgcatggct gtcgtcagct cgtgttgtga atgttgggt   9360 taagtcccgc aacgagcgca acccttatcc tttgttgcca gcggtccggc cgggaactca   9420
aaggagactg ccagtgataa actggaggaa ggtggggatg acgtcaagtc atcatggccc   9480
ttacgaccag ggctacacac gtgctacaat ggcgcataca agagaagcg acctcgcgag   9540 agcaagcgga cctcataaag tgcgtcgtag tccggattgg agtctgcaac tcgactccat   9600
gaagtcggaa tcgctagtaa tcgtggatca gaatgccacg gtgaatacgt tcccgggcct   9660
tgtacacacc gcccgtcaca ccatgggagt gggttgcaaa agaagtaggt agcttaacct   9720
tcgggagggc gcttaccact ttgtgattca tgactgggt gaagtcgtaa caaggtaacc   9780
```

```
gtaggggaac ctgcggttgg atcacctcct taccttaaag aagcgttctt tgaagtgctc      9840
acacagattg tctgatgaaa atgagcagta aaacctctac aggcttgtag ctcaggtggt      9900
tagagcgcac ccctgataag ggtgaggtcg gtggttcaag tccactcagg cctaccaaat      9960
ttgcacggca aatttgaaga ggttttaact acatgttatg gggctatagc tcagctggga     10020
gagcgcctgc tttgcacgca ggaggtctgc ggttcgatcc cgcatagctc caccatctct     10080
gtagtgatta aataaaaaat acttcagagt gtacctgcaa aggttcactg cgaagttttg     10140
ctctttaaaa atctggatca agctgaaaat tgaaacactg aacaacgaaa               10190

<210> SEQ ID NO 9
<211> LENGTH: 1522
<212> TYPE: DNA
<213> ORGANISM: Lactobacillus paracasei

<400> SEQUENCE: 9
gatgaacgct ggcggcgtgc ctaatacatg caagtcgaac gagttctcgt tgatgatcgg       60
tgcttgcacc gagattcaac atggaacgag tggcggacgg gtgagtaaca cgtgggtaac      120
ctgcccttaa gtgggggata acatttggaa acagatgcta ataccgcata atccaagaa       180 ccgcatggtt cttggctgaa agatggcgta agctatcgct tttggatgga cccgcggcgt      240
attagctagt tggtgaggta atggctcacc aaggcgatga tacgtagccg aactgagagg      300
ttgatcggcc acattgggac tgagacacgg cccaaactcc tacgggaggc agcagtaggg      360
aatcttccac aatggacgca agtctgatgg agcaacgccg cgtgagtgaa gaaggctttc      420
gggtcgtaaa actctgttgt tggagaagaa tggtcggcag agtaactgtt gtcggcgtga      480
cggtatccaa ccagaaagcc acggctaact acgtgccagc agccgcggta atacgtaggt      540
ggcaagcgtt atccggattt attgggcgta aagcgagcgc aggcggtttt ttaagtctga      600
tgtgaaagcc ctcggcttaa ccgaggaagc gcatcggaaa ctgggaaact tgagtgcaga      660
agaggacagt ggaactccat gtgtagcggt gaaatgcgta gatatatgga agaacaccag      720
tggcgaaggc ggctgtctgg tctgtaactg acgctgaggc tcgaaagcat gggtagcgaa      780
caggattaga taccctggta gtccatgccg taaacgatga atgctaggtg ttggagggtt      840
tccgcccttc agtgccgcag ctaacgcatt aagcattccg cctggggagt acgaccgcaa      900
ggttgaaact caaaggaatt gacggggccc cgcacaagcg gtggagcatg tggtttaatt      960
cgaagcaacg cgaagaacct taccaggtct tgacatcttt tgatcacctg agagatcagg     1020 tttcccttc ggggggcaaaa tgacaggtgg tgcatggttg tcgtcagctc gtgtcgtgag      1080
atgttgggtt aagtcccgca acgagcgcaa cccttatgac tagttgccag catttagttg     1140
ggcactctag taagactgcc ggtgacaaac cggaggaagg tggggatgac gtcaaatcat     1200
catgcccctt atgacctggg ctacacacgt gctacaatgg atggtacaac gagttgcgag     1260
accgcgaggt caagctaatc tcttaaagcc attctcagtt cggactgtag gctgcaactc     1320
gcctacacga agtcggaatc gctagtaatc gcggatcagc acgccgcggt gaatacgttc     1380
ccgggccttg tacacaccgc ccgtcacacc atgagagttt gtaacacccg aagccggtgg     1440
cgtaaccctt ttagggagcg agccgtctaa ggtgggacaa atgattaggg tgaagtcgta     1500
acaaggtagc cgtaggagaa cc                                              1522

<210> SEQ ID NO 10
<211> LENGTH: 1520
<212> TYPE: DNA
<213> ORGANISM: Lactobacillus casei
```

```
<220> FEATURE:
<221> NAME/KEY: modified_base
<222> LOCATION: (93)..(93)
<223> OTHER INFORMATION: a, c, t, g, unknown or other
<220> FEATURE:
<221> NAME/KEY: modified_base
<222> LOCATION: (1511)..(1511)
<223> OTHER INFORMATION: a, c, t, g, unknown or other
<220> FEATURE:
<221> NAME/KEY: modified_base
<222> LOCATION: (1516)..(1516)
<223> OTHER INFORMATION: a, c, t, g, unknown or other
<220> FEATURE:
<221> NAME/KEY: modified_base
<222> LOCATION: (1518)..(1518)
<223> OTHER INFORMATION: a, c, t, g, unknown or other

<400> SEQUENCE: 10
gatsaacgst sgcggcgtgc ctaatacatg caagtcgaac gagttctcgt tgatgatcgg      60
tgcttgcacc gagattcaac atggaacgwg tgncggacgg gtgagtaaca cgtgggtaac     120
ctgcccttaa gtgggggata acatttggaa acagatgcta ataccgcata gatccaagaa     180
ccgcatggtt cttggctgaa agatggcgta agctatcgct tttggatgga cccgcggcgt     240
attagctagt tggtgaggta atggctcacc aaggcgatga tacgtagccg aactgagagg     300
ttgatcggcc acattgggac tgagacacgg cccaaactct acggaggca gcagtaggga      360 atcttccaca atgacgcaa gtctgatgga gcaacgccgc gtgagtgaag aaggctttcg     420
ggtcgtaaaa ctctgttgtt ggagaagaat ggtcggcaga gtaactgttg tcggcgtgac     480
ggtatccaac cagaaagcca cggctaacta cgtgccagca gccgcggtaa tacgtaggtg     540
gcaagcgtta tccggattta ttgggcgtaa agcgagcgca ggcggttttt taagtctgat     600
gtgaaagccc tcggcttaac cgaggaagcg catcggaaac tgggaaactt gagtgcagaa     660
gaggacagtg gaactccatg tgtagcggtg aaatgcgtag atatatggaa gaacaccagt     720
ggcgaaggcg gctgtctggt ctgtaactga cgctgaggct cgaaagcatg ggtagcgaac     780
aggattagat accctggtag tccatgccgt aaacgatgaa tgctaggtgt tgagggtttc     840
ccgcccttca gtgccgcagc taacgcatta agcattccgc ctggggagta cgaccgcaag     900
gttgaaactc aaaggaattg acggggggccc gcacaagcgg tggagcatgt ggtttaattc     960
gaagcaacgc gaagaacctt accaggtctt gacatctttt gatcacctga gagatcaggt    1020
ttccccttcg ggggcaaaat gacaggtggt gcatggttgt cgtcagctcg tgtcgtgaga    1080
tgttgggtta agtcccgcaa cgagcgcaac ccttatgact agttgccagc atttagttgg    1140
gcactctagt aagactgccg gtgacaaacc ggaggaaggt ggggatgacg tcaaatcatc    1200
atgcccctta tgacctgggc tacacacgtg ctacaatgga tggtacaacg agttgcgaga    1260
ccgcgaggtc aagctaatct cttaaagcca ttctcagttc ggactgtagg ctgcaactcg    1320
cctacacgaa gtcggaatcg ctagtaatcg cggatcagca cgccgcggtg aatacgttcc    1380
cgggccttgt acacaccgcc cgtcacacca tgagagtttg taacacccga agccggtggc    1440 gtaaccctt tagggagcga gccgtctaag gtgggacaaa tgattagggt gaagtcgtaa     1500
caaggtagcc ntaggngnac                                                1520

<210> SEQ ID NO 11
<211> LENGTH: 1470
<212> TYPE: DNA
<213> ORGANISM: Staphylococcus warneri

<400> SEQUENCE: 11
gatgaacgct ggcggcgtgc ctaatacatg caagtcgagc gaacagataa ggagcttgct      60
```

```
cctttgacgt tagcggcgga cgggtgagta acacgtggat aacctaccta taagactggg    120
ataacttcgg gaaaccggag ctaataccgg ataacatatt gaaccgcatg gttcaatagt    180
gaaaggcggc tttgctgtca cttatagatg gatccgcgcc gtattagcta gttggtaagg    240
taacggctta ccaaggcaac gatacgtagc cgacctgaga gggtgatcgg ccacactgga    300
actgagacac ggtccagact cctacgggag gcagcagtag ggaatcttcc gcaatgggcg    360
aaagcctgac ggagcaacgc cgcgtgagtg atgaaggtct tcggatcgta aaactctgtt    420
atcagggaag aacaaatgtg taagtaactg tgcacatctt gacggtacct gatcagaaag    480
ccacggctaa ctacgtgcca gcagccgcgg taatacgtag gtggcaagcg ttatccggaa    540
ttattgggcg taaagcgcgc gtaggcggtt ttttaagtct gatgtgaaag cccacggctc    600
aaccgtggag ggtcattgga aactggaaaa cttgagtgca gaagaggaaa gtggaattcc    660
atgtgtagcg gtgaaatgcg cagagatatg gaggaacacc agtggcgaag gcgactttct    720
ggtctgtaac tgacgctgat gtgcgaaagc gtggggatca acaggatta gatacctgg     780 tagtccacgc cgtaaacgat gagtgctaag tgttaggggg tttccgcccc ttagtgctgc    840
agctaacgca ttaagcactc cgcctgggga gtacgaccgc aaggttgaaa ctcaaaggaa    900
ttgacgggga cccgcacaag cggtggagca tgtggtttaa ttcgaagcaa cgcgaagaac    960
cttaccaaat cttgacatcc tttgaccgct ctagagatag agtcttcccc ttcggggac    1020 aaagtgacag gtggtgcatg gttgtcgtca gctcgtgtcg tgagatgttg ggttaagtcc    1080
cgcaacgagc gcaacccttta agcttagttg ccatcattaa gttgggcact ctaagttgac    1140
tgccggtgac aaaccggagg aaggtgggga tgacgtcaaa tcatcatgcc ccttatgatt    1200
tgggctacac acgtgctaca atggacaata caaagggcag ctaaaccgcg aggtcaasca    1260
aatcccataa agttgttctc agttcggatt gtagtctgca actcgactac atgaagctgg    1320
aatcgctagt aatcgtagat cagcatgcta cggtgaatac gttcccgggt cttgtacaca    1380
ccgcccgtca caccacgaga gtttgtaaca cccgaagccg gtggagtaac catttatgga    1440
gctagccgtc gaaggtggga caaatgattg                                     1470
```

<210> SEQ ID NO 12
<211> LENGTH: 1419
<212> TYPE: DNA
<213> ORGANISM: Staphylococcus pasteuri

<400> SEQUENCE: 12

```
caagtcgagc gaacagataa ggagcttgct cctttgacgt tagcggcgga cgggtgagta     60
acacgtggat aacctaccta taagactggg ataacttcgg gaaaccggag ctaataccgg    120
ataagatttt gaaccgcatg gttcaatagt gaaagacggc cttgctgtca cttatagatg    180
gatccgcgcc gtattagcta gttggtaagg taacggctta ccaaggcaac gatacgtagc    240
cgacctgaga gggtgatcgg ccacactgga actgagacac ggtccagact cctacgggag    300
gcagcagtag ggaatcttcc gcaatgggcg aaagcctgac ggagcaacgc cgcgtgagtg    360
atgaaggtct tcggatcgta aaactctgtt atcagggaag aacaaacgtg taagtaactg    420
tgcacgtctt gacggtacct gatcagaaag ccacggctaa ctacgtgcca gcagccgcgg    480
taatacgtag gtggcaagcg ttatccggaa ttattgggcg taaagcgcgc gtaggcggtt    540
ttttaagtct gatgtgaaag cccacggctc aaccgtggag ggtcattgga aactggaaaa    600
cttgagtgca gaagaggaaa gtggaattcc atgtgtagcg gtgaaatgcg cagagatatg    660
gaggaacacc agtggcgaag gcgactttct ggtctgtaac tgacgctgat gtgcgaaagc    720
```

```
gtggggatca aacaggatta gataccctgg tagtccacgc cgtaaacgat gagtgctaag      780 tgttagggggg tttccgcccc ttagtgctgc agctaacgca ttaagcactc cgcctgggga    840
gtacgaccgc aaggttgaaa ctcaaaggaa ttgacgggga cccgcacaag cggtggagca      900
tgtggtttaa ttcgaagcaa cgcgaagaac cttaccaaat cttgacatcc tttgaccgct      960
ctagagatag agttttcccc ttcgggggac aaagtgacag gtggtgcatg gttgtcgtca     1020
gctcgtgtcg tgagatgttg ggttaagtcc cgcaacgagc gcaacccttg agcttagttg     1080
ccatcattaa gttgggcact ctaagttgac tgccggtgac aaaccggagg aaggtgggga     1140
tgacgtcaaa tcatcatgcc ccttatgatt tgggctacac acgtgctaca atggacaata     1200
caaagggcag ctaaaccgcg aggtcaagca aatcccataa agttgttctc agttcggatt     1260
gtagtctgca actcgactac atgaagctgg aatcgctagt aatcgtagat cagcatgcta     1320
cggtgaatac gttcccgggt cttgtacaca ccgcccgtca caccacgaga gtttgtaaca     1380
cccgaagccg gtggagtaac cattcctgga gctagccgt                            1419
```

<210> SEQ ID NO 13
<211> LENGTH: 1521
<212> TYPE: DNA
<213> ORGANISM: Lactobacillus casei
<220> FEATURE:
<221> NAME/KEY: modified_base
<222> LOCATION: (407)..(407)
<223> OTHER INFORMATION: a, c, t, g, unknown or other
<220> FEATURE:
<221> NAME/KEY: modified_base
<222> LOCATION: (655)..(655)
<223> OTHER INFORMATION: a, c, t, g, unknown or other
<220> FEATURE:
<221> NAME/KEY: modified_base
<222> LOCATION: (1476)..(1476)
<223> OTHER INFORMATION: a, c, t, g, unknown or other

<400> SEQUENCE: 13

```
grtsaacgct sgcggcgtgc ctaatacatg caagtcgaac gagttctgat tattgaaagg       60
tgcttgcatc ttgatttaat tttgaacgag tggcggacgg gtgagtaaca cgtgggtaac     120
ctgcccttaa gtgggggata acatttggaa acagatgcta ataccgcata atccaagaa     180 ccgcatggtt cttggctgaa agatggcgta agctatcgct tttggatgga cccgcggcgt     240
attagctagt tggtgaggta acggctcacc aaggcaatga tacgtagccg aactgagagg    300
ttgatcggcc acattgggac tgagacacgg cccaaactct acgggaggca gcagtaggga    360
atcttccaca atggacgcaa gtctgatgga gcaacgccgc gtgagtnaag aaggctttcg    420
ggtcgtaaaa ctctgttgtt ggagaagaat ggtcggcaga gtaactgttg tcggcgtgac    480
ggtatccaac cagaaagcca cggctaacta cgtgccagca gccgcggtaa tacgtaggtg    540
gcaagcgtta tccggattta ttgggcgtaa agcgagcgca ggcggttttt taagtctgat    600
gtgaaagccc tcggcttaac cgaggaagtg catcggaaac tgggaaactt gagtncagaa    660
gaggacagtg gaactccatg tgtagcggtg aaatgcgtag atatatggaa gaacaccagt    720
ggcgaaggcg gctgtctggt ctgtaactga cgctgaggct cgaaagcatg ggtagcgaac    780
aggattagat accctggtag tccatgccgt aaacgatgaa tgctaggtgt tgagggggttt    840 ccgcccttca gtgccgcagc taacgcatta agcattccgc ctggggagta cgaccgcaag    900
gttgaaactc aaaggaattg acgggggccc gcacaagcgg tggagcatgt ggtttaattc    960
gaagcaacgc gaagaacctt accaggtctt gacatctttt gatcacctga gagatcaggt   1020
ttccccttcg ggggcaaaat gacaggtggt gcatggttgt cgtcagctcg tgtcgtgaga   1080
```

```
tgttgggtta agtcccgcaa cgagcgcaac ccttatgact agttgccagc atttagttgg    1140
gcactctagt aagactgccg gtgacaaacc ggaggaaggt ggggatgacg tcaaatcatc    1200
atgcccctta tgacctgggc tacacacgtg ctacaatgga tggtacaacg agttgcgaga    1260
ccgcgaggtc aagctaatct cttaaagcca ttctcagttc ggactgtagg ctgcaactcg    1320
cctacacgaa gtcggaatcg ctagtaatcg cggatcagca cgccgcggtg aatacgttcc    1380
cgggccttgt acaccgccc gtcacacca tgagagtttg taacacccga gccggtggc     1440 gtaaccctt tagggagcga gccgtctaag gtgggncaaa tgattagggt gaagtcgtaa    1500
caaggtagcc gtaggagaac c                                             1521

<210> SEQ ID NO 14
<211> LENGTH: 1522
<212> TYPE: DNA
<213> ORGANISM: Lactobacillus zeae

<400> SEQUENCE: 14
gatgaacgct ggcggcgtgc ctaatacatg caagtcgaac gagttttggt cgatgaacgg     60
tgcttgcatc gtgattcaac ttaaaacgag tggcggacgg gtgagtaaca cgtgggtaac    120
ctgcccttaa gtgggggata catttggaa acagatgcta ataccgcata atccaagaa     180 ccgcatggtt cttggctgaa agatggcgta agctatcgct tttggatgga cccgcggcgt    240
attagctagt tggtgaggta acggctcacc aaggcgatga tacgtagccg aactgagagg    300
ttgatcggcc acattgggac tgagacacgg cccaaactcc tacgggaggc agcagtaggg    360
aatcttccac aatggacgca agtctgatgg agcaacgccg cgtgagtgaa gaaggctttc    420
gggtcgtaaa actctgttgt tggagaagaa tggtcggcag agtaactgtt gtcggcgtga    480
cggtatccaa ccagaaagcc acggctaact acgtgccagc agccgcggta atacgtaggt    540
ggcaagcgtt atccggattt attgggcgta aagcgagcgc aggcggtttt ttaagtctga    600
tgtgaaagcc ctcggcttaa ccgaggaagc gcatcggaaa ctgggaaact tgagtgcaga    660
agaggacagt ggaactccat gtgtagcggt gaaatgcgta gatatatgga agaacaccag    720
tggcgaaggc ggctgtctgg tctgtaactg acgctgaggc tcgaaagcat gggtagcgaa    780
caggattaga taccctggta gtccatgccg taaacgatga atgctaggtg ttggagggtt    840
tccgcccttc agtgccgcag ctaacgcatt aagcattccg cctggggagt acgaccgcaa    900
ggttgaaact caaaggaatt gacggggcc cgcacaagcg gtggagcatg tggtttaatt    960
cgaagcaacg cgaagaacct taccaggtct tgacatcttt tgatcacctg agagatcagg   1020 tttcccttc ggggcaaaa tgacaggtgg tgcatggttg tcgtcagctc gtgtcgtgag   1080
atgttgggtt aagtcccgca acgagcgcaa cccttatgac tagttgccag cattyagttg    1140
ggcactctag taagactgcc ggtgacaaac cggaggaagg tggggatgac gtcaaatcat    1200
catgcccctt atgacctggg ctacacacgt gctacaatgg atggtacaac gagttgcgag    1260
accgcgaggt caagctaatc tcttaaagcc attctcagtt cggactgtag gctgcaactc    1320
gcctacacga gtcggaatc gctagtaatc gcggatcagc acgccgcggt gaatacgttc    1380
ccgggccttg tacaccgcc cgtcacacc atgagagttt gtaacacccg aagccggtgg    1440
cgtaaccctt tagggagcg agccgtctaa ggtgggacaa tgattaggg tgaagtcgta    1500 acaaggtagc cgtaggagaa cc                                            1522
```